US011339150B2

(12) United States Patent
Piscopio et al.

(10) Patent No.: US 11,339,150 B2
(45) Date of Patent: May 24, 2022

(54) BENZIMIDAZOLE COMPOUNDS AS HDAC6 INHIBITORS

(71) Applicant: OnKure, Inc., Boulder, CO (US)

(72) Inventors: Anthony D. Piscopio, Longmont, CO (US); Gan Zhang, Niwot, CO (US); Kevin Hunt, Stephenville, TX (US)

(73) Assignee: OnKure, Inc., Boulder, CO (US)

( * ) Notice: Subject to any disclaimer, the term of this patent is extended or adjusted under 35 U.S.C. 154(b) by 0 days.

(21) Appl. No.: 17/421,658

(22) PCT Filed: Dec. 23, 2020

(86) PCT No.: PCT/US2020/066916
§ 371 (c)(1),
(2) Date: Jul. 8, 2021

(87) PCT Pub. No.: WO2021/133957
PCT Pub. Date: Jul. 1, 2021

(65) Prior Publication Data
US 2022/0041584 A1 Feb. 10, 2022

Related U.S. Application Data

(60) Provisional application No. 62/954,152, filed on Dec. 27, 2019.

(51) Int. Cl.
*C07D 413/14* (2006.01)
*A61K 45/06* (2006.01)
*C07D 417/14* (2006.01)

(52) U.S. Cl.
CPC ............ *C07D 413/14* (2013.01); *A61K 45/06* (2013.01); *C07D 417/14* (2013.01)

(58) Field of Classification Search
None
See application file for complete search history.

(56) References Cited

U.S. PATENT DOCUMENTS

| 8,772,305 B2 | 7/2014 | Dahmann et al. |
| 2013/0157977 A1 | 6/2013 | Rivero et al. |
| 2019/0185462 A1 | 6/2019 | Walji et al. |

FOREIGN PATENT DOCUMENTS

| WO | 2007114827 A1 | 10/2007 |
| WO | 2017065473 A1 | 4/2017 |

OTHER PUBLICATIONS

Bali et al., "Inhibition of Histone Deacetylase 6 Acetylates and Disrupts the Chaperone Function of Heat Shock Protein 90", JBC (2005) 280, pp. 26729-26734.
Bolden et al., "Anticancer activities of histone deacetylase inhibitors", Nature Rev. Drug. Discov. (2006) vol. 5, pp. 769-784.
Choudhary et al. "Lysine Acetylation Targets Protein Complexes and Co-Regulates Major Cellular Functions", Science (2009) 325, pp. 834-840.
Grozinger et al., "Three proteins define a class of human histone deacetylases related to yeast Hda1p", Proc. Natl. Acad. Sd. U.S.A. (1999) 96, pp. 4868-4873.
Haberland et al., "The many roles of histone deacetylases in development and physiology: implications for disease and therapy", Nature Rev. Genet. (2009) 10(1), pp. 32-42.
Hu et al., "Cloning and Characterization of a Novel Human Class I Histone Deacetylase That Functions as a Transcription Repressor", J. Biol. Chem. (2000) 275, pp. 15254-15264.
International Search Report and Written Opinion for International Application No. PCT/US2020/66916, dated Mar. 26, 2021, 11 pages.
Kao et al., "Isolation of a novel histone deacetylase reveals that class I and class II deacetylases promote SMRT-mediated repression", Genes Dev. (2000) 14, pp. 55-66.
Kawaguchi et al., "The Deacetylase HDAC6 Regulates Aggresome Formation and Cell Viability in Response to Misfolded Protein Stress", Cell (2003) 115, pp. 727-738.
Lavu et al., "Sirtuins—novel therapeutic targets to treat age-associated diseases", Nature Rev. Drug Discov. (2008) 7, pp. 841-853.
Lee et al., "HDAC6 controls autophagosome maturation essential for ubiquitin-selective quality-control autophagy", EMBO (2010) 29, pp. 969-980.
Minucci et al., "Histone deacetylase inhibitors and the promise of epigenetic (and more) treatments for cancer", Nature Rev. Cancer (2006) 6, pp. 38-51.
Van Helleputte et al., "The role of histone deacetylase 6 (HDAC6) in neurodegeneration", Research and Reports in Biology (2014) 5, pp. 1-13.
Venter et al., "The Sequence of the Human Genome", Science (2001) 291, pp. 1304-1351.
Yang et al., "Isolation and Characterization of cDNAs Corresponding to an Additional Member of the Human Histone Deacetylase Gene Family", J. Biol. Chem. (1997) 272, pp. 28001-28007.
Zhang et al., "HDAC6 Modulates Cell Motility by Altering the Acetylation Level of Cortactin", Mol. Cell. (2007) 27, pp. 197-213.
Zhou et al., "Cloning and characterization of a histone deacetylase, HDAC9", Proc. Natl. Acad. Sci U.S.A. (2001) 98, pp. 10572-10577.

(Continued)

*Primary Examiner* — Heidi Reese
(74) *Attorney, Agent, or Firm* — RatnerPrestia

(57) ABSTRACT

Novel compounds of Formula I are described, where the compounds are selective HDAC6 inhibitors suitable for treatment of diseases associated with HDAC6, where X, Y, Z, $A_1$, $A_2$, $Q_1$ and $Q_2$ are as described.

Formula I

23 Claims, 1 Drawing Sheet

(56) References Cited

OTHER PUBLICATIONS

Hassig et al., "Nuclear histone acetylases and deacetylases and transcriptional regulation: HATs off to HDACs", Current Opinion in Chemical Biology, 1997, 1:300-308.

Taunton et al., "A Mammalian Histone Deacetylase Related to the Yeast Transcriptional Regulator Rpd3p", Science, vol. 272, Apr. 19, 1996, pp. 408-411.

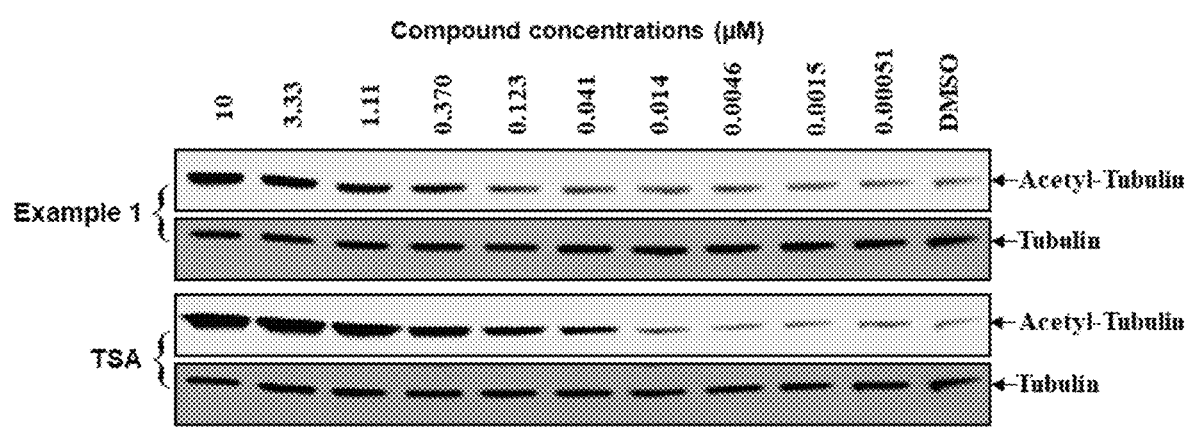

BENZIMIDAZOLE COMPOUNDS AS HDAC6 INHIBITORS

CROSS-REFERENCE TO RELATED APPLICATION

This application is the national phase of International Application No. PCT/US2020/066916, filed Dec. 23, 2020, which claims priority to U.S. Provisional Application No. 62/954,152, filed on Dec. 27, 2019, the contents of which applications are incorporated herein by reference in their entireties for all purposes.

BACKGROUND OF THE INVENTION

Post-translational modification of proteins through acetylation and deacetylation of lysine residues plays a critical role in regulating their cellular functions. Histone deacetylases (HDACs) are zinc-binding hydrolases that catalyze the deacetylation of lysine residues (Haberland et al., Nature Rev. Genet. (2009) 10, 32-42). HDACs participate in numerous cellular pathways that control cell shape, differentiation and proliferation, and HDAC inhibitors have been shown to be effective in treating cancer (Minucci et al., Nature Rev. Cancer (2006) 6, 38-51; Bolden et al., Nature Rev. Drug. Discov. (2006) 5, 769-784). HDAC inhibition results in hyperacetylation of chromatin, alterations in transcription, growth arrest, and apoptosis in cancer cell lines. Early phase clinical trials using available nonselective HDAC inhibitors demonstrate activities of these compounds against hematologic malignancies including multiple myeloma, although there is significant toxicity. It is known that HDACs can regulate the acetylation levels of a wide variety of proteins in addition to histones, thereby indicating a broad role for HDACs in numerous and critical cellular pathways in addition to transcriptional regulation (Choudhary et al., Science (2009) 325, 834-840).

Eleven human active site zinc-containing HDAC enzymes have currently been identified (Taunton et al., Science (1996) 272, 408-411; Yang et al., J. Biol. Chem. (1997) 272, 28001-28007; Grozinger et al., Proc. Natl. Acad. Sd. U.S.A. (1999) 96, 4868-4873; Kao et al., Genes Dev. (2000) 14, 55-66; Hu et al., J. Biol. Chem. (2000) 275, 15254-15264; Zhou et al., Proc. Natl. Acad. Sci U.S.A. (2001) 98, 10572-10577; Venter et al., Science (2001) 291, 1304-1351). These HDACs are classified into four families: Class I (HDAC1, HDAC2 and HDAC3), Class IIa (HDAC4, HDAC5, HDAC7 and HDAC9), Class IIb (HDAC6 and HDAC10) and Class IV (HDAC11). Class I modulates gene expression through deacetylation of the N-acetyl-lysine residues of histone proteins and other transcriptional regulators in the nucleus of the cell (Hassig et al., Curr. Opin. Chem. Biol. (1997) 1, 300-308). Class IIa can shuttle between the nucleus and the cytoplasm of the cell. However, the precise mechanism of transcriptional repression by Class IIa has not been fully elucidated.

An additional seven, structurally distinct HDACs known as the sirtuins, have been identified. Sirtuins use NAD as a cofactor (Lavu et al., Nature Rev. Drug Discov. (2008) 7, 841-853).

HDAC6 is unique among the known HDAC isoforms as it is the main cytoplasmic deacetylase in mammalian cells and is required for aggresome formation associated with ubiquitinated protein stress. For example, HDAC6 is involved with aggresome formation through regulation of acetylation of a-tubulin a component of microtubules and is essential for cellular viability in this context (Kawaguchi et al., Cell (2003) 115, 727-738; Lee et al., EMBO (2010) 29, 969-980). HDAC6 is believed to bind ubiquitinated proteins through a zinc finger domain and is known to interact with the dynein motor complex through another discrete binding motif, which allows transport of protein complexes along the microtubules. In addition, HDAC6 has been shown to regulate the acetylation state of the key heat shock protein Hsp90 (Bali et al., JBC (2005) 280, 26729-26734) and cortactin, a protein involved in cell motility (Zhang et al., Mol. Cell. (2007) 27, 197-213). Moreover, aberrant HDAC6 activity has been linked to various neurological and neurodegenerative disorders, including stroke, Huntington's disease, amyotrophic lateral sclerosis and Alzheimer's disease (Van Helleputte et al., Research and Reports in Biology (2014) 5, 1-13 and references cited therein).

There has been a significant research focus on the discovery of selective HDAC6 inhibitors, but many of the reported inhibitors undesirably retain moderate to significant inhibition of one or more off-target HDAC isoforms. This lack of selectivity for HDAC6 leads to mixed and often difficult to interpret results in preclinical assays and in vivo pharmacology models. Thus, there is a significant need for the development of HDAC6 inhibitors with improved selectivity and physiochemical profiles.

The present invention is directed towards novel compounds that selectively inhibit HDAC6 and use of the compounds for inhibiting HDAC6 and for treating diseases associated with HDAC6. It is understood that the embodiments of the invention discussed below with respect to the preferred variable selections can be taken alone or in combination with one or more embodiments, or preferred variable selections of the invention as if each combination were explicitly listed herein.

SUMMARY OF THE INVENTION

An aspect of the invention is a compound of Formula I:

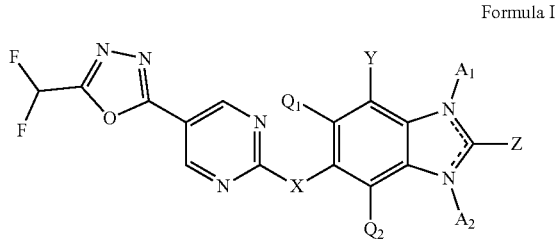

Formula I or pharmaceutically acceptable salts, co-crystals, tautomers, solvates, hydrates, polymorphs, isotopically enriched derivatives, or pro-drugs thereof, wherein:

X is $NR_1$ or O;

Y is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nC(O)NR_2R_3$, —$(CH_2)_nNR_2S(O)_2R_4$, —$(CH_2)_nS(O)R_4$, —$(CH_2)_nS(O)_2R_4$ or —$(CH_2)_nOR_2$, wherein Y is substituted with 0-3 independent $R_5$ substituents;

$Q_1$ is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nNR_2S(O)_2R_4$, —$(CH_2)_nS(O)R_4$, —$(CH_2)_nS(O)_2R_4$, or —$(CH_2)_nOR_2$, wherein $Q_1$ is substituted with 0-3 independent $R_5$ substituents; or X and $Q_1$ taken together with the other atoms to which X and $Q_1$ are attached form a heterocycloalkyl or heteroaryl ring; or Y and $Q_1$ taken together with the other atoms to which Y and $Q_1$ are attached form a cycloalkyl or aryl or heterocycloalkyl or heteroaryl ring; $Q_2$ is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nNR_2S(O)_2R_4$, —$(CH_2)_nS(O)R_4$, —$(CH_2)_nS(O)_2R_4$ or —$(CH_2)_nOR_2$, wherein $Q_2$ is substituted with 0-3 independent $R_5$ substituents; or X and $Q_2$ taken together with the other atoms to which X and $Q_2$ are attached form a heterocycloalkyl or heteroaryl ring; or $Q_2$ and $A_2$ taken together with the other atoms to which $Q_2$ and $A_2$ are attached form a heterocycloalkyl or heteroaryl ring;

Z is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nNR_2S(O)_2R_4$, —$(CH_2)_nS(O)R_4$, —$(CH_2)_nS(O)_2R_4$, or —$(CH_2)_nOR_2$, —$OR_2$ or oxygen where oxygen and the carbon to which is attached form a double bond;

$A_1$ and $A_2$ are each independently absent, hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl, —$(CH_2)_nNR_2R_3$, —$(CH_2)_nC(O)NR_2R_3$, —$(CH_2)_nNR_2C(O)R_4$, —$(CH_2)_nNR_2S(O)_2R_4$, —$(CH_2)_nCH(OH)CH_2(CH_2)_nOH$, —$(CH_2)_nC(O)R_4$ or —$(CH_2)_nOR_5$, —$(CH_2)_nS(O)R_4$, —$(CH_2)_nS(O)_2R_4$ wherein $A_1$ and $A_2$ are substituted with 0-3 independent $R_5$ substituents; or Y and $A_1$ taken together with the other atoms to which Y and $A_1$ are attached form a heterocycloalkyl or heteroaryl ring; or Z and $A_2$ taken together with the other atoms to which Z and $A_2$ are attached form a heterocycloalkyl or heteroaryl ring; or Z and $A_1$ taken together with the other atoms to which Z and $A_1$ are attached form a heterocycloalkyl or heteroaryl ring;

$R_1$ is hydrogen or $C_1$-$C_6$ alkyl;

$R_2$ and $R_3$ are each independently, hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl or —$(CH_2)_nOR_5$ wherein $R_2$ and $R_3$ are substituted with 0-3 independent $R_5$ substituents; or $R_2$ and $R_3$ taken together with the atom(s) to which $R_2$ and $R_3$ are attached form a heterocycloalkyl ring, where the heterocycloalkyl ring is substituted with 0-2 substituents selected from —$C_1$-$C_3$ alkyl, halogen, hydroxyl and amino;

$R_4$ is hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl, —$(CH_2)_nNR_6R_7$, —$(CH_2)_nOR_6$ wherein $R_4$ is substituted with 0-3 independent $R_5$ substituents; or $R_2$ and $R_4$ taken together with the atom(s) to which $R_2$ and $R_4$ are attached form a heterocycloalkyl ring;

each $R_5$ is independently hydrogen, halogen, acyl, carbamate, urea, alkoxyalkyl, —$C_1$-$C_6$ alkyl, —$C_1$-$C_6$ alkenyl, —$C_1$-$C_6$ alkynyl, heteroalkyl, haloalkyl, cycloalkyl, heterocycloalkyl, aryl, heteroaryl, arylalkyl, heteroarylalkyl, or heterocycloalkylalkyl;

$R_6$ and $R_7$ are each independently hydrogen, —$C_1$-$C_6$ alkyl and —$(CH_2)_nOH$; and n is independently 0, 1, 2, 3, 4, 5, 6, 7, 8, 9 or 10.

In an exemplary embodiment of Formula I, Y and $A_1$ taken together with the other atoms to which Y and $A_1$ are attached form a heterocycloalkyl or heteroaryl ring.

In an exemplary embodiment of Formula I, $Q_2$ and $A_2$ taken together with the other atoms to which $Q_2$ and $A_2$ are attached form a heterocycloalkyl or heteroaryl ring.

In an exemplary embodiment of Formula I, Z and $A_1$ taken together with the other atoms to which Z and $A_1$ are attached form a heterocycloalkyl or heteroaryl ring.

In an exemplary embodiment of Formula I, Z and $A_2$ taken together with the other atoms to which Z and $A_2$ are attached form a heterocycloalkyl or heteroaryl ring.

In an exemplary embodiment of Formula I, X and $Q_2$ taken together with the other atoms to which X and $Q_2$ are attached form a heterocycloalkyl or heteroaryl ring.

In an exemplary embodiment of Formula I, X and $Q_1$ taken together with the other atoms to which X and $Q_1$ are attached form a heterocycloalkyl or heteroaryl ring.

In an exemplary embodiment of Formula I, Y and $Q_1$ taken together with the other atoms to which Y and $Q_1$ are attached form a cycloalkyl or aryl or heterocycloalkyl or heteroaryl ring.

In an exemplary embodiment, the heterocycloalkyl ring formed by Y/$A_1$ or $Q_2$/$A_2$ or Z/$A_1$ or Z/$A_2$ or X/$Q_2$ or X/$Q_1$ or Y/$Q_1$ is a 5-10-membered ring or a 5-6-membered ring.

In an exemplary embodiment, the compound of Formula I is a compound of Formula II

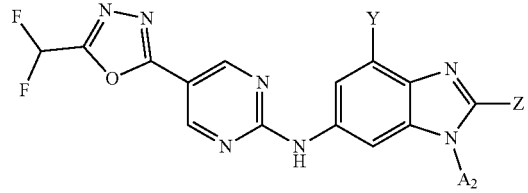

or pharmaceutically acceptable salts, co-crystals, tautomers, solvates, hydrates, polymorphs, isotopically enriched derivatives, or pro-drugs thereof, wherein:

Y is hydrogen, halogen, aryl, heteroaryl, —$(CH_2)_nC(O)NR_2R_3$ or —$(CH_2)_nS(O)_2R_4$;

$A_2$ is hydrogen, —$C_1$-$C_6$ alkyl, —$C_1$-$C_6$ alkenyl, —$(CH_2)_nOH$, —$(CH_2)_nNR_2R_3$ or —$(CH_2)_nCH(OH)CH_2(CH_2)_nOH$;

Z is H, —$C_1$-$C_3$ alkyl or —$NR_2R_3$, where $R_2$ and $R_3$ are each independently —$C_1$-$C_3$ alkyl or —$C_1$-$C_3$ alkenyl.

In an exemplary embodiment of Formula II, Z and $A_2$ taken together with the atoms attached to Z and $A_2$ form a heterocycloalkyl or heteroaryl ring.

In an exemplary embodiment of Formula II, Z is hydrogen and $A_2$ is hydrogen.

In an exemplary embodiment of Formula II, Y is phenyl, pyridyl, —$C(O)NR_2R_3$ or —$S(O)_2NH(CH_2)_nOH$; Z is hydrogen; and $A_2$ is hydrogen.

In an exemplary embodiment, the compound is selected from the group consisting of N-(5-(5-(difluoromethyl)-1,3,4-oxadiazol-2-yl)pyrimidin-2-yl)-4-phenyl-1H-benzo[d]imidazol-6-amine (1); 4-bromo-N-(5-(5-(difluoromethyl)-1,3,4-oxadiazol-2-yl)pyrimidin-2-yl)-1H-benzo[d]imidazol-6-amine (2); N-(5-(5-(difluoromethyl)-1,3,4-oxadiazol-2-yl)pyrimidin-2-yl)-4-(pyridin-3-yl)-1H-benzo[d]imidazol-6-amine hydrochloride (3); N-(5-(5-(difluoromethyl)-1,3,4-oxadiazol-2-yl)pyrimidin-2-yl)-1-methyl-4-phenyl-1H-benzo[d]imidazol-6-amine (4); N-(5-(5-(difluoromethyl)-1,3,4-oxadiazol-2-yl)pyrimidin-2-yl)-2-methyl-4-phenyl-1H-benzo[d]imidazol-6-amine (5); N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine 2,2,2- trifluoroacetate (6); N-(5-(5-(difluoromethyl)-1,3,4-oxadiazol-2-yl)pyrimidin-2-yl)-N-methyl-4-phenyl-1H-benzo[d]imidazol-6-amine (7); 6-((5-(5-(difluoromethyl)-1,3,4-oxadiazol-2-yl)pyrimidin-2-yl)amino)-N,N-dimethyl-1H-benzo[d]imidazole-4-carboxamide (8); N-(5-(5-(difluoromethyl)-1,3,4-oxadiazol-2-yl)pyrimidin-2-yl)-4-(2,4-difluorophenyl)-1H-benzo[d]imidazol-6-amine (9); N-(5-(5-(difluoromethyl)-1,3,4-oxadiazol-2-yl)pyrimidin-2-yl)-4-(pyridin-2-yl)-1H-benzo[d]imidazol-6-amine (10); 6-((5-(5-(difluoromethyl)-1,3,4-oxadiazol-2-yl)pyrimidin-2-yl)amino)-N-(2-hydroxyethyl)-1H-benzo[d]imidazole-4-sulfonamide (11); 1-allyl-N-(5-(5-(difluoromethyl)-1,3,4-oxadiazol-2-yl)pyrimidin-2-yl)-4-phenyl-1H-benzo[d]imidazol-6-amine (12); 3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol (13); 3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol (14); N-(5-(5-(difluoromethyl)-1,3,4-oxadiazol-2-yl)pyrimidin-2-yl)-1-(2-(dimethylamino)ethyl)-4-phenyl-1H-benzo[d]imidazol-6-amine (15); 1-(2-(6-((5-(5-(difluoromethyl)-1,3,4-oxadiazol-2-yl)pyrimidin-2-yl)amino)-4-phenyl-1H-benzo[d]imidazol-1-yl)ethyl)pyrrolidin-3-ol (16); N-(5-(5-(difluoromethyl)-1,3,4-oxadiazol-2-yl)pyrimidin-2-yl)-4-(4-morpholinophenyl)-1H-benzo[d]imidazol-6-amine (17); N-(5-(5-(difluoromethyl)-1,3,4-oxadiazol-2-yl)pyrimidin-2-yl)-4-(4-(morpholinomethyl)phenyl)-1H-benzo[d]imidazol-6-amine (18); N-(5-(5-(difluoromethyl)-1,3,4-oxadiazol-2-yl)pyrimidin-2-yl)-4-phenyl-1H-benzo[d]imidazol-6-amine (19) and a pharmaceutically acceptable salt of any one of compounds (1) through (19).

Another aspect of the invention is a pharmaceutical composition comprising a compound of Formula I or Formula II and a pharmaceutically acceptable carrier and/or excipient.

Another aspect of the invention is a method of treating a disease, disorder or symptom associated with HDAC6, comprising administering to a subject in need thereof a therapeutically effective amount of a compound of Formula I or Formula II.

In an exemplary embodiment, the compound of Formula I or Formula II is present as a pharmaceutical composition.

In an exemplary embodiment, the disease, disorder or symptom associated with HDAC6 is selected from the group consisting of cancer, a proliferative disease, a neurodegenerative disease, pain, an autoimmune or inflammatory disorder, an infection, a metabolic disorder, a hematologic disorder or a cardiovascular disease.

In an exemplary embodiment, the disorder or disease is cancer or a proliferative disease. In particular embodiments, the cancer or proliferative disease is selected from the group consisting of a carcinoma, a sarcoma, a leukemia, a blastoma, a lymphoma, a myeloma, a melanoma and a combination thereof. In particular embodiments, the disorder or disease is selected from the group consisting of multiple myeloma, melanoma, breast cancer, pancreatic cancer, ovarian cancer, prostate cancer, hepatocellular cancer, renal cancer, leukemia, T-cell lymphoma, cardiac cancer, bone cancer, glioblastoma, neuroblastoma, oral squamous cell carcinoma, urothelial cancer, lung cancer, cervical cancer, rectal cancer, liver cancer, pancreatic cancer, brain cancer, kidney cancer, stomach cancer, skin cancer, colon cancer, head and neck squamous cell carcinoma, Burkitt's Lymphoma, esophageal cancer, Hodgkin's lymphoma, bladder cancer, gastric cancer and a combination thereof.

In particular embodiments, the disorder or disease is selected from the group consisting of rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, eczema, psoriasis, sepsis, airway hyperresponsiveness, ulcerative colitis and a combination thereof.

In particular embodiments, the disorder or disease is selected from the group consisting of peripheral neuropathy, chemotherapy induced peripheral neuropathy, diabetic peripheral neuropathy, neuropathy, neuralgia, trigeminal neuralgia, postherpetic neuralgia, autoimmune peripheral neuropathy, Leber's hereditary optic neuropathy, POEMS syndrome, Cattleman disease, pain due to tumor infiltration, HIV related peripheral neuropathy, post-amputation phantom pain syndrome, Charcot-Marie-Tooth disease, medication induced peripheral neuropathy and a combination thereof.

In a particular embodiment, the disorder or disease is peripheral neuropathy, including drug induced peripheral neuropathy (e.g., chemotherapy induced peripheral neuropathy).

In an exemplary embodiment, the disorder or disease is peripheral neuropathy induced by treatment with an anti-cancer agent (e.g., alkylating agents, CAR-T cells, anti-CD38 antibodies, anti-CTLA-4 antibodies, epothilones, immunomodulatory agents, immuno-oncology agents, anti-PD-1 antibodies, anti-PD-LI antibodies, proteasome inhibitors, taxanes, platinum-based chemotherapeutic agents, and vinca alkaloids). In particular embodiments, the disorder or disease is peripheral neuropathy induced by treatment with arsenic trioxide, bortezomib, cabazitaxel, carboplatin, carfilzomib, cisplatin, carboplatin, oxaliplatin, cyclophosphamide, darzalex, docetaxel, elotuzumab, eribulin, fluorouracil (5-FU), gefitinib, gemcitabine hydrochloride, indatuximab, ixazomib, ravtansine, ipilimumab, ixabepilone, lenalidomide, nab-paclitaxel, nivolumab, oxaliplatin, paclitaxel, pomalidomide, temozolomide, thalidomide, vinblastine, vincristine, vindesine, or vinorelbine.

In an exemplary embodiment, the disorder or disease is peripheral neuropathy induced by treatment with a drug other than an anti-cancer agent (e.g., cardiovascular agents, statins, antimicrobial agents, immunosuppressants, anti-alcohol drugs, anticonvulsants, TNF-α inhibitors, and nucleoside analog reverse transcriptase inhibitors (NRTis)). In particular embodiments, the disorder or disease is peripheral neuropathy induced by treatment with atorvastatin, pitavastatin, lovastatin, simvastatin, pravastatin, fluvastatin, rosuvastatin, amiodarone, chloramphenicol, chloroquine, dapsone, fluoroquinolones, hydralazine, etanercept, ethambutol, isoniazid, linezolid, metronidazole, nitrofurantoin, leflunomide, phenytoin, didanosine, stavudine, or zalcitabine.

In an exemplary embodiment, the disorder or disease is cancer and peripheral neuropathy (e.g., chemotherapy induced peripheral neuropathy).

In exemplary embodiments, the disorder or disease is epilepsy, attention deficit disorder, depression, anxiety, Alzheimer's disease, Parkinson's Disease, Huntington's Disease, amyotrophic lateral sclerosis, spinal muscular atrophy, essential tremor, central nervous system trauma, multiple sclerosis, Charcot-Marie-Tooth (CMT), cerebral ischemia, stroke, Gulf War Illness, or a combination thereof.

In exemplary embodiments, the disorder or disease is an infection caused by virus, fungus, or bacteria, or a combination thereof.

In exemplary embodiments, the disorder or disease is metabolic syndrome, diabetes, obesity, high blood pressure, heart failure, cyst growth in autosomal dominant polycystic kidney disease (ADPKD), or a combination thereof.

In exemplary embodiments, the disorder or disease is cardiovascular stress, pressure overload, chronic ischemia, infarction-reperfusion injury, hypertension, atherosclerosis, peripheral artery disease, heart failure, hypertrophy, angina, arrhythmias, hypercholesterolemia, atherosclerosis, or stroke, or a combination thereof.

BRIEF DESCRIPTION OF THE DRAWINGS

The FIGURE shows the results of a comparison of Example 1 with reference compound TSA in a culture using U266B1 human myeloma cells.

DETAILED DESCRIPTION OF THE INVENTION

Definitions

The term "pharmaceutically acceptable" or "pharmacologically acceptable" as used herein, refer to molecular entities and compositions that do not produce adverse, allergic, or other untoward reactions when administered to an animal or a human.

The term, "pharmaceutically acceptable carrier" as used herein, includes any and all solvents, or a dispersion medium including, but not limited to, water, ethanol, a polyol (for example, glycerol, propylene glycol, and liquid polyethylene glycol, and the like), suitable mixtures thereof, and vegetable oils, coatings, isotonic and absorption delaying agents, liposomes, commercially available cleansers, and the like. Supplementary bioactive ingredients also can be incorporated into such carriers.

The term "alkyl", as used herein, means any straight chain or branched, non-cyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms, such as 6-10 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like.

Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as "cycloalkyls", "homocycles" or "homocyclic rings."

Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, refers to any aromatic carbocyclic moiety such as, but not limited to, phenyl or naphthyl.

The term "arylalkyl", or "aralkyl" as used herein, refers to any alkyl having at least one alkyl hydrogen atom replaced with an aryl moiety, such as benzyl, but not limited to, —(CH$_2$)$_2$phenyl, —(CH$_2$)$_3$phenyl, —CH(phenyl)$_2$, and the like.

The term "halogen" as used herein, refers to any fluoro, chloro, bromo, or iodo moiety.

The term "haloalkyl" as used herein, refers to any alkyl having at least one hydrogen atom replaced with halogen, such as trifluoromethyl, and the like.

The term "heteroaryl" as used herein, refers to any aromatic heterocycle ring of 5 to 10 members and having at least one heteroatom selected from nitrogen, oxygen and sulfur, and containing at least one carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl or quinazolinyl.

The term "heteroarylalkyl" as used herein, refers to any alkyl having at least one alkyl hydrogen atom replaced with a heteroaryl moiety, such as —CHpyridinyl, —CH$_2$-pyrimidinyl, and the like.

The term "heterocycloalkyl" or "heterocycle" or "heterocyclic ring", as used herein, refers to any 3- to 7-membered monocyclic or any 7- to 10-membered bicyclic ring which is either saturated or partially unsaturated, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycloalkyl ring may be attached via any heteroatom or carbon atom. Heterocycloalkyls include, but are not limited to, aziridinyl, azetidinyl, morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl and the like.

The term "heterocycloalkylalkyl", as used herein, refers to any alkyl having at least one alkyl hydrogen atom replaced with a heterocycloalkyl ring, such as —CH$_2$-morpholinyl, and the like.

The term "homocycle" or "cycloalkyl", as used herein, refers to any saturated or unsaturated (but not aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, refers to at least one alkyl moiety attached through a nitrogen bridge (i.e., —N-(alkyl)N, such as a dialkylamino) including, but not limited to, methylamino, ethylamino, dimethylamino, diethylamino, and the like.

The term "alkyloxy" or "alkoxy", as used herein, refers to any alkyl moiety attached through an oxygen bridge (i.e., —O-alkyl) such as, but not limited to, methoxy, ethoxy, and the like.

The term "alkylthio", as used herein, refers to any alkyl moiety attached through a sulfur bridge (i.e., —S— alkyl) such as, but not limited to, methylthio, ethylthio, and the like.

The term "alkenyl" refers to an unbranched or branched hydrocarbon chain having one or more double bonds therein. The double bond of an alkenyl group can be unconjugated or conjugated to another unsaturated group. Suitable alkenyl groups include, but are not limited to vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl group can be unsubstituted or substituted with one or two suitable substituents.

The term "alkynyl" refers to an unbranched or branched hydrocarbon chain having one or more triple bonds therein. The triple bond of an alkynyl group can be unconjugated or conjugated to another unsaturated group. Suitable alkynyl groups include, but are not limited to, ethynyl, propynyl, butynyl, pentynyl, hexynyl, methylpropynyl, 4-methyl-I-butynyl, 4-propyl-2-pentynyl- and 4-butyl-2-hexynyl. An alkynyl group can be unsubstituted or substituted with one or two suitable substituents.

The terms "alkylene", "alkenylene" and "alkynylene" as used herein refer to a divalent alkane, alkene and alkyne radical, respectively. It is understood that the alkylene, alkenylene and alkynylene may be straight or branched. An alkylene, alkenylene and alkynylene may also be substituted and unsubstituted.

The term "salts" as used herein, refers to any salt that complexes with identified compounds described herein. Examples of such salts include, but are not limited to, acid addition salts formed with inorganic acids (e.g., hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known to a person skilled in the art, which specifically includes the quaternary ammonium salts of the formula —NRR'R"$^+$Z$^-$, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

As used herein, the term "prodrug" refers to a derivative of a compound that can hydrolyze, oxidize, or otherwise react under biological conditions (in vitro or in vivo) to provide a compound of the invention. Prodrugs may only become active upon some reaction under biological conditions, but they may have activity in their unreacted forms. Examples of prodrugs contemplated herein include, without limitation, analogs or derivatives of compounds of the invention, and/or their salts when salt formation is possible, but in particular, derivatives of zinc binding thiol moiety. Examples of prodrug moieties include substituted and unsubstituted, branched or unbranched lower alkyl ester moieties, (e.g., a propionic acid ester), lower alkenyl esters, di-lower alkyl-amino lower-alkyl esters (e.g., a dimethylaminoethyl ester), acylamino lower alkyl esters (e.g., an acetyloxymethyl ester), acyloxy lower alkyl esters (e.g., a pivaloyloxymethyl ester), aryl esters (e.g., a phenyl ester), aryl-lower alkyl esters (e.g., a benzyl ester), heteroaryl esters (e.g., a nicotinate ester), substituted (e.g., with methyl, halo, or methoxy substituents) aryl and aryl-lower alkyl esters, amides, lower-alkyl amides, di-lower alkyl amides, and hydroxy amides. Naturally occurring amino acid esters or their enantiomers, dipeptide esters, phosphate esters, methoxyphosphate esters, disulfides and disulfide dimers may also qualify as prodrugs. Prodrugs and their uses are well known in the art (see, e.g., Berge et al. 1977). Prodrugs can typically be prepared using well-known methods, such as those described in Burger's Medicinal Chemistry and Drug Discovery (Manfred E. Wolff ed. 1995) and (Rautio, 2008).

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In various exemplary embodiments, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository, etc.

The term "patient", as used herein, is an animal, such as, for example, a mammal, such as, for example, a human. For example, out-patients and persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "subject" as used herein refers to a vertebrate, preferably a mammal, more preferably a primate, still more preferably a human. Mammals include, without limitation, humans, primates, wild animals, feral animals, farm animals, sports animals and pets.

In an exemplary embodiment, the invention provides a pharmaceutical comprising at least one pharmaceutically acceptable carrier, in addition to one or more compounds described herein. The composition can be present in any suitable form for the desired route of administration. A therapeutically effective amount of a compound as described herein depends upon the amounts and types of excipients employed, the amounts and specific types of active ingredients present in a dosage form, and the route by which the compound is to be administered to patients.

In an exemplary embodiment, dosage levels for the compounds of the invention range from about 0.001 to about 100 mg per kg of the subject's body weight and can be administered in single or multiple doses.

In an exemplary embodiment, the dose ranges from about 0.1 mg to about 2000 mg per day and can be given as a single once-a-day dose or, alternatively, as divided doses throughout the day or week or other predetermined time period. In a particular embodiment, the daily dose is administered twice daily in equally divided doses.

Suitable oral compositions in accordance with the invention include, without limitation, tablets, troches, lozenges, aqueous or oily suspensions, dispersible powders or granules, emulsion, hard or soft capsules, syrups or elixirs. Compositions suitable for oral use may be prepared according to any method known to the art for the manufacture of pharmaceutical compositions. For example, liquid formulations of the compounds can contain one or more agents selected from the group consisting of sweetening agents, flavoring agents, coloring agents and preserving agents in order to provide attractive and palatable preparations of the active agents.

For tablet compositions, typical pharmaceutically acceptable excipients include, without limitation, inert diluents such as calcium carbonate, sodium carbonate, lactose, calcium phosphate or sodium phosphate; granulating and disintegrating agents such as, for example, corn starch, or alginic acid; binding agents such as, for example, starch, gelatin or lubricating agents such as, for example, magnesium stearate, stearic acid or talc. The tablets may be uncoated or, alternatively, they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent such as, for example, calcium carbonate, calcium phosphate or kaolin, or as soft gelatin capsules wherein the active ingredient is mixed with water or an oil medium such as, for example peanut oil, liquid paraffin or olive oil.

For aqueous suspensions, the compound is admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth and gum acacia.

Oral suspensions may also contain dispersing or wetting agents, such as naturally-occurring phosphatide such as, for example, lecithin, or condensation products of an alkylene oxide with fatty acids such as, for example, polyoxyethylene stearate, or condensation products of ethylene oxide with long chain aliphatic alcohols such as, for example, heptadecaethyleneoxycetanol, or condensation products of ethylene oxide with partial esters derived from fatty acids and a hexitol such as, for example, polyoxyethylene sorbitol monooleate, or condensation products of ethylene oxide with partial esters derived from fatty acids and hexitol anhydrides such as, for example, polyethylene sorbitan monooleate. The aqueous suspensions may also contain one or more preservatives such as, for example, ethyl or n-propyl p-hydroxybenzoate, one or more coloring agents, one or more flavoring agents, and one or more sweetening agents such as sucrose or saccharin.

Sweetening agents such as those set forth above, and flavoring agents may be added to provide palatable oral preparations. The compositions may be preserved by the addition of an anti-oxidant such as ascorbic acid.

Dispersible powders and granules suitable for the preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients such as, for example, sweetening, flavoring and coloring agents, may also be present.

Syrups and elixirs may be formulated with sweetening agents such as, for example, glycerol, propylene glycol, sorbitol or sucrose. Such formulations may also contain a demulcent, a preservative, and flavoring and coloring agents.

Compositions for parenteral administrations are formulated in a sterile medium suitable for intravenous, intramuscular or intrathecal delivery. A sterile injectable preparation of the compounds may be in the form of a sterile injectable solution or sterile injectable suspension. Parentally acceptable diluents or solvents such as, for example, 1,3-butanediol can be used to formulate the parenteral compositions. Among acceptable vehicles and solvents that may be employed are water, Ringer's solution and isotonic sodium chloride solution. In addition, sterile oils also can be employed as a solvent or as a suspending medium. For this purpose, any bland fixed oil may be employed, including synthetic monoglycerides or diglycerides. In addition, fatty acids such as oleic acid can be used in the preparation of injectables.

Depending on the vehicle used and the concentration of the drug in the formulation, the parenteral formulation can contain other adjuvants such as local anesthetics, preservatives and buffering agents.

In yet another exemplary embodiment, a pharmaceutical composition according to the invention may contain one or more additional therapeutic agents, for example, to increase efficacy or to decrease side effects.

In various exemplary embodiments, the compounds and compositions described herein can be administered concurrently with, prior to, or subsequent to one or more additional therapeutic agents, which may be useful as, e.g., combination therapies. Therapeutic agents include therapeutically active agents. Therapeutic agents also include prophylactically active agents. Therapeutic agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In exemplary embodiments, the additional therapeutic agent is a therapeutic agent useful for treating and/or preventing a disease (e.g., cancer, proliferative disease, neurodegenerative disease, autoimmune or inflammatory disorder, infection, metabolic disorder, hematologic disorder, cardiovascular disease). Each additional therapeutic agent may be administered at a dose and/or on a time schedule determined as effective for that therapeutic agent. The additional therapeutic agents may also be administered together with each other and/or with the compound or composition described herein in a single dose or administered separately in different doses. The particular combination to employ in a regimen will take into account compatibility of the compound described herein with the additional therapeutic agent(s) and/or the desired therapeutic and/or prophylactic effect to be achieved. In general, it is expected that the additional therapeutic agent(s) in combination be utilized at levels that do not exceed the levels at which they are utilized individually. In some embodiments, the levels utilized in combination will be lower than those utilized individually.

In exemplary embodiments, the additional therapeutic agent (e.g., as part of a pharmaceutical composition or a combination therapy) may induce an undesired side effect (e.g., peripheral neuropathy). A compound of, for example, Formula I or Formula II is useful for treatment of the undesired side effect when administered in combination with the additional therapeutic agent (e.g., as part of a pharmaceutical composition or a combination therapy).

The additional therapeutic agents include, but are not limited to, anti-proliferative agents, anti-cancer agents, anti-angiogenesis agents, anti-inflammatory agents, and immunosuppressants. In certain embodiments, the additional therapeutic agent is an immunotherapy. In certain embodiments, the additional therapeutic agent is an anti-proliferative agent. In certain embodiments, the additional therapeutic agent is an anti-cancer agent. In certain embodiments, the anti-cancer agents include, but are not limited to, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum-based chemotherapeutic agents (e.g., cisplatin, carboplatin, oxaliplatin), vinca alkaloids (e.g., vincristine, vinblastine, vindesine, and vinorelbine), taxoids (e.g. paclitaxel or a paclitaxel) equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG 1005 (Angiopep-2 bound to three molecules of paclitaxel), paclitaxel-EC-1 (paclitaxel bound to the erbB2-recognizing peptide EC-1), and glucose-conjugated paclitaxel, (e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), thalidomide, lenalidomide, pomalidomide, tyrosine kinase inhibitors (e.g., axitinib (AG013736), bosutinib (SKI-606), cediranib (RECENTIN™, AZD2171), dasatinib (SPRYCEL™, BMS-354825), erlotinib (TARCEVA™), gefitinib (IRESSA™), imatinib (Gleevec®, CGP57148B, STI-571), lapatinib (TYKERB™, TYVERB™), lestaurtinib (CEP-701), neratinib (HKI-272), nilotinib (TASIGNA®), semaxanib (semaxinib, SU5416), sunitinib (SUTENT®, SU11248), toceranib (PALLADIA™), vandetanib (ZACTIMA™, ZD6474), vatalanib (PTK787, PTK/ZK), trastuzumab (HERCEPTIN™), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR™), everolimus (AFINITOR®), alemtuzumab (CAMPATH®), gemtuzumab ozogamicin (MYLOTARG™), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE), ixazomib (NINLARO)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL 765 (Sanofi Aventis), PF-4691502 (Pfizer), GDC0980 (Genetech), SF1126 (Semafoe) and OSI-027

(OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin and hexamethyl melamine.

In exemplary embodiments, the additional therapeutic agent is an immunotherapy. In particular embodiments, the immunotherapy is useful in the treatment of a cancer. Exemplary immunotherapies include, but are not limited to, T-cell therapies, interferons, cytokines (e.g., tumor necrosis factor, interferon a, interferon y), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In an exemplary embodiment, the immunotherapy is an antibody. In particular embodiments, the antibody is an anti-PD-1 antibody, an anti-PD-LI antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAMI antibody, an anti-BTLA antibody, an anti-LIGHT antibody, an anti-TIGIT antibody, an anti-VISTA antibody, an anti-HVEM antibody, an anti-Siglec antibody, an anti-GALI antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICE antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR00I, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDIO680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, trastuzumab, pertuzumab, obinutuzumab, cabiralizumab, margetuximab, enoblituzumab, mogamulizumab, panitumumab, carlumab, bevacizumab, rituximab or cetuximab.

EXAMPLES

The following examples which are set forth are offered to merely illustrate specific exemplary compounds, pharmaceutical compositions and methods of the present invention as described and are not to be construed in any way as limiting the scope of the invention.

General Experimental Procedures

Definitions of variables used in the structures in the schemes provided herein are commensurate with the variables of the corresponding positions in the chemical formulae delineated herein. The compounds of the Examples listed in Table 1 were characterized by HPLC, LCMS and/or $^1$HNMR. In some cases, crude reaction products were used in subsequent steps without characterization.

Common Abbreviations

ACN acetonitrile
aq. aqueous
Bn benzyl
br broad
CDI carbonyl diimidazole
d doublet
DCE 1,2-dichloroethane
DCM dichloromethane
dd doublet of doublets
dba dibenzylideneacetone
DFAA difluoroacetic anhydride
DIPEAq diisopropylethylamine
DMF dimethylformamide
DMSO dimethyl sulfoxide
dppf 1,1'-ferrocenediyl-bis(diphenylphosphine) ethyl acetate
eq equivalents
EA ethyl acetate
h hour(s)
HRMS high resolution mass spectrometry
HPLC high performance liquid chromatography
LCMS liquid chromatography and mass spectrometry
MS mass spectrometry
MW microwave
m multiplet
Me methyl
MeCN acetonitrile
min minutes
MeOH methanol
MHz megahertz
mL milliliter(s)
mmol millimoles
m/z mass to charge ratio
NBS N-bromo succinimide
NCS N-chloro succinimide
NMP N-methyl-2-pyrrolidone
NMR nuclear magnetic resonance
ppm parts per million
PPE petroleum ether
rt room temperature
s singlet
SM starting material
sol. solution
t triplet
pmol micromoles
TEA triethyl amine
TEOF triethyl orthoformate
TFA trifluoroacetic acid
TFAA trifluoroacetic anhydride
THP tetrahydropyranyl
TLC thin layer chromatography
p-TosOH para-toluenesulfonic acid Example 1. N-(5-(5-(difluoromethyl)-1,3,4-oxadiazol-2-yl)pyrimidin-2-yl)-4-phenyl-1H-benzo[d]imidazol-6-amine (1)

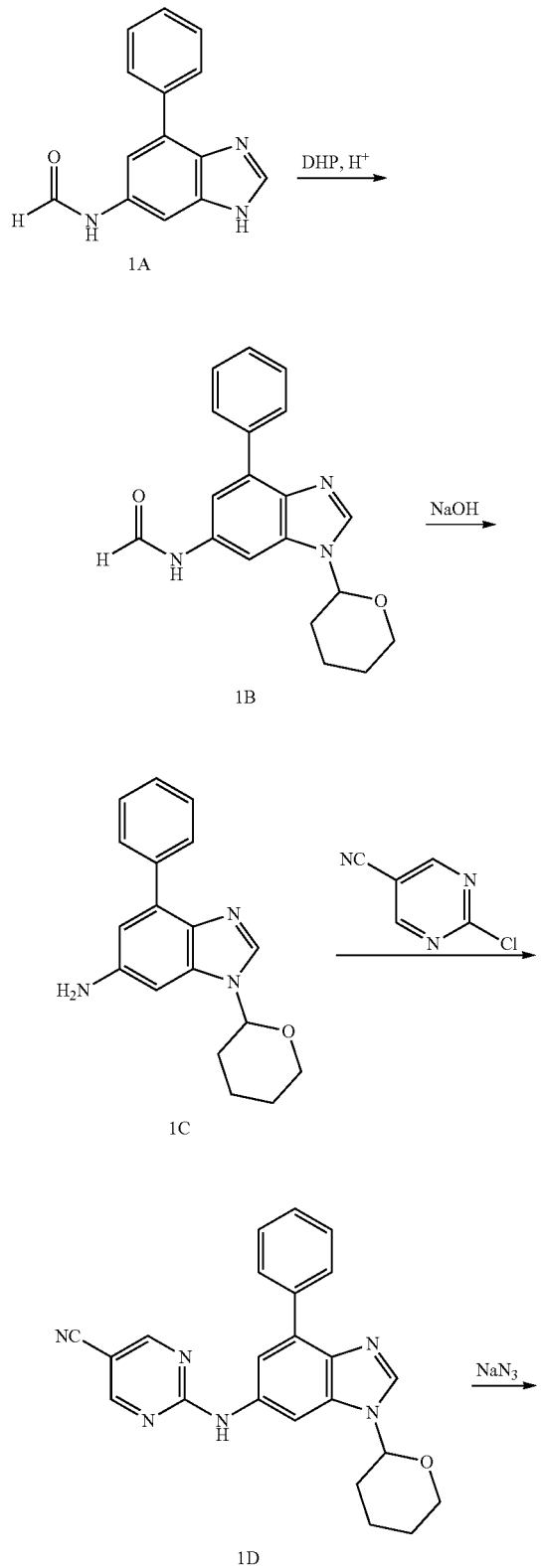

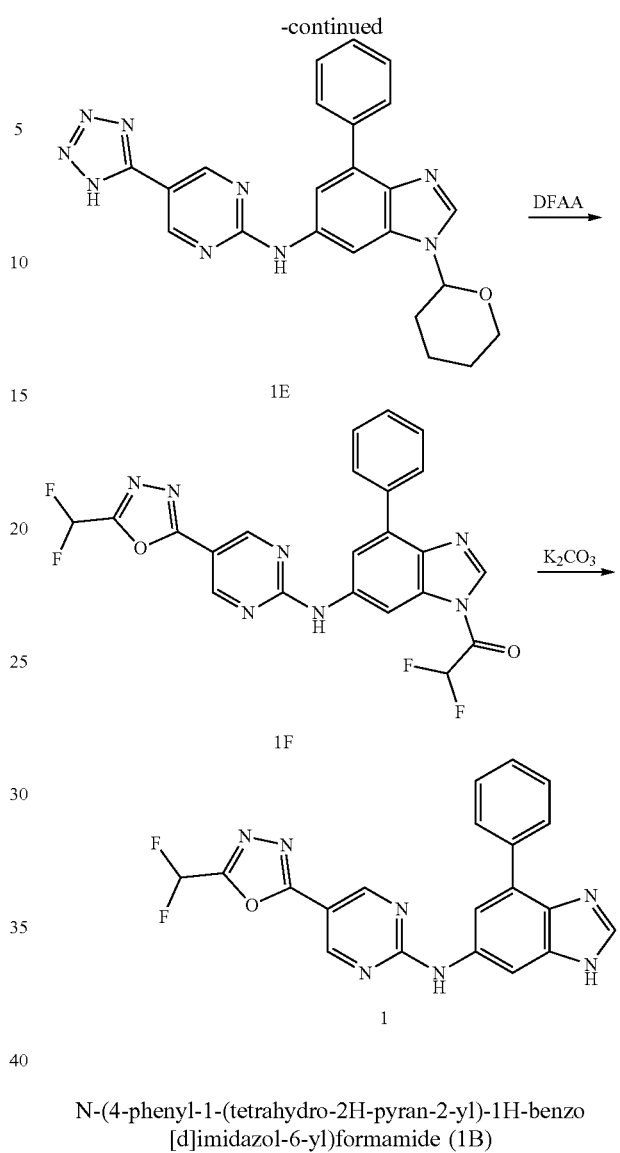

N-(4-phenyl-1-(tetrahydro-2H-pyran-2-yl)-1H-benzo[d]imidazol-6-yl)formamide (1B)

To a solution of compound 1A (synthesis described in WO 2007/114812 A1) (11.5 g, 48.5 mmol, 1.0 eq) in DMF (115 mL) was added DHP (40.8 g, 485 mmol, 44.3 mL, 10.0 eg) and TsOH.H$_2$O (922 mg, 4.85 mmol, 0.1 eq) at 15° C. The resulting mixture was heated to 65° C. and then stirred at 65° C. for 13 h. TLC (dichloromethane: methanol=8:1, R$_{f\text{-}SM}$=0.49) showed that the starting material was completely consumed. The reaction mixture was cooled to 25° C. and then combined with the mixture of a previous batch (2.0 g scale) for work-up. The mixture was poured into water (130 mL) and stirred for 5 min. The aqueous phase was extracted with ethyl acetate (100 mL, 60 mL). The combined organic phase was washed with brine (80 mL), dried with anhydrous Na$_2$SO$_4$, filtered and concentrated in vacuo. The residue was purified by column chromatography on silica gel (100-200 mesh silica gel, petroleum ether/ethyl acetate=2/1, 0/1) to give 1B (11.0 g, crude from two batches) as a red solid. $^1$H NMR: 400 MHz DMSO-d$_6$ δ 8.39 (s, 1H), 8.35 (d, J=1.6 Hz, 1H), 8.07 (d, J=1.6 Hz, 1H), 7.98-8.01 (m, 1H), 7.46-7.56 (m, 3H), 7.36-7.41 (m, 1H), 5.61-5.67 (m, 1H), 3.99-4.04 (m, 1H), 3.72-3.77 (m, 1H), 2.17-2.26 (m, 1H), 1.97-2.06 (m, 2H), 1.55-1.86 (m, 3H).

4-phenyl-1-(tetrahydro-2H-pyran-2-yl)-1H-benzo[d]imidazol-6-amine (1C)

To a solution of compound 1B (7.00 g, 21.8 mmol, 1.0 eq) in methanol (70 mL) was added a solution of sodium hydroxide (2.61 g, 65.3 mmol, 3.0 eq) in water (25 mL) at 15° C. The resulting mixture was stirred at 60° C. for 14 h. TLC (petroleum ether:ethyl acetate=0:1, $R_{f\text{-}SM}$=0.38, $R_{f\text{-}DP}$=0.45) showed that the starting material was completely consumed. The reaction mixture was cooled to 20° C. and then concentrated in vacuo to remove methanol. The residue was diluted with water (10 mL) and stirred for 3 min. The aqueous phase was extracted with ethyl acetate (30 mL, 15 mL). The combined organic phase was washed with dried with anhydrous $Na_2SO_4$, filtered and concentrated in vacuo. The residue was purified by column chromatography on silica gel (100-200 mesh silica gel, petroleum ether/ethyl acetate=2/1, 0/1) to give 1C (3.50 g, 11.4 mmol, 53% yield, 95.9% purity) as a pink solid. 1H NMR: 400 MHz DMSO-$d_6$ δ 8.07 (s, 1H), 7.97 (d, J=8.4 Hz, 2H), 7.44 (t, J=7.6 Hz, 2H), 7.33 (t, J=7.2 Hz, 1H), 6.80 (d, J=1.6 Hz, 1H), 6.72 (d, J=2.0 Hz, 1H), 5.47 (d, J=8.8 Hz, 1H), 5.09 (br. s, 2H), 3.97-4.05 (m, 1H), 3.67-3.73 (m, 1H), 2.12-2.25 (m, 1H), 1.94-2.02 (m, 2H), 1.56-1.81 (m, 3H).

2-((4-phenyl-1-(tetrahydro-2H-pyran-2-yl)-1H-benzo[d]imidazol-6-yl]amino)pyrimidine-5-carbonitrile (1D)

To a solution of 1C (200 mg, 682 umol, 1.0 eq) in i-PrOH (3.0 mL) was added 2-chloro-5-pyrimidinecarbonitrile (95.1 mg, 682 umol, 1.0 eq) and potassium carbonate (188 mg, 1.36 mmol, 2.0 eq) at 15. ° C. The resulting mixture was stirred at 90° C. for 5 h under nitrogen. TLC (petroleum ether:ethyl acetate=0:1, $R_{f\text{-}SM}$=0.45, $R_{f\text{-}DP}$=0.68) showed that the starting material was completely consumed. The mixture was cooled to 25° C. and then poured into water (5 mL). The aqueous phase was extracted with ethyl acetate (5 mL, 3 mL). The combined organic phase was dried with anhydrous $Na_2SO_4$, filtered and concentrated in vacuo to give 1D (260 mg, 656 umol, 96% yield) as a yellow solid, which was used in the next step directly without further purification. $^1$H NMR: (400 MHz, CDCl$_3$) δ 10.55 (s, 1H), 8.90 (s, 2H), 8.41 (s, 1H), 8.10 (s, 1H), 8.02 (d, J=7.6 Hz, 2H), 7.73 (s, 1H), 7.49 (t, J=7.6 Hz, 2H), 7.39 (t, J=7.2 Hz, 1H), 5.64 (d, J=9.6 Hz, 1H), 4.02 (d, J=10.8 Hz, 1H), 3.70-3.79 (m, 1H), 2.19-2.36 (m, 1H), 1.95-2.11 (m, 2H), 1.57-1.86 (m, 3H).

N-(5-(1H-tetrazol-5-yl)pyrimidin-2-yl)-4-phenyl-1-(tetrahydro-2H-pyran-2-yl)-1H-benzo[d]imidazol-6-amine (1E)

To a suspension of 1D (190 mg, 479 umol, 1.0 eq) and ammonium chloride (102 mg, 1.92 mmol, 4.0 eq) in DMF (4 mL) was added sodium azide (62.3 mg, 958 umol, 2.0 eq). The mixture was stirred at 110° C. for 12 h. LCMS showed that the reaction was complete, and the desired MS was detected. This mixture was combined with a corresponding mixture from a previous 50 mg reaction, and concentrated in vacuo to give 1E (500 mg, crude) as a brown solid, which was used in the next step directly without further purification.

N-(5-(5-(difluoromethyl)-1,3,4-oxadiazol-2-yl)pyrimidin-2-yl)-4-phenyl-1H-benzo[d]imidazol-6-amine (1)

To a solution of 1E (400 mg, 910 umol, 1.0 eq) in dichloromethane (4.0 mL) was added difluoroacetic anhydride (792 mg, 4.55 mmol, 5.0 eq) at 15° C. The resulting mixture was stirred at 35° C. for 35 h. Additional difluoroacetic anhydride (792 mg, 4.55 mmol, 5.0 eq) was added and the reaction was stirred at 35° C. for another 13 h. LCMS showed that main peaks were the desired product (1) and compound 1F. The reaction was combined with the mixture of a previous batch (100 mg scale). The combined, crude reaction mixtures were diluted with water (5.0 mL) and then potassium carbonate (3.0 eq) was added. The resulting mixture was stirred at 30° C. for 15 h. LCMS showed the compound 1F was completely consumed and the desired product was detected. The mixture was concentrated in vacuo to give 1.00 g of crude product. Residual potassium carbonate was removed by adding water (5.0 mL) and stirring for 5 min. The suspension was filtered, and the filter cake was dried under vacuum to give 150 mg of crude 1 as an off-white solid. The crude product (150 mg, 293.81 umol, 79.4% purity, 1.0 eq) was purified by Prep-HPLC (column: Waters Xbridge Prep OBD C18 150*40 mm*10 um; mobile phase: [water (10 mM NH$_4$HCO$_3$)-ACN]; B %: 20%-50%, 8 min) to give 1 (50.2 mg, 122 umol, 42% yield, 98.9% purity) as a light yellow solid. $^1$H NMR: (400 MHz, DMSO-$d_6$) δ 10.85 (s, 1H), 9.63 (s, 1H), 9.12 (s, 2H), 8.48 (s, 1H), 7.92 (s, 1H), 7.69 (d, J=6.8 Hz, 2H), 7.43-7.67 (m, 4H).

Example 2. 4-bromo-N-(5-(5-(difluoromethyl)-1,3,4-oxadiazol-2-yl)pyrimidin-2-yl)-1H-benzo[d]imidazol-6-amine

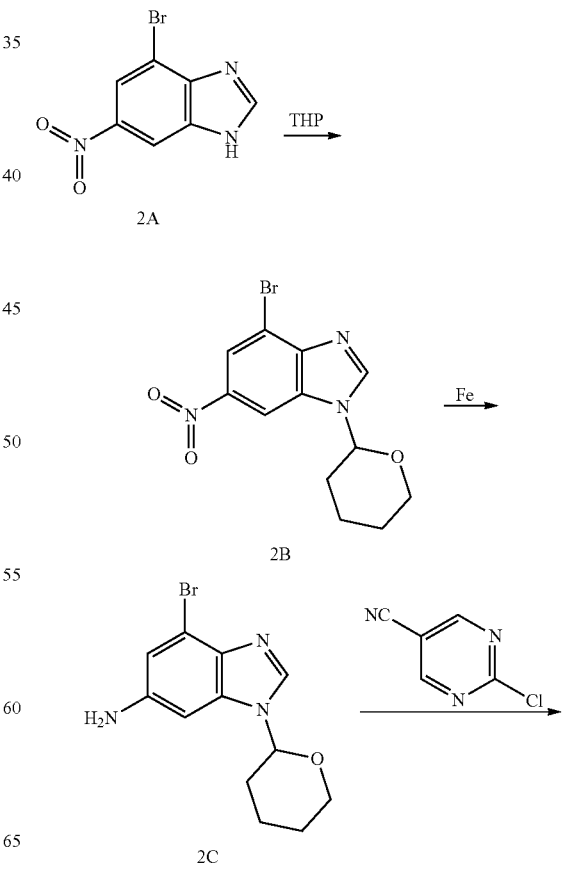

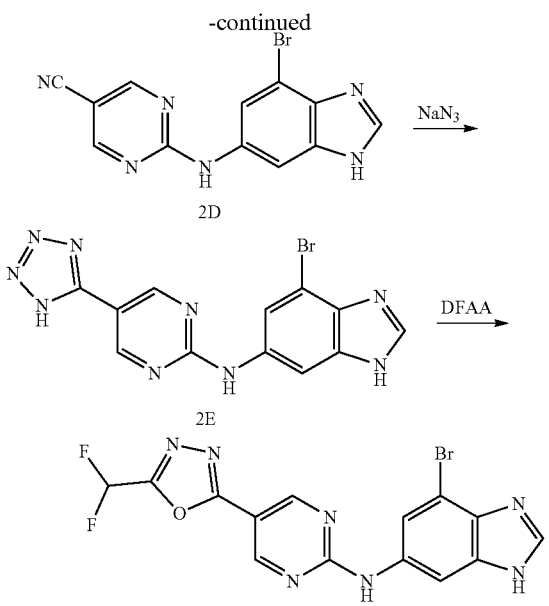

4-bromo-6-nitro-1-(tetrahydro-2H-pyran-2-yl)-1H-benzo[d]imidazole (2B)

To a solution of compound 4-bromo-6-nitro-1H-benzo[d]imidazole 2A (synthesis described in US2013/157977A1) (8.00 g, 33.1 mmol, 1 eq) in DHP (19.5 g, 231 mmol, 21.2 mL, 7 eq) was added TsOH (569 mg, 3.31 mmol, 0.1 eq). The reaction mixture was refluxed at 130° C. for 12 hrs. TLC (Ethyl acetate=1, R1, Rf=0.4, P1, Rf=0.8) showed the starting material was completely consumed. The reaction mixture was diluted with water (50 mL) and extracted with EtOAc (200 mL). The organic layer was washed with water (2×100 mL), dried over $Na_2SO_4$, filtered and concentrated under reduced pressure to give a residue. The residue was purified by column chromatography (SiO2, Petroleum ether:Ethyl acetate=20:1 to 1:1). 4-Bromo-6-nitro-1-(tetrahydro-2H-pyran-2-yl)-1H-benzo[d]imidazole 2B (4.50 g, 13.8 mmol, 42% yield) was obtained as a yellow solid. $^1$H NMR: (400 MHz DMSO-$d_6$) δ 8.90 (s, 1H), 8.88 (d, J=6.4 Hz, 1H), 8.31 (d, J=2.0 Hz, 1H), 5.90-5.93 (m, 1H), 3.85-4.00 (m, 1H), 3.81-3.84 (m, 1H), 2.17-2.22 (m, 1H), 2.10-2.17 (m, 1H), 1.97-2.1 (m, 1H), 1.61-1.64 (m, 1H), 1.59-1.61 (m, 2H).

4-bromo-6-amino-1-(tetrahydro-2H-pyran-2-yl)-1H-benzo[d]imidazole (2C)

To a solution of 2B (2.00 g, 6.13 mmol, 1.0 eq) in EtOH (20 mL) was added a solution of NH4Cl (1.64 g, 30.7 mmol, 5.0 eq) in $H_2O$ (10 mL), then Fe (1.03 g, 18.4 mmol, 3.0 eq) was added to the solution in one portion. The mixture was stirred at 80° C. for 12 hrs. TLC (Petroleum ether:Ethyl acetate=1:1, R1, Rf=0.4, P1, Rf=0.8) showed the starting material was consumed completely. The reaction solution was filtered and concentrated under reduced pressure to give 2C, 4-bromo-6-amino-1-(tetrahydro-2H-pyran-2-yl)-1H-benzo[d]imidazole (1.40 g, 4.73 mmol, 77% yield) as a brown solid. 1H NMR: (400 MHz DMSO-$d_6$) δ 8.09 (s, 1H), 6.81 (s, 1H), 6.70 (s, 1H), 5.42-5.45 (m, 1H), 3.95-4.02 (m, 1H), 3.60-3.72 (m, 1H), 1.95 (d, J=10.0 Hz, 2H), 1.67-1.79 (m, 2H), 1.57-1.58 (m, 3H), 1.39-1.45 (m, 1H).

2-((4-bromo-1H-benzo[d]imidazol-6-yl)amino)pyrimidine-5-carbonitrile (2D)

To a solution of 2C (1.40 g, 4.73 mmol, 1.0 eq) in i-PrOH (21 mL) was added 2-chloropyrimidine-5-carbonitrile (660 mg, 4.73 mmol, 1.0 eq) and $K_2CO_3$ (1.31 g, 9.45 mmol, 2 eq) at 15° C. The resulting mixture was stirred at 90° C. for 5 h under nitrogen. TLC (Petroleum ether:Ethyl acetate=0:1, R1, Rf=0.4, R2, Rf=0.5, P1, Rf=0.8) showed the starting material was consumed completely. The mixture was cooled to 25° C. and then poured into water (15 mL). The aqueous phase was extracted with ethyl acetate (20 mL). The combined organic phase was dried with anhydrous $Na_2SO_4$, filtered and concentrated in vacuo. Compound 2D (1.00 g, 2.50 mmol, 53% yield) was obtained as a brown solid. 1H NMR: (400 MHz DMSO-$d_6$) δ 8.92 (s, 2H), 8.43 (s, 1H), 8.10 (d, J=2.0 Hz, 1H), 7.86 (d, J=1.6 Hz, 1H), 5.59-5.62 (m, 1H), 3.98-4.03 (m, 1H), 3.69-3.77 (m, 2H), 2.15-2.24 (m, 1H), 1.97-2.03 (m, 3H), 1.69-1.80 (m, 2H), 1.60-1.65 (m, 3H), 1.44 (s, 2H), 1.32-1.39 (m, 1H), 1.17 (t, J=2.0 Hz, 1H).

N-(5-(1H-tetrazol-5-yl)pyrimidin-2-yl)-4-bromo-1H-benzo[d]imidazol-6-amine (2E)

Compound 2D (1.00 g, 2.50 mmol, 1.0 eq), NH4Cl (536 mg, 10.0 mmol, 4.0 eq) and sodium azide (326 mg, 5.01 mmol, 2.0 eq) in DMF (10 mL) was stirred at 100° C. for 12 hrs. LCMS (RT=1.014 min, MS+1=442) shown desired MS. The reaction mixture was diluted with water (30 mL) and extracted with EtOAc (20 mL×2). The combined organic layers were washed with brine (10 mL×2), dried over $Na_2SO_4$, filtered and concentrated under reduced pressure to give a residue. Compound 2E (500 mg, 1.13 mmol, 45.1% yield) was obtained as a brown solid. 4-bromo-N-(5-(5-(difluoromethyl)-1,3,4-oxadiazol-2-yl)pyrimidin-2-yl)-1H-benzo[d]imidazol-6-amine (2)

To a solution of compound 2E (140 mg, 317 umol, 1.0 eq) in DCM (3 mL) was added DFAA (275 mg, 1.58 mmol, 5.0 eq) at 15° C. The mixture was stirred at 35° C. for 48 hrs. The crude reaction mixture was purified by prep-HPLC (water (0.04% HCl)-ACN]; B %: 5%-30%, 8 min) to give 2 (15.0 mg, 11% yield, 97% purity) as a yellow solid. MS+1=408.0). 35.0 mg crude product was further purified by prep-HPLC (water (10 mM $NH_4HCO_3$)-ACN]; B %: 10%-40%, 3 min) to give addition 9.0 mg of 2 (9.00 mg, 6% yield, 91% purity) as a yellow solid.

Example 3. N-(5-(5-(difluoromethyl)-1,3,4-oxadiazol-2-yl)pyrimidin-2-yl)-4-(pyridin-3-yl)-1H-benzo[d]imidazol-6-amine hydrochloride (3)

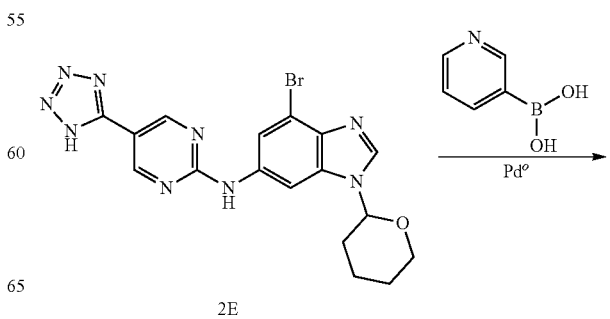

2E

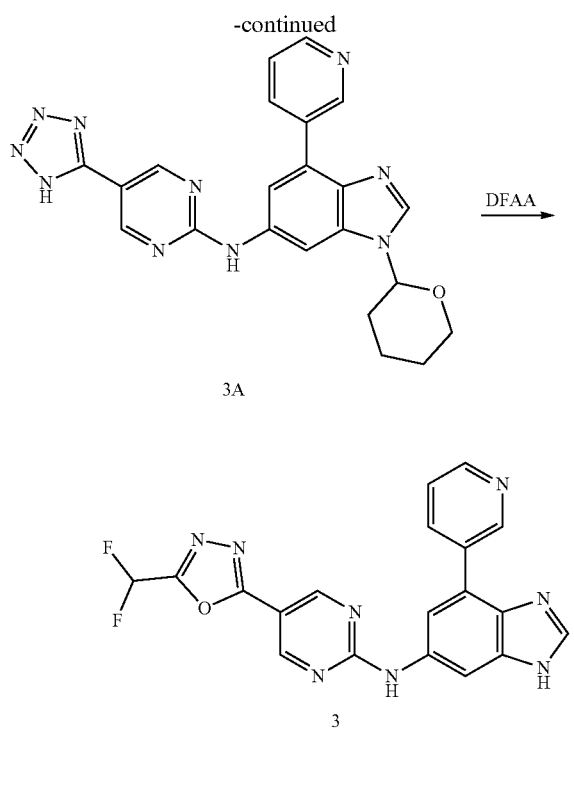

N-(5-(1H-tetrazol-5-yl)pyrimidin-2-yl)-4-(pyridin-3-yl)-1-(tetrahydro-2H-pyran-2-yl)-1H-benzo[d]imidazol-6-amine (3A)

To a solution of 2E (50.0 mg, 113 umol, 1.0 eq), 3-pyridylboronic acid (41.7 mg, 339 umol, 3 eq) Na₂CO₃ (55.1 mg, 520 umol, 4.60 eq) in DME (8 mL), H₂O (2 mL) and EtOH (4 mL). Then Pd(PPh₃)₄ (39.2 mg, 33.9 umol, 0.3 eq) was added, the solution was degassed and purged with N2 for 3 times. The reaction was stirred at 100° C. for 2 hrs. LCMS (RT=1.219 min, MS+1=441) shown desired MS. The reaction solution was filtered and concentrated in vacuo to give the residue. The residue was purified by prep-HPLC ([water (10 mM NH₄HCO₃)-ACN]; B %: 15%-40%, 7 min). 3A (20.0 mg, 42.0 umol, 37% yield) was obtained as a yellow solid.

N-(5-(5-(difluoromethyl)-1,3,4-oxadiazol-2-yl)pyrimidin-2-yl)-4-(pyridin-3-yl-1H-benzo[d]imidazol-6-amine hydrochloride (3)

To a solution of 3A (15.0 mg, 34.06 umol, 1.0 eq) in DCM (1.5 mL) was added DFAA (29.6 mg, 170 umol, 5.0 eq) at 15° C. The mixture was stirred at 35° C. for 48 hrs. LCMS (RT=1.006 min, MS+1=407) shown desired MS. The residue was purified by prep-HPLC (water (10 mM NH₄HCO₃)-ACN]; B %: 15%-45%, 8 min) to give 3 (7.00 mg, 17.1 umol, 50% yield, 99% purity) as a yellow solid. ¹H NMR: (400 MHz, MeOH) δ 9.08 (s, 2H), 9.03 (s, 1H), 8.59 (d, J=5.6 Hz, 1H), 8.32 (d, J=2.0 Hz, 1H), 8.21 (s, 1H), 7.59-7.63 (m, 2H), 7.22 (s, 1H), 2.15-2.24 (m, 1H), 1.97-2.03 (m, 3H), 1.69-1.80 (m, 2H), 1.60-1.65 (m, 3H), 1.44 (s, 2H), 1.32-1.39 (m, 1H), 1.17 (t, J=2.0 Hz, 1H).

Example 4. N-(5-(5-(difluoromethyl)-1,3,4-oxadiazol-2-yl)pyrimidin-2-yl)-1-methyl-4-phenyl-1H-benzo[d]imidazol-6-amine (4)

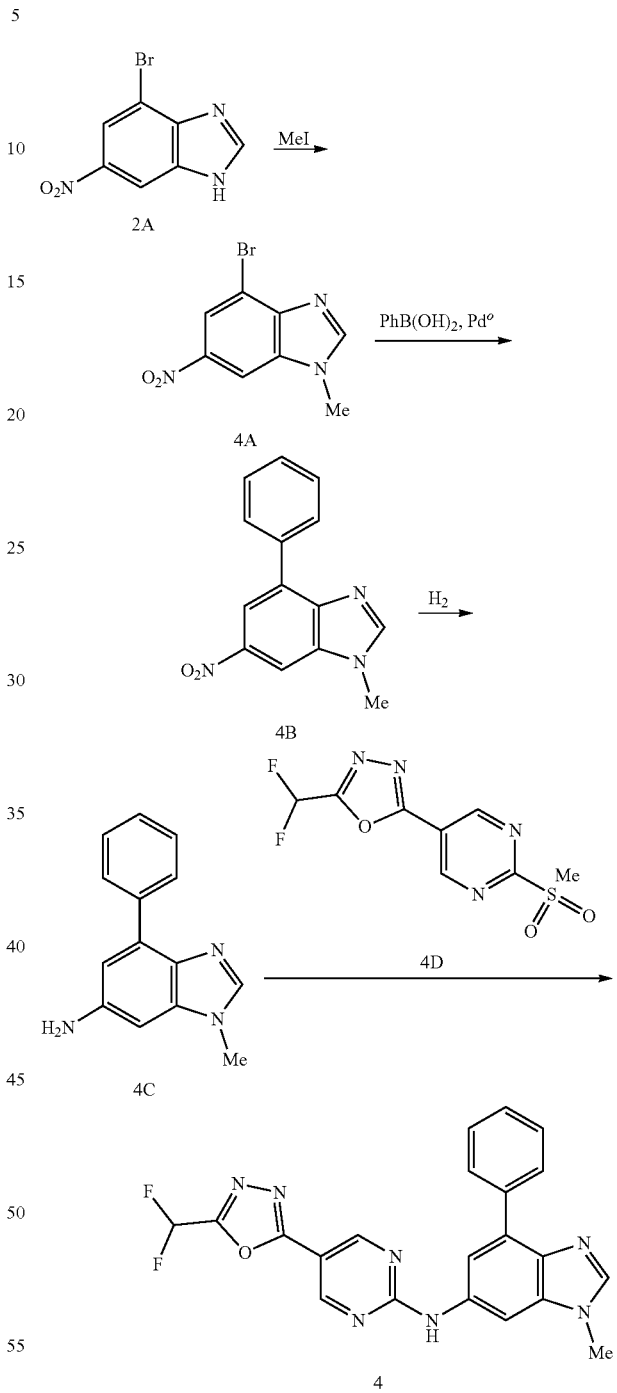

4-Bromo-1-methyl-6-nitro-1H-benzo[d]imidazole (4A)

To a solution of 4-Bromo-6-nitro-1H-benzo[d]imidazole 2A (1 g, 4.14 mmol) in acetone (10 mL) was added potassium carbonate (850 mg, 6.22 mmol) and iodomethane (880 mg, 6.22 mmol) at room temperature. The result mixture was stirred at room temperature overnight. The mixture was poured into water. The aqueous phase was extracted with ethyl acetate. The combined organic phase was dried with anhydrous Na₂SO₄, filtered and concentrated in vacuo to give 4-bromo-1-methyl-6-nitro-1H-benzo[d]imidazole 4A (1.2 g crude) as a yellow solid, which was used in the next step directly without further purification. LC-MS: (ES⁺): m/z 255.9 [M+H]⁺.

1-methyl-6-nitro-4-phenyl-1H-benzo[d]imidazole (4B)

To a solution of 4A (1.2 g, 4.70 mmol) in toluene/water (10 mL/4 mL) were added phenylboronic acid (861 mg, 7.06 mmol), Pd(dppf)Cl₂ (172 mg, 0.235 mmol) and Na₂CO₃ (1.04 g, 9.88 mmol) at rt. The solution was purged with nitrogen at rt for 10 min. The resulting solution was stirred at 100° C. for 3 h. After cooling to rt, the reaction was taken up with ethyl acetate. The combined organic layers were concentrated under vacuum. The residue was purified by silica gel with DCM~DCM/EA (10:1) to afford the desired product 1-methyl-6-nitro-4-phenyl-1H-benzo[d]imidazole 4B (500 mg, 42% yield) as a yellow solid. ¹H NMR: (400 MHz, DMSO) δ 8.39 (d, J=2 Hz, 1H), 8.33 (d, J=2 Hz, 1H), 8.14 (s, 1H), 8.01 (d, J=7.2 Hz, 2H), 7.52-7.54 (m, 2H), 7.40-7.46 (m, 1H), 3.98 (s, 3H).

1-methyl-4-phenyl-1H-benzo[d]imidazol-6-amine (4C)

To a stirring suspension of 4B (500 mg, 1.9 mmol) in methanol (20 mL) was added 10% Pd/C (250 mg, 50% purity) at rt. The resulting mixture was degassed with hydrogen for three times and stirred at rt for 12 h under hydrogen. LCMS showed the starting material was consumed completely and one main peak with desired mass was detected. The reaction mixture was filtered through a pad of Celite™ and the filtered cake was washed with methanol. The combined filtrate was concentrated in vacuo to give 1-methyl-4-phenyl-1H-benzo[d]imidazol-6-amine 4C (380 mg, crude) as a gray foamy solid, which was used in the next step without further purification. ¹H NMR (400 MHz, CDCl₃) δ7.944-7.926 (d, J=7.2 Hz, 2H), 7.727 (s, 1H), 7.492-7.453 (t, J=7.6 Hz, 2H), 7.369-7.332 (t, J=7.2 Hz, 1H), 6.849-6.844 (d, J=2.0 Hz, 1H), 6.633-6.628 (d, J=2.0 Hz, 1H), 3.752 (s, 3H).

Intermediate (4D). 2-(difluoromethyl)-5-(2-(methylsulfonyl)pyrimidin-5-yl)-1,3,4-oxadiazole

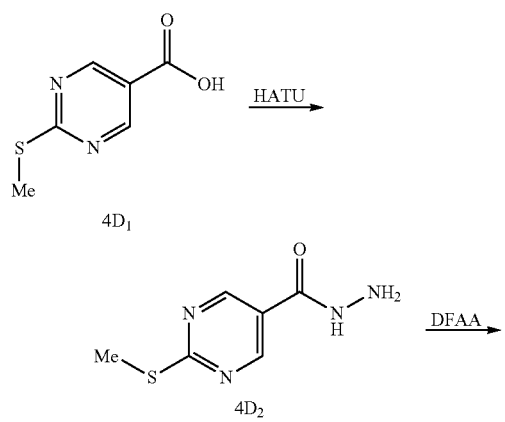

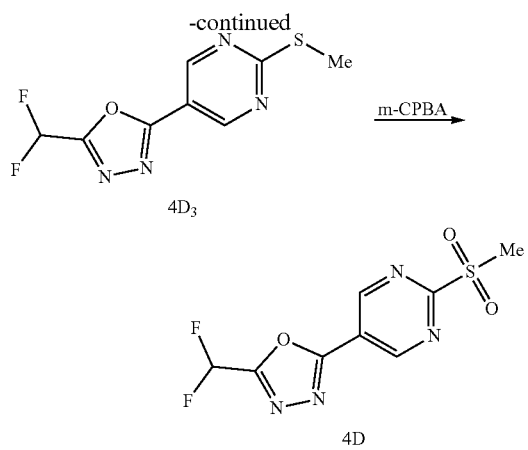

2-(methylthio)pyrimidine-5-carbohydrazide (4D2)

To a solution of 2-(methylthio)pyrimidine-5-carboxylic acid 4D1 (2.8 g, 16.5 mmol) in anhydrous dichloromethane (150 mL) was added anhydrous DIEA (6.38 g, 49.5 mmol), HATU (9.4 g, 24.75 mmol). The resulting solution was stirred at 0° C. for 20 min. Hydrazine hydrate (3.2 mL, 66 mmol) was added dropwise to the reaction mixture, and the resulting solution was stirred at room temperature for 30 min. LCMS showed the desired product was formed. Water (20 mL) was added, the layers were separated. The organic layer was washed with brine, dried, filtered, concentrated. The crude product was purified further by column chromatography with silica gel (eluent:PE,PE/EA=1:1,EA) to obtain 2-(methylthio)pyrimidine-5-carbohydrazide 4D2 (1.8 g, 60% yield) as a white solid. LC-MS: (ES⁺): m/z 185.1 [M+H]⁺.

2-(difluoromethyl)-5-(2-(methyl)pyrimidin-5-yl)-1,3,4-oxadiazole (4D₃)

To a solution of 2-(methylthio)pyrimidine-5-carbohydrazide (4D2) (1.8 g, 9.77 mmol) in THF (20 mL) was added Et₃N (1.98 g, 19.54 mmol), 2,2-difluoroacetic anhydride (3.4 g, 19.54 mmol). The resulting solution was stirred at 80° C. for 2 h. LCMS showed the desired product was formed. Saturated NaHCO₃ solution (50 mL) was added and mixture was extracted with ethyl acetate (3×60 mL). The combined organic layers were washed with brine, dried, filtered, concentrated. The crude product was purified by column chromatography with silica gel (eluent:PE,PE/EA=5:1,PE/EA=1:1) to obtain the title product 2-(difluoromethyl)-5-(2-(methylthio)pyrimidin-5-yl)-1,3,4-oxadiazole 4D3 (1.3 g, yield 55%) as a white solid. ¹H NMR: (400 MHz, DCCl₃) δ 9.160 (s, 2H), 7.067-6.809 (t, J=25.8 Hz, 1H), 2.652 (s, 3H).

2-(difluoromethyl)-5-(2-(methylsulfonyl)pyrimidin-5-yl)-1,3,4-oxadiazole (4D)

To a solution of 2-(difluoromethyl)-5-(2-(methylthio)pyrimidin-5-yl)-1,3,4-oxadiazole (4D3) (500 mg, 5.33 mmol) in dichloromethane (20 mL) was added m-chloroperoxybenzoic acid (2.3 g, 8.0 mmol). The resulting solution was stirred at room temperature for 2 h. A second aliquot of m-chloroperoxybenzoic acid (1.53 g, 5.33 mmol) was added and the resulting solution was stirred at rt for 1.5 h. LCMS showed the desired product was formed. The solution was filtered, the filtrate was concentrated and purified further by column chromatography with silica gel (eluent:PE,PE/EA=5:1,PE/EA=1:1) to obtain the title product 2-(difluoromethyl)-5-(2-(methylsulfonyl)pyrimidin-5-yl)-1,3,4-oxadiazole (4D) (480 mg, contained 30% 3-chlorobenzoic acid by HNMR, 89% yield) as a white solid. LC-MS: (ES+): 277.0 m/z [M+H]+; ¹H NMR: (400 MHz, CDCl₃) δ 9.615 (s, 2H), 7.131-6.873 (t, J=51.6 Hz, 1H), 3.450 (s, 3H).

N-(5-(5-(difluoromethyl)-1,3,4-oxadiazol-2-yl)pyrimidin-2-yl)-1-methyl-4-phenyl-1H-benzo[d]imidazol-6-amine (4)

In a microwave tube was placed 1-methyl-4-phenyl-1H-benzo[d]imidazol-6-amine (200 mg, 0.9 mmol) (4C), 2-(difluoromethyl)-5-(2-(methylsulfonyl)pyrimidin-5-yl)-1,3,4-oxadiazole (Intermediate 4D) (248 mg, 0.45 mmol), DMSO (3 mL), then the resulting solution was stirred at 80° C. for 30 min under microwave. Water (50 mL) was added to the solution and the mixture was extracted with ethyl acetate (50 mL×2). The combined organic extracts were washed with brine, dried over anhydrous Na₂SO₄ and concentrated. The crude product was purified by Prep-TLC (eluent:ethyl acetate) to obtain 45 mg which was subsequently washed with EA/MeOH (20:1, 2 mL) to obtain the title product N-(5-(5-(difluoromethyl)-1,3,4-oxadiazol-2-yl)pyrimidin-2-yl)-1-methyl-4-phenyl-1H-benzo[d]imidazol-6-amine (4) (25 mg, yield 7%) as faint yellow solid. LC-MS: (ES+): m/z 449.1 [M+H]+; ¹HNMR: (400 MHz, DMSO) δ10.535 (s, 1H), 9.091 (s, 2H), 8.205 (s, 1H), 8.098-8.077 (m, 3H), 7.743-7.369 (m, 5H), 3.233 (s, 3H).

Example 5. N-(5-(5-(difluoromethyl)-1,3,4-oxadiazol-2-yl)pyrimidin-2-yl)-2-methyl-4-phenyl-1H-benzo[d]imidazol-6-amine (5)

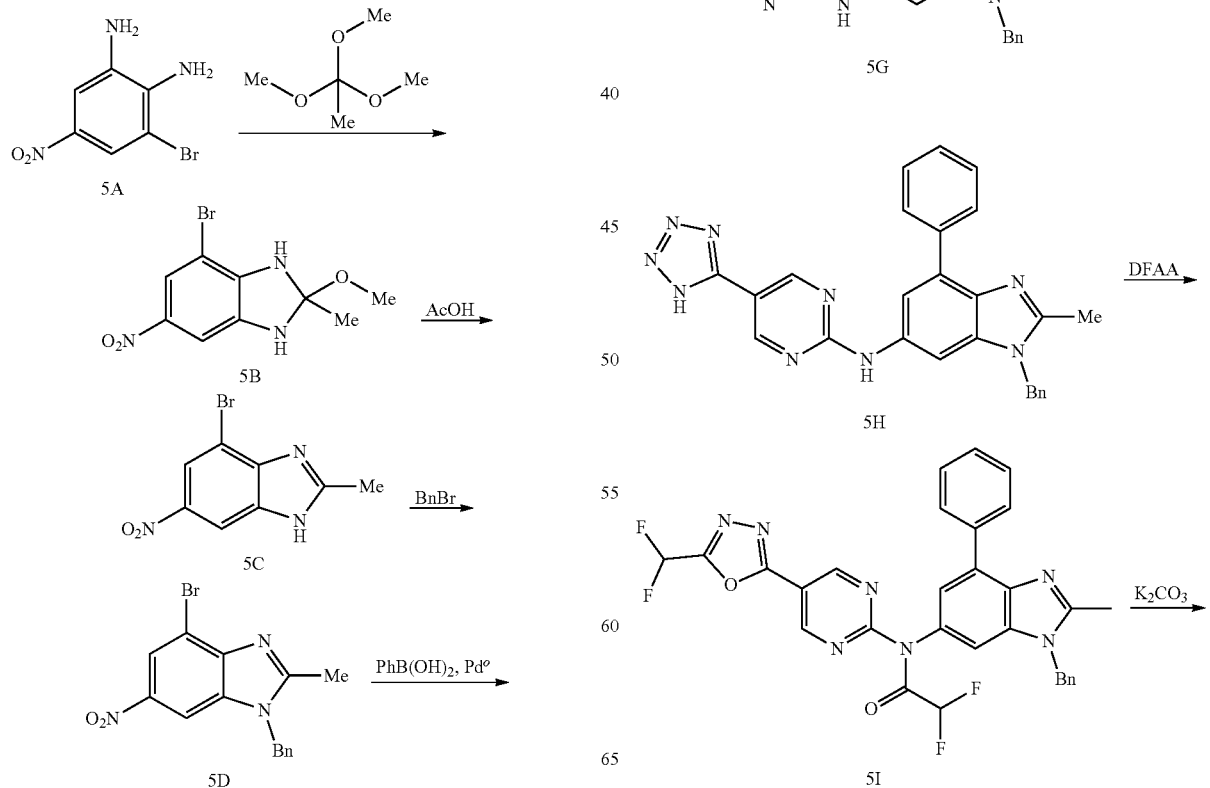

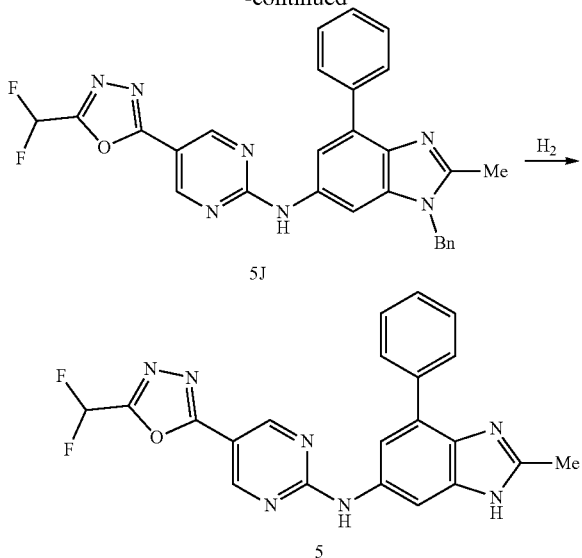

4-bromo-2-methoxy-2-methyl-6-nitro-2,3-dihydro-1H-benzo[d]imidazole (5B)

3-Bromo-5-nitro-1,2-diaminobenzene (5A) (2.98 g, 12.84 mmol) was dissolved in 20 mL 1,1,1-trimethoxyethane, the mixture was stirred overnight. The excess of 1,1,1-trimethoxyethane was removed under vacuum. The residue was used directly for the next step without further purification.

4-bromo-2-methyl-6-nitro-11H-benzo[d]imidazole (5C)

The crude 5B was dissolved in AcOH (15 mL) and then stirred for 4 hr. at 120° C. at which point the starting material was consumed. On cooling to room temperature, the reaction mixture was concentrated to dryness under vacuum. The residue was purified by silica gel column to give 1.3 g of 4-bromo-2-methyl-6-nitro-1H-benzo[d]imidazole (5C) as a solid.

1-benzyl-4-bromo-2-methyl-6-nitro-1H-benzo[d]imidazole (5D)

$K_2CO_3$ (808 mg, 5.85 mmol) and benzyl bromide (1.0 g, 5.85 mmol) were added into a solution of 5C (1.0 g, 3.9 mmol) in DMF(10 ml) at 0° C. The mixture was stirred for 1.5 h at 20~25° C. The reaction mixture was poured into a mixture of water (20 ml) and ethyl acetate (20 ml). The layers were separated, the organic phase was dried over $Na_2SO_4$ and concentrated to give a residue. The residue was purified by column chromatography on silica gel (PE: EA=5:1 to 1:1) to give a mixture of 1-benzyl-4-bromo-2-methyl-6-nitro-1H-benzo[d]imidazole (5D) and 3-benzyl-4-bromo-2-methyl-6-nitro-1H-benzo[d]imidazole isomer (1.25 g) as a solid. $^1$H NMR (400 MHz, CDCl$_3$) δ 8.396-8.393 (d, J=1.2 Hz, 1H), 8.153-8.149 (d, J=2.0 Hz, 1H), 7.356-7.340 (d, J=6.4 Hz, 3H), 7.053-7.034 (t, J=2 Hz, 2H), 5.398 (s, 2H), 2.682 (s, 3H).

1-benzyl-2-methyl-6-nitro-4-phenyl-1H-benzo[d]imidazole (5E)

$K_2CO_3$ (1.08 g, 7.7 mmol) and phenylboronic acid (951 mg, 7.7 mmol) was added into a solution of 5D (2.24 g, 6.47 mmol) in dioxane/$H_2O$ (40 ml/8 ml). Pd(PPh$_3$)$_4$ (75 mg, 0.06, mmol) was added into the mixture under nitrogen. The mixture was heated at reflux and stirred for 2.5 h. After cooling, the mixture was diluted with ethyl acetate (40 ml) and filtered through diatomite. The organic phase was washed with brine (20 ml×2), dried over $Na_2SO_4$ and concentrated to give a residue. The residue was purified by column chromatography on silica gel to afford 1-benzyl-2-methyl-6-nitro-4-phenyl-1H-benzo[d]imidazole (5E) (2.4 g, 100% yield) as solid. $^1$H NMR: (400 MHz, CDCl$_3$) δ 8.356-8.351 (d, J=2 Hz, 2H), 8.167-8.162 (d, J=2 Hz, 2H), 8.043-8.025 (d, J=7.2 Hz, 2H), 7.563-7.525 (t, J=7.6 Hz, 2H), 7.459-7.422 (t, J=7.6 Hz, 1H) 7.390-7.333 (m, 3H), 7.094-7.078 (d, J=6.4 Hz, 2H), 5.444 (s, 2H), 2.671 (s, 3H).

1-benzyl-2-methyl-4-phenyl-1H-benzo[d]imidazol-6-amine (5F)

Iron powder (1.2 g) was added into a mixture of 5E (2.4 g, 7 mmol) and NH$_4$Cl (2.4 g, 1×) in EtOH (60 ml) and water (30 ml). The mixture was heated to 70° C. and stirred for 1.5 h. After cooling, the mixture was combined with another batch of reaction mixture (78 mg was used) and filtered through diatomite. The mother liquid was concentrated in vacuo to remove EtOH. The remaining mixture was extracted with ethyl acetate (60 ml). The organic phase was dried over $Na_2SO_4$ and concentrated to give a residue. The residue was dissolved in DCM (40 ml), the organic phase was adjusted to pH~1 with 6 M HCl solution, the water phase was adjusted to pH~12 with 10% NaOH solution and extracted with DCM (30 ml×2). The combined organic layers were dried over $Na_2SO_4$ and evaporated to give (5F) 1-benzyl-2-methyl-4-phenyl-1H-benzo[d]imidazol-6-amine as white solid (1.66 g, 99%). $^1$H NMR: (400 MHz, CDCl$_3$) δ 7.957-7.938 (d, J=7.6 Hz, 2H), 7.484-7.448 (m, 2H), 7.356-7.259 (m, 4H), 7.079-7.062 (d, J=6.8 Hz, 2H), 6.780 (s, 1H), 6.479 (s, 1H), 5.247 (s, 2H), 2.527 (s, 3H).

2-((1-benzyl-2-methyl-4-phenyl-1H-benzo[d]imidazol-6-yl)amino)pyrimidine-5-carbonitrile (5G)

To a solution of 5F (500 mg, 1.59 mmol) in i-PrOH (8 mL) was added 2-chloropyrimidine-5-carbonitrile (223 mg, 1.59 mmol) and potassium carbonate (441 mg, 3.18 mmol). The resulting mixture was stirred at 90° C. for 2 h under nitrogen. The mixture was cooled to rt and then poured into water (5 mL). The aqueous phase was extracted with ethyl acetate. The combined organic phase was dried with anhydrous $Na_2SO_4$, filtered and concentrated in vacuo to give 2-((1-benzyl-2-methyl-4-phenyl-1H-benzo[d]imidazol-6-yl)amino)pyrimidine-5-carbonitrile (5G) (260 mg, 90% yield) as a yellow solid, which was used in the next step directly without further purification. LC-MS: (ES$^+$): m/z 417.2 [M+H]$^+$.

N-(5-(1H-tetrazol-5-yl)pyrimidin-2-yl)-1-benzyl-2-methyl-4-phenyl-1H-benzo[d]imidazol-6-amine (5H)

To a suspension of 5G (600 mg, 1.44 mmol) and cuprous iodide (55 mg, 0.288 mmol) in DMF (5 mL) was added sodium azide (187 mg, 2.88 mmol). The mixture was stirred at 110° C. for 4 h. LCMS showed that the reaction was completed, and the desired MS was detected. The mixture was concentrated in vacuo to give N-(5-(1H-tetrazol-5-yl)pyrimidin-2-yl)-1-benzyl-2-methyl-4-phenyl-1H-benzo[d]imidazol-6-amine (5H) (500 mg, crude) as a yellow solid,

N-(1-benzyl-2-methyl-4-phenyl-1H-benzo[d]imidazol-6-yl)-N-(5-(5-(difluoromethyl)-1,3,4-oxadiazol-2-yl)pyrimidin-2-yl)-2,2-difluoroacetamide (5I)

To a solution of 5H (500 mg, 1.08 mmol) in dioxane (5 mL) was added 2,2-difluoroacetic anhydride (947 mg, 5.44 mmol) at rt. The sealed vial was irradiated in the microwave on a Biotage Smith Synthesizer at 80° C. for 1 h. LCMS showed the reaction was completed. The mixture was cooled to rt and then poured into water. The aqueous phase was extracted with ethyl acetate. The combined organic phase was dried with anhydrous $Na_2SO_4$, filtered and concentrated in vacuo. The residue was the desired product N-(1-benzyl-2-methyl-4-phenyl-1H-benzo[d]imidazol-6-yl)-N-(5-(5-(difluoromethyl)-1,3,4-oxadiazol-2-yl)pyrimidin-2-yl)-2,2-difluoroacetamide (5I) (400 mg, crude), which was used in next step without further purification. LC-MS: (ES$^+$): m/z 589.1 [M+H]$^+$.

1-benzyl-N-(5-(5-(difluoromethyl)-1,3,4-oxadiazol-2-yl)pyrimidin-2-yl)-2-methyl-4-phenyl-1H-benzo[d]imidazol-6-amine (5J)

To a solution of 5I (400 mg, 0.681 mmol) in dioxane (5 mL) was added potassium carbonate (281 mg, 2.04 mmol) at rt. The mixture was stirred at 80° C. for 1 h. The mixture was cooled to rt and then poured into water. The aqueous phase was extracted with ethyl acetate. The combined organic phase was dried with anhydrous $Na_2SO_4$, filtered and concentrated in vacuo. The residue was purified by column chromatography on silica gel to give 1-benzyl-N-(5-(5-(difluoromethyl)-1,3,4-oxadiazol-2-yl)pyrimidin-2-yl)-2-methyl-4-phenyl-1H-benzo[d]imidazol-6-amine (5J) (280 mg) as a yellow solid. LC-MS: (ES$^+$): m/z 510.2 [M+H]$^+$.

N-(5-(5-(difluoromethyl)-1,3,4-oxadiazol-2-yl)pyrimidin-2-yl)-2-methyl-4-phenyl-1H-benzo[d]imidazol-6-amine (5)

To a stirring suspension of 1-benzyl-N-(5-(5-(difluoromethyl)-1,3,4-oxadiazol-2-yl)pyrimidin-2-yl)-2-methyl-4-phenyl-1H-benzo[d]imidazol-6-amine (5J) (280 mg, 0.55 mmol) in methanol (15 mL) was added Pd/C (1.4 g, 500% wt) at rt. The resulting mixture was degassed with hydrogen for three times and stirred at 50° C. for 3 h under hydrogen. LCMS showed the desired product was formed. The reaction mixture was filtered by a pad of Celite™ and the filtered cake was eluted with methanol. The combined filtrate was concentrated and purified by Prep-TLC (eluent:ethyl acetate) to obtain the title product N-(5-(5-(difluoromethyl)-1,3,4-oxadiazol-2-yl)pyrimidin-2-yl)-2-methyl-4-phenyl-1H-benzo[d]imidazol-6-amine (5) (16 mg, yield 6.9%) as faint yellow solid. LC-MS: (ES$^+$): m/z 420.1 [M+H]$^+$; $^1$H NMR: (400 MHz, DMSO) δ 12.332 (s, 1H), 10.435 (s, 1H), 9.063-9.055 (d, J=3.2 Hz, 2H), 8.020 (s, 2H), 7.690-7.385 (m, 6H), 3.318-3.311 (d, J=2.8 Hz, 3H).

Example 6. N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine (6)

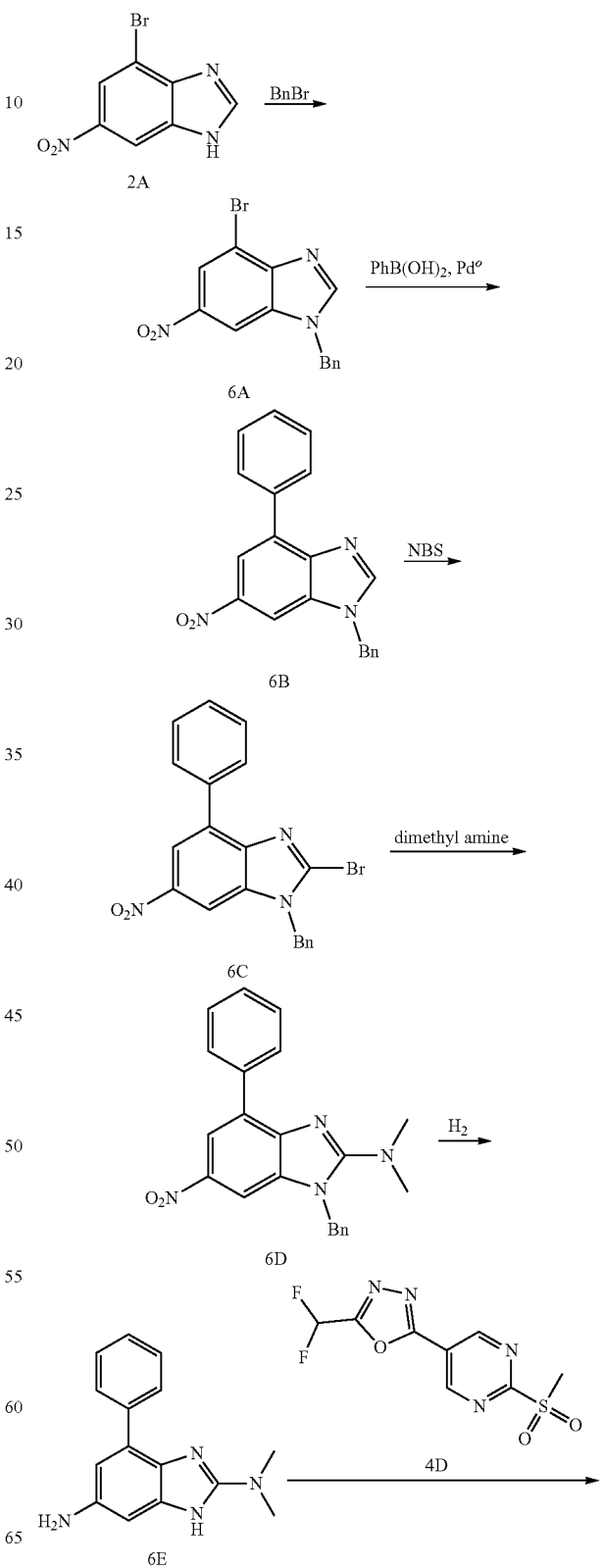

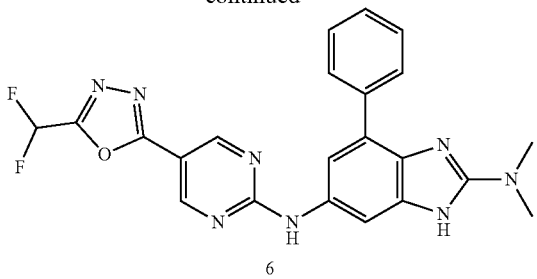

6

1-benzyl-4-bromo-6-nitro-1H-benzo[d]imidazole (6A)

K$_2$CO$_3$ (808 mg, 5.85 mmol) and BnBr (1.0 g, 5.85 mmol) were added into a solution of 2A (1.0 g, 4 mmol) in DMF(10 ml) at 0° C., the mixture was stirred for 1.5 h at 20~25° C. The mixture was poured into a mixture of water (20 ml) and EA (20 ml) to complete the reaction, the organic phase was dried over Na$_2$SO$_4$ and evaporated to give the crude residue. The residue was purified by column chromatography on silica gel (PE:EA=5:1 to 1:1) to give 6A (1.25 g, 100% concluding isomer) as a solid.

1-benzyl-6-nitro-4-phenyl-1H-benzo[d]imidazole (6B)

K$_2$CO$_3$ (1.2 g, 9 mmol) and phenylboronic acid (1.10 g, 9 mmol) was added into a solution of 6A (2.5 g, 7.5 mmol) in dioxane/H$_2$O (50 ml/10 ml), then Pd(PPh$_3$)$_4$ (86 mg, 0.075 mmol) was added into the mixture under N2. The mixture was heated at reflux and stirred for 2 hr after cooling, the mixture was diluted with EA (50 ml) and filtered through diatomite, the organic phase was washed with saturated NaCl solution (20 ml×2) and dried over Na$_2$SO$_4$ and evaporated to give the residue, the residue was purified by column chromatography on silica gel to afford the product 6B (2.2 g, 99%) as solid.

1-benzyl-2-bromo-6-nitro-4-phenyl-1H-benzo[d]imidazole (6C)

Compound 6B (1.2 g, 3.64 mmol) and N-Bromosuccinimide (1.9 g, 10.9 mmol, 1.5 eq) were combined in THF (20 mL) at rt and the resulting mixture was stirred at reflux for 1.5 h. The reaction mixture was cooled and diluted with ethyl acetate and water. The organic layer was further washed with brine, dried over Na$_2$SO$_4$, filtered and concentrated in vacuo to give a residue. The residue was purified by column chromatography on silica gel (petroleum ether:ethyl acetate=6:1) to give 1-benzyl-2-bromo-6-nitro-4-phenyl-1H-benzo[d]imidazole (6C) (1.2 g, 85% yield) as a yellow solid. LC-MS: (ES$^+$): m/z 409.2 [M+H]$^+$.

1-benzyl-N,N-dimethyl-6-nitro-4-phenyl-1H-benzo[d]imidazol-2-amine (6D)

To a solution of 6C (1.2 g, 2.94 mmol) in DMF (5 mL) was added dimethylamine (265 mg, 5.89 mmol) and triethylamine (595 mg, 5.89 mmol). The resulting mixture was stirred at 130° C. for 3 h. The reaction was diluted with ethyl acetate and water. The organic layer was further washed with brine, dried over Na$_2$SO$_4$, filtered and concentrated in vacuo to give a residue. The residue was purified by column chromatography on silica gel (petroleum ether:ethyl acetate=6:1) to give 1-benzyl-N,N-dimethyl-6-nitro-4-phenyl-1H-benzo[d]imidazol-2-amine (6D) (950 mg, 87% yield) as a yellow solid. LC-MS: (ES$^+$): m/z 374.1 [M+H]$^+$.

N2,N2-dimethyl-4-phenyl-1H-benzo[d]imidazole-2,6-diamine (6E)

To a stirring suspension of 1-benzyl-N,N-dimethyl-6-nitro-4-phenyl-1H-benzo[d]imidazol-2-amine (6D) (320 mg, 0.860 mmol) in methanol (20 mL) was added Pd/C (320 mg) and HCl/dioxane (1 mL) at rt. The resulting mixture was degassed with hydrogen three times and stirred at rt for 6 h under hydrogen. LCMS showed the desired product was formed. The reaction mixture was filtered through a pad of Celite™ and the filtered cake was eluted with methanol. The combined filtrate was concentrated and diluted with EA (60 mL), then the organic layer was washed with satd. NaHCO$_3$ solution (60 mL), brine, dried, concentrated to obtain the title product N2,N2-dimethyl-4-phenyl-1H-benzo[d]imidazole-2,6-diamine (6E) (180 mg, yield 76%) as a gray solid, and the product was used directly without further purification.

N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine (6)

In a microwave tube was placed N2,N2-dimethyl-4-phenyl-1H-benzo[d]imidazole-2,6-diamine (180 mg, 0.7 mmol), 2-(difluoromethyl)-5-(2-(methylsulfonyl)pyrimidin-5-yl)-1,3,4-oxadiazole (intermediate 4D) (197 mg, 0.7 mmol) and DMSO (3 mL). The resulting solution was stirred at 80° C. for 30 min under microwave. Water (50 mL) was added to the solution and the resulting mixture was extracted with ethyl acetate (50 mL×2). The combined organic extracts were washed with brine, dried over anhydrous Na$_2$SO$_4$ and concentrated. The crude product was purified by Prep-TLC (eluent:ethyl acetate) to obtain 52 mg crude product. It was further purified by Prep-HPLC to obtain the title product N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine (32 mg, yield 10%) as a white solid. LC-MS: (ES$^+$): m/z 449.1 [M+H]$^+$; $^1$H NMR: (400 MHz, DMSO) δ10.632 (s, 1H), 9.088 (s, 2H), 8.054-8.050 (d, J=1.6 Hz, 1H), 7.701-7.444 (m, 7H), 3.233 (s, 6H).

Example 7. N-(5-(5-(difluoromethyl)-1,3,4-oxadiazol-2-yl)pyrimidin-2-yl)-N-methyl-4-phenyl-1H-benzo[d]imidazol-6-amine (7)

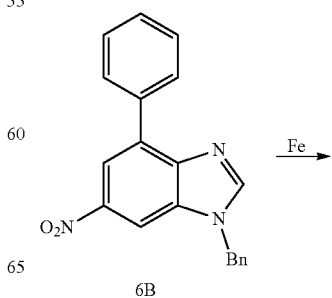

6B

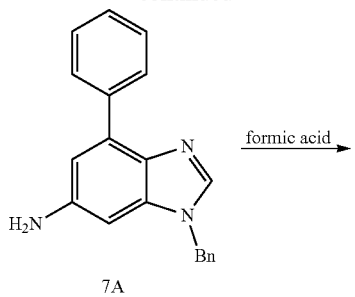

7A

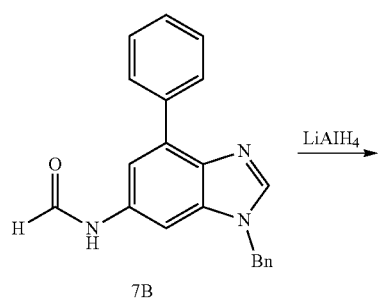

7B

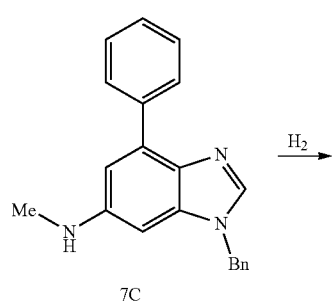

7C

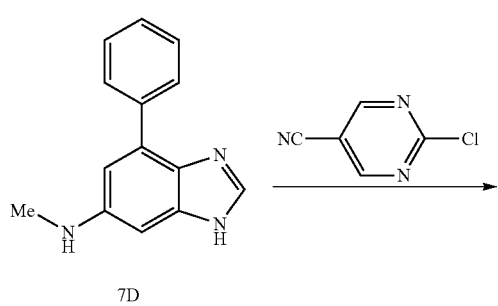

7D

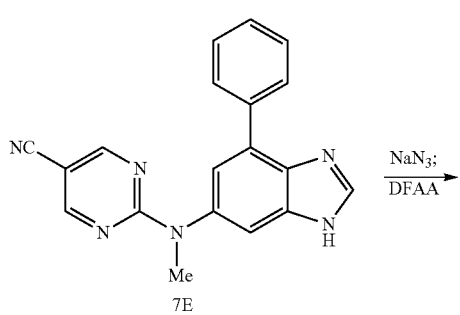

7E

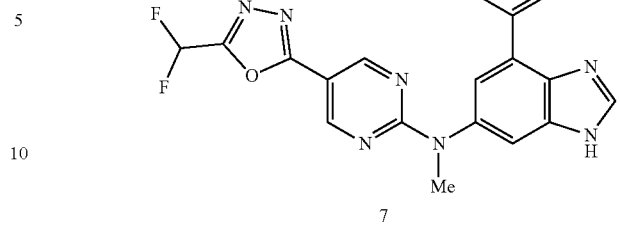

7

2-((1-benzyl-4-phenyl-1H-benzo[d]imidazol-6-yl)aminopyrimidine-5-carbonitrile (7A)

Fe powder (1.0 g, 0.5×) was added into a mixture of 6B (2.0 g, 6 mmol) and NH$_4$Cl (2.0 g, 1×) in EtOH (50 ml) and water (25 ml), the mixture was heated to 70° C. and stirred for overnight. After cooling, the mixture was filtered through diatomite, the mother liquid was concentrated in vacuo to remove EtOH, and extracted with EA (50 ml), the organic phase was dried over Na$_2$SO$_4$ and evaporated to give the residue, the residue was dissolved with DCM (40 ml), the organic phase was adjusted to pH~1 with 6 M HCl solution, the water phase was adjusted to pH~12 with 10% NaOH solution and extracted with DCM (30 ml×2), the combined organic layers were dried over Na$_2$SO$_4$ and evaporated to give the product (7A) as white solid (1.6 g, 88%).

N-(1-benzyl-4-phenyl-1H-benzo[d]imidazol-6-yl)formamide (7B)

A suspension of 7A (700 mg, 2.34 mmol) and formic acid (15 mL) was heated at 110° C. for 3 h. The solvent was removed under reduced pressure, the residue was diluted with satd. NaHCO$_3$ solution (50 mL), and extracted by ethyl acetate (3×30 mL). The combined organic layers were washed with brine, dried and concentrated. The crude product N-(1-benzyl-4-phenyl-1H-benzo[d]imidazol-6-yl)formamide (7B) (800 mg, crude) was used directly without further purification.

1-benzyl-N-methyl-4-phenyl-1H-benzo[d]imidazol-6-amine (7C)

7B (800 mg, 2.44 mmol) was suspended in THF (20 mL). The suspension was chilled to 0° C. LiAlH$_4$ (186 mg, 4.88 mmol) was added at this temperature. Then the solution was stirred at room temperature for 2 h. The reaction was quenched by the mixture solution (0.74 ml water and 10 ml THF) dropwise at 0° C., and the resulting solution was stirred at room temperature overnight. The solution was filtered, and the filtrate was concentrated. The crude product was purified by column chromatography with silica gel (eluent:PE/EA=0-50%) to give the product 1-benzyl-N-methyl-4-phenyl-1H-benzo[d]imidazol-6-amine (7C) (600 mg, two steps total yield 82%) as yellow solid. LC-MS: (ES$^+$): 314.2 m/z [M+H]$^+$.

N-methyl-4-phenyl-1H-benzo[d]imidazol-6-amine (7D)

To a solution of 7C (600 mg, 1.91 mmol) in AcOH (20 mL) was added Pd/C (300 mg, 50% wt). The resulting solution was stirred at 70° C. for 4 h under hydrogen atmosphere. The solution was filtered, and the filtrate was adjusted to pH=7-8 with satd. NaHCO₃ solution. The solution was extracted by ethyl acetate (3×60 mL). The combined organic layers were washed with water (60 mL), brine (60 mL), dried and concentrated to obtain the product N-methyl-4-phenyl-1H-benzo[d]imidazol-6-amine (7D) (300 mg, yield 70%) as gray solid. LC-MS: (ES⁺): 224.2 m/z [M+H]⁺.

2-(methyl(4-phenyl-1H-benzo[d]imidazol-6-yl) amino)pyrimidine-5-carbonitrile (7E)

In a microwave tube was placed 7D (170 mg, 0.76 mmol), 2-chloropyrimidine-5-carbonitrile (127 mg, 0.91 mmol), K₂CO₃ (210 mg, 1.52 mmol), i-PrOH (3 mL). The resulting solution was stirred at 110° C. for 1 h under microwave. Water (50 mL) was added to the solution and the mixture was extracted with DCM (50 mL×2). The combined organic extracts were washed with brine, dried over anhydrous Na₂SO₄ and concentrated. The crude product was purified further by Prep-TLC (eluent:ethyl acetate) to obtain the title product 2-(methyl(4-phenyl-1H-benzo[d]imidazol-6-yl) amino)pyrimidine-5-carbonitrile (7E) (120 mg, yield 48%) as yellow solid. LC-MS: (ES⁺): 327.1 m/z [M+H]⁺; ¹H NMR: (400 MHz, DMSO) δ12.682 (s, 1H), 8.757 (s, 2H), 8.319 (s, 1H), 8.112-8.035 (m, 2H), 7.504-7.369 (m, 5H), 3.610 (s, 3H).

N-(5-(5-(difluoromethyl)-1,3,4-oxadiazol-2-yl)pyrimidin-2-yl)-N-methyl-4-phenyl-1H-benzo[d]imidazol-6-amine (7)

In a microwave tube was placed 7E (120 mg, 0.37 mmol), sodium azide (48 mg, 0.74 mmol), CuI (24 mg, 20% wt), and DMF (5 mL). The resulting solution was stirred at 130° C. for 1 h by microwave under N2 atmosphere. LCMS showed that the reaction was completed, and the desired MS was detected. Then difluoroacetic anhydride (1.06 mg, 3.7 mmol) was added to the solution and the resulting solution was stirred at 80° C. for 40 min under microwave. LCMS showed that the starting material was consumed, and the desired product was detected. The reaction mixture was diluted with satd. NaHCO₃ solution (30 mL) and extracted with ethyl acetate (3×30 mL). The combined organic layers were washed with brine (2×30 mL), dried, concentrated. The crude product was purified by Prep-TLC (eluent:ethyl acetate) to obtain 70 mg crude product and then purified further by Prep-HPLC to obtain the title product N-(5-(5-(difluoromethyl)-1,3,4-oxadiazol-2-yl)pyrimidin-2-yl)-N-methyl-4-phenyl-1H-benzo[d]imidazol-6-amine (7) (43 mg, 28% yield) as a white solid. LC-MS: (ES⁺): 420.2 m/z [M+H]⁺; ¹H NMR: (400 MHz, DMSO) δ 10.774 (s, 1H), 9.158 (s, 2H), 9.100 (s, 1H), 8.378 (s, 1H), 7.842-7.802 (m, 3H), 7.606-7.484 (m, 3H).

Example 8. 6-((5-(5-(difluoromethyl)-1,3,4-oxadiazol-2-yl)pyrimidin-2-yl)amino)-N,N-dimethyl-1H-benzo[d]imidazole-4-carboxamide (8)

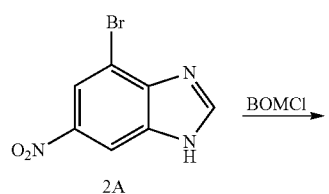

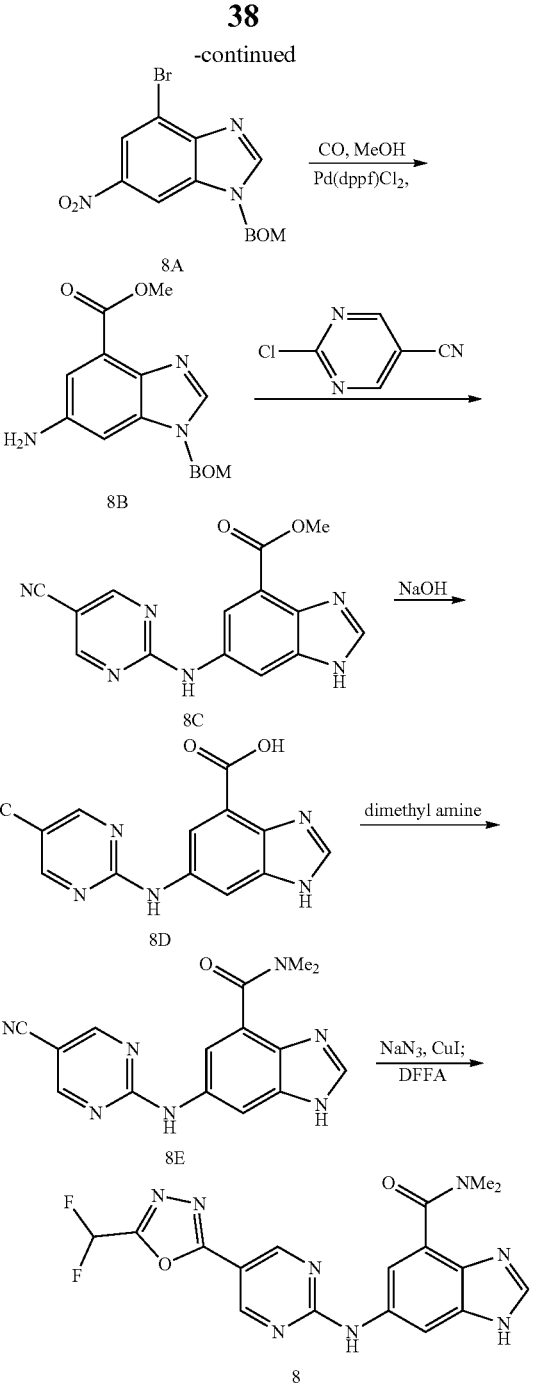

1-((benzyloxy)methyl)-4-bromo-6-nitro-1H-benzo[d]imidazole

NaH (2.48 g, 62.0 mmol) was added into a solution of 2A (5.0 g, 20.7 mmol) in DMF(50 ml) at 0° C., the solution was stirred for 30 min at 0° C., then BOMCl (8.62 ml, 62.0 mmol) was added into the solution and the solution was stirred for another 30 min, the solution was quenched with MeOH (5 ml) and poured into the mixture of ethyl acetate (50 ml) and water (50 ml). The layers were separated. The organic phase was combined with another batch of organic phase (100 mg was used). The mixture was washed with brine (30 ml×2), dried over Na₂SO₄ and evaporated to give a residue. The residue was purified by column chromatography on silica gel to afford 1-((benzyloxy)methyl)-4-bromo-6-nitro-1H-benzo[d]imidazole (8A) (5.7 g, 100%) as yellow solid.

methyl 6-amino-1-((benzyloxy)methyl)-1H-benzo[d]imidazole-4-carboxylate

To a solution of 8A (1.0 g, 2.76 mmol) in MeOH (100 mL) was added triethylamine (3.87 mL, 27.6 mmol), Pd(dppf)Cl$_2$ (319 g, 0.276 mmol), then the resulting solution was stirred at 100° C. under CO atmosphere for 17 h. LCMS showed the desired product was formed. The solvent was removed. The crude product was purified by column chromatography with silica gel (eluent:DCM/MeOH=0-10%) to obtain methyl 6-amino-1-((benzyloxy)methyl)-1H-benzo[d]imidazole-4-carboxylate (8B) (500 mg, yield 58%) as brown oil. LC-MS: (ES$^+$): 312.1 m/z [M+H]$^+$.

methyl 6-((5-cyanopyrimidin-2-yl)amino)-1H-benzo[d]imidazole-4-carboxylate (8C)

In a microwave tube was placed 8B (250 mg, 0.8 mmol), 2-chloropyrimidine-5-carbonitrile (117 mg, 0.84 mmol), K$_2$CO$_3$ (221 mg, 1.6 mmol), i-PrOH (10 mL), then the resulting solution was stirred at 100° C. for 2 h under microwave. LCMS showed the DP was formed. Water (50 mL) was added to the solution. The mixture was extracted with DCM (50 mL×2). The combined organic extracts were washed with brine, dried over anhydrous Na$_2$SO$_4$ and concentrated. The crude product was washed with MeOH (10 mL) to obtain the crude title product methyl 6-((5-cyanopyrimidin-2-yl)amino)-1H-benzo[d]imidazole-4-carboxylate (8C) (180 mg, yield 76%) as gray solid. LC-MS: (ES$^+$): 295.1 m/z [M+H]$^+$.

methyl 6-((5-cyanopyrimidin-2-yl)amino)-1H-benzo[d]imidazole-4-carboxylate (8D')

To a solution of methyl 8C (180 mg, 0.6 mmol) in MeOH/H$_2$O (12 mL, 3:1) was added NaOH (96 mg, 2.4 mmol). The solution was stirred at 60° C. for 6 h. LCMS showed the desired product was formed. The solvent was removed. Water (10 mL) was added to the solution and adjusted pH=5-6 with 1N HCl solution, filtered. The white solid was dryness to obtain the crude title product methyl 6-((5-cyanopyrimidin-2-yl)amino)-1H-benzo[d]imidazole-4-carboxylate (8D) (120 mg) and used straightly without purified further. LC-MS: (ES$^+$): 281.1 m/z [M+H]$^+$.

6-((5-cyanopyrimidin-2-yl)amino)-N,N-dimethyl-1H-benzo[d]imidazole-4-carboxamide (8E)

To a solution of 8D (120 mg, 0.43 mmol) in DMF (10 mL) was added DIEA (166 mg, 1.29 mmol), HATU (245 mg, 0.645 mmol), dimethylamine (2.0 M in THF solution, 1.1 mL, 2.15 mmol). The resulting solution was stirred at room temperature for 3 h. LCMS showed the desire product was formed. Water (20 mL) was added. The layers were separated, and the aqueous layer was extracted by ethyl acetate (2×30 mL). The combined organic layers were washed with brine, dried, filtered and concentrated. The crude product was purified further by Prep-TLC (eluent:DCM:MeOH=1:10) to obtain the title product 6-((5-cyanopyrimidin-2-yl)amino)-N,N-dimethyl-1H-benzo[d]imidazole-4-carboxamide (8E) (30 mg, yield 23%) as a yellow solid. LC-MS: (ES$^+$): 308.1 m/z [M+H]$^+$.

6-((5-(5-(difluoromethyl)-1,3,4-oxadiazol-2-yl)pyrimidin-2-Yl)amino)-N,N-dimethyl-1H-benzo[d]imidazole-4-carboxamide (8)

In a microwave tube was placed 8E (30 mg, 0.1 mmol,), sodium azide (13 mg, 0.2 mmol), CuI (6 mg, 20% wt), and DMF (1.5 mL). The resulting solution was stirred at 130° C. for 1 h by microwave under N2 atmosphere. LCMS showed that the reaction was completed, and the desired MS was detected. Difluoroacetic anhydride (174 mg, 1.0 mmol) was added to the solution and the resulting solution was stirred at 80° C. for 40 min under microwave. LCMS showed that the starting material was consumed, and the desired product was detected. The reaction mixture was diluted with satd. NaHCO$_3$ solution (30 mL) and extracted with ethyl acetate (2×30 mL). The combined organic layers were washed with brine (2×30 mL), dried, concentrated. The crude product was purified further by Prep-HPLC to obtain the title product 6-((5-(5-(difluoromethyl)-1,3,4-oxadiazol-2-yl)pyrimidin-2-yl)amino)-N,N-dimethyl-1H-benzo[d]imidazole-4-carboxamide (8) (12 mg, yield 31%) as a white solid. LC-MS: (ES$^+$): m/z 401.1 [M+H]$^+$; $^1$H NMR (400 MHz, DMSO) δ 10.731 (s, 1H), 9.130 (s, 2H), 9.007-98.972 (m, 1H), 8.394 (s, 1H), 7.730-7.702 (d, J=11.2 Hz, 3H), 3.092 (s, 3H), 2.937 (s, 3H).

Example 9. N-(5-(5-(difluoromethyl)-1,3,4-oxadiazol-2-yl)pyrimidin-2-yl)-4-(2,4-difluorophenyl)-1H-benzo[d]imidazol-6-amine (9)

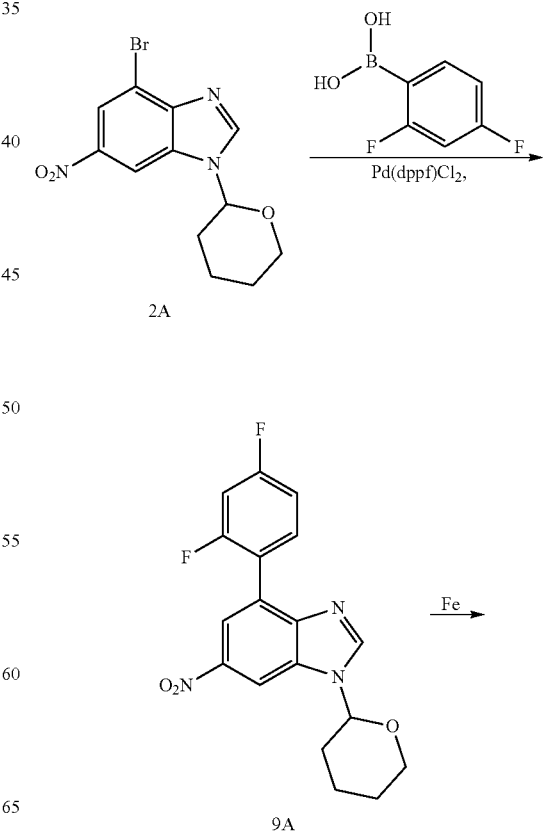

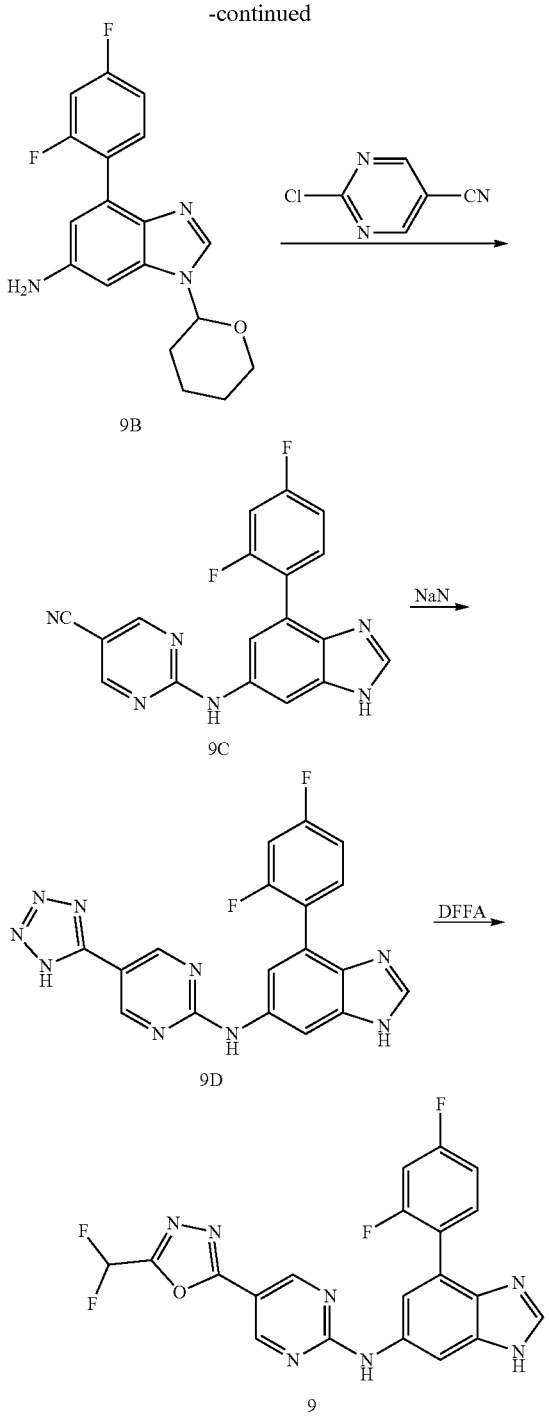

4-(2,4-difluorophenyl)-6-nitro-1-(tetrahydro-2H-pyran-2-yl)-1H-benzo[d]imidazole (9A)

To a solution of 2A (500 mg, 1.53 mmol) in Toluene/H$_2$O (5 mL/2 mL) were added (2,4-difluorophenyl)boronic acid (364 mg, 2.31 mmol), Pd(PPh$_3$)$_4$ (56 mg, 0.0765 mmol), Na$_2$CO$_3$ (342 mg, 3.21 mmol) at rt. The solution was purged with N2 at rt for 10 min to remove the excess 02. The resulting solution was stirred at 100° C. for 4 h. After cooling to rt, the reaction was taken up with EtOAc. The combined organic layers was concentrated under vacuum. The residue was purified by silica gel with DCM to afford 9A (500 mg, 91% yield) as a yellow solid. LC-MS: (ES$^+$/2): m/z 360.3 [M+H]$^+$.

4-(2,4-difluorophenyl)-1-(tetrahydro-2H-pyran-2-yl)-1H-benzo[d]imidazol-6-amine (9B)

To a solution of 9A (500 mg, 1.39 mmol) in EtOH/H$_2$O (10 mL/5 mL) was added ammonium chloride (372 mg, 6.96 mmol) and iron (233 mg, 4.17 mmol) at rt. The mixture was stirred at 75° C. for 2 h. The reaction mixture was cooled to 25° C. and then filtered. The filtrate was poured into water. The aqueous phase was extracted with ethyl acetate. The combined organic phases were washed with brine, dried with anhydrous Na$_2$SO$_4$, filtered and concentrated in vacuo. The 4-(2,4-difluorophenyl)-1-(tetrahydro-2H-pyran-2-yl)-1H-benzo[d]imidazol-6-amine (9B) (450 g, crude) was used straightly without further purification. LC-MS: (ES+): m/z 330.1 [M+H]$^+$.

2-((4-(2,4-difluorophenyl)-1H-benzo[d]imidazol-6-yl)amino)pyrimidine-5-carbonitrile (9C)

To a solution of 9B (450 mg, 1.36 mmol) in i-PrOH (10 mL) was added 2-chloropyrimidine-5-carbonitrile (191 mg, 1.36 mmol) and potassium carbonate (377 mg, 2.73 mmol). The resulting mixture was stirred at 90° C. for 4 h under nitrogen. The mixture was cooled to rt and then poured into water. The aqueous phase was extracted with ethyl acetate. The combined organic phase was dried with anhydrous Na$_2$SO$_4$, filtered and concentrated in vacuo. The residue was filtered, and the filtered cake was eluted with DCM. The filter cake is dried to give compound 2-((4-(2,4-difluorophenyl)-1H-benzo[d]imidazol-6-yl)amino)pyrimidine-5-carbonitrile 9C (400 mg, 84% yield) as a yellow solid.

N-(5-(1H-tetrazol-5-yl)pyrimidin-2-yl)-4-(2,4-difluorophenyl)-1H-benzo[d]imidazol-6-amine (9D)

To a solution of 9C (200 mg, 0.574 mmol) in DMF (3 mL) was added compound CuI (22 mg, 0.115 mmol) and sodium azide (75 mg, 1.15 mmol) under nitrogen at rt. The mixture was degassed with nitrogen for three times. The sealed vial was irradiated in the microwave on a Biotage Smith Synthesis at 130° C. for 1 h. LCMS showed the reaction was completed. The crude reaction mixture was directly for in the next step. LC-MS: (ES+): m/z 392.1 [M+H]$^+$.

N-(5-(5-(difluoromethyl)-1,3,4-oxadiazol-2-yl)pyrimidin-2-yl)-4-(2,4-difluorophenyl)-1H-benzo[d]imidazol-6-amine (9)

DFAA (500 mg, 2.87 mmol) was added to the previous to the reaction solution containing crude 9D (0.574 mmol). The sealed vial was irradiated in the microwave on a Biotage Smith Synthesis at 80° C. for 1 h. LCMS showed the reaction was completed. The mixture was cooled to rt and then poured into satd. Na$_2$HCO$_3$ solution. The aqueous phase was extracted with ethyl acetate. The combined organic phases were dried with anhydrous Na$_2$SO$_4$, filtered and concentrated in vacuo. The residue was purified by prep-HPLC to afford the desired product N-(5-(5-(difluoromethyl)-1,3,4-oxadiazol-2-yl)pyrimidin-2-yl)-4-(2,4-difluorophenyl)-1H-benzo [d]imidazol-6-amine (9) (39 mg, two steps total yield 15%) as a white solid. $^1$H NMR: (400 MHz, DMSO-d6): δ 10.76 (s, 1H), 9.20 (s, 1H), 9.13 (s, 2H), 8.48 (d, J=2 Hz, 1H), 7.69-7.76 (m, 3H), 7.44-7.56 (m, 1H), 7.30-7.31 (m, 1H). LC-MS: (ES+): m/z 442.1 [M+H]⁺.

Example 10. N-(5-(5-(difluoromethyl)-1,3,4-oxadiazol-2-yl)pyrimidin-2-yl)-4-(pyridin-2-yl)-1H-benzo[d]imidazol-6-amine (10)

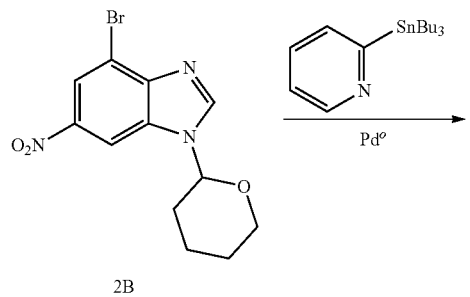

2B

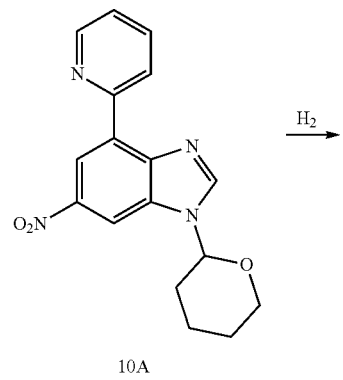

10A

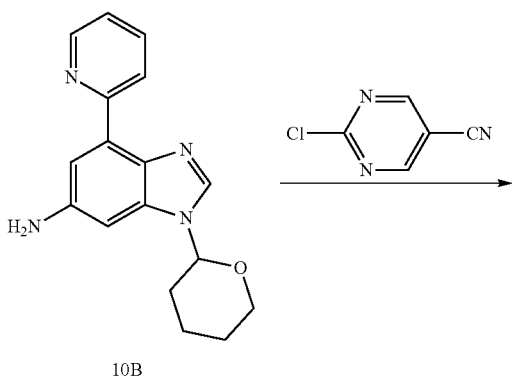

10B

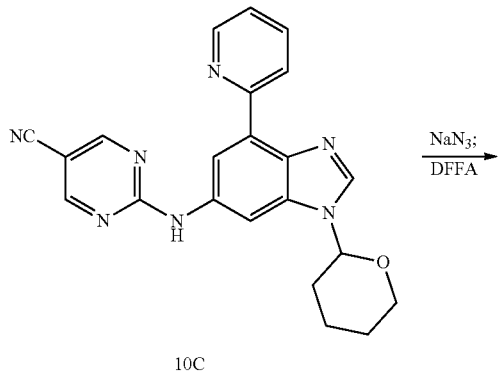

10C

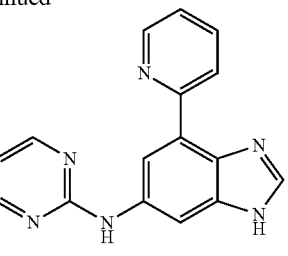

10

6-nitro-4-(pyridin-2-yl)-1-(tetrahydro-2H-pyran-2-yl)-1H-benzo[d]imidazole (10A)

To a solution of (2B) (500 mg, 1.53 mmol) in Toluene (5 mL) were added 2-(tributylstannyl)pyridine (364 mg, 2.31 mmol), Pd(PPh₃)₄ (56 mg, 0.0765 mmol) at rt. The solution was purged with N2 at rt for 10 min to remove the excess O2. The resulting solution was stirred at 100° C. for 4 h. The reaction was concentrated and was purified by silica gel with DCM/MeOH (0-15%) to afford the desired product 6-nitro-4-(pyridin-2-yl)-1-(tetrahydro-2H-pyran-2-yl)-1H-benzo[d]imidazole (10A) (480 mg, 97% yield) as a yellow solid. LC-MS: (ES+/2): 325.1 m/z [M+H]⁺.

4-(pyridin-2-yl)-1-(tetrahydro-2H-pyran-2-yl)-1H-benzo[d]imidazol-6-amine (10B)

To a solution of 10A (480 mg, 1.48 mmol) in MeOH (20 mL) was added Pd/C (100 mg) at rt. Then the reaction was stirred at rt for 4 h under H2 atmosphere. Then the reaction mixture was filtered, and the filtrate was concentrated. The crude product was purified by silica gel with DCM/MeOH (0-15%) to afford the desired product 4-(pyridin-2-yl)-1-(tetrahydro-2H-pyran-2-yl)-1H-benzo[d]imidazol-6-amine (10B) (200 mg, 46% yield) as a white solid. LC-MS: (ES+): 295.2 m/z [M+H]⁺.

2-((4-(pyridin-2-yl)-1-(tetrahydro-2H-pyran-2-yl)-1H-benzo[d]imidazol-6-yl)amino)pyrimidine-5-carbonitrile (10C)

To a solution of 10B (200 mg, 0.68 mmol) in i-PrOH (10 mL) was added 2-chloropyrimidine-5-carbonitrile (95 mg, 0.68 mmol) and potassium carbonate (188 mg, 1.36 mmol). The resulting mixture was stirred at 90° C. for 5 h under nitrogen. The mixture was cooled to rt and then poured into water. The aqueous phase was extracted with ethyl acetate. The combined organic phase was dried with anhydrous Na₂SO₄, filtered and concentrated in vacuo. The crude product was purified further by Prep-TLC to give compound 2-((4-(pyridin-2-yl)-1-(tetrahydro-2H-pyran-2-yl)-1H-benzo[d]imidazol-6-yl)amino)pyrimidine-5-carbonitrile (10C) (150 mg, 70% yield) as a yellow solid. LC-MS: (ES+): 398.1 m/z [M+H]⁺.

N-(5-(5-(difluoromethyl)-1,3,4-oxadiazol-2-yl)pyrimidin-2-yl)-4-(pyridin-2-yl)-1H-benzo[d]imidazol-6-amine (10)

To a solution of (10C) (150 mg, 0.479 mmol) in DMF (3 mL) was added compound CuI (18 mg, 0.096 mmol) and sodium azide (62 mg, 0.958 mmol) under nitrogen at rt. The mixture was degassed with nitrogen for three times. The sealed vial was irradiated in the microwave on a Biotage Smith Synthesis at 130° C. for 1 h. LCMS showed the reaction was completed. Then added DFAA (0.5 mL) to the reaction solution and the resulting solution was irradiated in the microwave on a Biotage Smith Synthesis at 80° C. for 40 min. LCMS showed the reaction was completed. The mixture was cooled to rt and then poured into satd. $Na_2HCO_3$ solution. The aqueous phase was extracted with ethyl acetate. The combined organic phases were dried with anhydrous $Na_2SO_4$, filtered and concentrated in vacuo. The residue was purified by prep-HPLC to afford N-(5-(5-(difluoromethyl)-1,3,4-oxadiazol-2-yl)pyrimidin-2-yl)-4-(pyridin-2-yl)-1H-benzo[d]imidazol-6-amine 10 (16.5 mg, two steps total yield 8%) as a white solid. LC-MS: (ES+): 441.1 m/z [M+H]+, LC-MS: (ES+): m/z 407.2 [M+H]$^+$; $^1$H NMR: (400 MHz, DMSO-d6): δ 10.774 (s, 1H), 9.253 (s, 1H), 9.157 (s, 2H), 8.836-8.822 (d, J=5.6 Hz, 1H), 8.482-8.470 (d, J=4.8 Hz, 1H), 8.251-8.231 (d, J=8.0 Hz, 1H), 8.093-8.050 (m, 1H), 7.712-7.456 (d, J=51.2 Hz, 1H), 7.537-7.506 (m, 1H).

Example 11. 6-((5-(5-(difluoromethyl)-1,3,4-oxadiazol-2-yl)pyrimidin-2-yl)amino)-N-(2-hydroxyethyl)-1H-benzo[d]imidazole-4-sulfonamide (11)

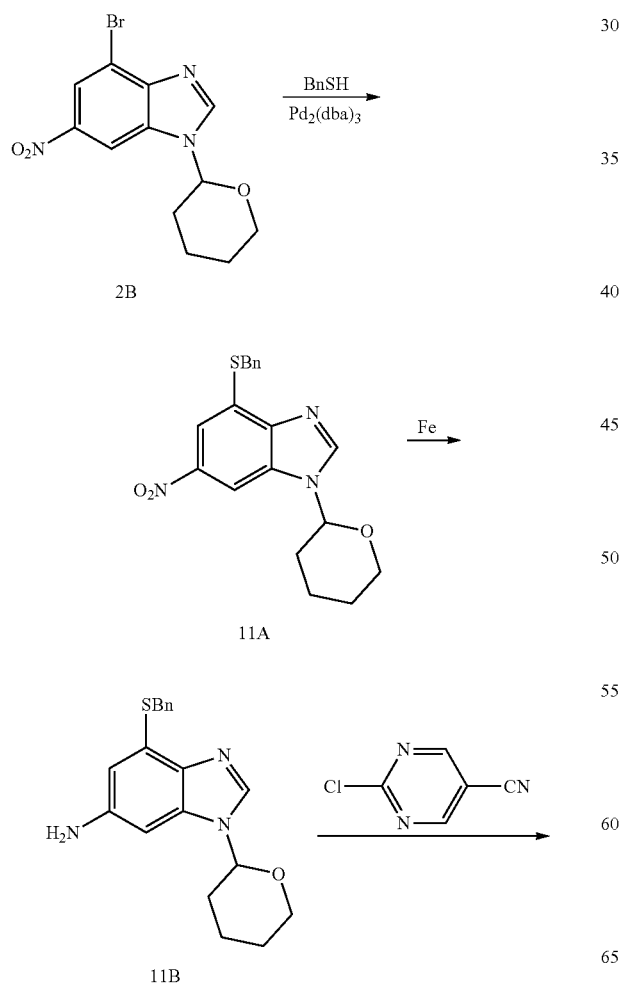

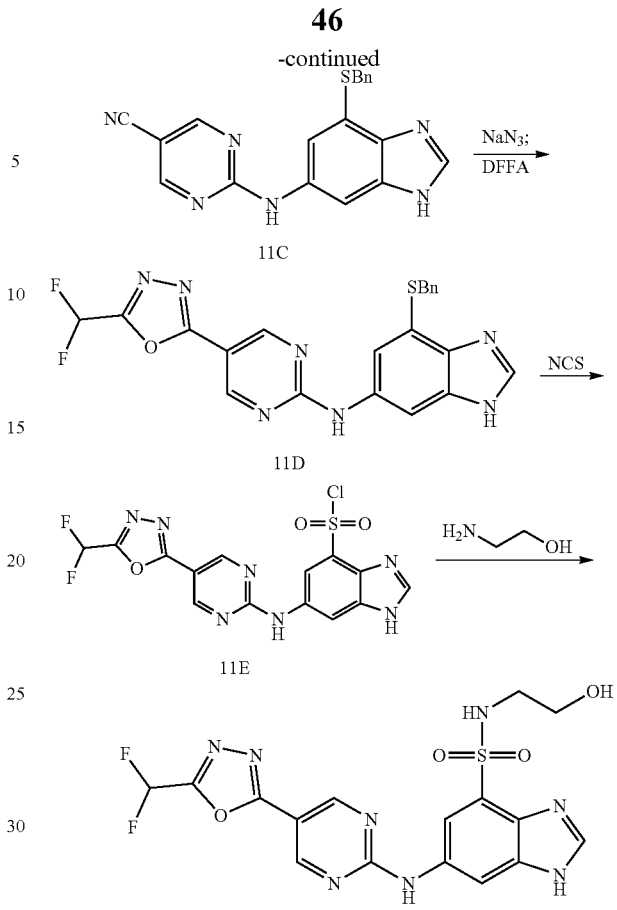

4-(benzylthio)-6-nitro-1-(tetrahydro-2H-pyran-2-yl)-1H-benzo[d]imidazole (11A)

BnSH (2.25 g, 18.4 mmol) was added into a mixture of 2B (3 g, 9.2 mmol), $Pd_2(dba)_3$ (843 mg, 0.92 mmol), xantphos (1.065 g, 1.84 mmol) and DIPEA (2.37 g, 18.4 mmol) in dioxane (15 ml) under N2 at 110° C., the mixture was stirred for 1 h at 110° C. After cooling, the reaction was poured into water (30 ml) and extracted with EA (50 ml×2). The combined organic layers were dried over $Na_2SO_4$ and concentrated. The crude product was purified by column chromatography on silica gel (EA/DCM=1/1) to obtain the product 4-(benzylthio)-6-nitro-1-(tetrahydro-2H-pyran-2-yl)-1H-benzo[d]imidazole (11A) as yellow solid (2.2 g, 62% yield). 1H NMR: (400 MHz, $CDCl_3$): δ 8.255 (s, 2H), 8.063 (s, 1H), 7.399-7.380 (d, J=7.6 Hz, 2H), 7.294-7.217 (m, 3H), 5.553-5.523 (t, J=6.4 Hz, 1H), 4.425 (s, 2H), 4.158-4.128 (d, J=12 Hz, 1H), 3.785 (m, 1H), 2.156-2.116 (m, 3H), 1.788-1.722 (m, 3H).

4-(benzylthio)-1-(tetrahydro-2H-pyran-2-yl)-1H-benzo[d]imidazol-6-amine (11B)

Fe powder (1 g, 0.5×) was added into a mixture of 11A (2 g, 5.4 mmol) and $NH_4Cl$ (2 g, 1×) in EtOH (50 ml) and water (25 ml), the mixture was heated to 70° C. and stirred for overnight. After cooling, the mixture was filtered through diatomite, the mother liquid was concentrated in vacuo to remove EtOH, and extracted with EA (50 ml), the organic phase was dried over $Na_2SO_4$ and evaporated to give the residue, the residue was purified by column chromatography on silica gel (PE/EA=10/1-1/1) to get the product 4-(benzylthio)-1-(tetrahydro-2H-pyran-2-yl)-1H-benzo[d]imidazol-6-amine (11B) as a yellow solid (1.5 g, 82% yield). $^1$H NMR (400 MHz, CDCl$_3$): δ 7.895 (s, 1H), 7.329-7.231 (m, 5H), 6.623-6.619 (d, J=1.6 Hz, 1H), 6.569-6.566 (d, J=1.2 Hz, 1H), 5.352-5.329 (d, J=9.2 Hz, 1H), 4.353 (s, 2H), 4.109-4.083 (d, J=10.4 Hz, 1H), 3.740-3.691 (m, 1H), 2.839 (s, 2H), 2.161-2.042 (m, 3H), 1.788-1.722 (m, 3H). LC-MS: (ES+/2): m/z 340.1 [M+H]$^+$.

2-((4-(benzylthio)-1H-benzo[d]imidazol-6-yl)amino)pyrimidine-5-carbonitrile (11C)

K$_2$CO$_3$ (1.22 g, 8.82 mmol) and 2-chloropyrimidine-5-carbonitrile (617 mg, 4.41 mmol) were added into a solution of 11B (1.5 g, 4.41 mmol) in i-PrOH https://www.chemicalbook.com/javascript:showMsqDetail ('ProductSynonyms.aspx?CBNumber=CB8854102&postData3=CN&SYMBOL_Type=A') (30 ml) under N2, then the mixture was heated to 90° C. and stirred for 2 h. After cooling, the mixture was poured into a mixture of water (30 ml) and extracted with EA (30 ml×2), the organic phases was washed with saturated NaCl solution (30 ml×2) and dried over Na$_2$SO$_4$ and evaporated to give the crude, the crude was purified by column chromatography on silica gel (PE/EA=1/1-1/10) to get the product 2-((4-(benzylthio)-1H-benzo[d]imidazol-6-yl)amino)pyrimidine-5-carbonitrile as a yellow solid (11C) (1.68 g, 74% yield). 1H NMR (400 MHz, CDCl$_3$): δ 8.583 (s, 2H), 7.978-7.953 (m, 2H), 7.676 (s, 1H), 7.203 (m, 5H), 4.088 (s, 2H). LC-MS: (ES+/2): m/z 359.1 [M+H]$^+$.

2-((4-(benzylthio)-1H-benzo[d]imidazol-6-yl)amino)pyrimidine-5-carbonitrile (11D)

CuI (40 mg, 0.21 mmol) and sodium azide (145 mg, 2.23 mmol) were added into a solution of 11C (400 mg, 1.11 mmol) in DMF (10 ml) under N2, the mixture was heated to 120° C. and stirred for overnight, after cooling to 90° C., then DFAA (2 ml) was added into the mixture and the mixture was stirred for 4 h at 90° C., the mixture was quenched with satd. aq. NaHCO$_3$ (20 ml) and extracted with EA (20 ml), the organic phase was dried over Na$_2$SO$_4$ and evaporated to give the residue, the residue was purified by column chromatography on silica gel (DCM/MeOH=10/1) to get the product 4-(benzylthio)-N-(5-(5-(difluoromethyl)-1,3,4-oxadiazol-2-yl)pyrimidin-2-yl)-1H-benzo[d]imidazol-6-amine (11D) as a yellow solid (250 mg, 50% yield for two steps). $^1$H NMR: (400 MHz, MeOD): δ 9.013 (s, 2H), 8.117-8.056 (m, 2H), 7.475 (s, 1H), 7.339-7.081 (m, 6H), 4.264 (s, 2H). LC-MS: (ES+/2): m/z 452.1 [M+H]$^+$.

6-((5-(5-(difluoromethyl)-1,3,4-oxadiazol-2-yl)pyrimidin-2-yl)amino)-benzo[d]imidazole-4-sulfonyl chloride (11E)

NCS (221 mg, 1.66 mmol) was added into the mixture of 11D (250 mg, 0.553 mmol) in AcOH/H$_2$O (5 ml, 9/1) at 25 to 30° C. and the mixture was stirred for 1 h, then the mixture was poured into a mixture of water (20 ml) and EA (20 ml), the organic phase was washed with saturated NaCl solution (10 ml×2) and dried over Na$_2$SO$_4$ and evaporated to give the crude 6-((5-(5-(difluoromethyl)-1,3,4-oxadiazol-2-yl)pyrimidin-2-yl)amino)-1H-benzo [d]imidazole-4-sulfonyl chloride (11E) (282 mg, crude), which was used for the next step without further purification. LC-MS: (ES+/2): m/z 428.0 [M+H]$^+$.

6-((5-(5-(difluoromethyl)-1,3,4-oxadiazol-2-yl)pyrimidin-2-yl)amino)-N-(2-hydroxyethyl)-1H-benzo[d]imidazole-4-sulfonamide (11)

11E (100 mg, 0.233 mmol) was added into the mixture of 2-aminoethan-1-ol (13.6 mg, 0.223 mmol) and TEA (25 mg, 0.247 mmol) in DCM(15 ml) and the mixture was stirred for 0.5 h at 25~30° C., then water and satd. NaHCO$_3$aq was added into the mixture and the mixture was extracted with DCM (30 ml×2), the organic phase was dried over Na$_2$SO$_4$ and evaporated to give the crude, the crude was purified by preparative HPLC to afford the product 11 (8.6 mg, 99%) as white solid. $^1$H NMR: (400 MHz, MeOD): δ 9.131 (s, 2H), 8.876-8.652 (m, 2H), 8.211 (s, 1H), 7.358-7.100 (t, J=51.6 Hz, 1H), 3.575-3.547 (t, J=5.6 Hz, 2H), 3.124-3.096 (t, J=5.6 Hz, 2H), LC-MS: (ES+/2): m/z 453.0 [M+H]$^+$.

Example 12. 1-allyl-N-(5-(5-(difluoromethyl)-1,3,4-oxadiazol-2-yl)pyrimidin-2-yl)-4-phenyl-1H-benzo[d]imidazol-6-amine (12)

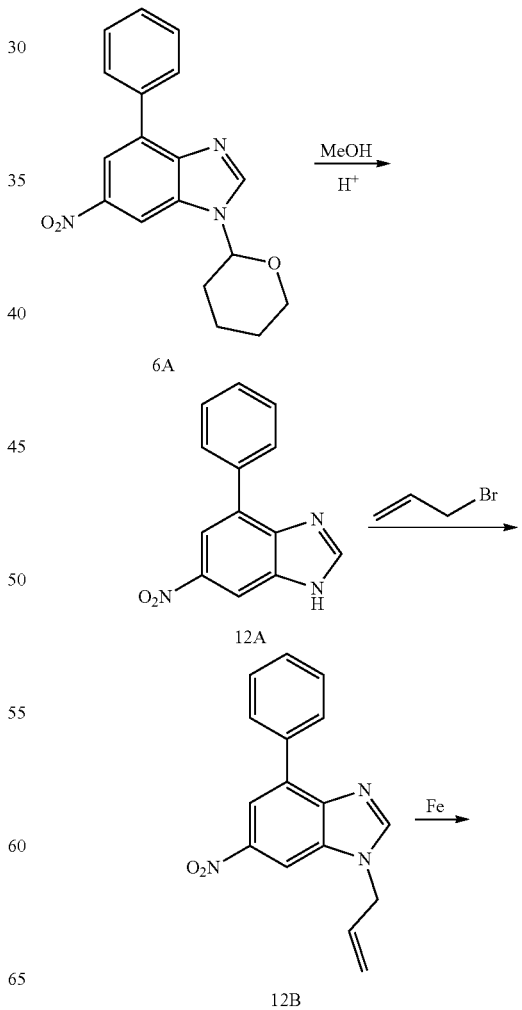

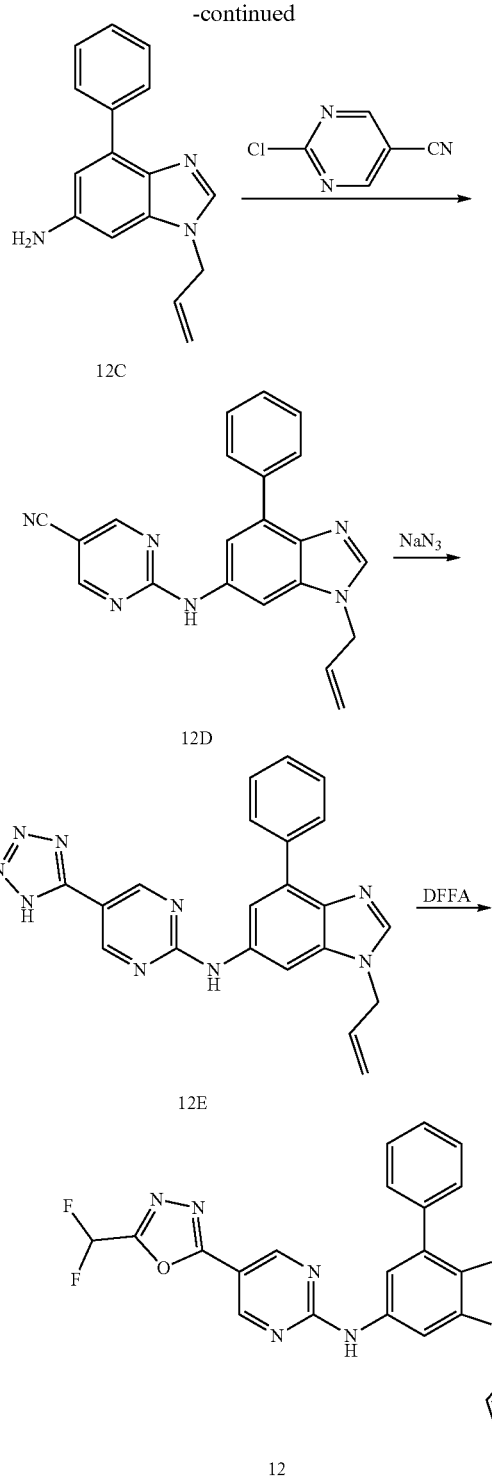

zole (12A) (2.9 g, crude), which was used in next step directly. LC-MS: (ES+): m/z 240.1 [M+H]+.

1-allyl-6-nitro-4-phenyl-1H-benzo[d]imidazole (12B)

To a solution of (12A) (2.9 g, 12.3 mmol) in DMF (20 mL) was added 3-bromoprop-1-ene (1.8 g, 14.8 mmol) and potassium carbonate (1.9 g, 13.5 mmol) at rt. The resulting solution was stirred for 4 h at rt. The mixture was poured into water. The aqueous phase was extracted with ethyl acetate. The combined organic phase was washed with brine, dried with anhydrous $Na_2SO_4$, filtered and concentrated in vacuo to give the crude 1-allyl-6-nitro-4-phenyl-1H-benzo [d]imidazole (12B) (2.7 g, crude) as a yellow solid, which was used for the next step directly without further purification. LC-MS: (ES+): m/z 280.1 [M+H]+.

1-allyl-4-phenyl-1H-benzo[d]imidazol-6-amine (12C)

To a solution of 12B (2.9 g, 10.4 mmol) in EtOH/$H_2O$ (20 mL/10 mL) was added ammonium chloride (2.2 g, 41.6 mmol) and iron (1.1 g, 20.8 mmol) at rt. The mixture was stirred at 70° C. for 2 h. The reaction mixture was cooled to 25° C. and then filtered. The filtrate was poured into water. The aqueous phase was extracted with ethyl acetate. The combined organic phase was washed with brine, dried with anhydrous $Na_2SO_4$, filtered and concentrated in vacuo. The residue was purified by column chromatography on silica gel (200-300 mesh silica gel, petroleum ether/ethyl acetate=2/1) to give compound 1-allyl-4-phenyl-1H-benzo [d]imidazol-6-amine (12C) (2.0 g, three steps total yield 81%) as a yellow oil. $^1$H: NMR (400 MHz, $CDCl_3$): δ 7.94 (d, J=7.2 Hz, 2H), 7.87 (s, 1H), 7.48-7.52 (m, 2H), 7.36-7.40 (m, 1H), 6.87 (d, J=2.4 Hz, 1H), 6.64 (d, J=2.0 Hz, 1H), 5.99-6.06 (m, 1H), 5.31-5.34 (m, 1H), 5.23 (d, J=16.8 Hz, 1H), 4.72-4.74 (m, 2H).

2-((1-allyl-4-phenyl-1H-benzo[d]imidazol-6-yl) amino)pyrimidine-5-carbonitrile (12D)

To a solution of 1-allyl-4-phenyl-1H-benzo[d]imidazol-6-amine (2 g, 8.03 mmol) in i-PrOH (20 mL) was added 2-chloropyrimidine-5-carbonitrile (1.12 g, 8.03 mmol) and potassium carbonate (2.2 g, 16.1 mmol). The resulting mixture was stirred at 90° C. for 4 h under nitrogen. The mixture was cooled to rt and then poured into water. The aqueous phase was extracted with ethyl acetate. The combined organic phase was dried with anhydrous $Na_2SO_4$, filtered and concentrated in vacuo. The residue was purified by column chromatography on silica gel (100-200 mesh silica gel, DCM/ethyl acetate=10/1) to give compound 2-((1-allyl-4-phenyl-1H-benzo[d]imidazol-6-yl)amino)pyrimidine-5-carbonitrile (12D) (2.4 g, 86% yield) as a yellow solid. LC-MS: (ES+): m/z 351.1 [M+H]+.

N-(5-(1H-tetrazol-5-yl)pyrimidin-2-yl)-1-allyl-4-phenyl-1H-benzo[d]imidazol-6-amine (12E)

To a solution of 12D (2.4 g, 6.82 mmol) and cuprous iodide (259 mg, 1.36 mmol) in DMF (20 mL) was added sodium azide (886 mg, 13.6 mmol). The mixture was stirred at 120° C. for 4 h. LCMS showed that the reaction was completed with the desired MS detected. The reaction 6-nitro-4-phenyl-1H-benzo[d]imidazole (12A)

To a solution of 6A (4.5 g, 13.9 mmol) in MeOH (50 mL) was added p-toluenesulfonic acid monohydrate (53 mg, 0.278 mmol) at rt. The resulting mixture was stirred reflux for overnight. The reaction was diluted with ethyl acetate and water. The organic layer was further washed with brine, dried over $Na_2SO_4$, filtered and concentrated in vacuo to give a crude product 6-nitro-4-phenyl-1H-benzo[d]imidasolution was used in the next step directly without purification. LC-MS: (ES+): m/z 396.2 [M+H]+.

1-allyl-N-(5-(5-(difluoromethyl)-1,3,4-oxadiazol-2-yl)pyrimidin-2-yl)-4-phenyl-1H-benzo[d]imidazol-6-amine (12)

DFAA (3.5 g, 20.4 mmol) was added to the reaction solution containing 12D (6.82 mmol) And the resulting mixture was stirred at 90° C. for 1 h. at which time LCMS showed the reaction was completed. The mixture was cooled to rt and then poured into solution of sodium bicarbonate and stirred for 10 min. The aqueous phase was extracted with ethyl acetate. The combined organic phase was dried with anhydrous $Na_2SO_4$, filtered and concentrated in vacuo. The residue was purified by column chromatography on silica gel (100-200 mesh silica gel, DCM/ethyl acetate=10/1) to afford the desired product 1-allyl-N-(5-(5-(difluoromethyl)-1,3,4-oxadiazol-2-yl)pyrimidin-2-yl)-4-phenyl-1H-benzo[d]imidazol-6-amine (12) (2.0 g, two steps total yield 67%) as a yellow solid. $^1$H NMR: (400 MHz, DMSO-d6): δ 10.68 (s, 1H), 9.12 (s, 2H), 8.87 (s, 1H), 8.33 (d, J=1.6 Hz, 1H), 7.91 (d, J=7.2 Hz, 2H), 7.81 (d, J=1.6 Hz, 1H), 7.44-7.69 (m, 4H), 6.07-6.14 (m, 1H), 5.31-5.40 (m, 2H), 5.03 (d, J=5.6 Hz, 2H).

Example 13. 3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol (13)

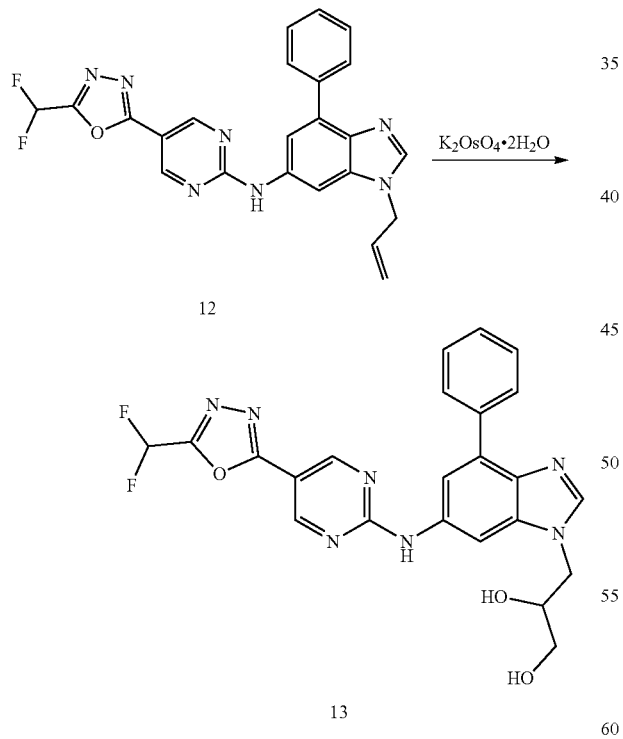

To a solution of 12 (1.9 g, 4.27 mmol) in a mixture of THF/tert-butanol (35 mL/5 mL) was added 4-methylmorpholine 4-oxide (1.0 g, 8.54 mmol) and potassium osmate (VI) dihydrate (63 mg, 0.171 mmol) and the reaction mixture was stirred at rt overnight. Then 40% solution of $Na_2SO_3$ was added and the mixture stirred for 30 min. Ethyl acetate was added and the organic layer separated, washed twice with water, dried over magnesium sulphate and concentrated to give 3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol (13) (1.2 g, yield 60%) as a yellow solid. 1H NMR (400 MHz, DMSO-d6): δ 10.67 (s, 1H), 9.11 (s, 2H), 8.87 (s, 1H), 8.36 (s, 1H), 7.80-7.90 (m, 3H), 7.48-7.59 (m, 4H), 4.50-4.53 (m, 1H), 4.23-4.29 (m, 1H), 3.94 (s, 3H). LC-MS: (ES+): m/z 480.1 [M+H]+.

Example 14. 2-(6-((5-(5-(difluoromethyl)-1,3,4-oxadiazol-2-yl)pyrimidin-2-yl)amino)-4-phenyl-1H-benzo[d]imidazol-1-yl)ethan-1-ol (14)

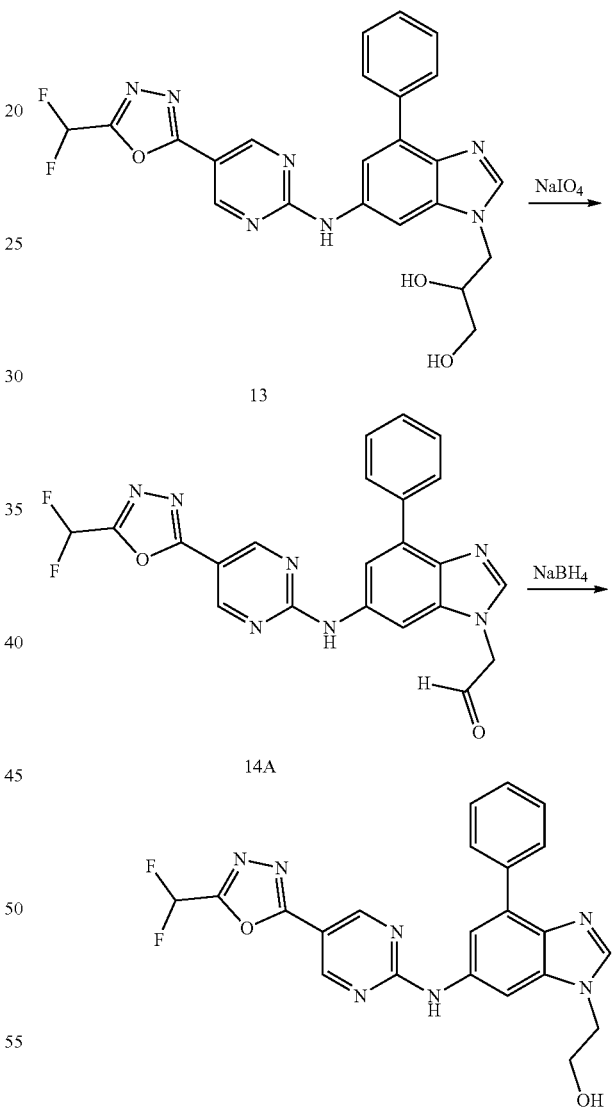

2-(6-((5-(5-(difluoromethyl)-1,3,4-oxadiazol-2-yl)pyrimidin-2-yl)amino)-4-phenyl-1H-benzo[d]imidazol-1-Yl)acetaldehyde (14A)

To a solution of (13) (200 mg, 0.417 mmol) in a mixture of DMSO/DCM (2 mL/10 mL) was added sodium periodate (load on silica gel, 446 mg, 2.08 mmol). The reaction mixture was stirred at rt for 40 min. Excess NaIO$_4$ was removed by filtration and the filtrate containing 14A was used directly in the next step without purification. LC-MS: (ES+18): m/z 466.1 [M+H]$^+$.

2-(6-((5-(5-(difluoromethyl)-1,3,4-oxadiazol-2-yl)pyrimidin-2-yl)amino)-4-phenyl-1H-benzo[d]imidazol-1-yl)ethanol (14)

To a solution of 14A from the previous step (150 mg, 0.335 mmol) in DCM (2 mL) was added sodium borohydride (25.5 mg, 0.671 mmol). The reaction mixture was stirred at rt for 5 min and then poured into water. The aqueous phase was extracted with ethyl acetate. The combined organic phase was washed with brine, dried with anhydrous Na$_2$SO$_4$, filtered and concentrated in vacuo. The residue was purified by prep-HPLC to afford the desired product 2-(6-((5-(5-(difluoromethyl)-1,3,4-oxadiazol-2-yl)pyrimidin-2-yl)amino)-4-phenyl-1H-benzo[d]imidazol-1-yl)ethan-1-ol (14) (4 mg) as a yellow solid. 1H NMR: (400 MHz, DMSO-d$_6$): δ 10.51 (s, 1H), 9.08 (s, 2H), 8.20 (s, 1H), 8.07-8.11 (m, 3H), 7.72 (s, 1H), 7.39-7.56 (m, 4H), 5.06 (t, J=5.2 Hz, 1H), 4.31 (t, J=4.8 Hz, 2H), 3.81 (d, J=5.2 Hz, 2H). LC-MS: (ES+): m/z 450.1 [M+H]$^+$.

Example 15. N-(5-(5-(difluoromethyl)-1,3,4-oxadiazol-2-yl)pyrimidin-2-yl)-1-(2-(dimethylamino)ethyl)-4-phenyl-1H-benzo[d]imidazol-6-amine (15)

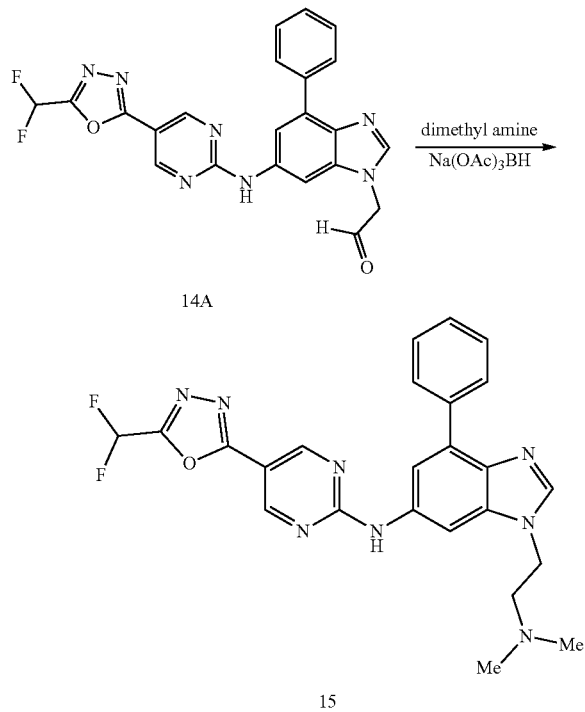

Dimethylamine (33 mg, 0.417 mmol) was added to a solution of 14A from Example 14 (0.417 mmol) and the resulting solution was stirred at rt for 30 min. Sodium triacetoxyborohydride (265 mg, 1.25 mmol) was added and the mixture was stirred at room temperature for overnight. The reaction was diluted with EtOAc and washed with water, saturated aqueous NaHCO$_3$, brine dried over sodium sulphate and concentrated in vacuo. The residue was purified by prep-HPLC to afford the desired product (15) (16 mg, two steps total yield 8%), as a yellow solid. $^1$H NMR: (400 MHz, DMSO-d6): δ 10.61 (s, 1H), 9.11 (s, 2H), 8.46 (s, 1H), 8.24 (s, 1H), 8.03 (d, J=7.6 Hz, 2H), 7.72 (s, 1H), 7.42-7.69 (m, 4H), 4.70-4.71 (m, 2H), 3.64 (m, 2H), 2.92 (s, 6H). LC-MS: (ES+): m/z 477.2 [M+H]$^+$.

Example 16. 1-(2-(6-((5-(5-(difluoromethyl)-1,3,4-oxadiazol-2-yl)pyrimidin-2-yl)amino)-4-phenyl-1H-benzo[d]imidazol-1-yl)ethyl)pyrrolidin-3-ol (16)

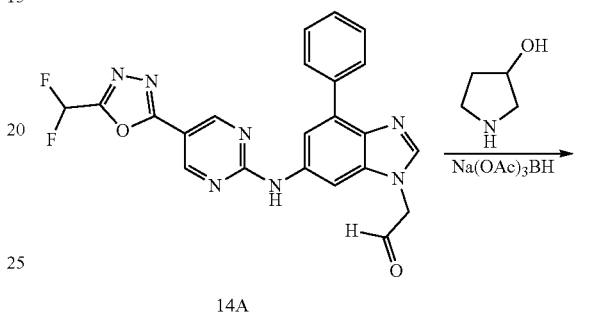

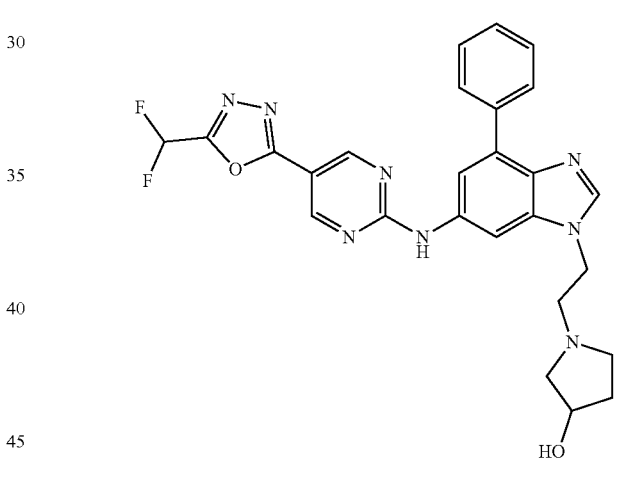

To a solution of 14A from Example 14 (150 mg, 0.335 mmol) and pyrrolidin-3-ol (29 mg, 0.335 mmol) in DCM (2 mL). The mixture solution was stirred at rt for 30 min. Sodium triacetoxyborohydride (213 mg, 1.01 mmol) was added and the mixture was stirred at room temperature for overnight. The reaction was diluted with EtOAc and washed with water, saturated aqueous NaHCO$_3$, brine dried over sodium sulphate and concentrated in vacuo. The residue was purified by prep-TLC to afford 1-(2-(6-((5-(5-(difluoromethyl)-1,3,4-oxadiazol-2-yl)pyrimidin-2-yl)amino)-4-phenyl-1H-benzo[d]imidazol-1-yl)ethyl)pyrrolidin-3-ol (16) (10 mg, yield 6%) as a yellow solid. $^1$H NMR: (400 MHz, CDCl$_3$+MeOD): δ 9.01 (s, 2H), 7.99 (s, 2H), 7.82-7.84 (s, 2H), 7.43-7.45 (m, 3H), 7.31-7.34 (m, 1H), 6.90 (m, 1H), 4.27-4.29 (m, 1H), 2.85-2.94 (m, 3H), 2.62 (s, 2H), 2.40-2.42 (m, 1H), 2.05-2.11 (m, 1H), 1.89-1.93 (m, 1H), 1.68-1.71 (m, 1H), 1.48-1.52 (m, 1H). LC-MS: (ES+): m/z 519.2 [M+H]$^+$.

Example 17. N-(5-(5-(difluoromethyl)-1,3,4-oxadiazol-2-yl)pyrimidin-2-yl)-4-(4-morpholinophenyl)-1H-benzo[d]imidazol-6-amine (17)

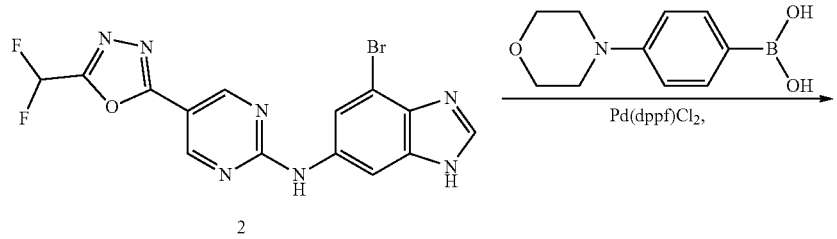

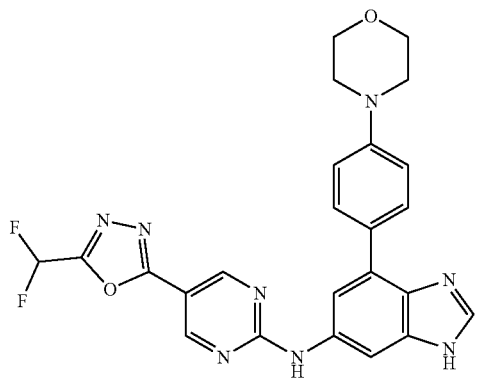

To a solution of 2 (150 mg, 0.367 mmol) in 1,4-Dioxane (2 mL) was added (4-morpholinophenyl)boronic acid (114 mg, 0.554 mmol), Pd(dppf)Cl$_2$ (14 mg, 0.0183 mmol), K$_2$CO$_3$ (102 mg, 0.739 mmol) at rt. The solution was purged with N2 at rt for 10 min to remove the excess O2. The resulting solution was stirred at 80° C. for overnight. After cooling to rt, the reaction was taken up with EtOAc. The combined organic layers was concentrated under vacuum. The residue was purified by prep-HPLC to afford the desired product N-(5-(5-(difluoromethyl)-1,3,4-oxadiazol-2-yl)pyrimidin-2-yl)-4-(4-morpholinophenyl)-1H-benzo[d]imidazol-6-amine (17) (20 mg, 11% yield) as a white solid. $^1$H NMR: (400 MHz, DMSO-d$_6$): δ 10.70 (s, 1H), 9.13 (s, 3H), 8.34 (s, 1H), 7.78 (s, 1H), 7.45-7.71 (m, 3H), 7.15 (d, J=8.8 Hz, 2H), 3.78-3.81 (m, 4H), 3.23-3.25 (m, 4H). LC-MS: (ES+): m/z 491.1 [M+H]$^+$.

Example 18. N-(5-(5-(difluoromethyl)-1,3,4-oxadiazol-2-yl)pyrimidin-2-yl)-4-(4-(morpholinomethyl)phenyl)-1H-benzo[d]imidazol-6-amine (18)

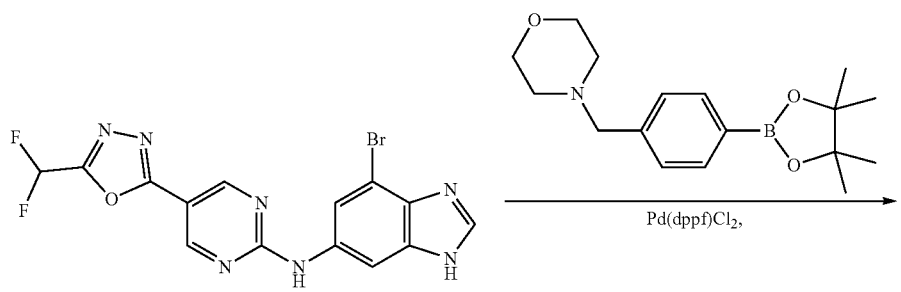

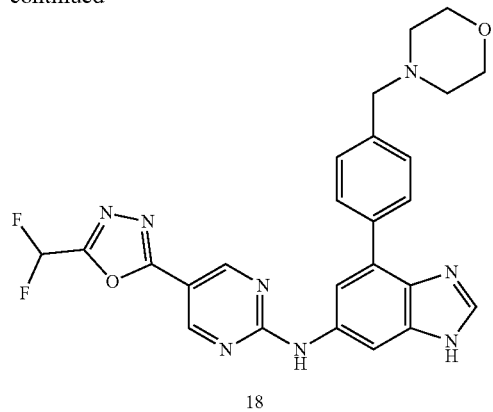

18

To a solution of 4-bromo-N-(5-(5-(difluoromethyl)-1,3,4-oxadiazol-2-yl)pyrimidin-2-yl)-1H-benzo[d]imidazol-6-amine (2) (100 mg, 0.246 mmol) in 1,4-Dioxane/H$_2$O (2 mL/0.2 mL) were added 4-(4-(4,4,5,5-tetramethyl-1,3,2-dioxaborolan-2-yl)benzyl)morpholine (112 mg, 0.369 mmol), Pd(dppf)Cl$_2$ (18 mg, 0.0246 mmol), K$_2$CO$_3$ (68 mg, 0.492 mmol) at rt. The solution was purged with N2 at rt for 10 min to remove the excess O2. The resulting solution was stirred at 60° C. for overnight. After cooling to rt, the reaction was taken up with EtOAc. The combined organic layers was concentrated under vacuum. The residue was purified by prep-HPLC to afford the desired product N-(5-(5-(difluoromethyl)-1,3,4-oxadiazol-2-yl)pyrimidin-2-yl)-4-(4-(morpholinomethyl)phenyl)-1H-benzo[d]imidazol-6-amine (18) (38 mg, 31% yield) as a white solid. $^1$H NMR: (400 MHz, DMSO-d$_6$): δ 10.69 (s, 1H), 9.12 (s, 2H), 8.90 (s, 1H), 8.34 (s, 1H), 8.00 (d, J=8 Hz, 2H), 7.85 (d, J=1.6 Hz, 1H), 7.44-7.70 (m, 3H), 4.46 (s, 2H), 3.91-4.05 (m, 4H), 3.33-3.15 (m, 4H). LC-MS: (ES+): m/z 505.1 [M+H]$^+$.

Example 19. N-(5-(5-(difluoromethyl)-1,3,4-oxadiazol-2-yl)pyrimidin-2-yl)-1H-benzo[d]imidazol-6-amine (19)

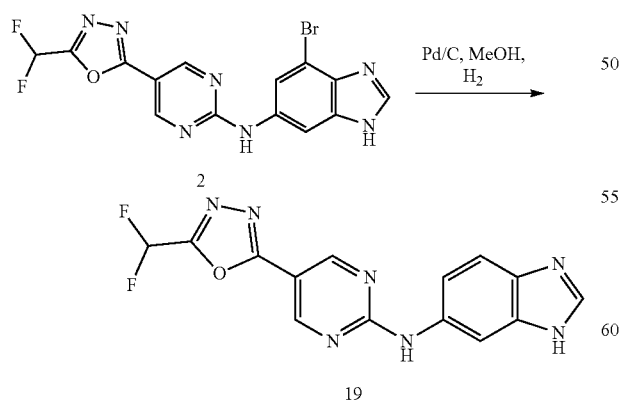

10% Pd/C (50 mg) was added to a solution of 2 (50 mg, 0.12 mmol) in MeOH (5 ml), the mixture was stirred for 1 h at 25~30° C. under H2. The reaction mixture was filtered through diatomite and evaporated to give the crude, the crude was purified by preparative HPLC to afford the product N-(5-(5-(difluoromethyl)-1,3,4-oxadiazol-2-yl)pyrimidin-2-yl)-1H-benzo[d]imidazol-6-amine (19) (2.75 mg, 7%) as white solid. $^1$H NMR: (400 MHz, MeOD): δ 9.119 (s, 4H), 8.639 (s, 1H), 7.739-7.719 (m, 3H), 7.351-7.093 (t, J=51.6 Hz, 1H) LC-MS: (ES+/2): m/z 328.0 [M+H]$^+$.

Example 20. 5-(5-(difluoromethyl)-1,3,4-oxadiazol-2-yl)-N-((4-phenyl-1H-benzo[d]imidazol-6-yl)methyl)pyrimidin-2-amine

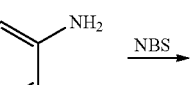

20A

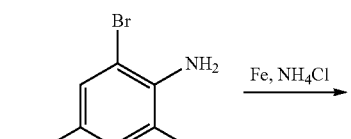

20B

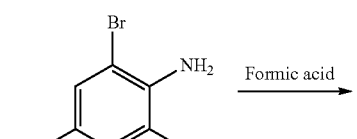

20C

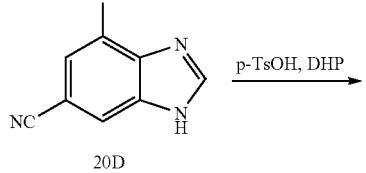

20D

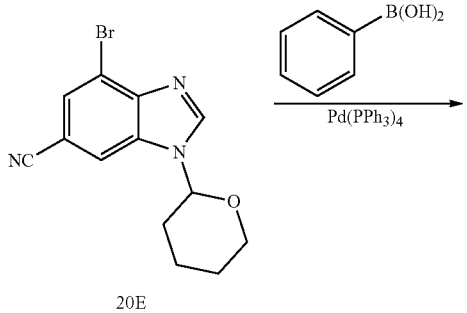

20E

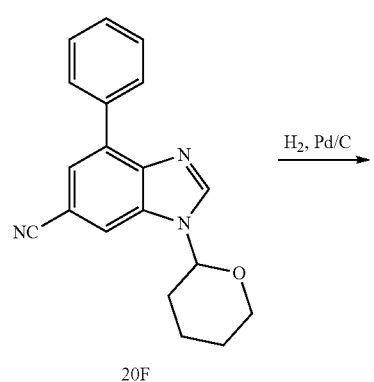

20F

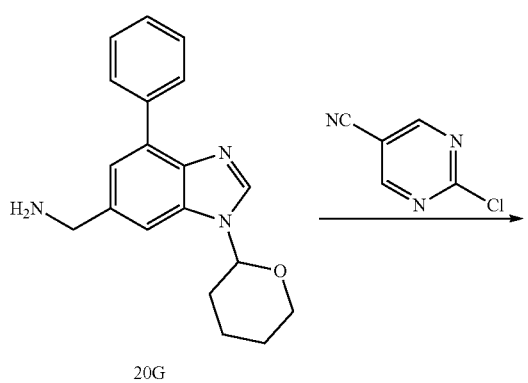

20G

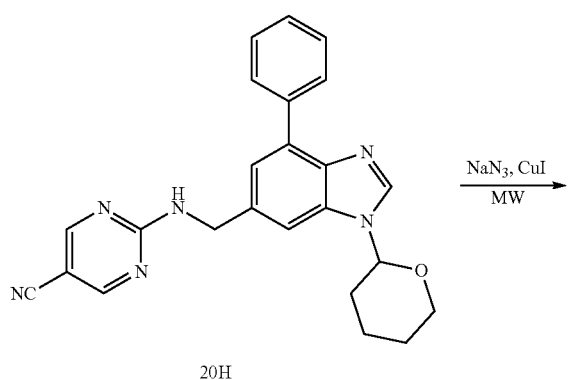

20H

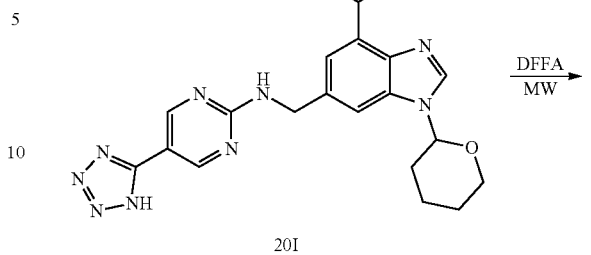

20I

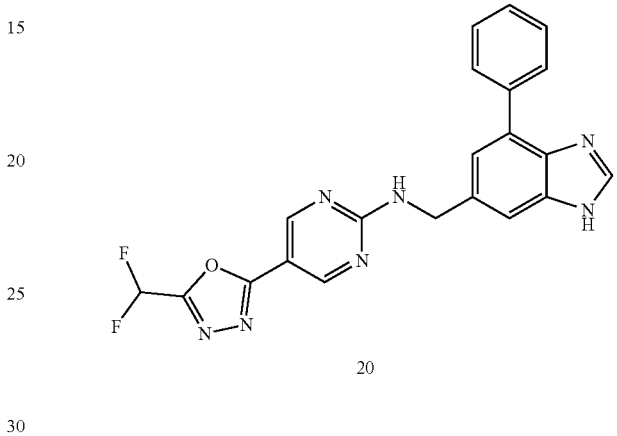

20

4-amino-3-bromo-5-nitrobenzonitrile (20B)

To a suspension of 4-amino-3-nitrobenzonitrile (20A) (4.89 g, 30 mmol) in acetonitrile (50 mL) was added NBS (6.4 g, 36 mmol) and the resulting mixture was stirred for 16 h at rt. The mixture was then concentrated in vacuum and extracted with EA (50 mL). The extract was washed with water, dried over $Na_2SO_4$ and evaporated. The crude product was purified by column chromatography with silica gel (PE/EA=8:1) to give 20B (6.2 g, yield 85%) as a yellow solid. LCMS: m/z 242.0 $[M+H]^+$ 1H NMR (400 MHz, $CDCl_3$) δ: 8.493 (s, 1H), 7.914 (s, 1H)

3,4-diamino-5-bromobenzonitrile (20C)

To a solution of 4-amino-3-bromo-5-nitrobenzonitrile (20B) (6.2 g, 25.6 mmol) in $EtOH/H_2O$ (2/1.75 mL) was added $NH_4Cl$ (5.28 g, 122.5 mmol) followed by Fe power (4.12 g, 73.5 mmol). The solution was then stirred at 75° C. for 2 h. The reaction was cooled, and concentrated in vacuum and the concentrate was extracted with EA, washed with brine, dried over anhydrous $Na_2SO_4$, filtered and concentrated in vacuum to give the 20C (4.7 g, yield 86%) as white solid which was used without further purification. LCMS: 212.0 m/z $[M+H]^+$

4-bromo-1H-benzo[d]imidazole-6-carbonitrile (20D)

A solution of 3,4-diamino-5-bromobenzonitrile (20C) (4.7 g, 22.2 mmol) in formic acid (40 mL) was stirred for 2 hours at 100° C. The solution was cooled, concentrated in vacuum and added to 40 mL of $H_2O$. The pH was adjusted to 13 with 6N NaOH, the mixture was extracted with EA and the organic phase was dried over anhydrous $Na_2SO_4$. Filtration and concentration in vacuo provided 20D (3.6 g, yield 73%) as a yellow solid. LCMS: 224.0 m/z $[M+H]^+$

4-bromo-1-(tetrahydro-2H-pyran-2-yl)-1H-benzo[d]imidazole-6-carbonitrile (20E)

To a solution of 4-bromo-1H-benzo[d]imidazole-6-carbonitrile (20D) (3.6 g, 16.22 mmol) in DMF (35 mL) was added p-TsOH (0.32 g, 1.62 mmol) and dihydropyaran (1.63 g, 19.46 mmol). The mixture was then stirred for 2 h at 60° C. at which time, the solution was poured into water, extracted with EA (50 mL) and washed with brine. Filtration and concentration in vacuo provided the crude product which was purified by column chromatography using silica gel (PE/EA=2:1) to give 20E (3.6 g, yield 72%) as a yellow solid which was used directly in the next step.

4-phenyl-1-(tetrahydro-2H-pyran-2-yl)-1H-benzo[d]imidazole-6-carbonitrile (20F)

To a solution of 4-bromo-1-(tetrahydro-2H-pyran-2-yl)-1H-benzo[d]Imidazole-6-carbonitrile (20D) (1.6 g, 5.21 mmol) in toluene/H$_2$O (v/v=4:1, 20 mL) was added Na$_2$CO$_3$ (1.65 g, 1.56 mmol), phenylboronic acid (0.76 g, 6.25 mmol) and Pd(dppf)Cl$_2$ (0.12 g, 0.26 mmol), and the resulting mixture was stirred for 4 hours at 90° C. under N2. The mixture was concentrated in vacuo and purified by column chromatography with silica gel (PE/EA=2:1) to provide (4-phenyl-1-(tetrahydro-2H-pyran-2-yl)-1H-benzo[d]imidazole-6-carbonitrile (0.85 g, yield 53%) as white solid. LCMS: 304.2 m/z [M+H]$^+$

(4-phenyl-1-(tetrahydro-2H-pyran-2-yl)-1H-benzo[d]imidazol-6-yl)methanamine (20G)

To a solution of 4-phenyl-1-(tetrahydro-2H-pyran-2-yl)-1H-benzo [d] imidazole-6-carbonitrile (20F) (0.85 g, 2.8 mmol) in MeOH (10 mL) was added Raney Ni (50 mg, 1.4 mmol) and the mixture was stirred for 16 h at rt under an atmosphere of H2. The solution was filtered and concentrated in vacuo to give 20G (0.65 g, yield 75%) as a white solid which was used directly in the next step. LC-MS: 308.2 m/z [M+H]$^+$

2-(((4-phenyl-1-(tetrahydro-2H-pyran-2-yl)-1H-benzo[d]imidazol-6-yl)methyl)amino)pyrimidine-5-carbonitrile (20H)

To a suspension of 4-phenyl-1-(tetrahydro-2H-pyran-2-yl)-1H-benzo[d]imidazole-6-carbonitrile (20G) (0.65 g, 1.95 mmol) in IPA (150 mL) was added K$_2$CO$_3$ (0.81 g, 5.85 mmol) and 2-chloropyrimidine-5-carbonitrile (0.32 g, 2.32 mmol), and the resulting mixture was stirred for 16 h at 100° C. The reaction was cooled to rt, water was added, and the mixture was extracted with EA (50 mL) and dried over anhydrous Na$_2$SO$_4$. After filtration and concentration, the crude product was purified by column chromatography with silica gel (DCM/MeOH=100:1) to give the 20H (0.55 g, yield 63%) as white solid. LCMS: 411.2 m/z [M+H]$^+$

N-((4-phenyl-1-(tetrahydro-2H-pyran-2-yl)-1H-benzo[d]imidazol-6-yl)methyl)-5-(1H-tetrazol-5-yl)pyrimidin-2-amine (20I)

To a solution of 2-(((4-phenyl-1-(tetrahydro-2H-pyran-2-yl)-1H-benzo[d]imidazol-6-yl)methyl)amino)pyrimidine-5-carbonitrile (20H) (0.2 g, 48.78 mmol) in DMF (10 mL) was added CuI (30 mg, 9.76 mmol) and sodium azide (64 mg, 97.56 mmol). The mixture was stirred for 2.5 hours under microwave radiation at 130° C. at which time, LCMS showed that the reaction was complete to give 20I. LCMS: 454.2 m/z [M+H]$^+$

5-(5-(difluoromethyl)-1,3,4-oxadiazol-2-yl)-N-((4-phenyl-1H-benzo[d]imidazol-6-yl)methyl)pyrimidin-2-amine (20)

(2,2-difluoroacetyl) 2,2-difluoroacetate (1.0 mL) was added to the crude solution of N-((4-phenyl-1-(tetrahydro-2H-pyran-2-yl)-1H-benzo[d]imidazol-6-yl)methyl)-5-(1H-tetrazol-5-yl)pyrimidin-2-amine (20I) from the previous experiment, and the resulting mixture was stirred at 65° C. for 30 min under microwave radiation at which time, LCMS showed that the starting material was consumed, and the desired product detected. The reaction mixture was diluted with sat. NaHCO$_3$ solution (30 mL) and extracted with EA (3×30 mL). The combined organic layers were washed with brine (2×30 mL), dried, and concentrated in vacuo. The crude product was purified by preparative HPLC to obtain (20) (182 mg, yield 88% two steps) as a white solid and as the corresponding TFA salt. LCMS: 420.2 m/z [M+H]$^+$ $^1$H NMR (400 MHz, DMSO) δ: 9.329 (s, 1H), 8.911-8.927 (d, J=6.4 Hz, 3H), 7.718-7.755 (t, J=14.8 Hz, 3H), 7.586-7.605 (d, J=7.6 Hz, 3H), 7.527-7.566 (d, J=15.6 Hz, 3H), 4.828-4.843 (d, J=6 Hz, 2H)$^{19}$F NMR (400 MHz, DMSO) δ: −74.12 ppm (s), −120.37 ppm (s)

Example 21. 2-(6-((5-(5-(difluoromethyl)-1,3,4-oxadiazol-2-yl)pyrimidin-2-yl)amino)-4-(pyridin-2-yl)-1H-benzo[d]imidazol-1-yl)ethan-1-ol

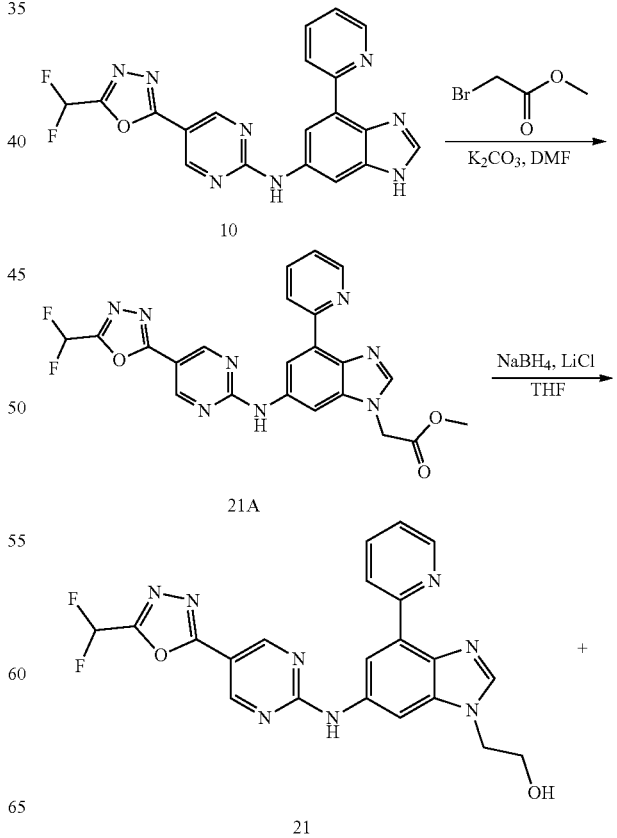

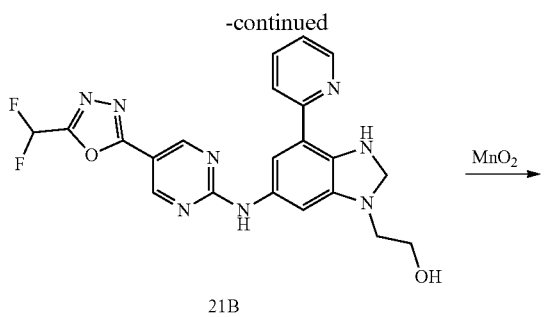

21B

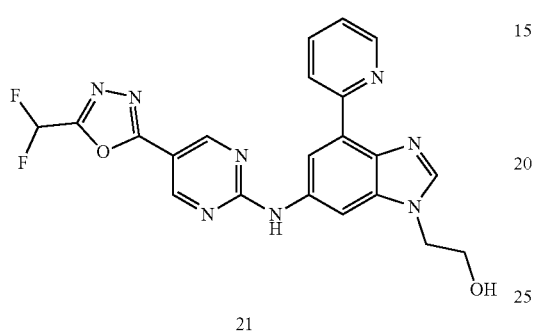

21 methyl 2-(6-((5-(5-(difluoromethyl)-1,3,4-oxadiazol-2-yl)pyrimidin-2-yl)amino)-4-(pyridin-2-yl)-1H-benzo[d]imidazol-1-yl)acetate (21A)

To a solution of N-(5-(5-(difluoromethyl)-1,3,4-oxadiazol-2-yl)pyrimidin-2-yl)-4-(pyridin-2-yl)-1H-benzo[d]imidazol-6-amine (10) (40 mg, 0.10 mmol) in DMF (5 mL) at rt was added methyl bromoacetate (18 mg, 0.12 mmol) and K$_2$CO$_3$ (28 mg, 0.22 mmol). The solution was stirred for 16 h and was then diluted with water. The precipitated solid was filtered, washed with water and hexane to give the crude product 21A (48 mg, yield 100%) which was used directly in the next step. LCMS: (ES+): m/z 479.1 [M+1]$^+$ 2-(6-((5-(5-(difluoromethyl)-1,3,4-oxadiazol-2-yl)pyrimidin-2-yl)amino)-4-(pyridin-2-yl)-1H-benzo[d]imidazol-1-yl)ethan-1-ol (21)

To a solution of methyl 2-(6-((5-(5-(difluoromethyl)-1,3,4-oxadiazol-2-yl)pyrimidin-2-yl)amino)-4-(pyridin-2-yl)-1H-benzo[d]imidazol-1-yl)acetate (21) (48 mg, 0.10 mmol) in THF was added lithium chloride (9.0 mg, 0.20 mmol) and NaBH$_4$ (8.0 mg, 0.20 mmol) at 0° C. The mixture was stirred at 0° C. for 3 h at which time HPLC showed the reaction was complete based on the formation of 21 and 21B in a 2:1 ratio. The mixture was concentrated and dried in vacuo, and the residue was dissolved in THF (3 mL) and DCM (3 mL) and treated with MnO$_2$ (200 mg). After stirring at rt for 16 h, the mixture was filtered, concentrated and the residue was purified by preparative HPLC to give the product 21 (7.3 mg, yield 16% for 2 steps) as a white solid. LCMS: (ES+): m/z 451.1 [M+1]$^+$ $^1$H NMR (400 MHz, CD$_3$OD): δ 9.07 (s, 2H), 8.68 (s, 1H), 8.35-8.39 (m, 2H), 8.23 (s, 1H), 7.92-7.99 (m, 2H), 7.43 (t, J=6.0 Hz, 1H), 7.22 (t, J=51.6 Hz, 1H), 4.43 (t, J=5.2 Hz, 2H), 3.97 (t, J=5.2 Hz, 2H).

Example 22. N-(5-(5-(difluoromethyl)-1,3,4-oxadiazol-2-yl)pyrimidin-2-yl)-4-(3,5-difluoropyridin-2-yl)-1H-benzo[d]imidazol-6-amine

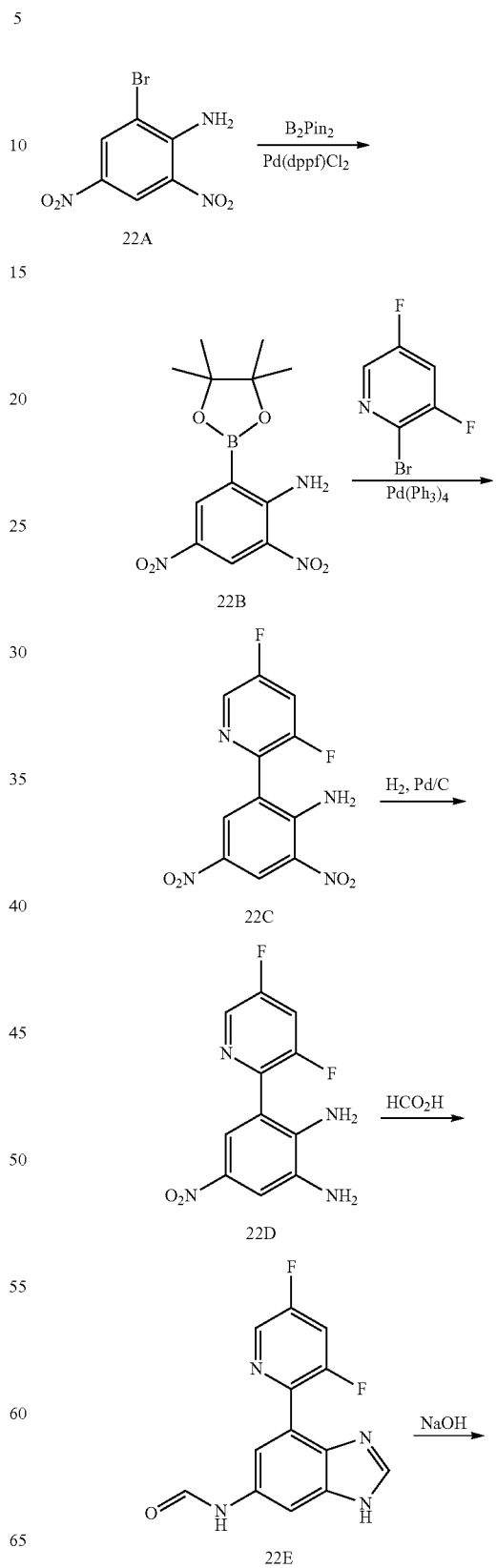

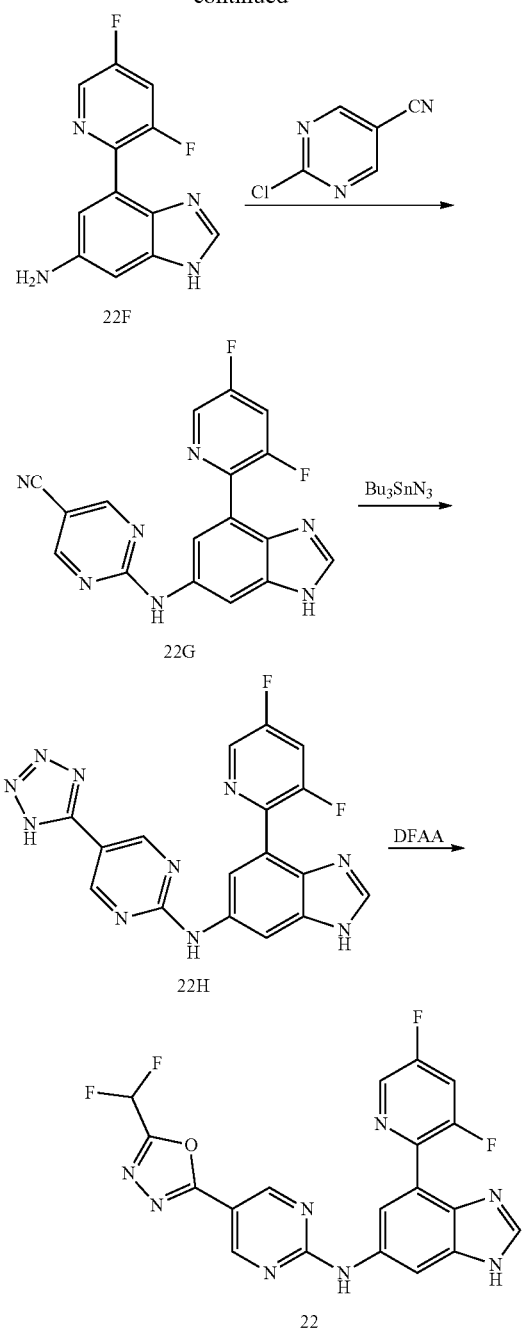

2,4-dinitro-6-(4,4,5,5-tetramethyl-1,3,2-dioxaborolan-2-yl)aniline (22B)

To a suspension of 2-bromo-4,6-dinitroaniline (1.0 g, 3.82 mmol) and KOAc (0.80 g, 8.16 mmol) in 1,4-dioxane (10 mL) was added bis(pinacolato)diboron (1.1 g, 4.20 mmol), and Pd(dppf)Cl$_2$ (0.30 g, 0.41 mmol). The mixture was stirred at 100° C. for 4 h at which time it was cooled to rt, poured into water and extracted with EA (50 mL). The organic phase was dried over anhydrous Na$_2$SO$_4$, filtered and concentrated. The corresponding residue was treated with Hexane/EA (20/1) which gave a precipitate that was filtered and dried to provide the crude product 22B (0.90 g, yield 76%) as brown solid.

2-(3,5-difluoropyridin-2-yl)-4,6-dinitroaniline (22C)

To a suspension of 2,4-dinitro-6-(4,4,5,5-tetramethyl-1,3,2-dioxaborolan-2-yl)aniline (22B) (0.50 g, 1.62 mmol), 2-bromo-3,5-difluoropyridine (470 mg, 2.43 mmol) and NaHCO$_3$ (0.42 g, 5.0 mmol) in 1,4-dioxane (1.0 mL) and water (1.0 mL) was added Pd(PPh$_3$)$_4$ (185 mg, 0.16 mmol). After stirring at 100° C. for 4 h, the mixture was cooled to rt, poured into water and extracted with EA (50 mL). The organic phase was dried over anhydrous Na$_2$SO$_4$, filtered, concentrated and purified by column chromatography (EA/PE=1/5 to 1/2) to give 22C (220 mg, yield 74%) as yellow solid. LCMS: (ES+) m/z 295.0 [M+H]$^+$ 6-(3,5-difluoropyridin-2-yl)benzene-1,2,4-triamine (22D)

A solution of 2-(3,5-difluoropyridin-2-yl)-4,6-dinitroaniline (22C) (120 mg, 0.41 mmol) in MeOH (15 mL) was added 10% Pd/C (24 mg). After stirring at 30° C. for 3 h under an atmosphere of H2, the mixture was filtered through Celite™, and the filtrate was concentrated in vacuo to give crude 22D (88 mg, yield 92%) which was used directly in the next step.

N-(4-(3,5-difluoropyridin-2-yl)-1H-benzo[d]imidazol-6-yl)formamide (22F)

A solution of 6-(3,5-difluoropyridin-2-yl)benzene-1,2,4-triamine (22D) (88 mg, 0.37 mmol) in formic acid (5.0 mL, 88%) was stirred at 100° C. for 1 h. The mixture was concentrated in vacuo to give crude 22E, which was dissolved in MeOH (2.0 mL) and added to 5.0 mL of 3N NaOH solution. The resulting mixture was stirred at 20° C. for 2 h. at which time, 1N HCl was added slowly to adjust pH to 8. The mixture was extracted with EA (50 mL), the organic phase was dried over anhydrous Na$_2$SO$_4$, filtered and concentrated in vacuo to give the crude product 22F (82 mg, yield 90%) as yellow solid which was used without further purification. LCMS: (ES+): m/z 247.1 [M+H]$^+$ 2-((4-(3,5-difluoropyridin-2-yl)-1H-benzo[d]imidazol-6-ylamino)pyrimidine-5-carbonitrile (22G)

A mixture of N-(4-(3,5-difluoropyridin-2-yl)-1H-benzo[d]imidazol-6-yl)formamide (22F) (82 mg, 0.33 mmol) and 2-chloropyrimidine-5-carbonitrile (42 mg, 0.30 mmol) in i-PrOH (5.0 mL) was stirred at 65° C. for 4 h. The mixture was cooled, concentrated and purified by column chromatography (EA/MeOH=25/1) to give 22G (56 mg, yield 53%). LCMS: (ES+): m/z 350.1 [M+H]$^+$ 2-bromo-4,6-dinitroaniline (22A)

To a suspension of 2-bromo-4,6-dinitroaniline (1.0 g, 3.82 mmol) and KOAc (0.80 g, 8.16 mmol) in 1,4-dioxane (10 mL) was added Pd(dppf)Cl$_2$ (0.30 g, 0.41 mmol). The mixture was stirred at 100° C. for 4 h and cooled to rt. The mixture was poured into water and the product was extracted with EA. The organic phase was dried over anhydrous Na$_2$SO$_4$, filtered and concentrated. The residue was treated with Hexane/EA (20/1) and the precipitate was filtered and dried to give the crude product 22A (0.90 g, yield 76%) as a brown solid.

N-(5-(5-(difluoromethyl)-1,3,4-oxadiazol-2-yl)pyrimidin-2-yl)-4-(3,5-difluoropyridin-2-yl)-1H-benzo[d]imidazol-6-amine (22)

A solution of 2-((4-(3,5-difluoropyridin-2-yl)-1H-benzo[d]imidazol-6-yl)amino)pyrimidine-5-carbonitrile (22G) (22 mg, 0.063 mmol) and azidotributylstannane (100 mg, 0.33 mmol) in toluene (3.0 mL) was stirred at 90° C. for 16 h. The mixture was cooled and concentrated in vacuo to give crude 22H, which was dissolved in DMF (3.0 mL) and treated with DFAA (122 mg, 0.80 mmol). The resulting mixture was warmed to 65° C. and stirred for 1 h. After cooling to rt, the mixture was poured into 1N NaHCO$_3$ solution (20 mL), and extracted with EA (20 mL), dried over anhydrous Na$_2$SO$_4$, filtered, concentrated and purified by preparative HPLC to give 22 (10 mg, yield 29%) as white solid and as the corresponding TFA salt. LCMS: (ES+): m/z 443.1 [M+H]$^+$ $^1$H NMR (400 MHz, CD$_3$OD): δ 9.35 (s, 1H), 9.17 (s, 2H), 8.82 (s, 1H), 8.68 (s, 1H), 8.46 (s, 1H), 7.91 (t, J=9.2 Hz, 1H), 7.26 (t, J=51.6 Hz, 1H).

Example 23. N-(5-(5-(difluoromethyl)-1,3,4-oxadiazol-2-yl)pyrimidin-2-yl)-4-(trifluoromethyl)-1H-benzo[d]imidazol-6-amine

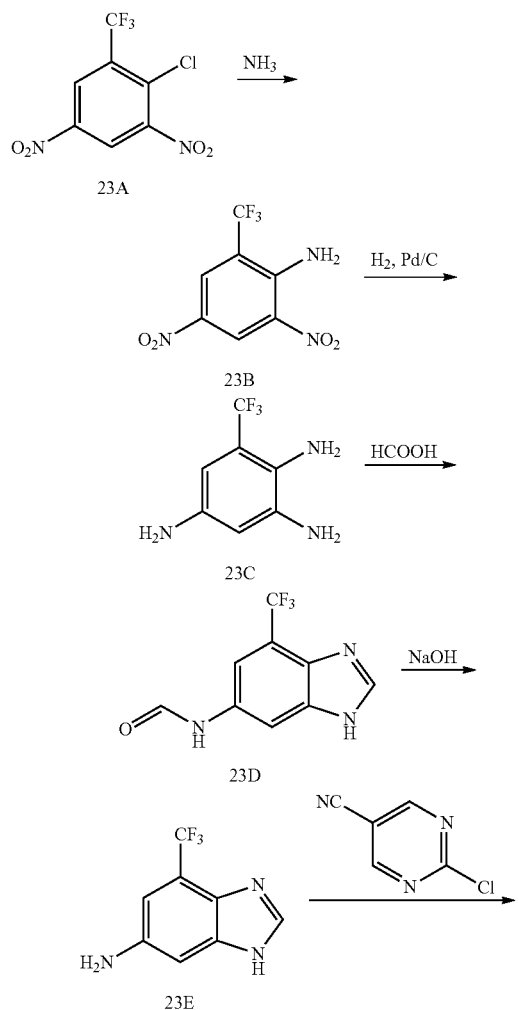

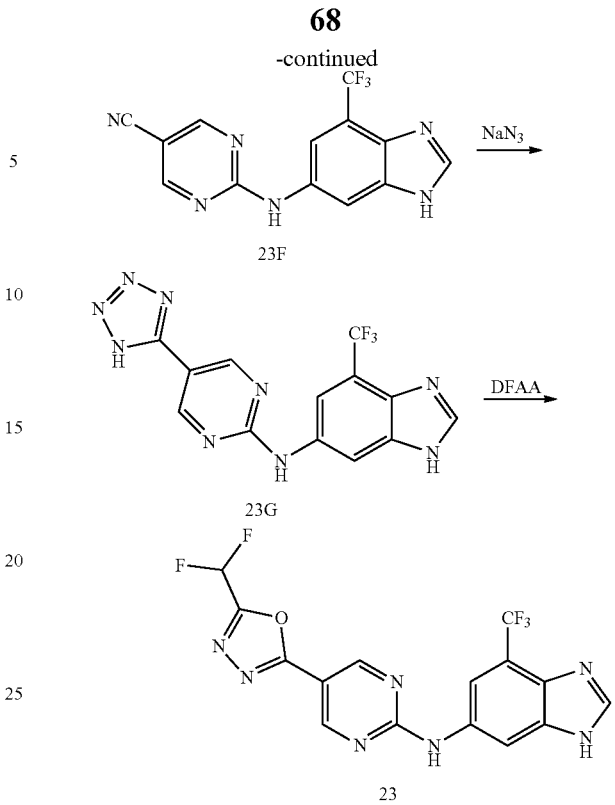

2,4-dinitro-6-(trifluoromethyl)aniline (23B)

To a solution of 2-chloro-1,5-dinitro-3-(trifluoromethyl)benzene (23A) (1.5 g, 5.6 mmol) in THF (5.0 mL) was added ammonium hydroxide sol. (33%, 10 mL). The resulting mixture was stirred at 25° C. for 16 h and was then concentrated. The residue was diluted with water (10 mL) and the resulting precipitate was filtered and washed with water (10 mL). The solid was then dried in vacuo to give 23B (1.3 g, yield 93%) as yellow solid which was used directly in the next step.

6-(trifluoromethyl)benzene-1,2,4-triamine (23C)

A solution of 2,4-dinitro-6-(trifluoromethyl)aniline (23B) (1.3 g, 5.18 mmol) in MeOH (15 mL) was added 10% Pd/C (0.25 g). The mixture was stirred under an atmosphere of hydrogen at 30° C. for 3 h, filtered through celite, and the filtrate was concentrated in vacuo to give 23C (0.97 g, yield 98%) which was used without purification. LCMS: (ES+): m/z 192.1, [M+1]$^+$

4-(trifluoromethyl)-1H-benzo[d]imidazol-6-amine (23E)

A solution of 6-(trifluoromethyl)benzene-1,2,4-triamine (23C) (0.80 g, 4.19 mmol) in formic acid (88%) was stirred at 100° C. for 1 h. The mixture was cooled and concentrated in vacuo to give crude 23D (1.1 g). LCMS: (ES+): m/z 230.1, [M+1]$^+$. The residue was diluted with MeOH (2.0 mL) and added to 10 mL of 3N NaOH sol. The mixture was stirred at 20° C. for 2 h, at which time, 1N HCl was added slowly to adjust the pH to 8. The mixture was extracted with EA and the organic phase was dried over anhydrous Na$_2$SO$_4$, filtered and concentrated in vacuo to give 23E (0.68 g, 97% yield for two steps) as yellow solid. LCMS: (ES+): m/z 202.1, [M+1]$^+$ 2-((4-(trifluoromethyl)-1H-benzo[d]imidazol-6-yl)amino)pyrimidine-5-carbonitrile (23F)

A mixture of 4-(trifluoromethyl)-1H-benzo[d]imidazol-6-amine (23E) (0.40 g, 2.0 mmol) and 2-chloropyrimidine-5-carbonitrile (292 mg, 2.1 mmol) in i-PrOH (5.0 mL) was stirred at 65° C. for 2 h. The mixture was cooled, concentrated and diluted with 1N NaHCO$_3$ sol. The precipitated solid was filtered, dried and recrystallized from EA to give 23F (350 mg, yield 58%). LCMS: (ES+): m/z 305.1, [M+1]$^+$.

N-(5-(5-(difluoromethyl)-1,3,4-oxadiazol-2-yl)pyrimidin-2-yl)-4-(trifluoromethyl)-1H-benzo[d]imidazol-6-amine (23)

To a solution of 2-((4-(trifluoromethyl)-1H-benzo[d]imidazol-6-yl)amino)pyrimidine-5-carbonitrile (23F) (150 mg, 0.5 mmol) and sodium azide (65 mg, 1.0 mmol) in DMF (5.0 mL) was added CuI (20 mg, 0.1 mmol). The mixture was stirred at 120° C. for 2 h at which time LCMS showed the reaction was complete to give crude 23G. The mixture was then cooled to 10° C., and DFAA (870 mg) was added. The mixture was heated to 90° C. and stirred for 1 h. The mixture was cooled to rt, poured into 1N NaHCO$_3$ sol. (20 mL), and was extracted with EA (20 mL). The organic phase was dried over anhydrous Na$_2$SO$_4$, filtered and concentrated. The residue was purified by silica gel column chromatography (EA/MeOH=25/1) to give 23 (130 mg, yield 66% for 2 steps) as a white solid. LCMS: (ES+): m/z 398.0, [M+1]$^+$ 1H NMR (400 MHz, DMSO-d6) δ 12.87 (br s, 1H), 10.66 (br s, 1H), 9.11 (s, 2H), 8.45 (s, 1H), 8.35 (s, 1H), 7.89 (s, 1H), 7.57 (t, J=51.6 Hz, 1H).

Example 24. 2-(5-((5-(5-(difluoromethyl)-1,3,4-oxadiazol-2-yl)pyrimidin-2-yl)amino)-7-phenyl-1H-benzo[d]imidazol-1-yl)ethan-1-ol

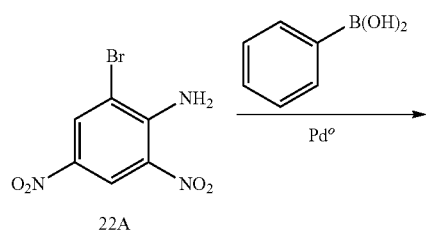

22A

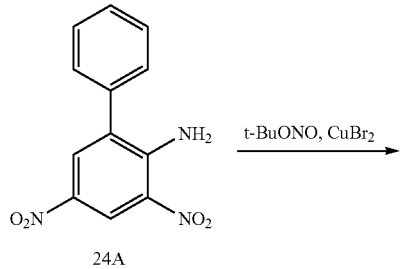

24A

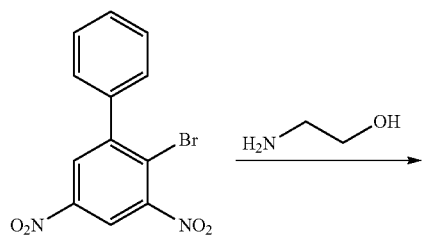

24B

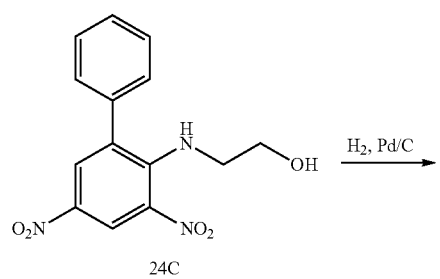

24C

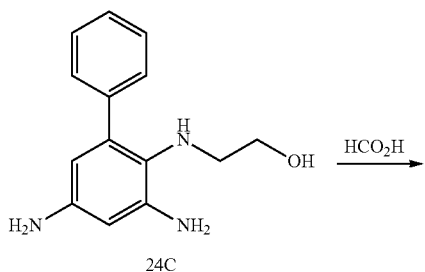

24C

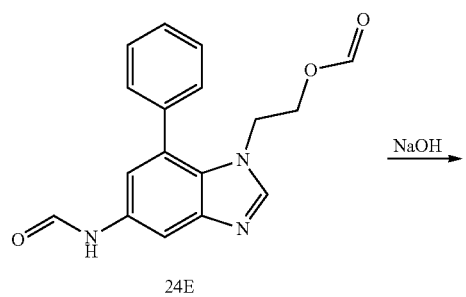

24E

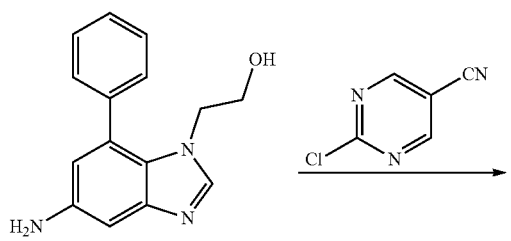

24F

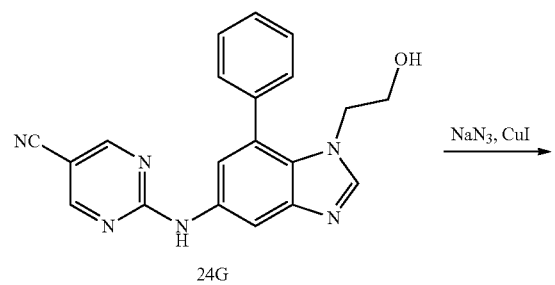

24G

-continued

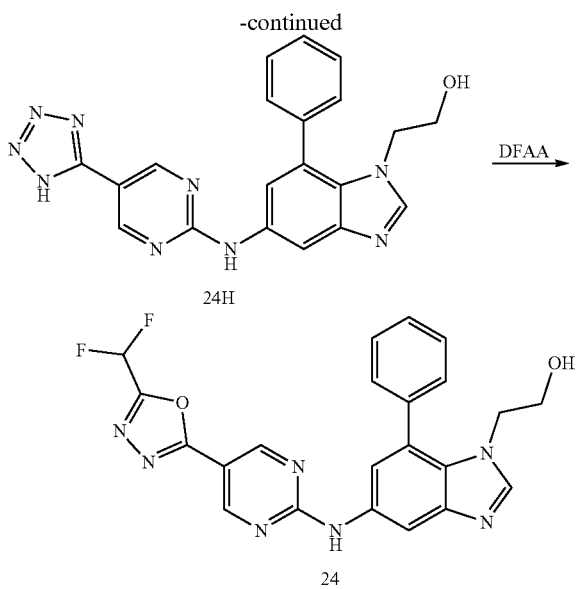

3,5-dinitro-[1,1'-biphenyl]-2-amine (24A)

A mixture of 2-bromo-4, 6-dinitroaniline (2.0 g, 7.6 mmol), phenylboronic acid (1.12 g, 9.2 mmol), Pd(PPh$_3$)$_4$ (460 mg, 0.40 mmol) and Na$_2$CO$_3$ (1.62 g, 15.3 mmol) in dioxane/water (24 mL/3 mL) was stirred for 2 h at 110° C. under N2 at which time, LCMS showed the reaction was complete. The reaction was poured into ice water (150 mL), the product was extracted with DCM (20 mL×3), and the combined organic layers were dried over anhydrous Na$_2$SO$_4$, filtered, concentrated and recrystallized with EA to give 24A (1.75 g, yield 88%). LCMS: (ES+): m/z 260.06 [M+H]$^+$ 2-bromo-3,5-dinitro-1,1'-biphenyl (24B)

To a solution of 3,5-dinitro-[1,1'-biphenyl]-2-amine (24A) (1.50 g, 5.79 mmol) in CH$_3$CN (15 mL) was added cupric bromide (1.94 g, 8.70 mmol) and tert-butyl nitrite (1.42 g, 13.7 mmol). The mixture was stirred at 70° C. for 2 h at which time, LCMS showed the reaction was complete. The reaction was quenched with 1N HCl and extracted with EA (20 mL×3). The combined organic layers were washed with water and brine, and dried over anhydrous Na$_2$SO$_4$. Filtration and solvent removal by rotary evaporation to give 24B (1.92 g, yield 103%), which was used directly in the next step without further purification.

2-((3,5-dinitro-[1,1'-biphenyl]-2-yl)amino)ethan-1-ol (24C)

To a solution of 2-bromo-3,5-dinitro-1,1'-biphenyl (24B) (1.92 g, 5.79 mmol) in CH$_3$CN (10 mL) was added ethanolamine (1.81 g, 29.7 mmol). The mixture was stirred at 50° C. for 2 h at which time, LCMS showed the reaction was complete. The reaction mixture was diluted with water and extracted with EA (20 mL×3), and the combined organic layers were washed with water, brine, and dried over anhydrous Na$_2$SO$_4$. Filtration and solvent removal by rotary evaporation to give 24C (1.95 g, yield 111%), which was used directly in next step without further purification. LCMS: (ES+): m/z 304.1 [M+H]$^+$.

2-((3,5-diamino-[1,1'-biphenyl]-2-yl)amino)ethan-1-ol (24D)

A mixture of 2-((3,5-dinitro-[1,1'-biphenyl]-2-yl)amino)ethan-1-ol (24C) (1.11 g, 3.65 mmol) and 10% Pd/C (230 mg) in methanol (50 mL) was stirred for 3 h at 25° C. under an atmosphere of H2. The mixture was filtered through a Celite™ pad, and the filtrate was concentrated to give 24D (913 mg, yield 98%), which was used in next step without further purification. LCMS: (ES+): m/z 244.1 [M+H]$^+$.

2-(5-amino-7-phenyl-1H-benzo[d]imidazol-1-yl)ethan-1-ol (24F)

A solution of 2-((3,5-diamino-[1,1'-biphenyl]-2-yl)amino)ethan-1-ol (24D) (904 mg 3.71 mmol) in 5.0 mL formic acid was stirred for 30 min at 90° C. at which time, LCMS showed the reaction was complete. The reaction mixture was concentrated directly to give crude 24E which was used in next step without further purification. 24E (750 mg 2.66 mmol) was dissolved in 3.0 mL MeOH and 45 mL 3N NaOH sol. The reaction mixture was stirred for 16 h at rt at which time, LCMS showed the reaction was complete. HBr was added slowly to adjust the pH to 8, and the mixture was extracted with EA (50 mL×3). The combined organic layers were washed with water, brine, and dried over anhydrous Na$_2$SO$_4$. Filtration and solvent evaporation gave 24F (600 mg, yield 89%), which was used in next step without further purification. LCMS: (ES+): m/z 254.1 [M+H]$^+$.

2-((1-(2-hydroxyeth)yl)-7-phenyl-1H-benzo[d]imidazol-5-yl)amino)pyrimidine-5-carbonitrile (24G)

To a solution of 2-(5-amino-7-phenyl-1H-benzo[d]imidazol-1-yl)ethan-1-ol (24F) (68 mg, 0.27 mmol) in i-PrOH (5.0 mL) was added 2-chloropyrimidine-5-carbonitrile (42 mg, 0.30 mmol). The mixture was stirred at 60° C. for 4 h at which time, LCMS showed the reaction was complete. The reaction mixture was concentrated, and the product recrystallized from EA to give 24G (61 mg, yield 63%). LCMS: (ES+): m/z 357.1 [M+H]$^+$ 2-(5-((5-(5-(difluoromethyl)-1,3,4-oxadiazol-2-yl)pyrimidin-2-yl)amino)-7-phenyl-1H-benzo[d]imidazol-1-yl)ethan-1-ol (24)

To a solution of 2-((1-(2-hydroxyethyl)-7-phenyl-1H-benzo[d]imidazol-5-yl)amino)pyrimidine-5-carbonitrile (24G) (35 mg, 0.10 mmol) and sodium azide (20 mg, 0.29 mmol) in DMF (3.0 mL) was added CuI (55 mg, 0.29 mmol). The mixture was stirred at 120° C. for 3 h at which time, LCMS showed the reaction was complete. The mixture was cooled to 10° C. and DFAA (0.50 g) was added. The mixture was then stirred at 90° C. for 1 hr, cooled to room temperature, poured into 1N NaHCO$_3$ sol. (20 mL) and extracted with EA (20 mL). The organic phase was dried over anhydrous Na$_2$SO$_4$, filtered and concentrated. The residue was recrystallized from 10:1 DCM:MeOH to give 24 (17 mg, yield 31%). LCMS: (ES+): m/z 450.1 [M+H]$^+$ $^1$H NMR (400 MHz, CD$_3$OD): δ 9.30 (s, 1H), 9.17 (s, 2H), 8.79 (s, 1H), 7.50-7.65 (m, 6H), 7.26 (s, J=51.6 Hz, 1H), 4.14 (t, J=5.2 Hz, 2H), 3.41 (t, J=5.2 Hz, 2H).

Example 25. 2-(6-((5-(5-(difluoromethyl)-1,3,4-oxadiazol-2-yl)pyrimidin-2-yl)amino)-4-phenyl-1H-benzo[d]imidazol-1-yl)-N,N-dimethylacetamide

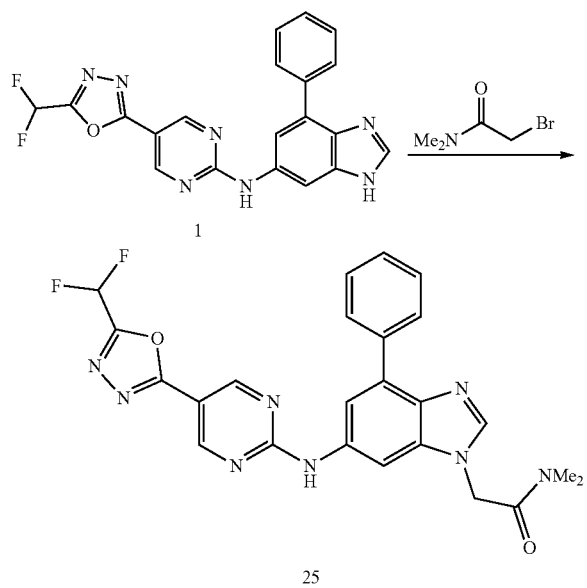

2-(6-((5-(5-(difluoromethyl)-1,3,4-oxadiazol-2-yl)pyrimidin-2-yl)amino)-4-phenyl-1H-benzo[d]imidazol-1-yl)-N,N-dimethylacetamide (25)

N-(5-(5-(difluoromethyl)-1,3,4-oxadiazol-2-yl)pyrimidin-2-yl)-4-phenyl-1H-benzo[d]imidazol-6-amine (1) (40 mg, 0.099 mmol) was dissolved in DMF (5.0 ml) and 2-bromo-N,N-dimethylacetamide (16.3 mg, 0.099 mmol) was added, followed by $K_2CO_3$ (13.7 mg, 0.099 mmol). The reaction mixture was stirred at rt for 5 h at which time, LCMS showed little SM remaining. The reaction was quenched with water and extracted with EA (100 mL×3). The combined organic layers were washed with water, brine, and dried over anhydrous $Na_2SO_4$. Filtration and concentration provided the crude product which was purified by silica gel column chromatography (PE/EA=2/1) to afford 25 (18.5 mg, yield 38%). LCMS: (ES+): m/z 491.1 [M+H]$^+$ $^1$H NMR (400 MHz, DMSO-d$_6$): δ 10.46 (br s, 1H), 9.06 (s, 2H), 8.17-8.06 (m, 3H), 7.93 (s, 1H), 7.72 (s, 1H), 7.71-7.44 (m, 3H), 7.39 (t, J=7.2 Hz, 1H), 5.28 (s, 2H), 3.17 (s, 3H), 2.90 (s, 3H).

Example 26. N-(cyclopropylmethyl)-6-((5-(5-(difluoromethyl)-1,3,4-oxadiazol-2-yl)pyrimidin-2-yl)amino)-1-(2-hydroxyethyl)-1H-benzo[d]imidazole-4-sulfonamide

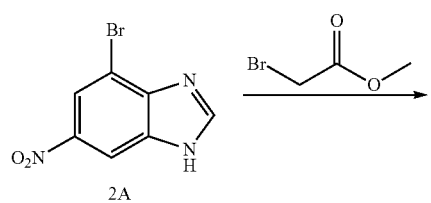

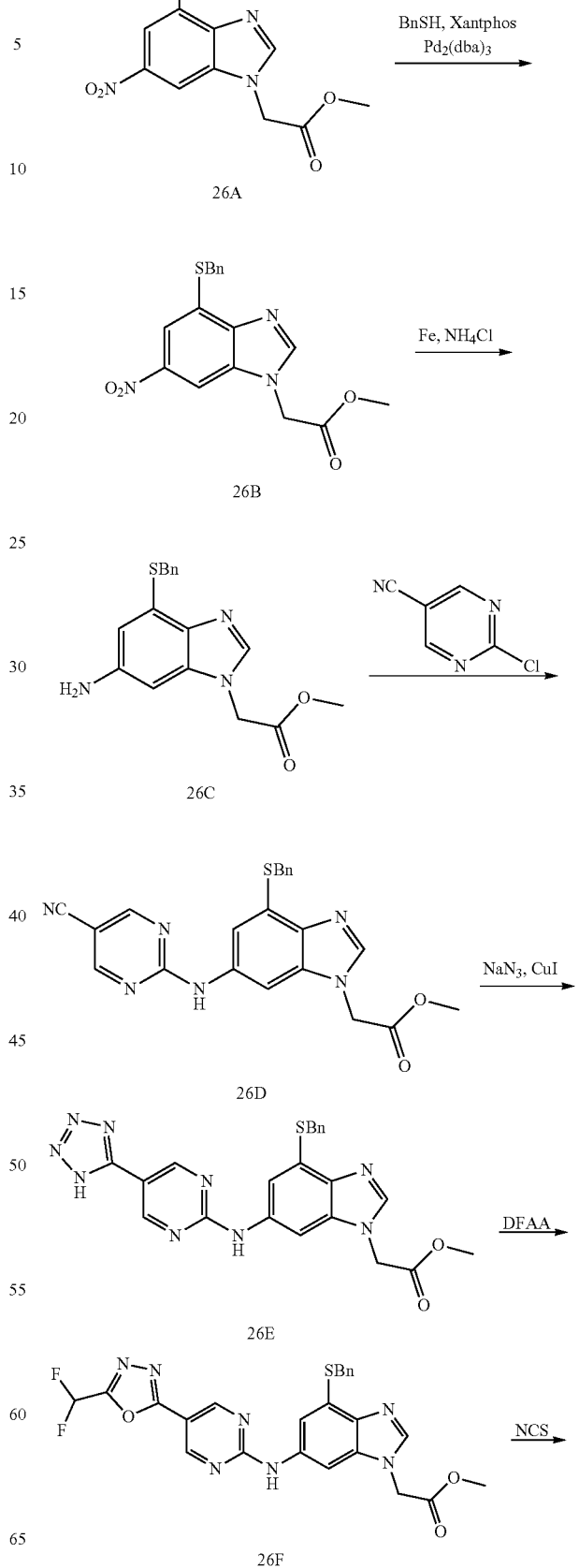

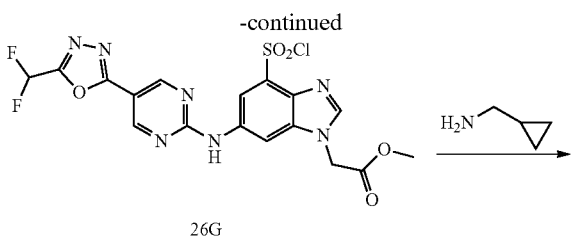

26G

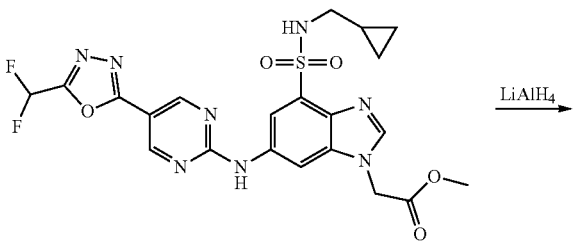

26H

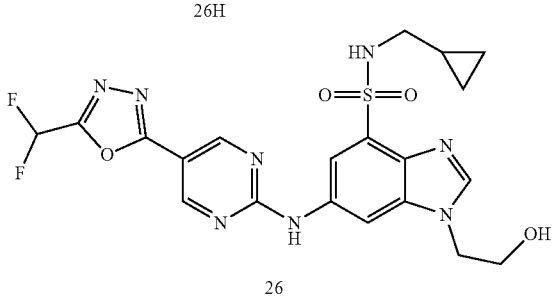

26 methyl 2-(4-bromo-6-nitro-1H-benzo[d]imidazol-1-yl)acetate (26A)

To a mixture of 2-bromo-4,6-dinitroaniline (2A) (1.5 g, 6.2 mmol) and K$_2$CO$_3$ (1.71 g, 12.4 mmol) in DMF at 25° C. (30 mL) was added methyl bromoacetate (1.42 g, 9.3 mmol) and the resulting mixture was stirred for 16 h. EA (100 mL) was added, and the mixture was washed with water (100 mL×2), and brine (80 mL×2). The organic phase was dried with anhydrous MgSO$_4$. Filtration and concentration provided the crude product which was purified by column chromatography (EA/PE=1:2) to afford 26A (1.5 g, yield 77%) as a yellow solid. LC-MS: (ES$^+$): m/z 314.0 [M+H]$^+$.

methyl 2-(4-(benzylthio)-6-nitro-1H-benzo[d]imidazol-1-yl)acetate (26B)

A mixture of methyl 2-(4-bromo-6-nitro-1H-benzo[d]imidazol-1-yl)acetate (26A) (1.2 g, 3.82 mmol), BnSH (0.71 g, 5.73 mmol), Xantphos (0.44 g, 0.76 mmol), Pd$_2$(dba)$_3$ (0.35 g, 0.38 mmol) and DIPEA (0.99 g, 7.64 mmol) in 1,4-dioxane (30 mL) was stirred for 16 h at 100° C. under N2. The mixture was cooled and concentrated, and the residue was purified by column chromatography (EA/PE=1:2) to afford 26B (0.98 g, yield 72%) as a yellow solid. LC-MS: (ES$^+$): m/z 358.1 [M+H]$^+$.

methyl 2-(6-amino-4-(benzylthio)-1H-benzo[d]imidazol-1-yl)acetate (26C)

A mixture of methyl 2-(4-(benzylthio)-6-nitro-1H-benzo[d]imidazol-1-yl)acetate (26B) (1.0 g, 2.80 mmol), iron powder (0.78 g, 14.0 mmol) and NH$_4$Cl (1.5 g, 28.0 mmol) in MeOH (40 mL) and water (4.0 mL) was stirred for 3 h at 68° C. under N2. The mixture was cooled, filtered through a Celite™ pad, and concentrated. The residue was taken up in EA (60 mL) and washed with water (60 mL×2), brine (60 mL×1), and was dried over anhydrous MgSO$_4$. Filtration and concentration provided crude 26C (0.76 g, 83% yield) as a white solid.

methyl 2-(4-(benzylthio)-6-((5-cyanopyrimidin-2-yl)amino)-1H-benzo[d]imidazol-1-yl)acetate (26D)

A mixture of methyl 2-(6-amino-4-(benzylthio)-1H-benzo[d]imidazol-1-yl)acetate (26C) (0.70 g, 2.14 mmol) and 2-chloropyrimidine-5-carbonitrile (0.27 g, 1.93 mmol) in IPA (10 mL) was stirred for 3 h at 70° C. under N2. The mixture was cooled, filtered, and the filter cake was dried to give 26D (0.65 g, yield 71%) as grey solid. LC-MS: (ES$^+$): m/z 431.1 [M+H]$^+$.

methyl 2-(6-((5-(1H-tetrazol-5-yl)pyrimidin-2-yl)amino)-4-(benzylthio)-1H-benzo[d]imidazol-1-yl)acetate (26E)

A mixture of methyl 2-(4-(benzylthio)-6-((5-cyanopyrimidin-2-yl)amino)-1H-benzo[d]imidazol-1-yl)acetate (26D) (200 mg, 0.46 mmol), sodium azide (59.8 mg, 0.92 mmol) and CuI (17.5 mg, 0.09 mmol) in DMF (10 mL) was stirred for 3 h at 120° C. under N2 to give crude 26E which was used directly in the next step.

methyl 2-(4-(benzylthio)-6-((5-(5-(difluoromethyl)-1,3,4-oxadiazol-2-yl)pyrimidin-2-yl)amino)-1H-benzo[d]imidazol-1-yl)acetate (26F)

To the crude solution of 26E in DMF from the previous experiment was added DFAA (800 mg, 4.6 mmol) under N2 and the mixture was stirred for 1 h at 90° C. The reaction mixture was cooled to rt, poured into saturated NaHCO$_3$ solution (30 mL) and stirred for 30 min at 25° C. EA (50 mL) was added and the organics were washed with water (50 mL, containing 1 mL of ammonium hydroxide sol.) and brine (100 mL). The organic phase was dried with anhydrous MgSO$_4$, filtered and concentrated. The residue was recrystallized from EA containing a small amount of PE to give 26F (165 mg, yield 68%) as a yellow solid. LC-MS: (ES$^+$): m/z 524.0 [M+H]$^+$.

methyl 2-(4-(chlorosulfonyl)-6-((5-(5-(difluoromethyl)-1,3,4-oxadiazol-2-yl)pyrimidin-2-yl)amino)-1H-benzo[d]imidazol-1-yl)acetate (26G)

A mixture of methyl 2-(4-(benzylthio)-6-((5-(5-(difluoromethyl)-1,3,4-oxadiazol-2-yl)pyrimidin-2-yl)amino)-1H-benzo[d]imidazol-1-yl)acetate (26F) (80 mg, 0.15 mmol) in AcOH (5.0 mL) and H$_2$O (0.50 mL) was cooled to 5° C. and NCS (60 mg, 0.45 mmol) was added under N2. The mixture was stirred at 20° C. for 3 h, and was concentrated in vacuo to give crude 26G, which was used directly in the next step.

methyl 2-(4-(N-(cyclopropylmethyl)sulfamoyl)-6-((5-(5-(difluoromethyl)-1,3,4-oxadiazol-2-yl)pyrimidin-2-yl)amino)-1H-benzo[d]imidazol-1-yl)acetate (26H)

To a stirred solution of cyclopropylmethanamine (35.6 mg, 0.50 mmol) in pyridine (2 mL) was added a solution of methyl 2-(4-(chlorosulfonyl)-6-((5-(5-(difluoromethyl)-1,3,4-oxadiazol-2-yl)pyrimidin-2-yl)amino)-1H-benzo[d]imidazol-1-yl)acetate (26G) (0.15 mmol) in DCM. The reaction mixture was stirred at 20° C. for 1 h at which time, the solvents were removed under reduced pressure. The residue was purified by column chromatography (70% EA/PE) to give 26H (52 mg, 65% yield for two steps) as a yellow solid. LC-MS: (ES+): m/z 535.1 [M+H]+.

N-(cyclopropylmethyl)-6-((5-(5-(difluoromethyl)-1,3,4-oxadiazol-2-yl)pyrimidin-2-yl)amino)-1-(2-hydroxyethyl)-1H-benzo[d]imidazole-4-sulfonamide (26)

To a stirred solution of methyl 2-(4-(N-(cyclopropylmethyl)sulfamoyl)-6-((5-(5-(difluoromethyl)-1,3,4-oxadiazol-2-yl)pyrimidin-2-yl)amino)-1H-benzo[d]imidazol-1-yl)acetate (26H) (52 mg, 0.097 mmol) in THF (2.0 mL) at 0° C. was added LiAlH$_4$ (3.68 mg, 0.097 mmol) under N2. The reaction mixture was stirred at 0° C. for 1 h and was quenched by the addition of EA (5 mL) at 0° C. Additional EA (50 mL) was added, and the organics were washed with water. (50 mL) and brine (50 mL). The organics were dried (MgSO$_4$), filtered and concentrated to provide the crude product which was purified by preparative HPLC followed by preparative TLC to give 26 (9.2 mg, yield 19%) as a white solid. LCMS: (ES+): m/z 507.2 [M+H]+ $^1$H NMR (400 MHz, CD$_3$OD): δ 9.10 (m, 2H), 8.55 (s, 1H), 8.31 (s, 1H), 8.05 (s, 1H), 7.22 (t, J=51.6 Hz, 1H), 4.40-4.48 (m, 2H), 3.91-4.00 (m, 2H), 2.78 (d, J=6.8 Hz, 2H), 0.75-0.82 (m, 1H), 0.30-0.40 (m, 2H), 0.02-0.07 (m, 2H).

Example 27. 2-(6-((5-(5-(difluoromethyl)-1,3,4-oxadiazol-2-yl)pyrimidin-2-ylamino)-4-(thiazol-4-yl)-1H-benzo[d]imidazol-1-yl)ethan-1-ol

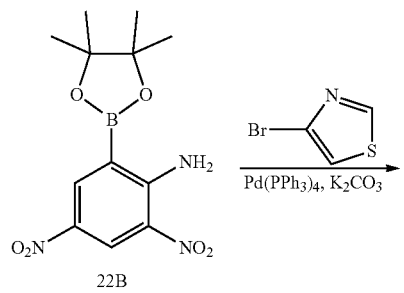

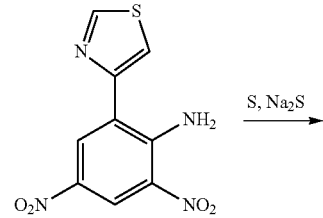

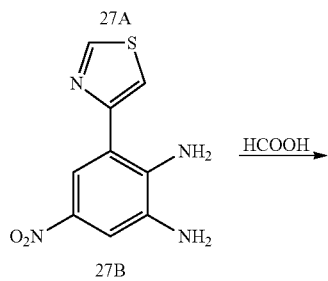

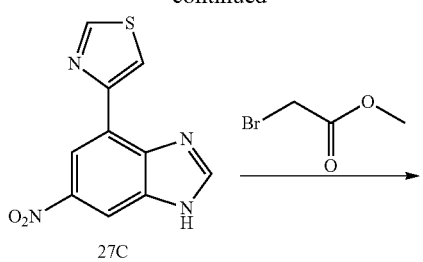

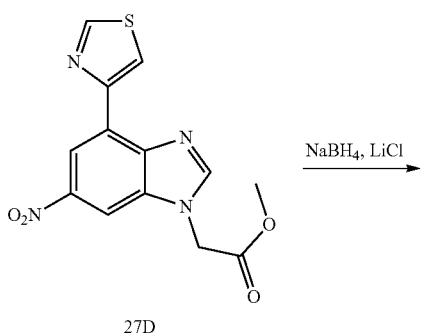

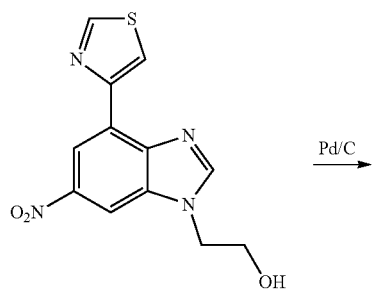

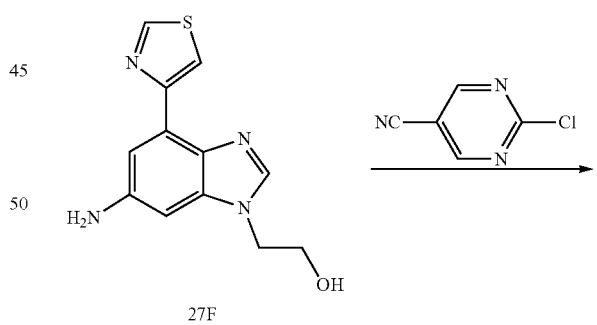

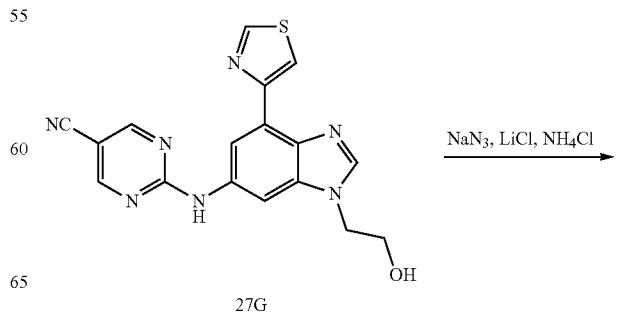

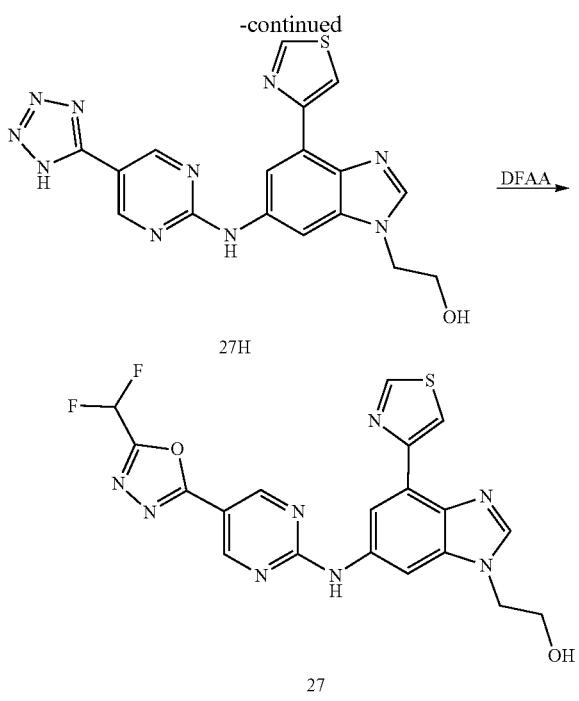

2,4-dinitro-6-(thiazol-4-yl)aniline (27A)

A suspension of 2,4-dinitro-6-(4,4,5,5-tetramethyl-1,3,2-dioxaborolan-2-yl)aniline (22B) (1.0 g, 3.24 mmol), 4-bromothiazole (820 mg, 5.0 mmol), $K_2CO_3$ (0.90 g, 6.5 mmol) and $Pd(PPh_3)_4$ (370 mg, 0.32 mmol) in 1,4-dioxane (10 mL) and water (2 mL) was stirred at 100° C. for 6 h at which time it was cooled and poured into water (50 mL). The mixture was extracted with EA and the organic phase was dried over anhydrous $Na_2SO_4$, filtered and concentrated. The residue was purified by column chromatography (EA/PE=1/4 to 1/2) to give 27A (662 mg, yield 77%) as yellow solid.

5-nitro-3-(thiazol-4-yl)benzene-1,2-diamine (27B)

A mixture of sodium sulfide (150 mg, 1.9 mmol) and sulfur (61 mg, 1.9 mmol) in $H_2O$ (4.0 mL) and EtOH (2.0 mL) was heated at reflux under N2 for 1 h. The solution was cooled and then added to a stirred suspension of 2,4-dinitro-6-(thiazol-4-yl)aniline (27A) (500 mg, 1.88 mmol) and $NH_4Cl$ (0.10 g, 1.9 mmol) in $H_2O$ (2.0 mL) and EtOH (3.0 mL). The mixture was stirred at 65° C. for 30 min, at which time 2N NaOH solution (2.0 mL) was added dropwise and the mixture was stirred for an additional 15 minutes at 65° C. After cooling, the mixture was poured into water (20 mL) and 2N HCl (2.0 mL) was added. The resulting mixture was extracted with EA and the combined organic layers were dried over $Na_2SO_4$, filtered and evaporated to give the crude product 5-nitro-3-(thiazol-4-yl)benzene-1,2-diamine (27B) (341 mg, yield 7⁶%) as a rust-colored solid which was used in the next step without further purification.

4-(6-nitro-1H-benzo[d]imidazol-4-yl)thiazole (27C)

A solution of 5-nitro-3-(thiazol-4-yl)benzene-1,2-diamine (27B) (341 mg, 1.44 mmol) in formic acid (5.0 mL, 88%) was stirred at 100° C. for 1 h. The mixture was cooled, concentrated in vacuo, diluted with MeOH (2.0 mL) and added to a 10 mL solution of sat. aq. $Na_2CO_3$. The mixture was stirred at 20° C. for 2 h, 1N HCl was added slowly to adjust the pH to 8, and the mixture was extracted with EA. The organic phase was dried over anhydrous $Na_2SO_4$, filtered and concentrated in vacuo. The residue was recrystallized from DCM/hexane to give 27C (191 mg, yield 54%) as a yellow solid.

methyl 2-(6-nitro-4-(thiazol-4-yl)-1H-benzo[d]imidazol-1-yl)acetate (27D)

To a solution of 4-(6-nitro-1H-benzo[d]imidazol-4-yl)thiazole (27C) (180 mg, 0.73 mmol) in DMF (5.0 mL) was added $K_2CO_3$ (152 mg, 1.1 mmol) and methyl 2-bromoacetate (135 mg, 0.88 mmol). The mixture was stirred at 20° C. for 16 h at which time water (20 mL) was added. The resulting solid was filtered, washed with water and hexane to give crude 27D (210 mg, yield 66%) which was used directly in the next step. LCMS: (ES+): m/z 319.0 $[M+H]^+$.

2-(6-nitro-4-(thiazol-4-yl)-1H-benzo[d]imidazol-1-yl)ethan-1-ol (27E)

To a solution of methyl 2-(6-nitro-4-(thiazol-4-yl)-1H-benzo[d]imidazol-1-yl)acetate (27D) (180 mg, 0.57 mmol) in THF (5.0 mL) and water(1.0 mL) was added LiCl (48 mg, 1.14 mmol) and $NaBH_4$ (43 mg, 1.14 mmol) at 0° C., and the resulting mixture was stirred at 0° C. for 3 h. The mixture was diluted with water (20 mL), extracted with EA and the organic phase was dried over $Na_2SO_4$, filtered and concentrated in vacuo to give the crude product 27E (216 mg, yield 74%) which was used directly in the next step. LCMS: (ES+): m/z 291.1 $[M+H]^+$.

2-(6-amino-4-(thiazol-4-yl)-1H-benzo[d]imidazol-1-yl)ethan-1-ol (27F)

To a solution of crude 2-(6-nitro-4-(thiazol-4-yl)-1H-benzo[d]imidazol-1-yl)ethan-1-ol (27E) (216 mg, 0.74 mmol) in THF (3.0 mL) and MeOH (3.0 mL) was added 10% Pd/C (40 mg). The mixture was stirred at 20° C. for 3 h under an atmosphere of $H_2$. The mixture was filtered through Celite™, and the Celite™ pad washed with THF/MeOH (3/1). The filtrate was concentrated in vacuo to give the crude product 27F (140 mg, yield 73%) which was used in the next step without further purification.

2-((1-(2-hydroxyethyl)-4-(thiazol-4-yl)-1H-benzo[d]imidazol-6-yl)amino)pyrimidine-5-carbonitrile (27G)

A mixture of 2-(6-amino-4-(thiazol-4-yl)-1H-benzo[d]imidazol-1-yl)ethan-1-ol (27F) (80 mg, 0.31 mmol) and 2-chloropyrimidine-5-carbonitrile (48 mg, 0.34 mmol) in i-PrOH (5.0 mL) was stirred at 65° C. for 4 h. The precipitated solid was filtered, washed with methanol and dried in vacuo to give the 27G (82 mg, yield 73%) as a yellow solid which was used without further purification. LCMS: (ES+): m/z 364.1 $[M+H]^+$.

2-(6-((5-(5-(difluoromethyl)-1,3,4-oxadiazol-2-yl)pyrimidin-2-yl)amino)-4-(thiazol-4-yl)-1H-benzo[d]imidazol-1-yl)ethan-1-ol (27)

To a solution of 2-((1-(2-hydroxyethyl)-4-(thiazol-4-yl)-1H-benzo[d]imidazol-6-yl)amino)pyrimidine-5-carbonitrile (27G) (50 mg, 0.14 mmol) and sodium azide (65 mg, 1.0 mmol) in DMF (3.0 mL) was added NH₄Cl (38 mg, 0.70 mmol) and LiCl (30 mg, 0.70 mmol). The mixture was stirred at 120° C. for 24 h at which time, LCMS showed the reaction was complete to give crude 27H. The mixture was then cooled to 10° C., and DFAA (600 mg, 3.5 mmol) was added. The mixture was heated at 90° C. with stirring for 2 h, cooled to rt and poured into a solution of 1N Na₂CO₃ (20 mL). The mixture was stirred at rt for 2 h and extracted with EA (20 mL×2). The combined organic layers were dried over anhydrous Na₂SO₄, filtered and concentrated. The residue was purified by preparative HPLC to give 27 (26 mg, yield 41%) as a light-yellow solid. LCMS: (ES+): m/z 457.1 [M+H]⁺ ¹H NMR (400 MHz, DMSO-d₆): δ 10.50 (s, 1H), 9.23 (s, 1H), 9.07 (s, 2H), 8.99 (s, 1H), 8.33 (s, 1H), 8.28 (s, 1H), 8.14 (s, 1H), 7.56 (t, J=50.8 Hz, 1H), 5.02 (s, 1H), 4.30-4.34 (m, 2H), 3.80-3.85 (m, 2H).

Example 28. 6-((5-(5-(difluoromethyl)-1,3,4-oxadiazol-2-yl)pyrimidin-2-yl)amino)-N-methyl-4-phenyl-1H-benzo[d]imidazole-1-carboxamide

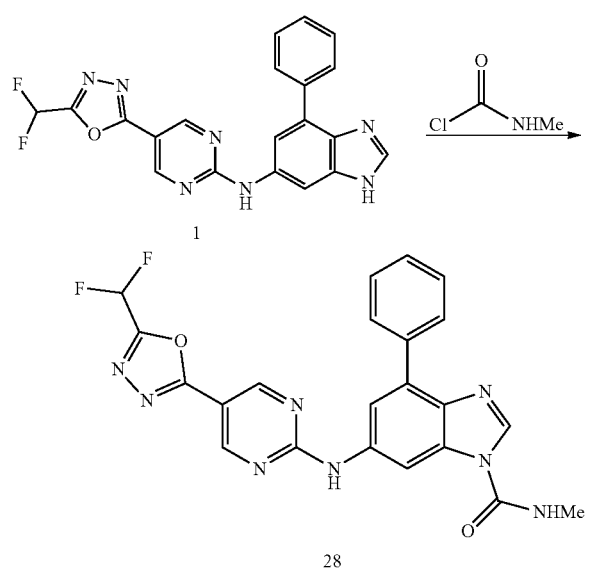

6-((5-(5-(difluoromethyl)-1,3,4-oxadiazol-2-yl)pyrimidin-2-yl amino)-N-methyl-4-phenyl-1H-benzo[d]imidazole-1-carboxamide (28)

To a mixture of N-(5-(5-(difluoromethyl)-1,3,4-oxadiazol-2-yl)pyrimidin-2-yl)-4-phenyl-1H-benzo[d]imidazol-6-amine (1) (50 mg, 0.123 mmol) and TEA (40 mg, 0.369 mmol) in DCM (3.0 mL) was added a solution of methylcarbamoyl chloride (11.5 mg, 0.123 mmol) in DCM (1.0 mL) at 20° C. slowly. The reaction mixture was stirred at 20° C. for 3 h, at which time, LCMS showed little SM remaining. The mixture was quenched with ice water and extracted with EA (10 mL×3). The combined organic layers were washed with water, brine, and dried over anhydrous Na₂SO₄. Filtration and evaporation provided a residue which was purified by silica gel chromatography (EA) to obtain 28 (35 mg, yield 61%) as a yellow solid. LCMS: (ES+): m/z 463.1 [M+H]⁺ ¹H NMR (400 MHz, CD₃OD): δ 9.08 (s, 1H), 8.73 (s, 1H), 8.64 (s, 1H), 7.84 (d, J=7.6 Hz, 2H), 7.76 (s, 1H), 7.51 (t, J=7.6 Hz, 2H), 7.42 (t, J=7.2 Hz, 1H), 7.22 (t, J=51.6 Hz, 1H), 3.03 (s, 3H).

Example 29. 2-(6-((5-(5-(difluoromethyl)-1,3,4-oxadiazol-2-yl)pyrimidin-2-yl)amino)-4-phenyl-1H-benzo[d]imidazol-1-yl)propan-1-ol

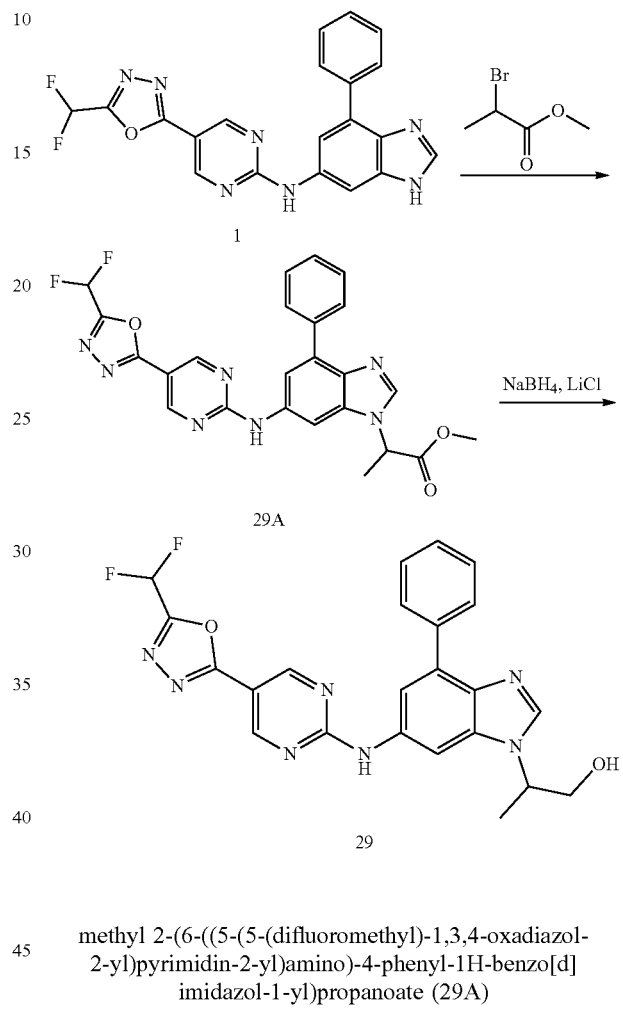

methyl 2-(6-((5-(5-(difluoromethyl)-1,3,4-oxadiazol-2-yl)pyrimidin-2-yl)amino)-4-phenyl-1H-benzo[d]imidazol-1-yl)propanoate (29A)

A suspension of N-(5-(5-(difluoromethyl)-1,3,4-oxadiazol-2-yl)pyrimidin-2-yl)-4-phenyl-1H-benzo[d]imidazol-6-amine (1) (100 mg, 0.25 mmol), methyl 2-bromopropanoate (82 mg, 0.49 mmol) and K₂CO₃ (104 mg, 0.75 mmol) in DMF (5.0 ml) was stirred at rt for 5 h at which time, LCMS showed little SM remained. The reaction was quenched with water and extracted with EA (10 mL×3). The combined organic layers were washed with water, brine, and dried over anhydrous Na₂SO₄. Filtration and evaporation provided a residue which was purified by silica gel column chromatography (PE/EA=2/1) to afford 29A (81 mg, yield 66%). LCMS: (ES+): m/z 492.1 [M+H]⁺.

To a solution of methyl 2-(6-((5-(5-(difluoromethyl)-1,3,4-oxadiazol-2-yl)pyrimidin-2-yl)amino)-4-phenyl-1H-benzo[d]imidazol-1-yl)propanoate (29A) (100 mg, 0.203 mmol) in THF (12 mL) and H₂O (3.0 mL) under N2 was added NaBH₄ (11.6 mg, 0.0.305 mmol) and LiCl (12.8 mg, 0.638 mmol) at 0° C. The reaction was stirred at 20° C. for 3 h and the solvent was evaporated. The residue was diluted with 50 ml of EA, and the organics were washed with brine, dried over anhydrous Na$_2$SO$_4$, filtered and concentrated. The residue was purified by preparative HPLC to give 29 (16.7 mg, yield 16%) which was isolated as a mixture of the free base and corresponding TFA salt. LCMS: (ES+): m/z 464.1 [M+H]$^+$ $^1$H NMR (400 MHz, CD$_3$OD): δ 9.37 (s, 1H), 9.16 (s, 2H), 8.70 (s, 1H), 7.82 (s, 1H), 7.71 (d, J=7.5 Hz, 2H), 7.61 (t, J=7.4 Hz, 2H), 7.57-7.51 (m, 1H), 7.23 (t, J=51.6 Hz, 1H), 5.01 (d, J=6.4 Hz, 1H), 4.01 (d, J=5.2 Hz, 2H), 1.77 (d, J=6.8 Hz, 3H).

Example 30. 2-(6-((5-(5-(difluoromethyl)-1,3,4-oxadiazol-2-yl)pyrimidin-2-yl)amino)-2-methyl-4-phenyl-1H-benzo[d]imidazol-1-yl)ethan-1-ol

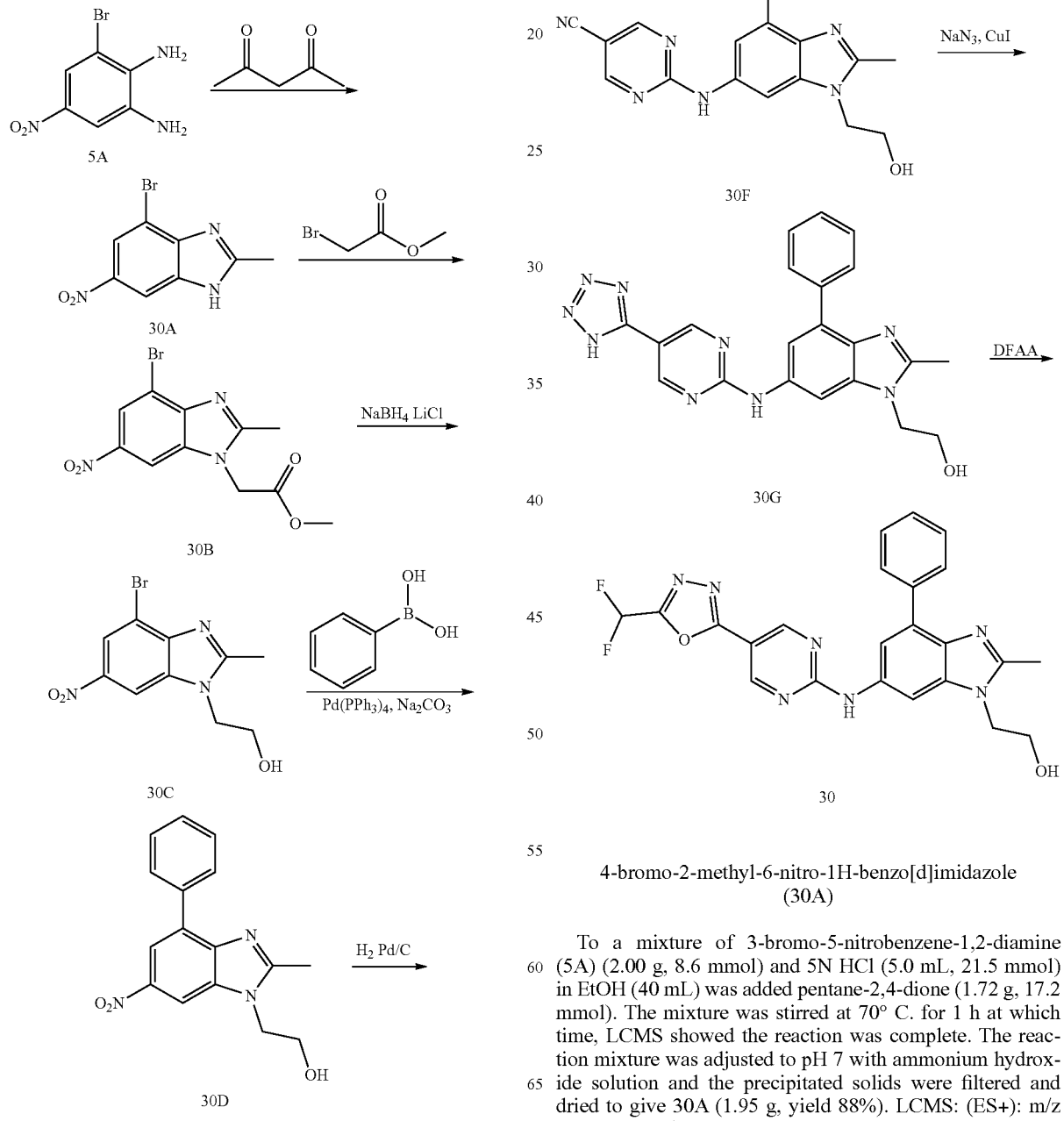

4-bromo-2-methyl-6-nitro-1H-benzo[d]imidazole (30A)

To a mixture of 3-bromo-5-nitrobenzene-1,2-diamine (5A) (2.00 g, 8.6 mmol) and 5N HCl (5.0 mL, 21.5 mmol) in EtOH (40 mL) was added pentane-2,4-dione (1.72 g, 17.2 mmol). The mixture was stirred at 70° C. for 1 h at which time, LCMS showed the reaction was complete. The reaction mixture was adjusted to pH 7 with ammonium hydroxide solution and the precipitated solids were filtered and dried to give 30A (1.95 g, yield 88%). LCMS: (ES+): m/z 256.0 [M+H]$^+$.

methyl 2-(4-bromo-2-methyl-6-nitro-1H-benzo[d]imidazol-1-yl)acetate (30B)

To a mixture of 4-bromo-2-methyl-6-nitro-1H-benzo[d]imidazole (30A) (1.01 g, 4.0 mmol) and $K_2CO_3$ (1.08 g, 7.8 mmol) in DMF (10 mL) was added methyl 2-bromoacetate (0.90 g, 5.9 mmol). The mixture was stirred at rt for 2 h at which time, LCMS showed the reaction was complete. The reaction mixture was concentrated and recrystallized from (PE:EA=1:2) to give 30B (1.07 g, yield 82%). LCMS: (ES+): m/z 328.0 [M+H]$^+$.

2-(4-bromo-2-methyl-6-nitro-1H-benzo[d]imidazol-1-yl)ethan-1-ol (30C)

To a solution of methyl 2-(4-bromo-2-methyl-6-nitro-1H-benzo[d]imidazol-1-yl)acetate (30B) (36 mg, 0.10 mmol) in THF (2.5 mL) and $H_2O$ (0.50 mL) was added $NaBH_4$ (7.0 mg, 0.17 mmol) and LiCl (8.0 mg, 0.17 mmol). The mixture was stirred at rt for 1 h and was then poured into water (10 mL). The mixture was extracted with EA (20 mL) and the organic phase was dried over anhydrous $Na_2SO_4$, filtered and concentrated. The residue was recrystallized (PE:EA=1:1) to give 30C (21 mg, yield 64%). LCMS: (ES+): m/z 300.0 [M+H]$^+$.

2-(2-methyl-6-nitro-4-phenyl-1H-benzo[d]imidazol-1-yl)ethan-1-ol (30D)

To a solution of 2-(4-bromo-2-methyl-6-nitro-1H-benzo[d]imidazol-1-yl)ethan-1-ol (30C) (110 mg, 0.37 mmol) in dioxane (8.0 mL) and $H_2O$ (1.0 mL) was added $Na_2CO_3$ (79 mg, 0.74 mmol), followed by Pd(PPh$_3$)$_4$ (24 mg, 0.020 mmol) and phenylboronic acid (54 mg, 0.44 mmol). The mixture was then stirred at 100° C. for 8 h. After cooling to .rt, the mixture was poured into water (20 mL), extracted with EA (20 mL), dried over anhydrous $Na_2SO_4$, filtered and concentrated. The residue was purified by preparative TLC (EA) to give 30D (83 mg, yield 7$^6$%). LCMS: (ES+): m/z 298.1 [M+H]$^+$.

2-(6-amino-2-methyl-4-phenyl-1H-benzo[d]imidazol-1-yl)ethan-1-ol (30E)

To a solution of 2-(2-methyl-6-nitro-4-phenyl-1H-benzo[d]imidazol-1-yl)ethan-1-ol (30D) (83 mg, 0.28 mmol) in MeOH (4 mL) was added Pd/C (40 mg). The mixture was stirred at 30° C. for 1 h under an atmosphere of H2, and was then filtered and concentrated to provide 30E (72 mg, yield 96%) which was used without further purification. LCMS: (ES+): m/z 268.1 [M+H]$^+$.

2-((1-(2-hydroxyethyl)-2-methyl-4-phenyl-1H-benzo[d]imidazol-6-yl)amino)pyrimidine-5-carbonitrile (30F)

To a solution of 2-(6-amino-2-methyl-4-phenyl-1H-benzo[d]imidazol-1-yl)ethan-1-ol (30E) (72 mg, 0.27 mmol) in i-PrOH (5 mL) was added 2-chloropyrimidine-5-carbonitrile (38 mg, 0.27 mmol). The mixture was stirred at 70° C. for 6 h. After cooling to rt, the reaction mixture was concentrated and recrystallized (PE:EA=1:1) to give 30F (68 mg, yield 68%). LCMS: (ES+): m/z 371.1 [M+H]$^+$.

2-(6-((5-(5-(difluoromethyl)-1,3,4-oxadiazol-2-yl)pyrimidin-2-yl)amino)-2-methyl-4-phenyl-1H-benzo[d]imidazol-1-yl)ethan-1-ol (30)

To a solution of 2-((1-(2-hydroxyethyl)-2-methyl-4-phenyl-1H-benzo[d]imidazol-6-yl)amino)pyrimidine-5-carbonitrile (30F) (29 mg, 0.080 mmol) and sodium azide (24 mg, 0.24 mmol) in DMF (4.0 mL) was added CuI (46 mg, 0.24 mmol). The mixture was stirred at 120° C. for 3 h at which time, LCMS showed the reaction was complete to provide 30G. The mixture was cooled to 10° C. and DFAA (0.50 g) was added. The mixture was stirred at 90° C. for 1 h, cooled to rt and was poured into 1N NaHCO$_3$ (20 mL) sol. The mixture was extracted with EA (20 mL) and the organic phase was dried over anhydrous $Na_2SO_4$, filtered and concentrated. The residue was purified by preparative HPLC to give 30 (19 mg, 52% yield for 2 steps). LCMS: (ES+): m/z 464.2 [M+H]$^+$ $^1$H NMR (400 MHz, CD$_3$OD): δ 9.06 (s, 2H), 8.05 (s, 1H), 7.83 (d, J=7.2 Hz, 2H), 7.41-7.50 (m, 3H), 7.35-7.40 (m, 1H), 7.21 (t, J=51.6 Hz, 1H), 4.36 (t, J=5.2 Hz, 2H), 3.95 (t, J=5.2 Hz, 2H), 2.64 (s, 3H).

Example 31. 2-(4-bromo-6-((5-(5-(difluoromethyl)-1,3,4-oxadiazol-2-yl)pyrimidin-2-yl)amino)-1H-benzo[d]imidazol-1-yl)ethan-1-ol

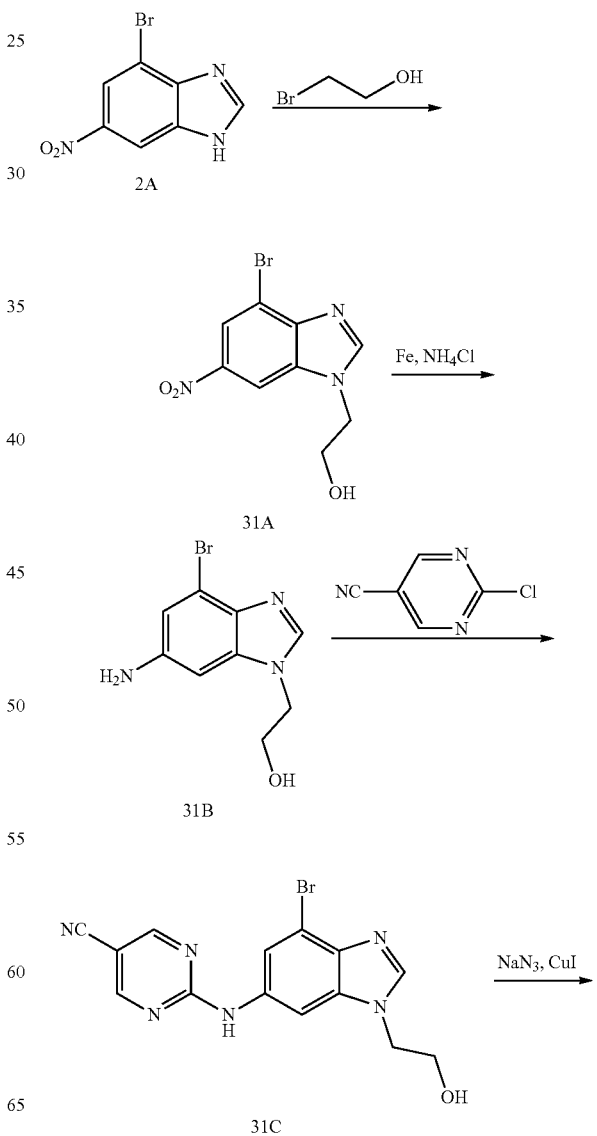

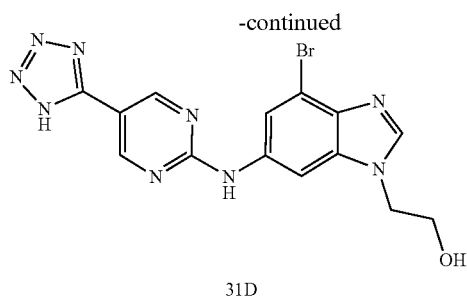

31D

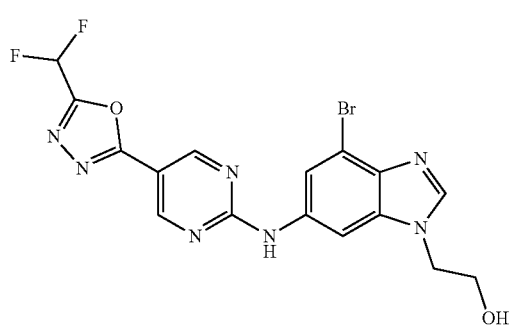

31

2-(4-bromo-6-nitro-1H-benzo[d]imidazol-1-yl)ethan-1-ol (31A)

To a solution of compound 4-bromo-6-nitro-1H-benzo[d]imidazole 2A (2.0 g, 8.3 mmol) in DMF (30 mL) was added 2-bromoethan-1-ol (2.06 g, 16.6 mmol) and Cs$_2$CO$_3$ (8.15 g, 24.9 mmol). The mixture was stirred at 120° C. for 76 h at which time, LCMS showed the reaction was complete. The reaction mixture was cooled to rt and concentrated, and the residue was recrystallized (DCM:MeOH=20:1) to give 31A (900 mg, yield 38%). LCMS: (ES+): m/z 287.1 [M+H]$^+$, $^1$H NMR (400 MHz, DMSO-d$_6$): δ 8.71 (s, 1H) 8.62 (s, 1H), 8.26 (s, 1H), 5.04 (s, 1H), 4.46 (s, 2H), 3.77 (m, 2H).

2-(6-amino-4-bromo-1H-benzo[d]imidazol-1-yl)ethan-1-ol (31B)

To a solution of 2-(4-bromo-6-nitro-1H-benzo[d]imidazol-1-yl)ethan-1-ol (31A) (0.90 g, 3.16 mmol) in EtOH (30 mL) and H$_2$O (3.0 mL) was added iron powder (885 mg, 15.8 mmol) and NH$_4$Cl (1.71 g, 31.6 mmol), and the mixture was stirred at 80° C. for 3 h. After cooling to rt, the mixture was concentrated, and the residue was diluted with EA and filtered. The filtrate was washed with brine, dried over anhydrous Na$_2$SO$_4$, filtered and concentrated. The residue was purified by silica gel column chromatography to give 31B (678 mg, yield 84%). LCMS: (ES+): m/z 257.1 [M+H]$^+$.

2-((4-bromo-1-(2-hydroxyethyl)-1H-benzo[d]imidazol-6-yl)amino)pyrimidine-5-carbonitrile (31C)

To a solution of 2-(6-amino-4-bromo-1H-benzo[d]imidazol-1-yl)ethan-1-ol (31B) (678 mg, 2.66 mmol) in i-PrOH (10 mL) was added 2-chloropyrimidine-5-carbonitrile (370 mg, 2.66 mmol). The mixture was stirred at 70° C. for 6 h at which time, LCMS showed the reaction was complete. The reaction mixture was cooled to rt and was concentrated. The residue was recrystallized (PE:EA=2:1) to give 31C (515 mg, yield 54%). $^1$H NMR (400 MHz, DMSO): δ 10.59 (s, 1H), 8.92 (s, 2H), 8.35 (s, 1H), 8.02 (s, 1H), 7.80 (s, 1H), 4.27 (s, 2H), 3.76 (t, J=4.8 Hz, 2H).

2-(4-bromo-6-((5-(5-(difluoromethyl)-1,3,4-oxadiazol-2-yl)pyrimidin-2-yl)amino)-1H-benzo[d]imidazol-1-yl)ethan-1-ol (31)

To a solution of 2-((4-bromo-1-(2-hydroxyethyl)-1H-benzo[d]imidazol-6-yl)amino)pyrimidine-5-carbonitrile (31C) (515 mg, 1.44 mmol) and sodium azide (187 mg, 2.88 mmol) in DMF (10 mL) was added CuI (54.9 mg, 0.288 mmol). The mixture was stirred at 120° C. for 3 h at which time, LCMS showed the reaction was complete to give 31D. The mixture was cooled to 10° C. and DFAA (1.9 g) was added. The mixture was stirred at 90° C. for 1 h, was cooled to rt and poured into 1N NaHCO$_3$ (20 mL). The mixture was extracted with EA (20 mL) and the organic phase was dried over anhydrous Na$_2$SO$_4$, filtered and concentrated. The residue was recrystallized from 1:1 EA:Hexane to give 31 (136 mg, yield 21%). LCMS: (ES+): m/z 453.1 [M+H]$^+$.

Example 32. 2-(6-((5-(5-(difluoromethyl)-1,3,4-oxadiazol-2-yl)pyrimidin-2-ylamino)-4-(2,4-difluorophenyl)-1H-benzo[d]imidazol-1-yl)ethan-1-ol

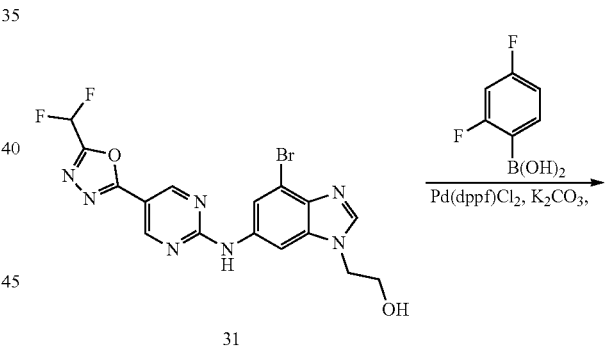

31

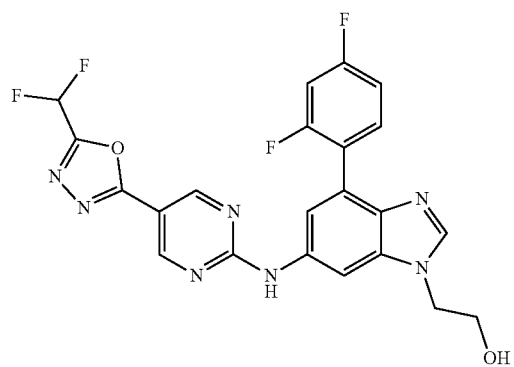

32

2-(6-((5-(5-(difluoromethyl)-1,3,4-oxadiazol-2-yl)pyrimidin-2-yl)amino)-4-(2,4-difluorophenyl)-1H-benzo[d]imidazol-1-yl)ethan-1-ol (32)

A mixture of 2-(4-bromo-6-((5-(5-(difluoromethyl)-1,3,4-oxadiazol-2-yl)pyrimidin-2-yl)amino)-1H-benzo[d]imidazol-1-yl)ethan-1-ol (31) (50 mg, 0.11 mmol), (2,4-difluorophenyl)boronic acid (24 mg, 0.15 mmol), Pd(dppf)Cl$_2$ (7.3 mg, 0.010 mmol) and Na$_2$CO$_3$ (21, 0.20 mmol) in 1,4-dioxane (5.0 mL) and water (1.0 mL) was stirred at 80° C. for 8 h. The reaction mixture was cooled to rt, quenched with water and extracted with EA. The organic layer was washed with brine and dried over anhydrous Na$_2$SO$_4$, filtered and concentrated. The residue was purified by preparative HPLC to afford 32 (7.3 mg, yield 11%) as the corresponding TFA salt. LCMS: (ES+): m/z 486.1 [M+H]$^+$ $^1$H NMR (400 MHz, CD$_3$OD): δ 9.40 (s, 1H), 9.16 (s, 2H), 8.75 (s, 1H), 7.83 (s, 1H), 7.68 (d, J=6.5 Hz, 1H), 7.37-7.06 (m, 3H), 4.72-4.58 (m, 2H), 4.13-3.98 (m, 2H).

Example 33. 2-(6-((5-(5-(difluoromethyl)-1,3,4-oxadiazol-2-yl)pyrimidin-2-yl)amino)-4-(4-fluoro-2-(trifluoromethyl)phenyl)-1H-benzo[d]imidazol-1-yl)ethan-1-ol

2-(6-((5-(5-(difluoromethyl)-1,3,4-oxadiazol-2-yl)pyrimidin-2-yl)amino)-4-(4-fluoro-2-(trifluoromethyl)phenyl)-1H-benzo[d]imidazol-1-yl)ethan-1-ol (33)

A mixture of 2-(4-bromo-6-((5-(5-(difluoromethyl)-1,3,4-oxadiazol-2-yl)pyrimidin-2-yl)amino)-1H-benzo[d]imidazol-1-yl)ethan-1-ol (31) (41 mg, 0.090 mmol), (4-fluoro-2-(trifluoromethyl)phenyl)boronic acid (31 g, 0.15 mmol), Pd(dppf)Cl$_2$ (7.3 mg, 0.010 mmol) and Na$_2$CO$_3$ (21, 0.20 mmol) in 1,4-dioxane (5.0 mL) and water (1.0 mL) was stirred at 80° C. for 8 h. The reaction mixture was cooled to rt, quenched with water and extracted with EA. The organic layer was washed with brine and dried over anhydrous Na$_2$SO$_4$, filtered and concentrated. The residue was purified by preparative HPLC to afford 33 (16 mg, yield 27%) as the corresponding TFA salt. LCMS: (ES+): m/z 536.2 [M]$^+$ $^1$H NMR (400 MHz, CD$_3$OD): δ 9.37 (s, 1H), 9.16 (s, 2H), 8.80 (d, J=1.3 Hz, 1H), 7.75 (d, J=7.6 Hz, 2H), 7.60 (d, J=6.0 Hz, 2H), 7.23 (t, J=51.6 Hz, 1H), 4.66 (t, J=4.8 Hz, 2H), 4.07 (t, J=4.8 Hz, 2H).

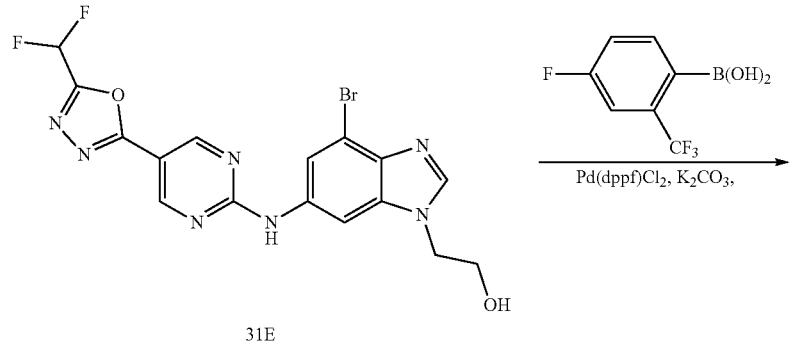

31E

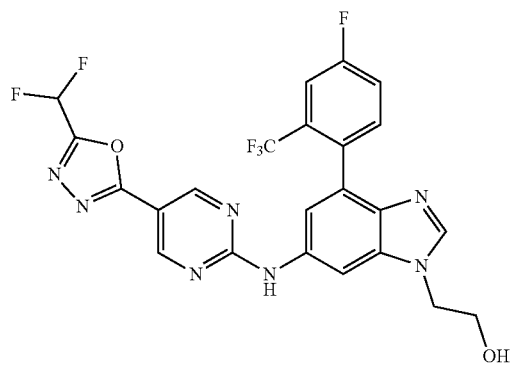

33

Example 34. 2-(4-(tert-butyl)-6-((5-(5-(difluoromethyl)-1,3,4-oxadiazol-2-yl)pyrimidin-2-yl)amino)-1H-benzo[d]imidazol-1-yl)ethan-1-ol

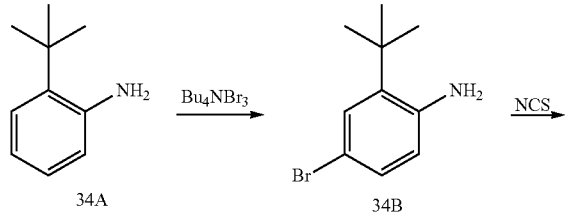
34A, 34B

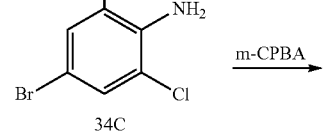
34C

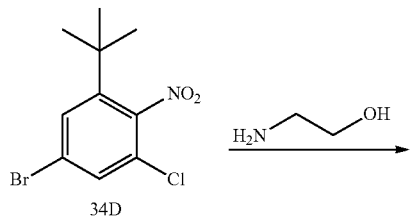
34D

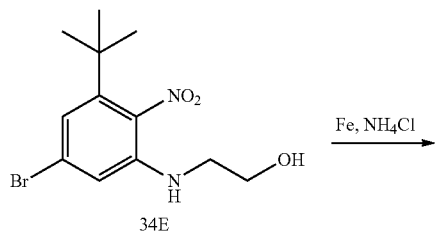
34E

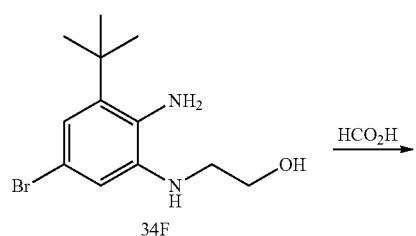
34F

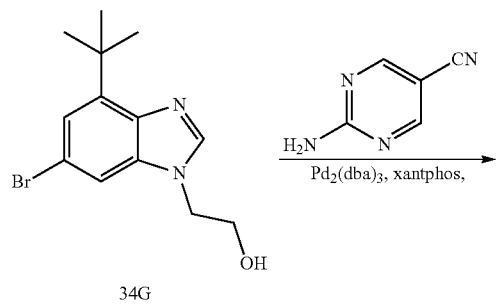
34G

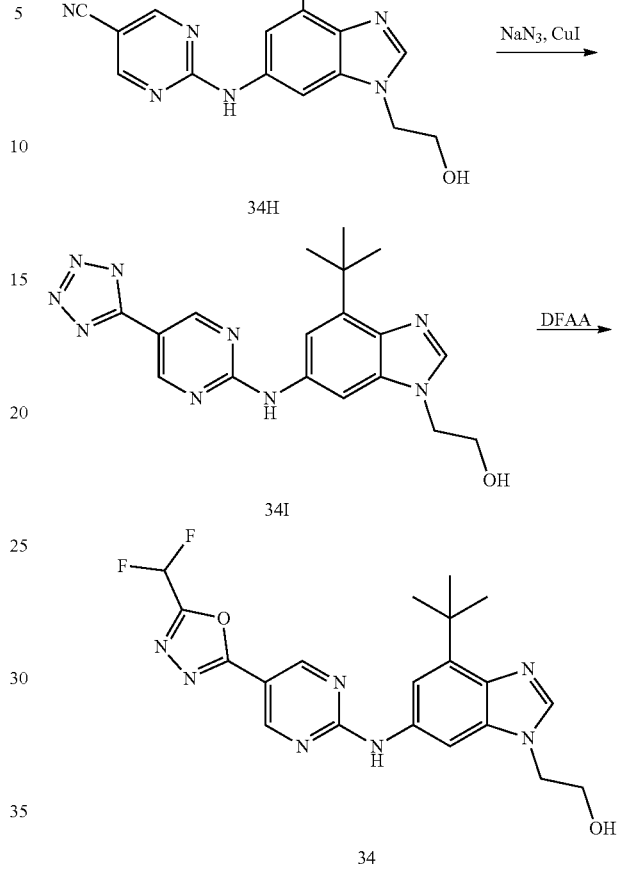
34H, 34I, 34

4-bromo-2-(tert-butyl)aniline (34B)

To a solution of 2-(tert-butyl)aniline (10 g, 67 mmol) in THF (200 mL) was added tetrabutylammonium tribromide (32.1 g, 67 mmol) at 5° C. portion wise at a rate such that the temperature did not rise significantly. After the addition, the reaction was allowed to warm to rt. Stirring continued for 30 minutes at which time, the reaction mixture was diluted with water and extracted with ethyl acetate. The organic layer was washed with brine, dried over anhydrous $Na_2SO_4$, filtered and concentrated. The residue was purified by silica chromatography eluting with 25% dichloromethane in hexane to give 34B (12.2 g, yield 80%) as light-red oil. $^1$H NMR (400 MHz, $CD_3OD$): δ 7.22 (d, J=2.0 Hz, 1H), 7.03 (dd, J=8.4, 2.0 Hz, 1H), 6.59 (d, J=8.4 Hz, 1H), 1.37 (s, 9H).

4-bromo-2-(tert-butyl)-6-chloroaniline (34C)

To a solution of 4-bromo-2-(tert-butyl)aniline (34B) (2.2 g, 10 mmol) in MeCN (50 mL) was added NCS (1.4 g, 10.5 mmol), and the mixture was stirred at 65° C. for 16 h. The reaction was cooled to rt and the mixture was concentrated in vacuo. Water was then added, and the resulting mixture was extracted with EA/hexane (1/5; 50 mL×2). The combined organic layers were dried over anhydrous $Na_2SO_4$, filtered and concentrated to give crude 34C (2.6 g, yield 99%). ¹H NMR (400 MHz, CDCl₃): δ 7.31 (d, J=2.4 Hz, 1H), 7.23 (d, J=2.4 Hz, 1H), 4.34 (br s, 2H), 1.40 (s, 9H).

5-bromo-1-(tert-butyl)-3-chloro-2-nitrobenzene (34D)

To a solution of 4-bromo-2-(tert-butyl)-6-chloroaniline (34C) (2.6 g, 9.9 mmol) in DCE (40 mL) was added 3-chloroperoxybenzoic acid (6.0 g, 30 mmol, 85% purity). The mixture was stirred at rt for 30 min and then heated at 50° C. for 30 mins. The mixture was cooled to rt, quenched with water, and extracted with DCM (2×50 ml). The combined organic layers were washed with sat. aq. NaHCO₃ sol., aq. sodium thiosulfate solution, brine, and dried over anhydrous Na₂SO₄. Filtration and concentration provided a residue which was purified by silica gel chromatography (EA/hexane=1/10) to give 34D (2.5 g, yield 86%).

2-((5-bromo-3-(tert-butyl)-2-nitrophenyl)amino) ethan-1-ol (34E)

To a solution of 5-bromo-1-(tert-butyl)-3-chloro-2-nitrobenzene (34D) (1.0 g, 3.4 mmol) in THF (10 mL) was added 2-aminoethan-1-ol (1.0 g, 17 mmol) and the resulting mixture was stirred at 20° C. for 16 h. The reaction mixture was then poured into water and extracted with EA. The organic phase was dried over anhydrous Na₂SO₄, filtered and concentrated. The residue was purified by silica chromatography (EA/hexane=1/3) to give 34E (0.32 g, yield 30%) as a yellow solid. ¹H NMR (400 MHz, CDCl₃): δ 7.04 (d, J=1.6 Hz, 1H), 6.94 (d, J=1.6 Hz, 1H), 3.92 (t, J=5.2 Hz, 2H), 3.42 (t, J=5.2 Hz, 2H), 1.60 (s, 9H).

2-((2-amino-5-bromo-3-(tert-butyl)phenyl)amino) ethan-1-ol (34F)

To a solution of 2-((5-bromo-3-(tert-butyl)-2-nitrophenyl) amino)ethan-1-ol (34E) (0.22 g, 0.70 mmol) in EtOH (8.0 mL) and H₂O (1.0 mL) was added iron powder (0.40 g, 7.0 mmol) and NH₄Cl (0.75 g, 14 mmol). The mixture was stirred at 80° C. for 3 h and after cooling, the mixture was poured into water and extracted with EA (2×50 mL). The combined organic layers were dried over anhydrous Na₂SO₄, filtered and evaporated to give the crude product 34F (0.20 g, yield 100%) which was used directly in the next step.

2-(6-bromo-4-(tert-butyl)-1H-benzo[d]imidazol-1-yl)ethan-1-ol (34G)

A solution of crude 2-((2-amino-5-bromo-3-(tert-butyl) phenyl)amino)ethan-1-ol (34F) (200 mg, 0.70 mmol) in formic acid (5.0 mL, 88%) was stirred at 100° C. for 1 h. The mixture was cooled, concentrated in vacuo, diluted with MeOH (2.0 mL) and added to 1N Na₂CO₃ sol. (10 mL). The mixture was stirred at 20° C. for 2 h at which time, 1N HCl was added slowly to adjust the pH to 8. The mixture was extracted with EA and the organic phase was dried over anhydrous Na₂SO₄, filtered and concentrated in vacuo. The residue was recrystallized from DCM/hexane to give 34G (170 mg, yield 82%) as a light-yellow solid.

2-((4-(tert-butyl)-1-(2-hydroxyethyl)-1H-benzo[d] imidazol-6-v amino)pyrimidine-5-carbonitrile (34H)

A mixture of 2-(6-bromo-4-(tert-butyl)-1H-benzo[d]imidazol-1-yl)ethan-1-ol (34G) (170 mg, 0.57 mmol), 2-aminopyrimidine-5-carbonitrile (84 mg, 0.70 mmol), Pd₂(dba)₃ (46 mg, 0.050 mmol), XantPhos (58 mg, 0.10 mmol) and Cs₂CO₃ (330 mg, 1.0 mmol) in DMF was stirred at 100° C. under N2 for 16 h. The mixture was cooled, poured into water, extracted with EA, dried over anhydrous Na₂SO₄, filtered and concentrated. The residue was purified by preparative TLC (EA/hexane=2/1) to give 34H (36 mg, yield 19%) as a light-yellow solid.

2-(4-(tert-butyl)-6-((5-(5-(difluoromethyl)-1,3,4-oxadiazol-2-yl)pyrimidin-2-yl)amino)-1H-benzo[d] imidazol-1-yl)ethan-1-ol (34)

To a solution of 2-((4-(tert-butyl)-1-(2-hydroxyethyl)-1H-benzo[d]imidazol-6-yl)amino)pyrimidine-5-carbonitrile (34H) (36 mg, 0.11 mmol) and sodium azide (21 mg, 0.33 mmol) in DMF (3.0 mL) was added CuI (38 mg, 0.20 mmol). The mixture was stirred at 120° C. for 3 h at which time, LCMS showed the reaction was complete to give 34I. The mixture was cooled to 10° C. and DFAA (290 mg, 1.65 mmol) was added. The mixture was warmed to 90° C. and stirred for 2 h. The mixture was then cooled to rt, poured into 1N Na₂CO₃ (20 mL) and stirred for 2 h. The mixture was extracted with EA (20 mL×2) and the combined organic layers were dried over anhydrous Na₂SO₄, filtered and concentrated. The residue was purified by preparative TLC (EtOAc/hexane=2/1) to give 34 (17 mg, yield 37%) as white solid. LCMS: (ES+): m/z 430.1 [M+H]⁺ ¹H NMR (400 MHz, CD₃OD): δ 9.07 (s, 2H), 8.14 (d, J=1.6 Hz, 1H), 8.10 (s, 1H), 7.32 (d, J=1.6 Hz, 1H), 7.23 (s, J=52 Hz, 1H), 4.37 (t, J=5.2 Hz, 2H), 3.95 (t, J=5.2 Hz, 2H), 1.59 (s, 9H).

Example 35. N-(5-(5-(difluoromethyl)-1,3,4-oxadiazol-2-yl)pyrimidin-2-yl)-4-(pyridin-4-yl)-1H-benzo [d]imidazol-6-amine

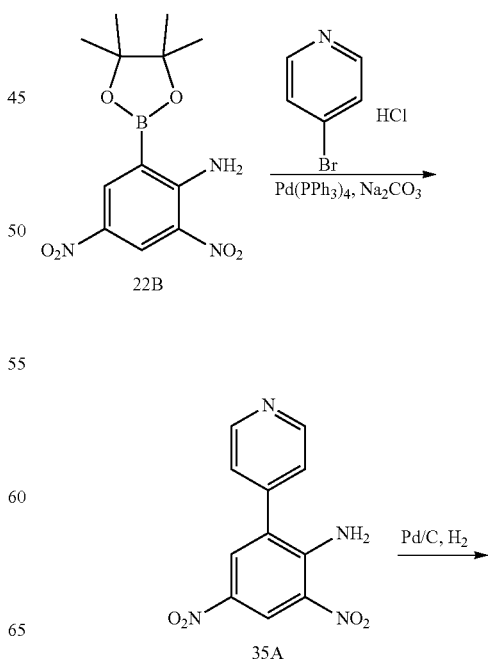

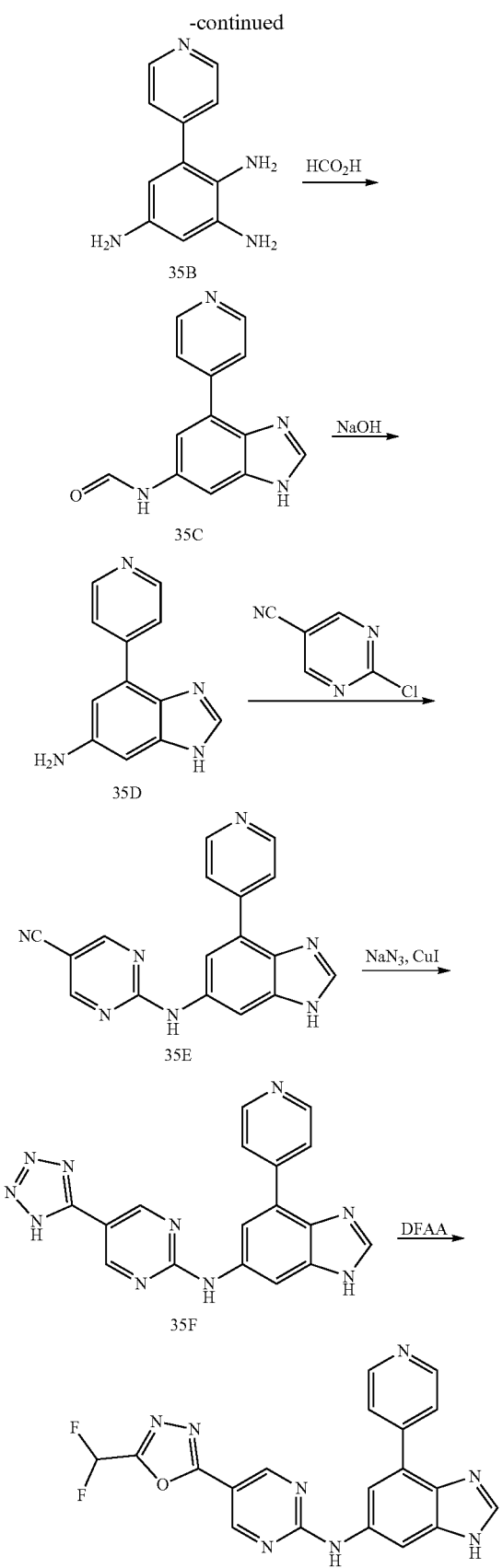

2,4-dinitro-6-(pyridin-4-yl)aniline (35A)

A mixture of 2,4-dinitro-6-(4,4,5,5-tetramethyl-1,3,2-dioxaborolan-2-yl)aniline (22B) (1.0 g, 3.24 mmol), 4-bromopyridine hydrochloride (1.26 g, 6.48 mmol), Pd(PPh$_3$)$_4$ (187 mg, 0.16 mmol) and Na$_2$CO$_3$ (1.72 g, 16.2 mmol) in dioxane (30 mL) and H$_2$O (3.0 mL) was stirred under N$_2$ at 80° C. for 6 hrs. The reaction mixture was cooled, taken up in EA (60 mL) and washed with water (60 mL×2) and brine (60 mL×2). The organic layer was dried over anhydrous MgSO$_4$, filtered and concentrated. The residue was purified by column chromatography (20-60% EA/PE) to give 35A (600 mg, yield 71%) as a brown solid. LC-MS: (ES$^+$): m/z 261.1 [M–H]$^+$.

6-(pyridin-4-yl)benzene-1,2,4-triamine (35B)

A mixture of 2,4-dinitro-6-(pyridin-4-yl)aniline (35A) (600 mg, 2.3 mmol) and 10% Pd/C (120 mg) in MeOH (20 mL) was stirred at 25° C. for 16 h under an atmosphere of H$_2$. The mixture was filtered through a Celite™ pad, and the filtrate was concentrated to give 35B (410 mg, yield 8⁹%) as yellow solid which was used directly in the next step. LC-MS: (ES$^+$): m/z 201.1 [M+H]$^+$.

N-(4-(pyridin-4-yl)-1H-benzo[d]imidazol-6-yl)formamide (35C)

A mixture of 6-(pyridin-4-yl)benzene-1,2,4-triamine (35B) (410 mg, 2.05 mmol) in formic acid (20 mL) was stirred for 2 h at 90° C. under N2. The mixture was cooled and concentrated to give a crude 35C (500 mg, 100%) which was obtained as a grey solid and used directly in the next step. LC-MS: (ES$^+$): m/z 239.2 [M+H]$^+$.

4-(pyridin-4-yl)-1H-benzo[d]imidazol-6-amine (35D)

A mixture of N-(4-(pyridin-4-yl)-1H-benzo[d]imidazol-6-yl)formamide (35C) (500 mg, 2.05 mmol) in 3N NaOH (30 mL) was stirred for 2 h at 25° C. The mixture was adjusted to pH 8 with 1M HCl and taken up in EA (40 mL). The organic layer was washed with water (40 mL×2), brine (40 mL×2) and dried over anhydrous MgSO$_4$. Filtration and concentration provided 35D (350 mg, 81% yield for two steps) as a brown solid which was used directly in the next step. LC-MS: (ES$^+$): m/z 211.1 [M+H]$^+$.

2-((4-(pyridin-4-yl)-1H-benzo[d]imidazol-6-yl)amino)pyrimidine-5-carbonitrile (35E)

A mixture of 4-(pyridin-4-yl)-1H-benzo[d]imidazol-6-amine (35D) (150 mg, 0.71 mmol) and 2-chloropyrimidine-5-carbonitrile (89.6 mg, 0.64 mmol) in IPA (8.0 mL) was stirred at 65° C. for 2 h under N2. The mixture was concentrated to give a residue which was purified by column chromatography (0-20% MeOH/EA) to give 35E (20 mg, yield 10%) as a brown solid, and an additional 75 mg of impure 35E which was subjected to repurification.

N-(5-(5-(difluoromethyl)-1,3,4-oxadiazol-2-yl)pyrimidin-2-yl)-4-(pyridin-4-yl)-1H-benzo[d]imidazol-6-amine (35)

A mixture of 2-((4-(pyridin-4-yl)-1H-benzo[d]imidazol-6-yl)amino)pyrimidine-5-carbonitrile (35E) (20 mg, 0.064 mmol), sodium azide (7.8 mg, 0.12 mmol) and CuI (2.3 mg, 0.012 mmol) in IPA (8.0 mL) was stirred for 3 h at 120° C. under N2 to give 35F. The mixture was cooled to rt and DFAA (104 mg, 0.60 mmol) was added. The mixture was then stirred at 90° C. for 1 h, and cooled to rt. The reaction mixture was poured into sat. aq. NaHCO₃ sol. (30 mL) and stirred for 30 min at 25° C. EA (30 mL) was added and the organics were washed with water (30 mL, containing 1 mL ammonium hydroxide sol.) and brine (30 mL). The organic phase was dried with anhydrous MgSO₄, filtered and concentrated. The residue was purified by preparative HPLC to give 35 (14.5 mg, yield 56%) as a yellow solid. LC-MS: (ES⁺): m/z 407.1 [M+H]⁺ ¹H NMR (400 MHz, DMSO-d₆): δ 10.59 (s, 1H), 9.10 (s, 2H), 8.76 (br s, 2H), 8.40 (s, 1H), 8.22-8.30 (m, 3H), 7.97 (s, 1H), 7.42-7.70 (t, J=51.2 Hz, 1H).

Example 36. N-(5-(5-(difluoromethyl)-1,3,4-oxadiazol-2-yl)pyrimidin-2-yl)-4-(1H-pyrazol-5-yl)-1H-benzo[d]imidazol-6-amine

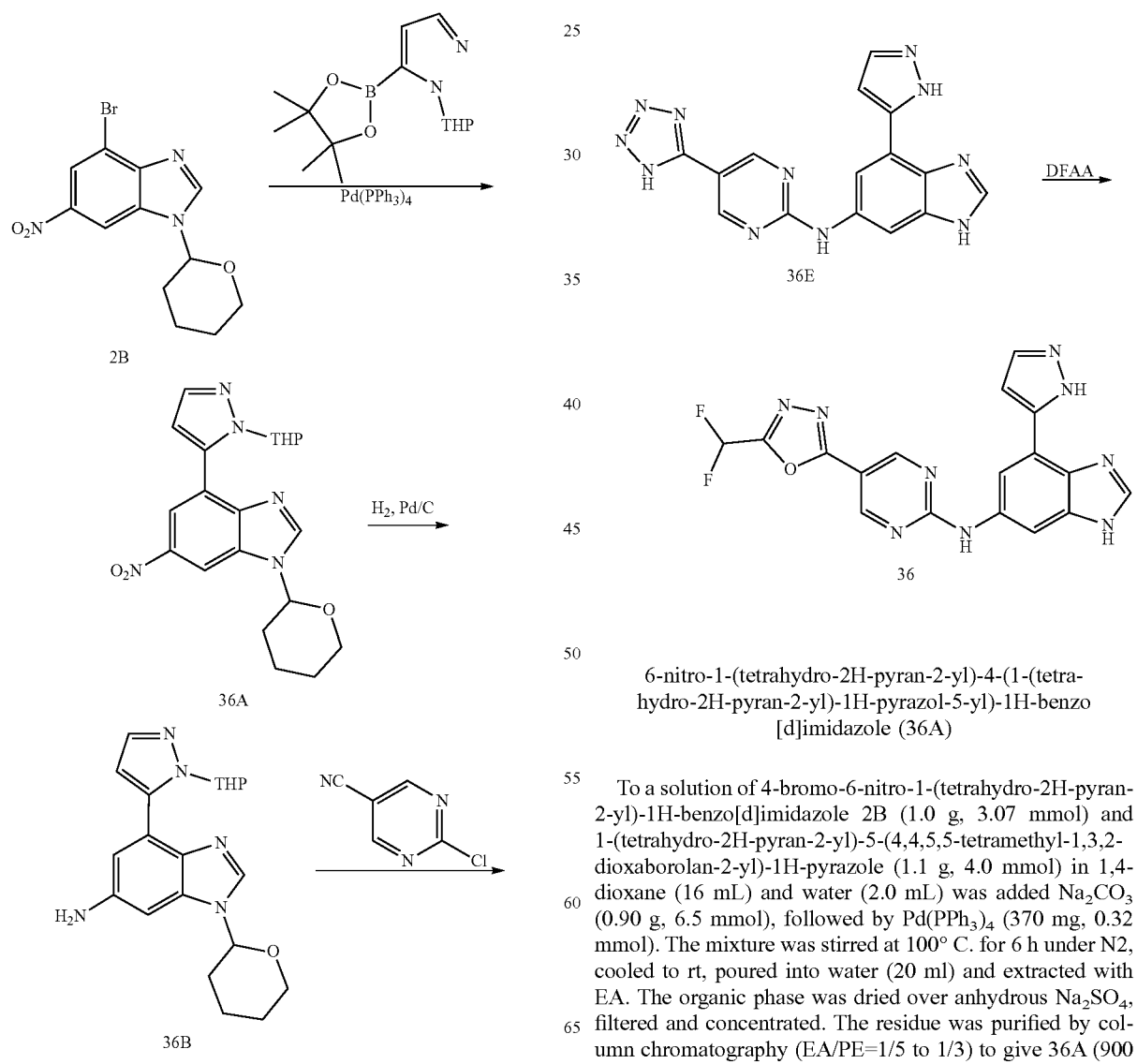

6-nitro-1-(tetrahydro-2H-pyran-2-yl)-4-(1-(tetrahydro-2H-pyran-2-yl)-1H-pyrazol-5-yl)-1H-benzo[d]imidazole (36A)

To a solution of 4-bromo-6-nitro-1-(tetrahydro-2H-pyran-2-yl)-1H-benzo[d]imidazole 2B (1.0 g, 3.07 mmol) and 1-(tetrahydro-2H-pyran-2-yl)-5-(4,4,5,5-tetramethyl-1,3,2-dioxaborolan-2-yl)-1H-pyrazole (1.1 g, 4.0 mmol) in 1,4-dioxane (16 mL) and water (2.0 mL) was added Na₂CO₃ (0.90 g, 6.5 mmol), followed by Pd(PPh₃)₄ (370 mg, 0.32 mmol). The mixture was stirred at 100° C. for 6 h under N2, cooled to rt, poured into water (20 ml) and extracted with EA. The organic phase was dried over anhydrous Na₂SO₄, filtered and concentrated. The residue was purified by column chromatography (EA/PE=1/5 to 1/3) to give 36A (900 mg, yield 74%) as a yellow solid.

1-(tetrahydro-2H-pyran-2-yl)-4-(1-(tetrahydro-2H-pyran-2-yl)-1H-pyrazol-5-yl)-1H-benzo[d]imidazol-6-amine (36B)

To a solution of 6-nitro-1-(tetrahydro-2H-pyran-2-yl)-4-(1-(tetrahydro-2H-pyran-2-yl)-1H-pyrazol-5-yl)-1H-benzo[d]imidazole (36A) (900 mg, 2.26 mmol) in MeOH (10 mL) was added Pd/C (100 mg). The mixture was stirred at 30° C. for 5 h under an atmosphere of H2. The mixture was filtered through Celite™, and the Celite™ pad was washed with THF/MeOH (3/1). The filtrate was concentrated in vacuo to give the crude product 36B (720 mg, 87%) which was used directly in the next step.

2-((4-(1-(tetrahydro-2H-pyran-2-yl)-1H-pyrazol-5-yl)-1H-benzo[d]imidazol-6-yl)amino)pyrimidine-5-carbonitrile (36C)

A mixture of 1-(tetrahydro-2H-pyran-2-yl)-4-(1-(tetrahydro-2H-pyran-2-yl)-1H-pyrazol-5-yl)-1H-benzo[d]imidazol-6-amine (36B) (200 mg, 0.54 mmol), 2-aminopyrimidine-5-carbonitrile (70 mg, 0.50 mmol) in i-PrOH (5.0 mL) was stirred at 65° C. for 4 h. The precipitated solids were filtered, washed with methanol and dried in vacuo to give crude 36C (90 mg, yield 46%) which was used directly in the next step. LCMS: (ES+): m/z 387.1 [M+H]+.

2-((4-(1H-pyrazol-5-yl)-1H-benzo[d]imidazol-6-yl)amino)pyrimidine-5-carbonitrile (36D)

A solution of 2-((4-(1-(tetrahydro-2H-pyran-2-yl)-1H-pyrazol-5-yl)-1H-benzo[d]imidazol-6-yl)amino)pyrimidine-5-carbonitrile (36C) (45 mg, 0.12 mmol) in EtOH (5.0 mL) and concentrated HCl (2 mL) was stirred at rt for 16 h. The mixture was concentrated in vacuo at 20° C. and freeze-dried to give crude 36D (40 mg) which was used directly in the next step. LCMS: (ES+): m/z 303.1 [M+H]+.

N-(5-(5-(difluoromethyl)-1,3,4-oxadiazol-2-yl)pyrimidin-2-yl)-4-(1H-pyrazol-5-yl)-1H-benzo[d]imidazol-6-amine (36)

To a solution of 2-((4-(1H-pyrazol-5-yl)-1H-benzo[d]imidazol-6-yl)amino)pyrimidine-5-carbonitrile (36D) (40 mg, 0.12 mmol) and sodium azide (25 mg, 0.40 mmol) in DMF (3.0 mL) was added CuI (57 mg, 0.30 mmol). The mixture was stirred at 120° C. for 3 h at which time, LCMS showed the reaction was complete to give 36E. The mixture was cooled to 10° C., and DFAA (290 mg, 1.65 mmol) was added. The mixture was warmed to 90° C., and stirred for 2 h. The mixture was cooled to rt, poured into 1N Na2CO3 sol. (20 mL), and stirred at rt for 2 h. The reaction mixture was extracted with EA/THF (20 mL/10 mL)×2 and the combined organic layers were dried over anhydrous Na2SO4, filtered and concentrated. The residue was purified by preparative HPLC to give 36 (8.2 mg, yield 17% for 3 steps) as a white solid. LCMS: (ES+): m/z 396.1 [M+H]+ 1H NMR (400 MHz, DMSO-d6): δ 10.45 (br s, 1H), 9.07 (s, 2H), 8.22 (s, 1H), 8.08 (s, 1H), 7.96 (s, 1H), 7.81 (s, 1H), 7.57 (t, J=51.6 Hz, 1H).

Example 37. 2-(6-((5-(5-(difluoromethyl)-1,3,4-oxadiazol-2-yl)pyrimidin-2-yl)amino)-4-(1H-pyrazol-5-yl)-1H-benzo[d]imidazol-1-yl)ethan-1-ol

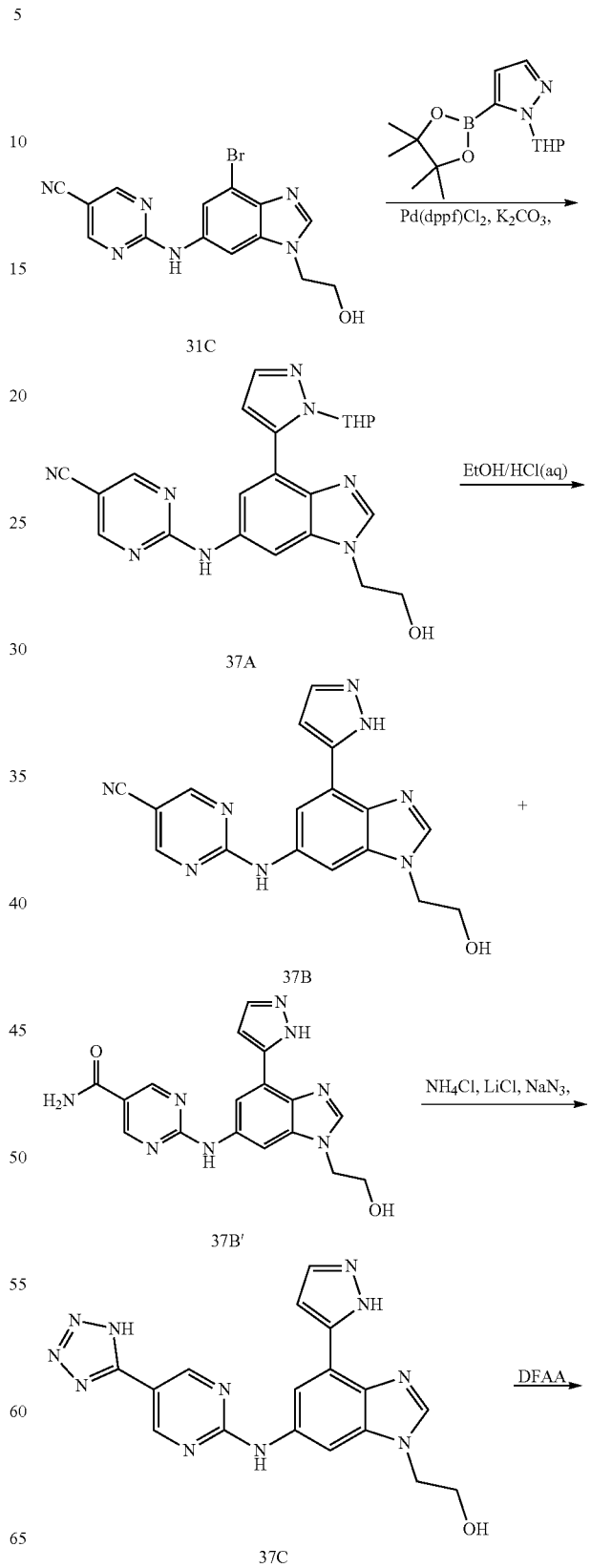

-continued

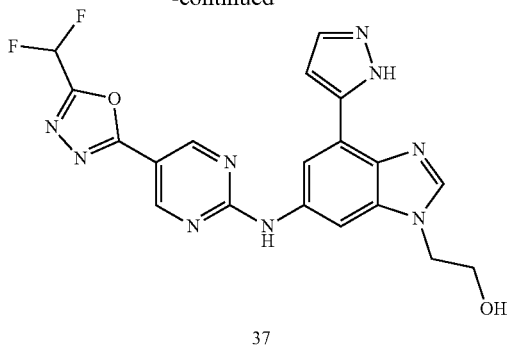

37

2-((1-(2-hydroxyethyl)-4-(1-(tetrahydro-2H-pyran-2-yl)-1H-pyrazol-5-yl)-1H-benzo[d]imidazol-6-yl)amino)pyrimidine-5-carbonitrile (37A)

To a suspension of 2-((4-bromo-1-(2-hydroxyethyl)-1H-benzo[d]imidazol-6-yl)amino)pyrimidine-5-carbonitrile (31C) (90 mg, 0.25 mmol), and 1-(tetrahydro-2H-pyran-2-yl)-5-(4,4,5,5-tetramethyl-1,3,2-dioxaborolan-2-yl)-1H-pyrazole (84 mg, 0.30 mmol) in 1,4-dioxane (9.0 mL) and water (1.0 mL) was added Na$_2$CO$_3$ (53 mg, 0.50 mmol), followed by Pd(dppf)Cl$_2$ (18 mg, 0.025 mmol). The reaction mixture was stirred at 85° C. for 8 h under N$_2$, and cooled to rt. The reaction mixture was diluted with water, extracted with EA, and the organic layer was washed with brine, dried over anhydrous Na$_2$SO$_4$, filtered and concentrated. The residue was purified by column chromatography (DCM/MeOH=20/1) to afford compound 37A (62 mg, yield 58%). LCMS: (ES+): m/z 431.1 [M+H]$^+$.

2-((1-(2-hydroxyethyl)-4-(1H-pyrazol-5-yl)-1H-benzo[d]imidazol-6-yl)amino)pyrimidine-5-carbonitrile (37B)

A solution of 2-((1-(2-hydroxyethyl)-4-(1-(tetrahydro-2H-pyran-2-yl)-1H-pyrazol-5-yl)-1H-benzo[d]imidazol-6-yl)amino)pyrimidine-5-carbonitrile (37A) (62 mg, 0.144 mmol) in EtOH (10 ml) and concentrated HCl (2.0 ml) was stirred at rt for 16 h. The solvent was concentrated under reduced pressure to afford an inseparable mixture (58 mg) of 37B (35%) and 37B' (65%). 37B LCMS: (ES+): m/z 347.1 [M+H]$^+$ 37B'LCMS: (ES+): m/z 365.1 [M+H]$^+$.

2-(6-((5-(5-(difluoromethyl)-1,3,4-oxadiazol-2-yl)pyrimidin-2-yl)amino)-4-(1H-pyrazol-5-yl)-1H-benzo[d]imidazol-1-yl)ethan-1-ol (37)

To a mixture (58 mg, ~0.17 mmol) of 2-((1-(2-hydroxyethyl)-4-(1H-pyrazol-5-yl)-1H-benzo[d]imidazol-6-yl)amino)pyrimidine-5-carbonitrile (37B) (35%) and 37B' (65%) in DMF (3.0 mL) was added sodium azide (32.5 mg, 0.50 mmol), NH$_4$Cl (27 mg, 0.50 mmol) and LiCl (21 mg, 0.50 mmol). The mixture was stirred at 120° C. for 3 h to give 37C together with 37B'. The mixture was cooled to 10° C. and DFAA (0.50 g) was added. The mixture was then stirred at 90° C. for 1 h, cooled to rt and poured into 1N NaHCO$_3$ (20 mL) sol. The mixture was extracted with EA (20 mL), dried over anhydrous Na$_2$SO$_4$, filtered and concentrated. The residue was purified by preparative HPLC to give 37 (8.2 mg, yield 13%) LCMS: (ES+): m/z 440.1 [M+H]$^+$, $^1$H NMR (400 MHz, DMSO-d$_6$): δ 10.55 (br s, 1H), 9.12 (s, 2H), 8.30 (s, 1H), 8.07 (d, J=3.2 Hz, 2H), 7.80 (s, 1H), 7.62 (t, J=51.6 Hz, 1H), 7.35 (s, 1H), 5.11 (br s, 1H), 4.36 (t, J=4.8 Hz, 2H), 3.85 (t, J=4.8 Hz, 2H).

Example 38. N-(5-(5-(difluoromethyl)-1,3,4-oxadiazol-2-yl)pyrimidin-2-yl)-5-fluoro-4-phenyl-1H-benzo[d]imidazol-6-amine

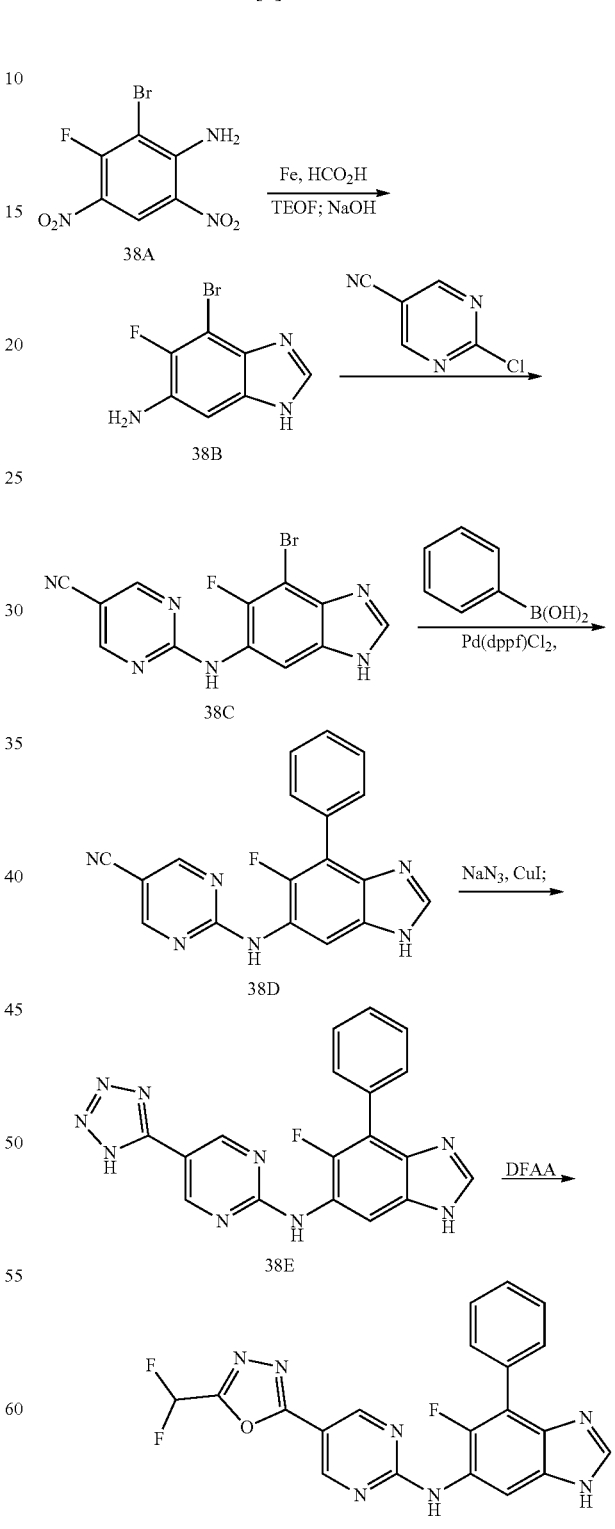

4-bromo-5-fluoro-1H-benzo[d]imidazol-6-amine (38B)

To a solution of 2-bromo-3-fluoro-4,6-dinitroaniline (38A; prepared as described in WO 2016/041849 A1) (1.6 g, 6.96 mmol) in MeOH (100 mL) was added iron powder (3.9 g, 69.6 mmol), trimethyl orthoformate (7.4 g, 69.6 mmol) and formic acid (3.2 g, 69.6 mmol) at rt under N2. The mixture was heated to 65° C. for 16 h, cooled to rt, filtered, and concentrated in vacuum. 3N NaOH solution (15 mL) was added and the resulting mixture was stirred for 1 h at 25° C., adjusted to pH~8 with 4N HCl, and extracted with EA (30 mL). The organic phase was dried over anhydrous $Na_2SO_4$, filtered and concentrated to give the crude product, which was purified by chromatography column with DCM:MeOH=10:1 to give 38B (560 mg, Yield: 35%) as a yellow solid. LCMS: (ES+): m/z 230.0.

2-((4-bromo-5-fluoro-1H-benzo[d]imidazol-6-ylamino)pyrimidine-5-carbonitrile (38C)

To a mixture of 4-bromo-5-fluoro-1H-benzo[d]imidazol-6-amine (38B) (100 mg, 0.435 mmol) in i-PrOH (3 mL) was added $K_2CO_3$ (120 mg, 0.87 mmol) and 2-chloropyrimidine-5-carbonitrile (60 mg, 0.435 mmol) at rt. The resulting mixture was then stirred at 90° C. under N2 for 16 h and cooled to rt. The mixture was diluted with $H_2O$ (20 mL) and extracted with EA (30 mL). The organic phase was dried over anhydrous $Na_2SO_4$, filtered and concentrated in vacuum to give the crude product, which was purified by preparative TLC to give 38C (30 mg, Yield: 21%) as a yellow solid. LCMS: (ES+): m/z 333.0.

2-((5-fluoro-4-phenyl-1H-benzo[d]imidazol-6-yl)amino)pyrimidine-5-carbonitrile (38D)

To a mixture of 2-((4-bromo-5-fluoro-1H-benzo[d]imidazol-6-yl)amino)pyrimidine-5-carbonitrile (38C) (30 mg, 0.090 mmol) in $H_2O$ (0.4 mL) and dioxane (2 mL) was added phenylboronic acid (16.5 mg, 0.135 mmol), $Na_2CO_3$ (19 mg, 0.18 mmol) and Pd(dppf)Cl$_2$ (6.6 mg, 0.0090 mmol) under N2. The mixture was stirred at 90° C. for 3 h, cooled to rt, diluted with $H_2O$ (10 mL), and extracted with EA (2×10 mL). The combined organic phases were dried over anhydrous $Na_2SO_4$ and concentrated. The residue was purified by preparative TLC to give 38D (20 mg, Yield: 67%) as a yellow solid. LCMS: (ES+): m/z 331.1.

N-(5-(5-(difluoromethyl)-1,3,4-oxadiazol-2-yl)pyrimidin-2-yl)-5-fluoro-4-phenyl-1H-benzo[d]imidazol-6-amine (38)

To a solution of 2-((5-fluoro-4-phenyl-11H-benzo[d]imidazol-6-yl)amino)pyrimidine-5-carbonitrile (38D) (20 mg, 0.0605 mmol) in DMF (2 mL) was added sodium azide (8 mg, 0.12 mmol) and CuI (19 mg, 0.12 mmol) under $N_2$. The mixture was stirred at 130° C. for 1 h at which time LCMS showed the reaction was complete to give 38E. The mixture was cooled to 10° C. and DFAA (53 mg, 0.3 mmol) was added. The resulting mixture was warmed to 80° C., and stirred for 1 h. The mixture was then cooled to rt, poured into a solution of 1M NaHCO$_3$ (5 mL), and stirred at rt for 15 min. The precipitated solid was filtered and purified by preparative HPLC to give (37) (7.3 mg, Yield: 28%) as a yellow solid and as the corresponding TFA salt. LCMS: (ES+): m/z 424.1 1H NMR (400 MHz, DMSO-d$_6$): δ 12.57-12.65 (m, 1H), 10.03-10.05 (m, 1H), 8.98-9.00 (m, 2H), 8.21-8.27 (m, 1H), 7.72-7.78 (m, 2H), 7.42-7.59 (m, 5H).

Example 39. N-(5-(5-(difluoromethyl)-1,3,4-oxadiazol-2-yl)pyrimidin-2-yl)-7-fluoro-4-phenyl-1H-benzo[d]imidazol-6-amine

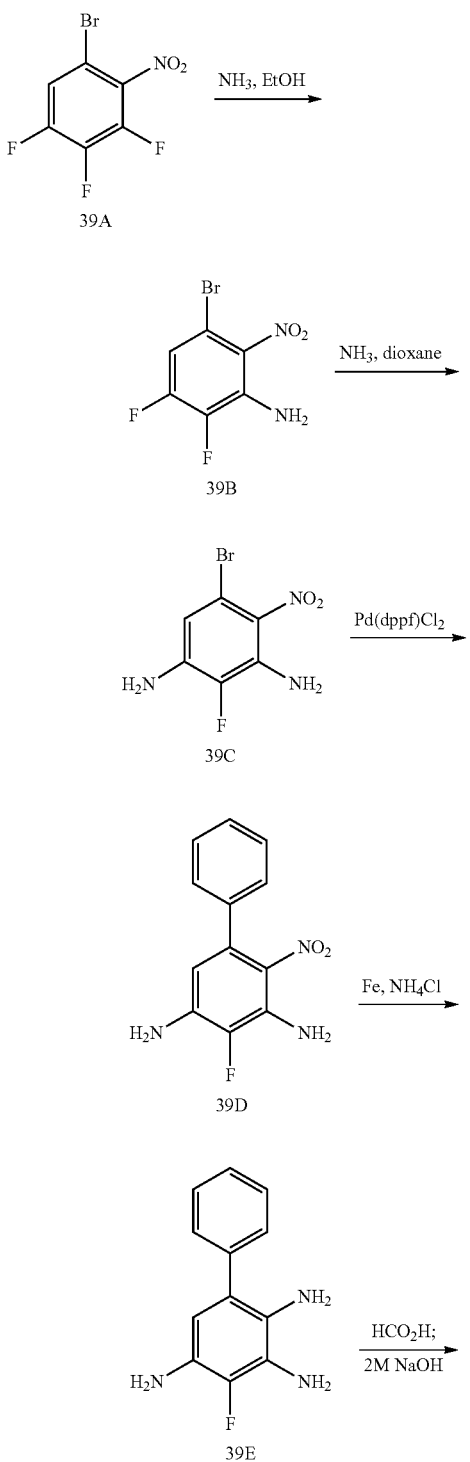

-continued

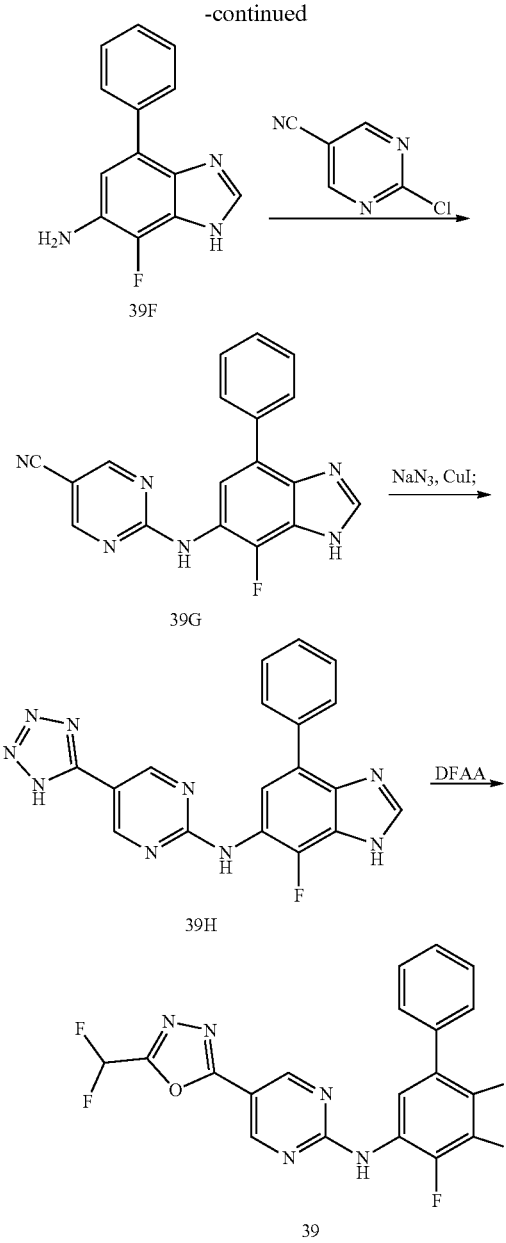

3-bromo-5,6-difluoro-2-nitroaniline (39B)

To a solution of 1-bromo-3,4,5-trifluoro-2-nitrobenzene (39A) (1.0 g, 3.92 mmol) in EtOH (10 mL) was added ammonium hydroxide sol. (0.5 mL) and the mixture was stirred at 25° C. for 3 h. The solution was concentrated in vacuum, and the residue purified by column chromatography (EA/PE=1/50) to give (39B) (800 mg, Yield: 81%) as a yellow solid.

5-bromo-2-fluoro-4-nitrobenzene-1,3-diamine (39C)

To a solution of 3-bromo-5,6-difluoro-2-nitroaniline (39B) (800 mg) in EtOH (10 mL) was added ammonium hydroxide sol. (1.5 mL) and the mixture was stirred at 100° C. for 12 h. The solution was concentrated in vacuum and the residue purified by column chromatography (EA/PE=1/20) to give (39C) (700 mg, Yield: 88%) as a yellow solid. LCMS: (ES+): m/z 250.0.

4-fluoro-2-nitro-[1,1'-biphenyl]-3,5-diamine (39D)

To a suspension of 5-bromo-2-fluoro-4-nitrobenzene-1,3-diamine (39C) (700 mg, 2.8 mmol), phenylboronic acid (686 mg, 5.6 mmol) and $K_2CO_3$ (773 mg, 5.6 mmol) in 1,4-dioxane (20 mL) and water (2 mL) was added Pd(dppf)Cl$_2$ (220 mg, 0.3 mmol), and the resulting mixture was stirred at 90° C. for 12 h under N2. The mixture was then cooled to rt, poured into water (20 mL) and extracted with EA. The organic phase was dried over anhydrous $Na_2SO_4$, filtered and concentrated in vacuum. The residue was purified by preparative TLC (EA/PE=1/3) to give (39D) (650 mg, Yield: 93%) as a yellow solid. LCMS: (ES+): m/z 228.1.

4-fluoro-[1,1'-biphenyl]-2,3,5-triamine (39E)

To a suspension of 4-fluoro-2-nitro-[1,1'-biphenyl]-3,5-diamine (39D) (680 mg, 2.75 mmol) and iron powder (462 mg, 8.25 mmol) in EtOH/$H_2O$ (20/2 mL) was added $NH_4Cl$ (735 mg, 13.8 mmol), and the mixture was stirred at 80° C. for 4 h. The mixture was cooled to rt, filtered through Celite™, and the filtrate was concentrated in vacuum. The crude product was purified by preparative TLC (EA/PE=1/3) to give (39E) (300 mg, Yield: 50%) as a yellow solid. LCMS: (ES+): m/z 218.1.

7-fluoro-4-phenyl-1H-benzo[d]imidazol-6-amine (39F)

A solution of 4-fluoro-[1,1'-biphenyl]-2,3,5-triamine (39E) (300 mg, 1.38 mmol) in formic acid (5 mL) was stirred at 90° C. for 1 h. The mixture was concentrated in vacuum to give the crude corresponding benzimidazole derivative which was dissolved in MeOH (2 mL). Aqueous NaOH (3.0 N, 5.0 mL) was then added and resulting mixture was stirred at 20° C. for 2 h. Aqueous HCl (1.0 N) was added slowly to adjust the pH to 8, and the product was extracted with EA. The organic phase was dried over anhydrous $Na_2SO_4$, filtered and concentrated in vacuum to give the crude product (39F) (200 mg, Yield: 64%) as a yellow solid which was used directly in the next step. LCMS: (ES+): m/z 228.1.

2-((7-fluoro-4-phenyl-1H-benzo[d]imidazol-6-yl)amino)pyrimidine-5-carbonitrile (39G)

To a mixture of 7-fluoro-4-phenyl-1H-benzo[d]imidazol-6-amine (39F) (200 mg, 0.88 mmol) and 2-chloropyrimidine-5-carbonitrile (135 mg, 0.97 mmol) in i-PrOH (5 mL), was added $K_2CO_3$ (243 mg, 1.76 mmol) and the solution was stirred at 90° C. for 12 h. The mixture was cooled to rt, diluted with EA and washed with brine (2×). The organic phase was dried over anhydrous $Na_2SO_4$, filtered and concentrated in vacuum. The residue was recrystallized with EA:PE=1:1 to obtain (39G) (200 mg, Yield: 69%) as a yellow solid. LCMS: (ES+): m/z 331.1.

N-(5-(5-(difluoromethyl)-1,3,4-oxadiazol-2-yl)pyrimidin-2-yl)-7-fluoro-4-phenyl-1H-benzo[d]imidazol-6-amine (39)

To a solution of 2-((7-fluoro-4-phenyl-1H-benzo[d]imidazol-6-yl)amino)pyrimidine-5-carbonitrile (39G) (100 mg, 0.303 mmol) and sodium azide (65 mg, 1.0 mmol) in DMF (3.0 mL) was added CuI (11.4 mg, 0.060 mmol). The mixture was stirred at 120° C. for 3 h at which time, LCMS showed the reaction was complete to give 39H. The mixture was cooled to 10° C., and DFAA (0.3 mL) was added. The mixture was warmed to 90° C. and stirred for 3 h. The mixture was cooled to rt, poured into 1N Na$_2$CO$_3$ sol. (20 mL) and stirred for 2 h. The reaction mixture was extracted with EA (20 mL×2) and the combined organic layers were dried over anhydrous Na$_2$SO$_4$, filtered, and concentrated in vacuum. The residue was purified by preparative HPLC to give (39) (11.5 mg, Yield: 9.0%) as a light-yellow solid and as the corresponding TFA salt. LCMS: (ES+): m/z 424.2 $^1$H NMR (400 MHz, DMSO-d$_6$): ☐ 10.19 (s, 1H), 9.00 (s, 2H), 8.61 (s, 1H), 7.80-7.82 (d, J=8.0 Hz, 2H), 7.42-7.68 (m, 6H).

Example 40. N-(5-(5-(difluoromethyl)-1,3,4-oxadiazol-2-yl)pyrimidin-2-yl)-4-(1-methyl-1H-pyrazol-5-yl)-1H-benzo[d]imidazol-6-amine

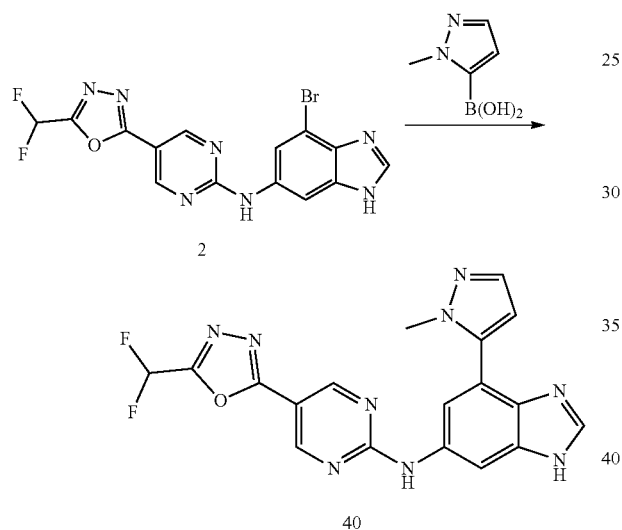

N-(5-(5-(difluoromethyl)-1,3,4-oxadiazol-2-yl)pyrimidin-2-yl)-4-(1-methyl-1H-pyrazol-5-yl)-1H-benzo[d]imidazol-6-amine (40)

To a solution of 4-bromo-N-(5-(5-(difluoromethyl)-1,3,4-oxadiazol-2-yl)pyrimidin-2-yl)-1H-benzo[d]imidazol-6-amine (2) (200 mg, 0.49 mmol) and (1-methyl-1H-pyrazol-5-yl) boronic acid (124 mg, 0.98 mmol) in dioxane/H$_2$O (10.0 mL/1.0 mL) was added Pd(dppf)Cl$_2$ (36.6 mg, 0.050 mmol) and K$_2$CO$_3$ (203 mg, 1.47 mmol). The mixture was stirred at 90° C. for 12 h under N2 at which time, LCMS showed the reaction was complete. The solution was cooled to rt, diluted with EA, and washed with brine three times. The organic layer was dried over anhydrous Na$_2$SO$_4$, filtered, concentrated in vacuum and the residue was purified by preparative HPLC to give (40) (23.0 mg, yield: 9.3%) as a white solid and as the corresponding TFA salt. LCMS: (ES+): m/z 410.2 [M+1]+, $^1$H NMR (400 MHz, DMSO-d$_6$): δ 10.79 (s, 1H), 9.13-9.15 (m, 3H), 8.44 (s, 1H), 7.82 (s, 1H), 7.63 (s, 1H), 7.58 (t, J=51.2 Hz, 1H), 6.60 (s, 1H), 3.85 (s, 3H).

Example 41. 2-(6-((5-(5-(difluoromethyl)-1,3,4-oxadiazol-2-yl)pyrimidin-2-yl)amino)-4-phenyl-2-(trifluoromethyl)-1H-benzo[d]imidazol-1-yl)ethan-1-ol

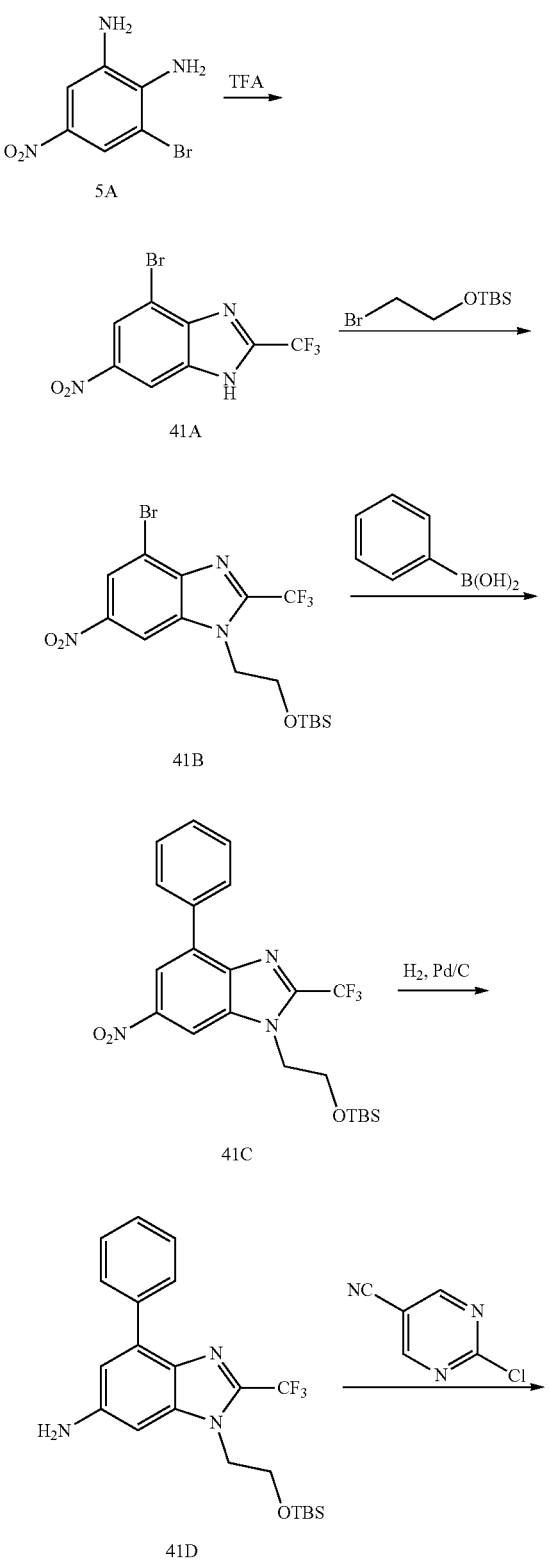

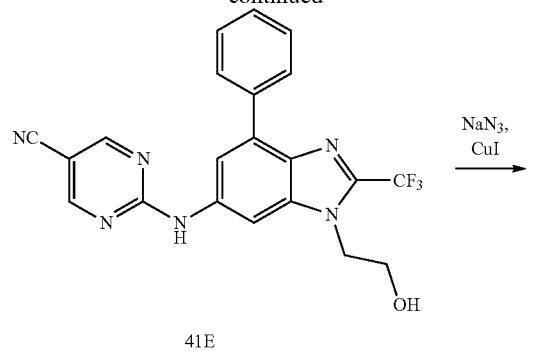

41E

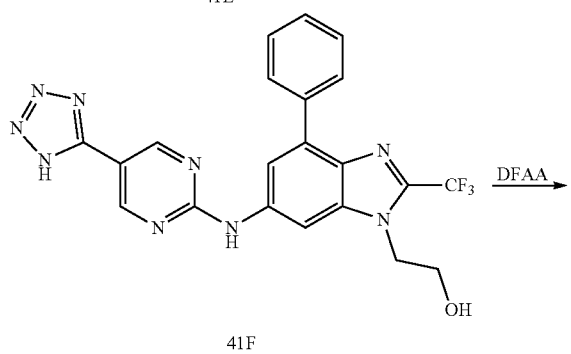

41F

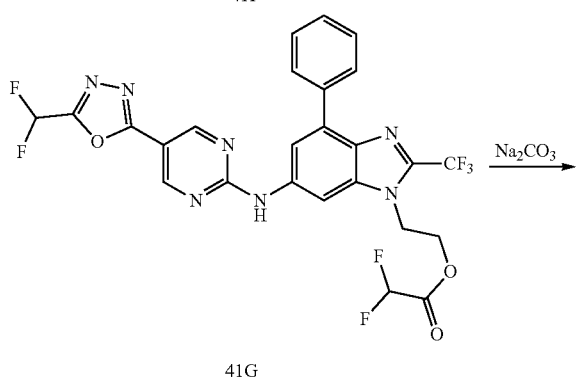

41G

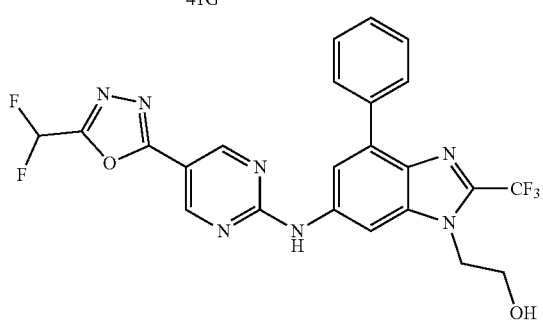

41

4-bromo-6-nitro-2-(trifluoromethyl)-1H-benzo[d]imidazole (41A)

A solution of 3-bromo-5-nitrobenzene-1,2-diamine (5A) (3.0 g, 12.9 mmol) in trifluoroacetic acid (10.3 g, 90.5 mmol) was stirred at 90° C. for 16 h. The mixture was diluted with water (15 mL) and extracted with EA. The organic phase was dried over anhydrous Na$_2$SO$_4$, filtered and concentrated in vacuum. The residue was purified by column chromatography (EA/PE=1/4 to 1/2) to give 41A (3.2 g, yield: 80%) as a yellow solid. LCMS: (ES+): m/z 310.0 [M+1]$^+$.

4-bromo-1-(2-((tert-butyldimethylsilyl)oxy)ethyl)-6-nitro-2-(trifluoromethyl)-1H-benzo[d]imidazole (41B)

To a solution of 4-bromo-6-nitro-2-(trifluoromethyl)-1H-benzo[d]imidazole (1.0 g, 3.23 mmol) (41A) in DMF (10 mL) was added K$_2$CO$_3$ (890 mg, 6.45 mmol) and 2-bromoethoxy tert-butyldimethylsilane (2.32 mg, 9.7 mmol). The mixture was stirred at 80° C. for 16 h, cooled, diluted with water (20 mL), and extracted with EA. The organic phase was dried over anhydrous Na$_2$SO$_4$, filtered and concentrated in vacuum. The residue was purified by column chromatography (EA/PE=1/20 to 1/10) to give (41B1) (0.85 g, yield: 54%) as an orange solid. LCMS: (ES+): m/z 468.0 [M+1]$^+$.

1-(2-((tert-butyldimethylsilyl)oxy)ethyl)-6-nitro-4-phenyl-2-(trifluoromethyl)-1H-benzo[d]imidazole (41C)

To a suspension of 4-bromo-1-(2-((tert-butyldimethylsilyl)oxy)ethyl)-6-nitro-2-(trifluoromethyl)-1H-benzo[d]imidazole (41B) (850 mg, 1.81 mmol), 4-bromothiazole (340 mg, 2.72 mmol) and K$_2$CO$_3$ (0.65 g, 3.63 mmol) in 1,4-dioxane (8.0 mL) and water (1.0 mL) was added Pd(dppf)Cl$_2$ (133 mg, 0.18 mmol). The mixture was stirred at 90° C. for 16 h, cooled to rt, poured into water and extracted with EA. The organic phase was dried over anhydrous Na$_2$SO$_4$, filtered and concentrated. The residue was purified by column chromatography (EA:PE=1:20 to 1:10) to give (41C) (700 mg, yield: 83%) as an orange oil. LCMS: (ES+): m/z 466.1 [M+1]$^+$.

1-(2-((tert-butyldimethylsilyl)oxy)ethyl)-4-phenyl-2-(trifluoromethyl)-1H-benzo[d]imidazol-6-amine (41D)

To a solution of 1-(2-((tert-butyldimethylsilyl)oxy)ethyl)-6-nitro-4-phenyl-2-(trifluoromethyl)-1H-benzo[d]imidazole (41C) (0.95 mg, 2.04 mmol) in MeOH (10 mL) was added Pd/C (500 mg). The mixture was stirred at 20° C. for 3 h under an atmosphere of H2. The mixture was filtered through Celite™, and the Celite™ pad was washed with MeOH. The filtrate was concentrated in vacuum to give crude 41D (700 mg, yield: 80%) as an orange oil which was used directly in the next step. LCMS: (ES+): m/z 436.2 [M+1]$^+$.

2-((1-(2-hydroxyethyl)-4-phenyl-2-(trifluoromethyl)-1H-benzo[d]imidazol-6-yl)amino)pyrimidine-5-carbonitrile (41E)

A mixture of 1-(2-((tert-butyldimethylsilyl)oxy)ethyl)-4-phenyl-2-(trifluoromethyl)-1H-benzo[d]imidazol-6-amine (41D) (700 mg, 1.61 mmol), 2-chloropyrimidine-5-carbonitrile (230 mg, 1.61 mmol) and K$_2$CO$_3$ (444 mg, 3.22 mmol) in i-PrOH (20 mL) was stirred at 65° C. for 4 h. The reaction was cooled and the precipitate was filtered, washed with methanol and dried in vacuo to give 41E (500 mg, yield: 73%) as a yellow solid. LCMS: (ES+): m/z 425.1 [M+1]$^+$.

2-(6-((5-(5-(difluoromethyl)-1,3,4-oxadiazol-2-yl)pyrimidin-2-yl)amino)-4-phenyl-2-(trifluoromethyl)-1H-benzo[d]imidazol-1-yl)ethan-1-ol (41)

To a solution of 2-((1-(2-hydroxyethyl)-4-phenyl-2-(trifluoromethyl)-1H-benzo[d]imidazol-6-yl)amino)pyrimidine- 5-carbonitrile (41E) (200 mg, 0.472 mmol) and sodium azide (62 mg, 0.954 mmol) in DMF (5.0 mL) was added CuI (18 mg, 0.095 mmol). The mixture was stirred at 130° C. for 1.0 h at which time, LCMS showed the reaction was complete to give (41F). The mixture was then cooled to 20° C. and DFAA (820 mg, 4.71 mmol) was added. The mixture was warmed to 80° C., stirred for 1 h, and cooled to rt to provide crude (41G). The solution containing (41G) was then poured into a flask containing 1N Na$_2$CO$_3$ sol. (20 mL), and the mixture was stirred at rt for 2 h, at which time it was extracted with EA (20 mL×2). The combined organic layers were dried over anhydrous Na$_2$SO$_4$, filtered, and concentrated, and the residue was purified by preparative HPLC to give (41) (110 mg, yield: 45%) as a light-yellow solid. LCMS: (ES+): m/z 518.1 [M+1]$^+$ $^1$HNMR (400 MHz, DMSO-d$_6$): δ 10.68 (s, 1H), 9.13 (s, 2H), 8.34 (s, 1H), 7.98 (d, J=7.6 Hz, 2H), 7.85 (s, 1H), 7.70-7.44 (m, 4H), 5.12 (t, J=5.6 Hz, 1H), 4.42-4.48 (m, 2H), 3.82-3.88 (m, 2H).

Example 42. N-(5-(5-(difluoromethyl)-1,3,4-oxadiazol-2-yl)pyrimidin-2-yl)-4-(2-fluoro-4-iodophenyl)-1H-benzo[d]imidazol-6-amine

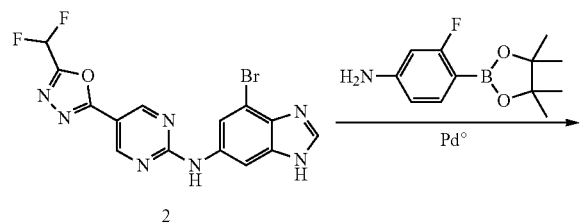

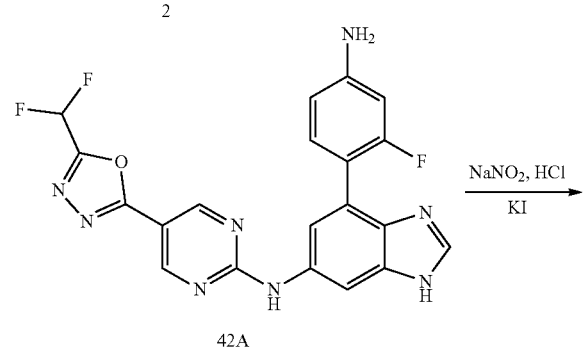

4-(4-amino-2-fluorophenyl)-N-(5-(5-(difluoromethyl)-1,3,4-oxadiazol-2-yl)pyrimidin-2-yl)-1H-benzo[d]imidazol-6-amine (42A)

To a solution of 4-bromo-N-(5-(5-(difluoromethyl)-1,3,4-oxadiazol-2-yl)pyrimidin-2-yl)-1H-benzo[d]imidazol-6-amine (2) (200 mg, 0.49 mmol) and 3-fluoro-4-(4,4,5,5-tetramethyl-1,3,2-dioxaborolan-2-yl)aniline (232 mg, 0.98 mmol) in dioxane/H$_2$O (10.0 mL/1.0 mL) was added Pd(dppf)Cl$_2$ (36.6 mg, 0.050 mmol) and K$_2$CO$_3$ (203 mg, 1.47 mmol). The mixture was stirred at 90° C. for 12 h under N2 at which time, LCMS showed the reaction was complete. The solution was diluted with EA, and washed with brine three times. The organic layer was dried over anhydrous Na$_2$SO$_4$, filtered, and concentrated. The residue was purified by preparative TLC to give (42A) (150 mg, yield: 70%) as a yellow solid. LCMS: (ES+): m/z 439.1 [M+1]$^+$.

N-(5-(5-(difluoromethyl)-1,3,4-oxadiazol-2-yl)pyrimidin-2-yl)-4-(2-fluoro-4-iodophenyl)-1H-benzo[d]imidazol-6-amine (42)

To a solution of hydrochloric acid (4N, 3.0 mL) at −10° C. was added 4-(4-amino-2-fluorophenyl)-N-(5-(5-(difluoromethyl)-1,3,4-oxadiazol-2-yl)pyrimidin-2-yl)-1H benzo[d]imidazol-6-amine (42A) (150 mg, 0.34 mmol), followed by a solution of sodium nitrite (500 mg, 7.25 mmol) in water (2.0 mL) while maintaining the temperature below 0° C. After the addition, the reaction mixture was stirred for 15 min to obtain the corresponding diazonium salt solution. In a separate 50 mL three-necked flask was added KI (1.00 g, 6.02 mmol), water (6.0 mL) and the diazonium salt solution prepared above dropwise with stirring while maintaining the temperature below 0° C. After the addition, the reaction mixture was stirred for 12 h at 0° C. The solution was adjusted to pH>8 with 1N Na$_2$CO$_3$ sol. and extracted with EA (2×50 mL). The combined organic layers were dried over anhydrous Na$_2$SO$_4$, filtered and concentrated. The residue was purified by preparative HPLC to give (42) (13.0 mg, yield: 6%) as a white solid as the corresponding TFA salt. LCMS: (ES+): m/z 550.1 [M+1]$^+$ $^1$H NMR (400 MHz, DMSO-d$_6$): δ 10.80 (s, 1H), 9.23 (s, 1H), 9.13 (s, 2H), 8.50 (s, 1H), 7.89 (d, J=9.6 Hz, 1H), 7.77-7.82 (m, 2H), 7.42-7.68 (m, 2H).

Example 43. N-(5-(5-(difluoromethyl)-1,3,4-oxadiazol-2-yl)pyrimidin-2-yl)-2-((dimethylamino)methyl)-4-phenyl-1H-benzo[d]imidazol-6-amine

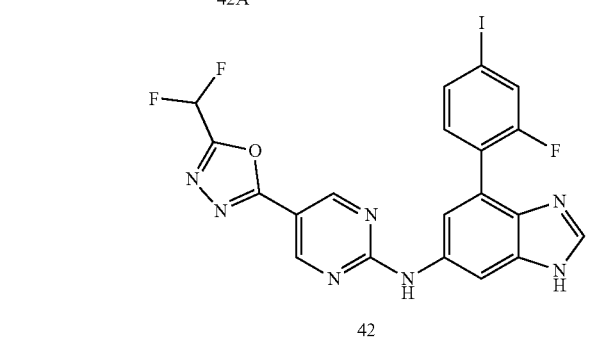

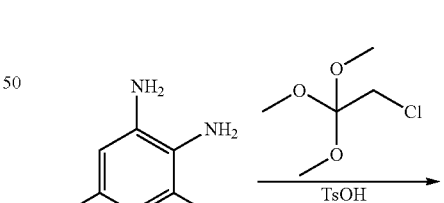

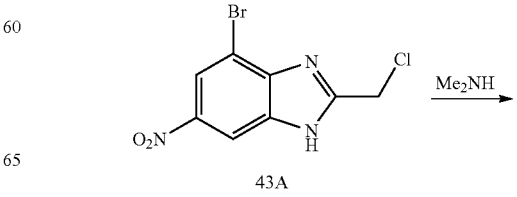

113
-continued

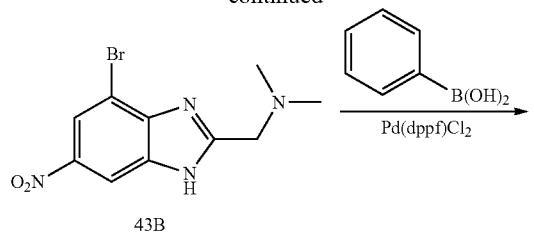

43B

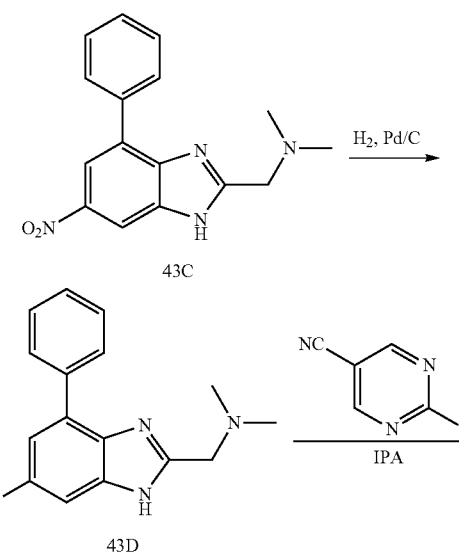

43C

43D

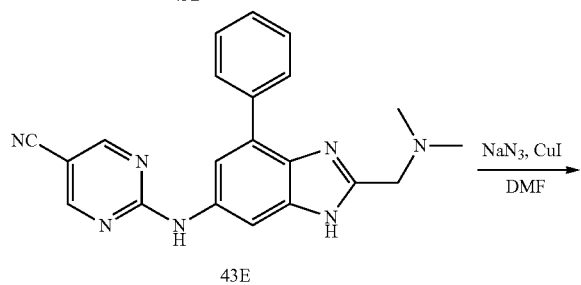

43E

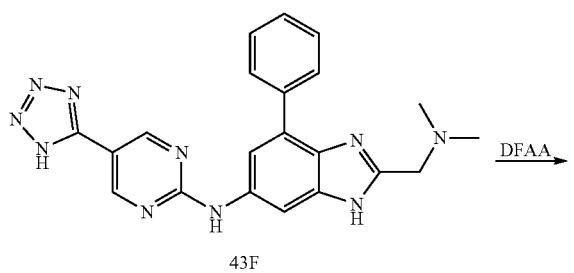

43F

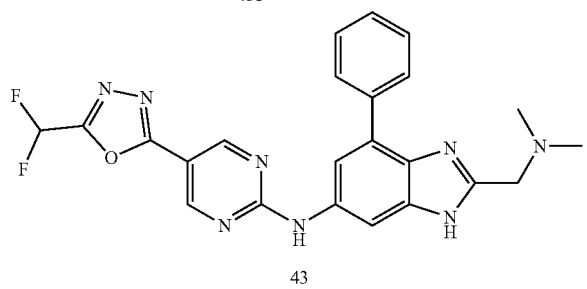

43

114

4-bromo-2-(chloromethyl)-6-nitro-1H-benzo[d]imidazole (43A)

To a solution of 3-Bromo-5-nitro-1,2-diaminobenzene (5A) (5.0 g, 22 mmol) in DCM (100 mL) under N2 was added 2-chloro-1,1,1-trimethoxyethane (6.65 g, 108 mmol) and p-TsOH.H$_2$O (0.41 g, 2.2 mmol). The mixture was stirred 25° C. for 16 h at which time, it was diluted with water (50 mL) and extracted with DCM (50 mL). The organic phase was dried over anhydrous Na$_2$SO$_4$ and concentrated in vacuo. The residue was purified by column chromatography (PE:EA=10:1~6:1) to give (43A) (5.1 g, yield: 80%) as a yellow solid. LCMS: (ES+): m/z 290.0 [M+1]$^+$.

1-(4-bromo-6-nitro-1H-benzo[d]imidazol-2-yl)-N,N-dimethylmethanamine (43B)

To a solution of 4-bromo-2-(chloromethyl)-6-nitro-1H-benzo[d]imidazole (43A) (6.0 g, 20.6 mmol) in MeCN (120 mL) was added Me$_2$NH (30 mL, 2N in MeOH) at 25° C. and the resulting mixture was stirred at 25° C. for 10 h. The mixture was diluted with water (50 mL) and extracted with EA (50 mL×2). The combined organic layers were dried over anhydrous Na$_2$SO$_4$ and concentrated in vacuo to give the crude product, which was purified by column chromatography (DCM:MeOH=10:1) to give (42B) (4.1 g, yield: 66%) as a yellow solid.

N,N-dimethyl-1-(6-nitro-4-phenyl-1H-benzo[d]imidazol-2-yl)methanamine (43C)

To a mixture of 1-(4-bromo-6-nitro-1H-benzo[d]imidazol-2-yl)-N,N-dimethylmethanamine (43B) (2.5 g, 8.36 mmol) in H$_2$O (5.0 mL) and dioxane (25 mL) was added phenylboronic acid (1.5 g, 12.5 mmol), Na$_2$CO$_3$ (1.78 g, 16.72 mmol) and Pd(dppf)Cl$_2$ (0.6 g, 0.836 mmol) under N2. The mixture was stirred at 90° C. for 16 h and cooled to rt. The mixture was then diluted with H$_2$O (50 mL), extracted with DCM:MeOH=10:1 (50 mL×2), dried over Na$_2$SO$_4$ and concentrated in vacuo to give the crude product, which was purified by column chromatography (DCM:MeOH=10:1) to give (43C) (1.68 g, yield: 68%) as a yellow solid. LCMS: (ES+) m/z 297.2 [M+1]$^+$.

2-((dimethylamino)methyl)-4-phenyl-1H-benzo[d]imidazol-6-amine (43D)

To a mixture of N,N-dimethyl-1-(6-nitro-4-phenyl-1H-benzo[d]imidazol-2-yl)methanamine (43C) (1.68 g, 5.67 mol) in MeOH (30 mL) was added 10% Pd/C (150 mg) at 25° C. under an atmosphere of H2. The mixture was stirred at 25° C. for 10 h and filtered through Celite™. Evaporation gave (43D) (1.5 g, yield: 99%) as a yellow oil which was used directly in the next step. LCMS: (ES+): m/z 267.1 [M+1]$^+$.

2-((2-((dimethylamino)methyl)-4-phenyl-1H-benzo[d]imidazol-6-yl)amino)pyrimidine-5-carbonitrile (43E)

A mixture of 2-((dimethylamino)methyl)-4-phenyl-1H-benzo[d]imidazol-6-amine (43D) (900 mg, 3.38 mmol) and 2-chloropyrimidine-5-carbonitrile (470 mg, 3.38 mmol) in i-PrOH (18 mL) was stirred at 90° C. for 16 h. The mixture was cooled to rt and concentrated, and the residue was purified by chromatography to give (43E) (120 mg, yield: 9.6%) as a yellow solid. LCMS: (ES+): m/z 370.2 [M+1]+.

N-(5-(5-(difluoromethyl)-1,3,4-oxadiazol-2-yl)pyrimidin-2-yl)-2-((dimethylamino)methyl-4-phenyl-1H-benzo[d]imidazol-6-amine (43)

To a solution of 2-((2-((dimethylamino)methyl-4-phenyl-1H-benzo[d]imidazol-6-yl)amino)pyrimidine-5-carbonitrile (43E) (120 mg, 0.452 mmol) in DMF (5.0 mL) was added sodium azide (60 mg, 0.923 mmol) and CuI (144 mg, 0.756 mmol) under N2. The mixture was stirred at 130° C. for 1 h at which time, LCMS showed the reaction was complete to give (43F). The mixture was then cooled to 10° C. and DFAA (1.17 g, 6.78 mmol) was added. The resulting mixture was stirred at 80° C. for 1 hr, cooled to rt, and added to 1N NaHCO₃ sol. (20 mL). The mixture was stirred at rt for 15 min and extracted with EA (50 mL). The organic layer was dried with anhydrous Na₂SO₄, filtered and concentrated. The residue was purified by preparative HPLC to give (43) (18.8 mg, yield: 7.4%) as a yellow solid and as the corresponding TFA salt. LCMS: (ES+): m/z 463.2 [M+1]⁺.

Example 44. N-(5-(5-(difluoromethyl)-1,3,4-oxadiazol-2-yl)pyrimidin-2-yl)-4-(1H-pyrazol-4-yl)-1H-benzo[d]imidazol-6-amine

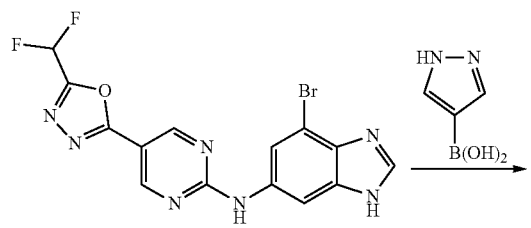

N-(5-(5-(difluoromethyl)-1,3,4-oxadiazol-2-yl)pyrimidin-2-yl)-4-(1H-pyrazol-4-yl)-1H-benzo[d]imidazol-6-amine (44)

To a solution of 4-bromo-N-(5-(5-(difluoromethyl)-1,3,4-oxadiazol-2-yl)pyrimidin-2-yl)-1H-benzo[d]imidazol-6-amine (2) (200 mg, 0.49 mmol) and (1H-pyrazol-4-yl) boronic acid (110 mg, 0.98 mmol) in dioxane/H₂O (10.0 mL/1.0 mL) was added Pd(dppf)Cl₂ (36.6 mg, 0.05 mmol) and K₂CO₃ (203 mg, 1.47). The mixture was stirred at 90° C. for 12 h under N2, at which time, LCMS showed the reaction was complete. The solution was cooled, diluted with EA (50 mL), and washed with brine (50 mL×3). The organic layer was dried over anhydrous Na₂SO₄, filtered, and concentrated, and the residue was purified by preparative HPLC to give (44) (22.0 mg, yield: 11%) as a white solid and as the corresponding TFA salt. LCMS: (ES+): m/z 396.2 [M+1]⁺¹H NMR (400 MHz, DMSO-d₆): δ 10.63 (s, 1H), 9.10-9.13 (m, 3H), 8.22-8.27 (m, 3H), 7.91 (s, 1H), 7.58 (t, J=51.2 Hz, 1H).

Example 45. 4-(5-chloro-2-fluorophenyl)-N-(5-(5-(difluoromethyl)-1,3,4-oxadiazol-2-yl)pyrimidin-2-yl)-1H-benzo[d]imidazol-6-amine

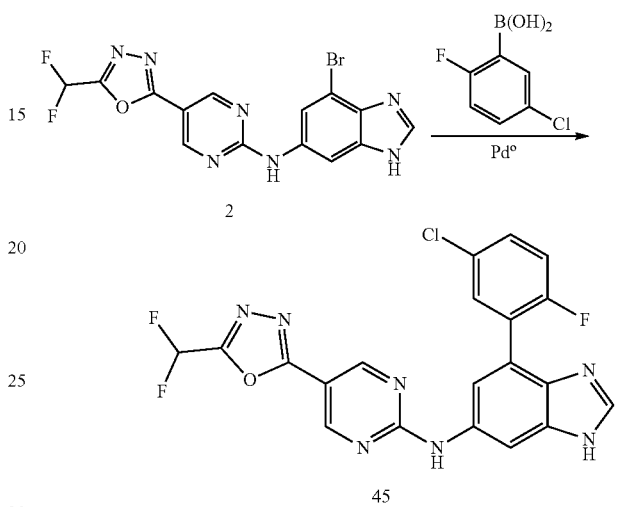

4-(5-chloro-2-fluorophenyl)-N-(5-(5-(difluoromethyl)-1,3,4-oxadiazol-2-yl)pyrimidin-2-yl)-1H-benzo[d]imidazol-6-amine (45)

To a solution of 4-bromo-N-(5-(5-(difluoromethyl)-1,3,4-oxadiazol-2-yl)pyrimidin-2-yl)-1H-benzo[d]imidazol-6-amine (2) (100 mg, 0.246 mmol), (5-chloro-2-fluorophenyl) boronic acid (64.3 mg, 0.369 mmol) and K₂CO₃ (67.8 mg, 0.492 mmol) in 1,4-dioxane (2.0 mL) and water (0.20 mL) was added Pd(dppf)Cl₂ (18.0 mg, 0.025 mmol). The mixture was stirred at 90° C. for 12 h at which time, LCMS showed the reaction was complete. The solution was cooled, diluted with EA (50 mL), and washed with brine (50 mL×3). The organic layer was dried over anhydrous Na₂SO₄, filtered, and concentrated, and the residue was purified by preparative HPLC to give 45 (33.2 mg, yield: 29%) as a light-yellow solid. LCMS: (ES+): m/z 458.1 [M+1]⁺ ¹H NMR (400 MHz, DMSO-d₆): δ 10.71 (s, 1H), 9.13 (s, 2H), 8.97 (br s, 1H), 8.44 (s, 1H), 7.45-7.80 (m, 6H).

Example 46. 2-(6-((5-(5-(difluoromethyl)-1,3,4-oxadiazol-2-yl)pyrimidin-2-yl)amino)-4-(1H-pyrazol-4-yl)-1H-benzo[d]imidazol-1-yl)ethan-1-ol

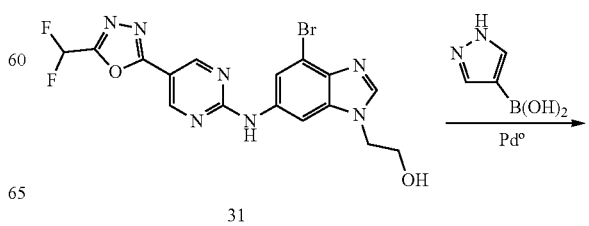

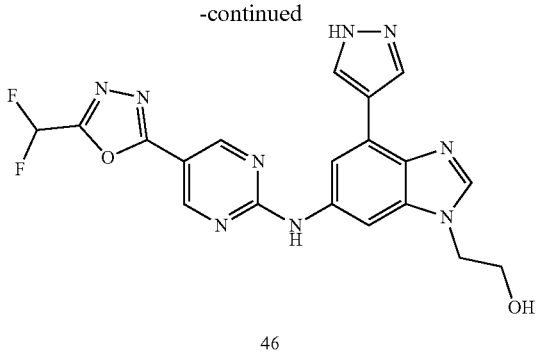

46

2-(6-((5-(5-(difluoromethyl)-1,3,4-oxadiazol-2-yl)pyrimidin-2-yl)amino)-4-(1H-pyrazol-4-yl)-1H-benzo[d]imidazol-1-yl)ethan-1-ol (46)

To a solution of 2-(4-bromo-6-((5-(5-(difluoromethyl)-1,3,4-oxadiazol-2-yl)pyrimidin-2-yl)amino)-1H-benzo[d]imidazol-1-yl)ethan-1-ol (31) (100 mg, 0.246 mmol), (5-chloro-2-fluorophenyl) boronic acid (64.3 mg, 0.369 mmol) and $K_2CO_3$ (67.8 mg, 0.492 mmol) in 1,4-dioxane (2.0 mL) and water (0.20 mL) was added Pd(dppf)Cl$_2$ (18.0 mg, 0.025 mmol). The mixture was stirred at 90° C. for 12 h, cooled to rt, poured into water (20 mL) and extracted with EA (20 mL). The organic phase was dried over anhydrous $Na_2SO_4$, filtered and concentrated. The residue was purified by preparative HPLC to give (46) (33.2 mg, yield: 29%) as a light-yellow solid. LCMS: (ES+): m/z 458.1 [M+1]$^+$=3.37 min. 1H NMR (400 MHz, DMSO-d$_6$): δ 10.71 (s, 1H), 9.13 (s, 2H), 8.97 (br s, 1H), 8.44 (s, 1H), 7.45-7.80 (m, 6H).

Example 47

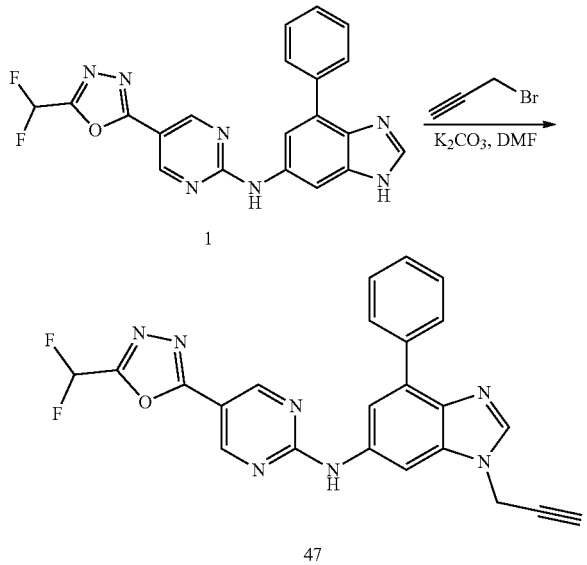

To a solution of N-(5-(5-(difluoromethyl)-1,3,4-oxadiazol-2-yl)pyrimidin-2-yl)-4-phenyl-1H-benzo[d]imidazol-6-amine (1) (40 mg, 0.0987 mmol) and 3-bromoprop-1-yne (17.7 mg, 0.15 mmol) in DMF was added $K_2CO_3$ (27.6 g, 0.20 mmol). The solution was stirred at 25° C. for 12 h. The mixture was diluted with EA (50 mL), and washed twice with brine. The organic layer was dried over anhydrous $Na_2SO_4$, filtered and concentrated. The residue was purified by preparative HPLC to give 47 (6.8 mg, yield: 16%) as a white solid. LCMS: (ES+): m/z 444.1 [M+1]$^+$ $^1$H NMR (400 MHz, DMSO-d$_6$): δ 10.59 (s, 1H), 9.10 (s, 2H), 8.24-8.29 (m, 2H), 8.07 (d, J=7.2 Hz, 2H), 7.78 (s, 1H), 7.31-7.70 (m, 4H), 5.23 (s, 2H), 3.59 (s, 1H).

Example 48. N-(5-(5-(difluoromethyl)-1,3,4-oxadiazol-2-yl)pyrimidin-2-yl)-4-phenyl-1-(2,2,2-trifluoroethyl)-1H-benzo[d]imidazol-6-amine

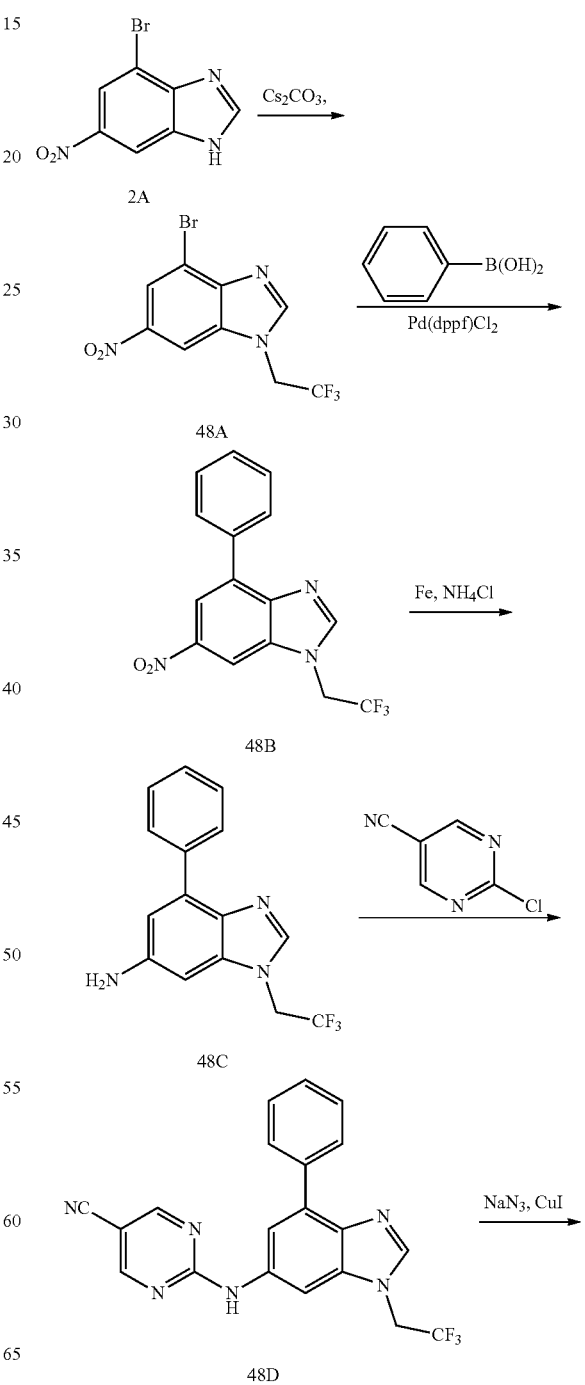

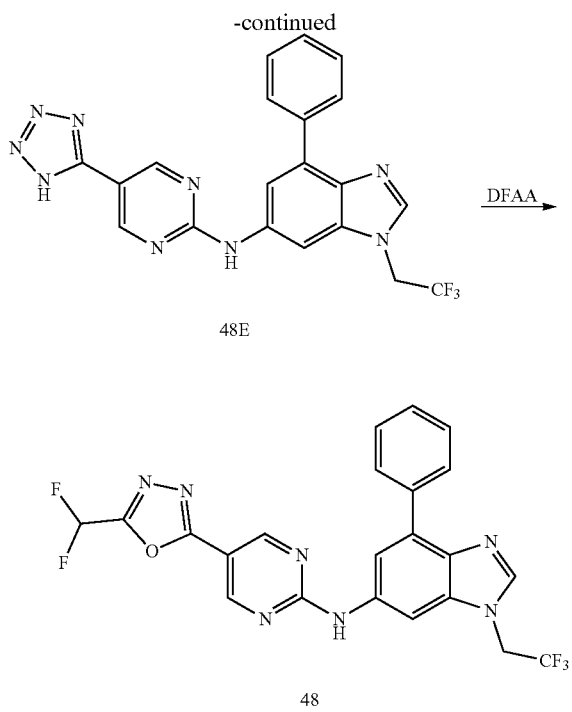

48E

48

4-bromo-6-nitro-1-(2,2,2-trifluoroethyl)-1H-benzo[d]imidazole (48A)

To a solution of 4-bromo-6-nitro-1H-benzo[d]imidazole (2A) (synthesis described in US2013/157977, 2013, A1) (0.50 g, 2.07 mmol) and Cs$_2$CO$_3$ (1.35 g, 4.15 mmol) in DMF (10.0 mL) was added 2,2,2-trifluoroethyl trifluoromethanesulfonate (0.53 g, 2.28 mmol). The mixture was stirred at rt for 12 h. The mixture was diluted with EA, and washed with aq. NH$_4$Cl. The organic phase was dried over anhydrous Na$_2$SO$_4$, filtered and concentrated. The residue was purified by column chromatography (EA/PE=1/10 to 1/5) to give 48A (400 mg, yield: 60%) as a yellow solid. LCMS: (ES+): m/z 324.0 [M+1]$^+$.

6-nitro-4-phenyl-1-(2,2,2-trifluoroethyl)-1H-benzo[d]imidazole (48B)

To a suspension of 4-bromo-6-nitro-1-(2,2,2-trifluoroethyl)-1H-benzo[d]imidazole (48A) (400 mg, 1.24 mmol), phenylboronic acid (303 mg, 2.48 mmol) and K$_2$CO$_3$ (394 mg, 3.72 mmol) in 1,4-dioxane (10.0 mL) and water (2.0 mL) was added Pd(dppf)Cl$_2$ (88.0 mg, 0.12 mmol). The mixture was stirred at 90° C. for 12 h. The mixture was poured into water, extracted with EA (50 mL), and the organic phase was dried over anhydrous Na$_2$SO$_4$, filtered and concentrated. The residue was purified by preparative TLC (EA/PE=1/2) to give (48B) (320 mg, yield: 80%) as a yellow solid and confirmed by 1D-NOE. $^1$H NMR (400 MHz, DMSO-d$_6$): δ 8.87 (s, 1H), 8.75 (s, 1H), 8.31 (s, 1H), 8.08-8.10 (d, J=7.2 Hz, 2H), 7.50-7.58 (m, 2H), 7.43-7.49 (m, 1H), 5.55-5.70 (m, 2H).

4-phenyl-1-(2,2,2-trifluoroethyl)-1H-benzo[d]imidazol-6-amine (48C)

To a mixture of H$_2$O (1.0 mL) and EtOH (10 mL) was added 6-nitro-4-phenyl-1-(2,2,2-trifluoroethyl)-1H-benzo[d]imidazole (48B) (320 mg, 0.99 mmol), iron powder (168 mg, 3.00 mmol) and NH$_4$Cl (268 mg, 5.00 mmol), and the resulting mixture was heated at reflux for 2 h. After cooling, the mixture was poured into water and extracted with EA (2×50 mL). The combined organic layers were dried over anhydrous Na$_2$SO$_4$, filtered and concentrated to give (48C) (150 mg, yield: 52%) as yellow solid, which was used in the next step without further purification. LCMS: (ES+): m/z 292.1 [M+1]$^+$.

2-((4-phenyl-1-(2,2,2-trifluoroethyl)-1H-benzo[d]imidazol-6-yl)amino)pyrimidine-5-carbonitrile (48D)

A mixture of 4-phenyl-1-(2,2,2-trifluoroethyl)-1H-benzo[d]imidazol-6-amine (47C) (150 mg, 0.52 mmol), 2-chloropyrimidine-5-carbonitrile (79 mg, 0.57 mmol) and K$_2$CO$_3$ (144 mg, 1.04 mmol) in i-PrOH (5.0 mL) was stirred at 90° C. for 12 h. The mixture was cooled and concentrated in vacuo and the residue was purified by preparative TLC (EA) to give (48D) (120 mg, yield: 58%) as a yellow solid. LCMS: (ES+): m/z 395.1 [M+1]$^+$.

N-(5-(5-(difluoromethyl)-1,3,4-oxadiazol-2-yl)pyrimidin-2-yl)-4-phenyl-1-(2,2,2-trifluoroethyl)-1H-benzo[d]imidazol-6-amine (48)

To a solution of 2-((4-phenyl-1-(2,2,2-trifluoroethyl)-1H-benzo[d]imidazol-6-yl)amino)pyrimidine-5-carbonitrile (48D) (120 mg, 0.30 mmol) and sodium azide (65.0 mg, 1.0 mmol) in DMF (3.0 mL) was added CuI (11.4 mg, 0.060 mmol). The mixture was stirred at 120° C. for 3 h at which time, LCMS showed the reaction was complete to provide crude (48E). The mixture was allowed to cool to 25° C., DFAA (0.30 mL) was added and the resulting mixture was stirred at 90° C. for 3 h. The reaction mixture then was cooled to rt and was poured into 1N Na$_2$CO$_3$ sol (20.0 mL). The mixture was stirred at rt for 2 h and was then extracted with EA (20 mL×2). The combined organic layers were dried over anhydrous Na$_2$SO$_4$, filtered, and concentrated. The residue was purified by preparative HPLC to give 48 (26.2 mg, yield: 15%) as a white solid and as the corresponding TFA salt. LCMS: (ES+): m/z 488.2 [M+1]$^+$. $^1$H NMR (400 MHz, DMSO-d6): δ 10.61 (s, 1H), 9.09 (s, 2H), 8.41 (s, 1H), 8.26 (s, 1H), 8.03 (d, J=7.2 Hz, 2H), 7.78 (s, 1H), 7.40-7.70 (m, 4H), 5.35-5.42 (m, 2H).

Example 49. N-(5-(5-(difluoromethyl)-1,3,4-oxadiazol-2-yl)pyrimidin-2-yl)-4-phenyl-1-(thiazol-2-yl)-1H-benzo[d]imidazol-6-amine

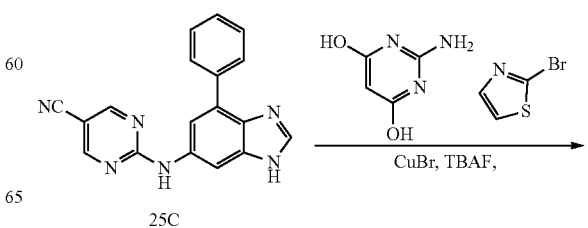

25C

121

-continued

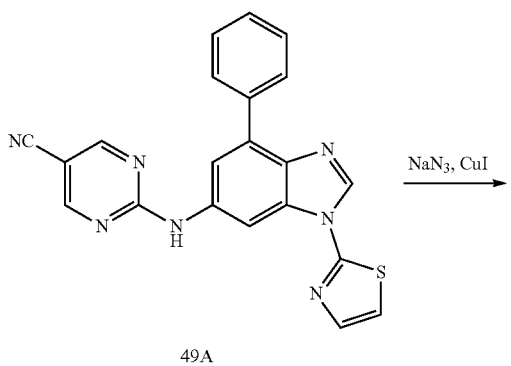

49A

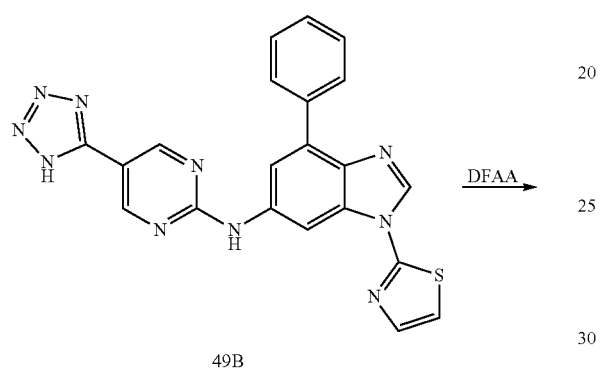

49B

49

2-((4-phenyl-1-(thiazol-2-yl)-1H-benzo[d]imidazol-6-yl)amino)pyrimidine-5-carbonitrile (49A)

A mixture of 2-((4-phenyl-1H-benzo[d]imidazol-6-yl)amino)pyrimidine-5-carbonitrile (25C) (1.30 g, 4.16 mmol), 2-aminopyrimidine-4,6-diol (107 mg, 0.84 mmol), 2-bromothiazole (1.03 g, 6.3 mmol), CuBr (61 mg, 0.42 mmol), and TBAF.3H$_2$O (3.98 g, 12.6 mmol) was stirred at 150° C. for 24 h. The mixture was cooled to rt, diluted with EA, and washed with brine twice. The organic layer was dried over anhydrous Na$_2$SO$_4$, filtered and concentrated. The residue was purified by column chromatography (DCM/MeOH=50/1) to give 49A (100 mg, yield: 6.1%) as a yellow solid. LCMS: (ES+): m/z 396.1 [M+1]$^+$.

122

((4-phenyl-1H-benzo[d]imidazol-6-yl)amino)pyrimidine-5-carbonitrile (49)

To a solution of 2-((4-phenyl-1-(thiazol-2-yl)-1H-benzo[d]imidazol-6-yl)amino)pyrimidine-5-carbonitrile (49A) (100 mg, 0.25 mmol) and sodium azide (65.0 mg, 1.00 mmol) in DMF (3.0 mL) was added CuI (11.4 mg, 0.060 mmol). The mixture was stirred at 120° C. for 3 h at which time, LCMS showed the reaction was complete to give 49B. The mixture was allowed to cool to rt and DFAA (0.30 mL) was added. The mixture was stirred at 90° C. for 3 h, cooled to rt, and was poured into 1N Na$_2$CO$_3$ solution (20 mL). The mixture was stirred at rt for 2 h, and then extracted with EA (20 mL×2). The combined organic layers were dried over anhydrous Na$_2$SO$_4$, filtered and concentrated. The residue was purified by preparative HPLC to give 49 (7.2 mg, yield: 5.8%) as a white solid. LCMS: (ES+): m/z 489.1 [M+1]$^+$ $^1$H NMR (400 MHz, DMSO-d$_6$): δ 10.74 (s, 1H), 9.15 (s, 2H), 8.90-8.95 (m, 2H), 8.04 (d, J=6.8 Hz, 2H), 7.87-7.93 (m, 2H), 7.77 (s, 1H), 7.40-7.71 (m, 4H).

Example 50. 1-(6-((5-(5-(difluoromethyl)-1,3,4-oxadiazol-2-yl)pyrimidin-2-yl)amino)-1H-benzo[d]imidazol-4-yl)pyrrolidin-2-one

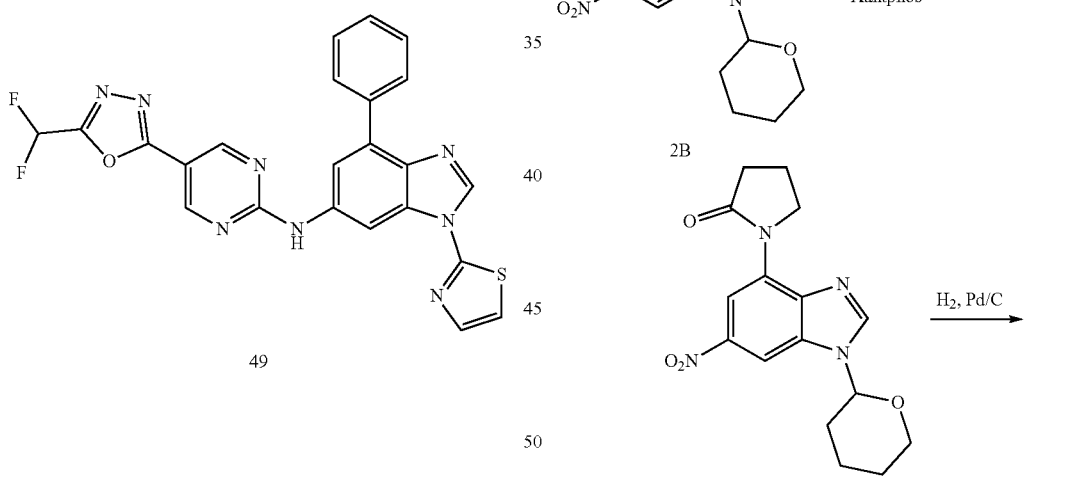

2B

50A

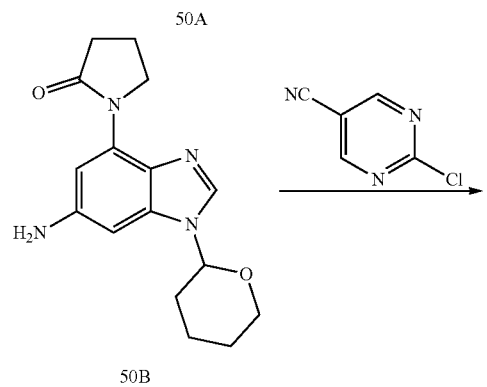

50B

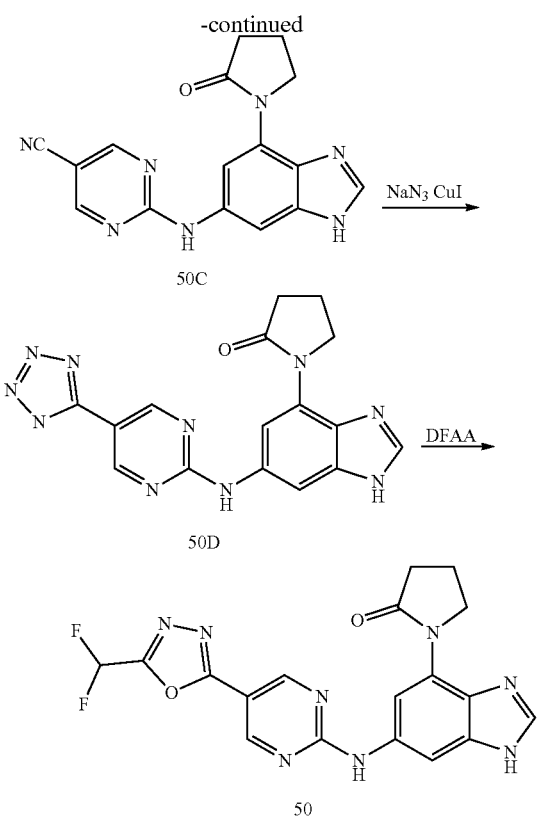

1-(6-nitro-1-(tetrahydro-2H-pyran-2-yl)-1H-benzo[d]imidazol-4-yl)pyrrolidin-2-one (50A)

To a suspension of 4-bromo-6-nitro-1-(tetrahydro-2H-pyran-2-yl)-1H-benzo[d]imidazole 2B (200 mg, 0.615 mmol), pyrrolidin-2-one (78.5 mg, 0.923 mmol) and Cs$_2$CO$_3$ (400 mg, 1.22 mmol) in 1,4-dioxane (8.0 mL) was added Xanthos (53.4 mg, 0.092 mmol), followed by Pd$_2$(dba)$_3$ (56.0 mg, 0.061 mmol) under N2. The mixture was stirred at 100° C. for 16 h, cooled to rt, poured into water (50 mL) and extracted with EA. The organic phase was dried over anhydrous Na$_2$SO$_4$, filtered and concentrated. The residue was purified by column chromatography (EA/PE=1/20 to 1/10) to give 50A (200 mg, yield: 60%) as a yellow solid. LCMS: (ES+): m/z 333.1 [M+1]$^+$.

1-(6-amino-1-(tetrahydro-2H-pyran-2-yl)-1H-benzo[d]imidazol-4-yl)pyrrolidin-2-one (50B)

To a solution of 1-(6-nitro-1-(tetrahydro-2H-pyran-2-yl)-1H-benzo[d]imidazol-4-yl)pyrrolidin-2-one (50A) (200 mg, 0.606 mmol) in MeOH (5.0 mL) was added 10% Pd/C (100 mg). The mixture was stirred at 20° C. for 3 h under an H2 atmosphere. The mixture was filtered through Celite™ and the filtrate was concentrated in vacuo to give 50B (180 mg, yield: 89%) as an orange solid which was used directly in the next step. LCMS: (ES+): m/z 301.2 [M+1]$^+$.

2-((4-(2-oxopyrrolidin-1-yl)-1-(tetrahydro-2H-pyran-2-yl)-1H-benzo[d]imidazol-6-yl)amino)pyrimidine-5-carbonitrile (49C)

A mixture of 1-(6-amino-1-(tetrahydro-2H-pyran-2-yl)-1H-benzo[d]imidazol-4-yl)pyrrolidin-2-one (50B) (100 mg, 0.333 mmol) and 2-chloropyrimidine-5-carbonitrile (47 mg, 0.33 mmol) in i-PrOH (5.0 mL) and K$_2$CO$_3$ (91.9 mg, 0.666 mmol) was stirred at 90° C. for 16 h. The precipitate was filtered, washed with methanol and dried in vacuo to give 50C (80 mg, yield: 60%) as a yellow solid. LCMS: (ES+): m/z 404.2 [M+1]$^+$.

1-(6-((5-(5-(difluoromethyl)-1,3,4-oxadiazol-2-yl)pyrimidin-2-yl)amino)-1H-benzo[d]imidazol-4-yl)pyrrolidin-2-one (50)

To a solution of 2-((4-(2-oxopyrrolidin-1-yl)-1-(tetrahydro-2H-pyran-2-yl)-1H-benzo[d]imidazol-6-yl)amino)pyrimidine-5-carbonitrile (50C) (80 mg, 0.199 mmol) and sodium azide (25.8 mg, 0.397 mmol) in DMF (2.0 mL) was added CuI (7.55 mg, 0.040 mmol). The mixture was stirred at 130° C. for 1.0 h at which time, LCMS showed the reaction was complete to give 50D. The solution was cooled to 10° C., DFAA (345 mg, 1.98 mmol) was added and the mixture was stirred at 80° C. for 1 h. The mixture was then was cooled to rt and poured into 1N Na$_2$CO$_3$ sol. (20 mL). The mixture was stirred at rt for 2 h and extracted with EA (20 mL×2). The combined organic layers were dried over anhydrous Na$_2$SO$_4$, filtered and concentrated. The residue was purified by preparative HPLC to give 50 (9.7 mg, yield: 9.6%) as a light-yellow solid and as the corresponding TFA salt. LCMS: (ES+): m/z 413.2 [M+1]$^+$ $^1$H NMR (400 MHz, DMSO-d$_6$): δ 10.71 (s, 1H), 9.12 (s, 2H), 9.09 (br s, 1H), 8.26 (s, 1H), 7.71 (s, 1H), 7.58 (t, J=51.2 Hz, 1H), 3.99 (t, J=7.2 Hz, 2H), 2.57 (t, J=8.0 Hz, 2H), 2.15-2.25 (m, 2H).

Example 51. N-(5-(5-(difluoromethyl)-1,3,4-oxadiazol-2-yl)pyrimidin-2-yl)-4-(1H-pyrazol-1-yl)-1H-benzo[d]imidazol-6-amine

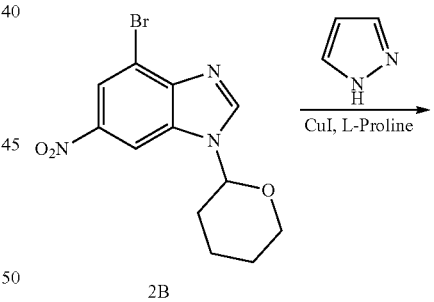

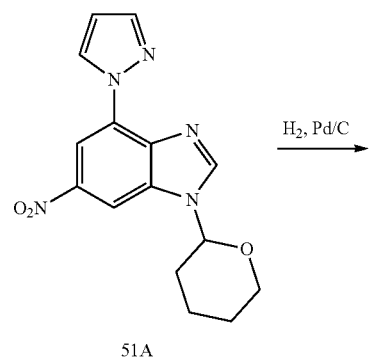

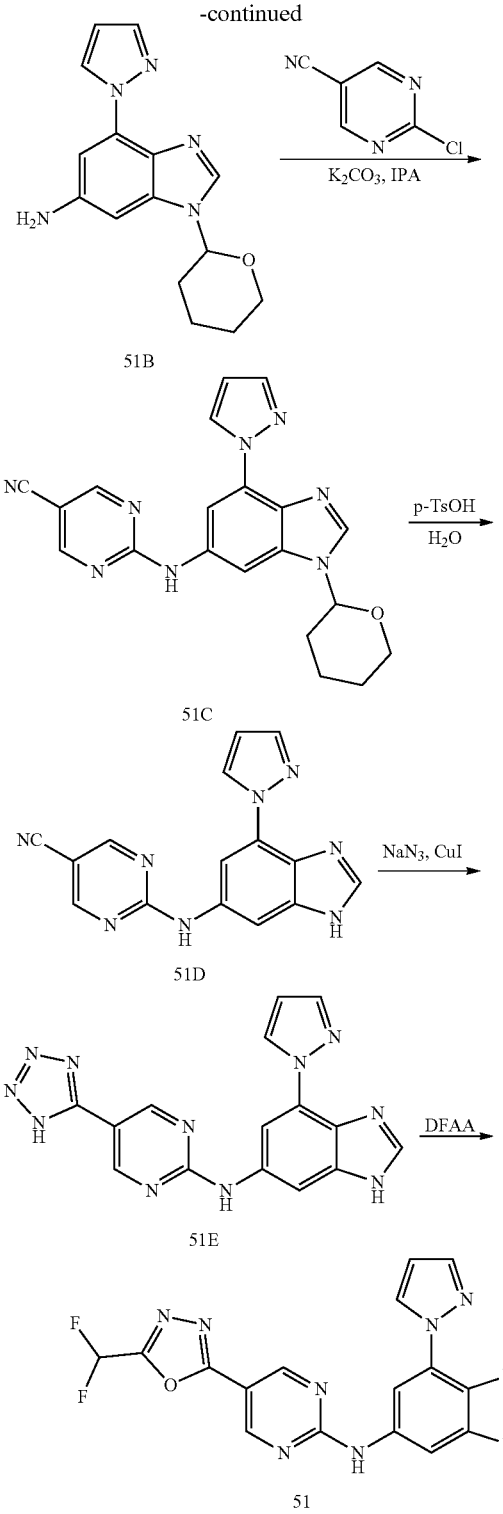

6-Nitro-4-(1H-pyrazol-1-yl)-1-(tetrahydro-2H-pyran-2-yl)-1H-benzo[d]imidazole (51A)

To a solution of 4-bromo-6-nitro-1-(tetrahydro-2H-pyran-2-yl)-1H-benzo[d] imidazole 2B (1.0 g, 3.07 mmol) in DMF (20 mL) was added 1H-pyrazole (0.42 g, 6.14 mmol), L-Proline (0.176 g, 1.53 mmol), CuI (0.25 g, 1.53 mmol) and $Cs_2CO_3$ (2 g, 6.14 mmol) under N2. The mixture was stirred at 100° C. for 16 h. The reaction mixture was cooled to rt, diluted with $H_2O$ (50 mL) and extracted with EA (50 mL×2). The combined organic layers were dried over anhydrous $Na_2SO_4$ and concentrated, and the residue was purified by column chromatography (PE:EA=1:1) to give 51A (190 mg, yield: 20%) as a yellow solid. LCMS: (ES+): m/z 314.2 $[M+1]^+$.

4-(1H-Pyrazol-1-yl)-1-(tetrahydro-2H-pyran-2-yl)-1H-benzo[d]imidazol-6-amine (51B)

To a mixture of 6-Nitro-4-(1H-pyrazol-1-yl)-1-(tetrahydro-2H-pyran-2-yl)-1H-benzo[d]imidazole (51A) (190 mg, 0.606 mmol) in MeOH (5.0 mL) was added 10% Pd/C (20 mg) at rt and the resulting mixture was stirred under an atmosphere of H2 for 5 h. The mixture was filtered through Celite™ and concentrated to give the product 51B (160 mg, yield: 93%) as a yellow oil. LCMS: (ES+): m/z 284.2 $[M+1]^+$.

2-((4-(1H-Pyrazol-1-yl)-1-(tetrahydro-2H-pyran-2-yl)-1H-benzo[d]imidazol-6-yl)amino)pyrimidine-5-carbonitrile (51C)

To a mixture of 4-(1H-Pyrazol-1-yl)-1-(tetrahydro-2H-pyran-2-yl)-1H-benzo[d]imidazol-6-amine (51B) (160 mg, 0.565 mmol) in i-PrOH (3 mL) was added $K_2CO_3$ (156 mg, 1.13 mmol) and 2-chloropyrimidine-5-carbonitrile (79 mg, 0.565 mmol) at rt under N2. The resulting mixture was then stirred at 90° C. for 5 h. After cooling to rt, the mixture was diluted with $H_2O$ (20 mL), extracted with EA (30 mL) and the organic phase was dried over anhydrous $Na_2SO_4$, filtered and concentrated to give 51C (130 mg, yield: 60%) as a yellow solid. LCMS: (ES+): m/z 387.2 $[M+1]^+$.

2-((4-(1H-Pyrazol-1-yl)-1H-benzo[d]imidazol-6-yl)amino)pyrimidine-5-carbonitrile (51D)

To a mixture of 2-((4-(1H-Pyrazol-1-yl)-1-(tetrahydro-2H-pyran-2-yl)-1H-benzo[d]imidazol-6-yl)amino)pyrimidine-5-carbonitrile (51C) (110 mg, 0.285 mmol) in $H_2O$ (0.4 mL) and dioxane (2 mL) was added p-TsOH·$H_2O$ (220 mg, 0.854 mmol) at 25° C. under N2. The mixture was stirred at 80° C. for 3 h at which time, the mixture was cooled, diluted with $H_2O$ (10 mL), and extracted with EA (10 mL×2). The combined organic layers were dried over anhydrous $Na_2SO_4$, filtered and concentrated in vacuo to give crude 51C (90 mg, yield: 100%) as a yellow solid. LCMS: (ES+): m/z 303.1 [M+1]+.

N-(5-(5-(Difluoromethyl)-1,3,4-oxadiazol-2-yl)pyrimidin-2-yl)-4-(1H-pyrazol-1-yl)-1H-benzo[d]imidazol-6-amine (51)

To a solution of 2-((4-(1H-Pyrazol-1-yl)-1H-benzo[d]imidazol-6-yl)amino)pyrimidine-5-carbonitrile (51D)(90 mg, 0.285 mmol) in DMF (2.0 mL) was added sodium azide (39 mg, 0.595 mmol) and CuI (96 mg, 0.595 mmol) under N2. The mixture was stirred at 130° C. for 1 h at which time, LCMS showed the reaction was complete to give (51E). The solution was cooled to 10° C., DFAA (518 mg, 2.98 mmol) was added and the mixture was stirred at 80° C. for 1 h. The mixture was then cooled to rt and poured into 1N $Na_2CO_3$ sol. (20 mL). The mixture was stirred at rt for 2 h and extracted with EA (20 mL×2). The combined organic layers were dried over anhydrous $Na_2SO_4$, filtered and concentrated. The residue was purified by preparative HPLC to give (51) as a yellow solid. LCMS: (ES+): m/z 396.1 [M+1]+ $^{1}$H NMR (400 MHz, DMSO-d$_6$): δ 10.57 (br s, 1H), 9.33 (br s, 1H), 9.08 (s, 2H), 8.28 (s, 1H), 8.10-8.16 (m, 2H), 7.80 (s, 1H), 7.57 (t, J=51.2 Hz, 1H), 6.58 (s, 1H).

Example 52. N-(5-(5-(difluoromethyl)-1,3,4-oxadiazol-2-yl)pyrimidin-2-yl)-4-(2,6-difluorophenyl)-1H-benzo[d]imidazol-6-amine

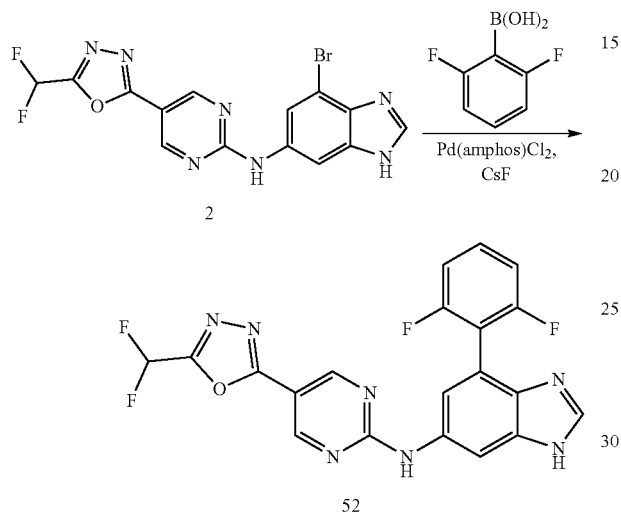

To a solution of 4-bromo-N-(5-(5-(difluoromethyl)-1,3,4-oxadiazol-2-yl)pyrimidin-2-yl)-1H-benzo[d]imidazol-6-amine (2) (60.0 mg, 0.15 mmol) and (2,6-difluorophenyl) boronic acid (47.4 mg, 0.30 mmol) in dioxane/H$_2$O (3.0 mL/0.3 mL) was added Pd(amphos)Cl$_2$ (14.0 mg, 0.020 mmol) and CsF (46.0 mg, 0.30 mmol). The mixture was stirred at 90° C. for 12 h under N2 at which time, LCMS showed the reaction was complete. The solution was diluted with EA, and washed with brine three times. The organic layer was dried over anhydrous Na$_2$SO$_4$, filtered and concentrated. The residue was purified by preparative HPLC to give 52 (6.8 mg, yield: 8.4%) as a white solid and as the corresponding TFA salt. LCMS: (ES+): m/z 442.1 [M+1]+ $^{1}$H NMR (400 MHz, DMSO-d$_6$): δ 10.76 (s, 1H), 9.13 (s, 2H), 9.03 (br s, 1H), 8.50 (s, 1H), 7.57-7.74 (m, 3H), 7.30-7.45 (m, 2H).

Example 53. N-(5-(5-(difluoromethyl)-1,3,4-oxadiazol-2-yl)pyrimidin-2-yl)-4-(2,6-difluorophenyl)-1H-benzo[d]imidazol-6-amine

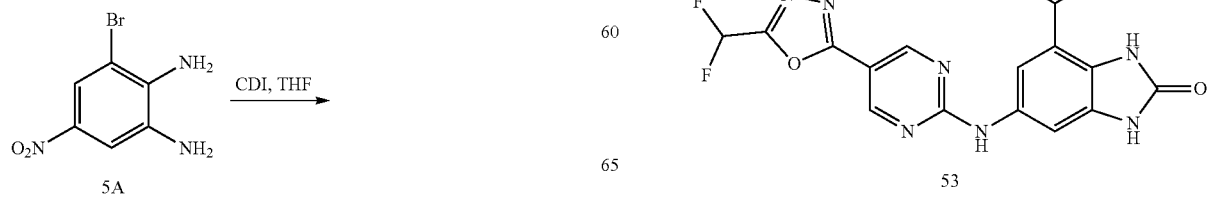

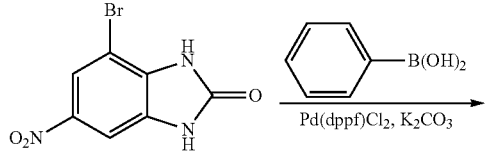

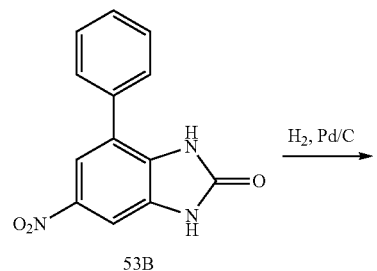

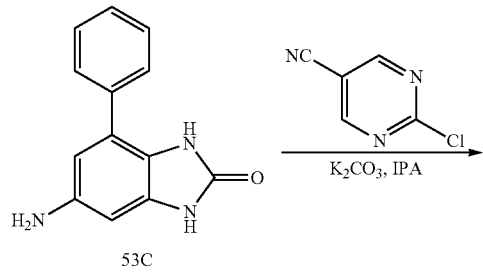

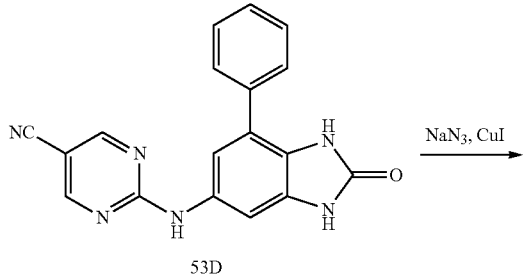

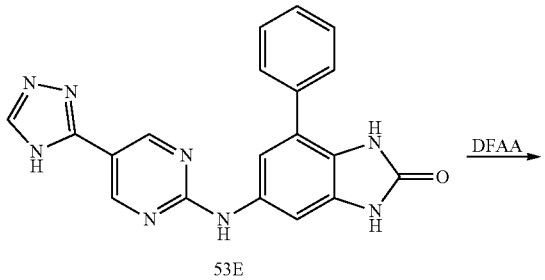

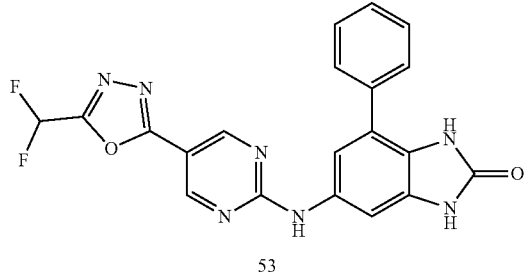

N-(5-(5-(Difluoromethyl)-1,3,4-oxadiazol-2-yl)pyrimidin-2-yl)-4-(1H-pyrazol-1-yl)-1H-benzo[d]imidazol-6-amine (53A)

A mixture of 3-bromo-5-nitrobenzene-1,2-diamine (5A) (0.50 g, 2.15 mmol) and carbonyl diimidazole (713 mg, 4.40 mmol) in THF (20.0 mL) was stirred at rt for 12 h. The solvent was evaporated, and EA (10 mL) and water (1m mL) were added. The resulting solid was filtered, and the filter cake was washed with EA and dried in vacuo to give 53A (450 mg, yield: 81%) as a yellow solid. LCMS: (ES+): m/z 258.0 [M+1]$^+$.

6-nitro-4-phenyl-1,3-dihydro-2H-benzo[d]imidazol-2-one (53B)

To a suspension of N-(5-(5-(Difluoromethyl)-1,3,4-oxadiazol-2-yl)pyrimidin-2-yl)-4-(1H-pyrazol-1-yl)-1H-benzo[d]imidazol-6-amine (53A) (450 mg, 1.75 mmol), phenylboronic acid (427 mg, 3.50 mmol) and K$_2$CO$_3$ (483 mg, 3.50 mmol) in 1,4-dioxane (10.0 mL) and water (2.0 mL) was added Pd(dppf)Cl$_2$ (132 mg, 0.18 mmol). The mixture was stirred at 90° C. for 12 h. The mixture was then cooled, poured into water and extracted with EA (20 mL×2). The combined organic layers were dried over anhydrous Na$_2$SO$_4$, filtered and concentrated. The residue was purified by preparative TLC (EA/DCM=1/1) to give 53B (380 mg, yield: 85%) as a yellow solid. LCMS: (ES+): m/z 256.1 [M+1]$^+$.

6-amino-4-phenyl-1H-benzo[d]imidazol-2(3H)-one (53C)

A mixture of 6-nitro-4-phenyl-1,3-dihydro-2H-benzo[d]imidazol-2-one (53B) (380 mg, 1.49 mmol) and Pd/C (300 mg) in a MeOH (10.0 mL) was stirred at under an H2 atmosphere at 25° C. for 3 h. The mixture was filtered through Celite™ and the filtrate was concentrated in vacuo to give 52C (300 mg, yield: 79%) which was used directly without further purification. LCMS: (ES+): m/z 226.1 [M+1]$^+$.

2-((2-oxo-7-phenyl-2,3-dihydro-1H-benzo[d]imidazol-5-yl)amino)pyrimidine-5-carbonitrile (53D)

To a mixture of 6-amino-4-phenyl-1H-benzo[d]imidazol-2(3H)-one (53C) (300 mg, 1.33 mmol) and 2-chloropyrimidine-5-carbonitrile (222 mg, 1.60 mmol) in i-PrOH (5.0 mL), was added K$_2$CO$_3$ (267 mg, 2.66 mmol). The resulting mixture was stirred at 90° C. for 12 h, cooled, and concentrated, and the residue purified by column chromatography (EA/PE=1/1) to give 53D (200 mg, yield: 46%) as a yellow solid. LCMS: (ES+): m/z 329.1 [M+1]$^+$.

((5-(5-(difluoromethyl)-1,3,4-oxadiazol-2-yl)pyrimidin-2-yl)amino)-4-phenyl-1H-benzo[d]imidazol-2(3H)-one (53)

To a solution of 2-((2-oxo-7-phenyl-2,3-dihydro-1H-benzo[d]imidazol-5-yl)amino)pyrimidine-5-carbonitrile (53D) (100 mg, 0.31 mmol) and sodium azide (61.0 mg, 0.93 mmol) in DMF (3.0 mL) was added CuI (11.8 mg, 0.060 mmol). The mixture was stirred at 120° C. for 3 h at which time, LCMS showed the reaction was complete to give crude 53E. The solution was cooled to 10° C., DFAA (0.3 mL) was added and the mixture was stirred at 80° C. for 1 h. The mixture was then was cooled to rt and poured into 1N Na$_2$CO$_3$ sol. (20 mL). The mixture was stirred at rt for 2 h and extracted with EA (20 mL×2). The combined organic layers were dried over anhydrous Na$_2$SO$_4$, filtered and concentrated. The residue was purified by preparative HPLC to give (53) as a white solid. LCMS: (ES−): m/z 420.1 [M+1]$^+$ $^1$H NMR (400 MHz, DMSO-d$_6$): δ 10.78 (s, 1H), 10.62 (s, 1H), 10.36 (s, 1H), 9.04 (s, 2H), 7.30-7.70 (m, 8H).

Example 54. N-(5-(5-(difluoromethyl)-1,3,4-oxadiazol-2-yl)pyrimidin-2-yl)-7-fluoro-4-phenyl-1H-benzo[d]imidazol-5-amine

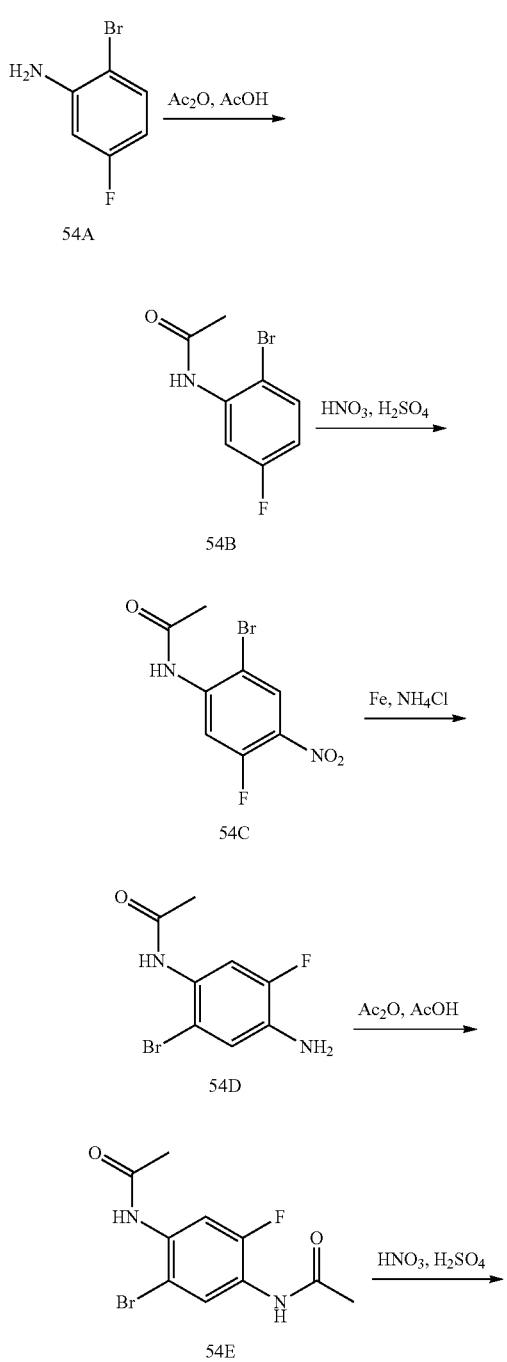

-continued

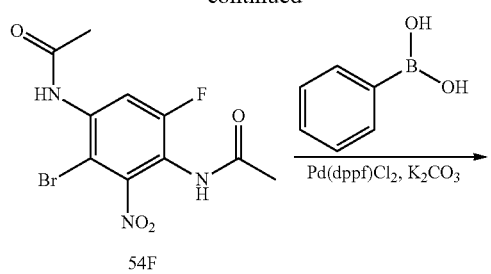

54F

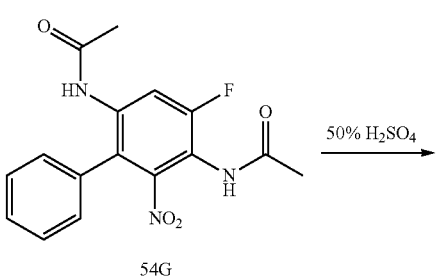

54G

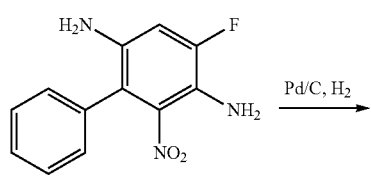

54H

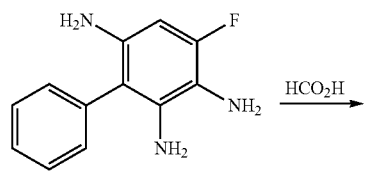

54I

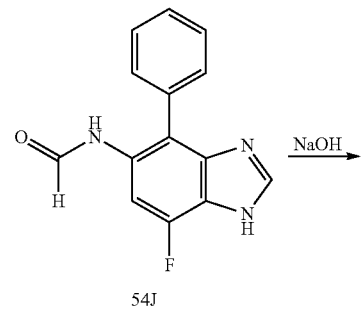

54J

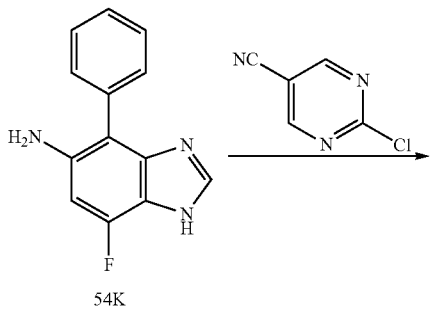

54K

-continued

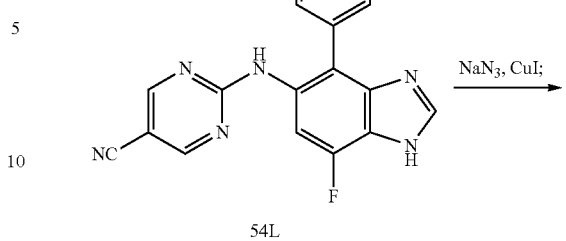

54L

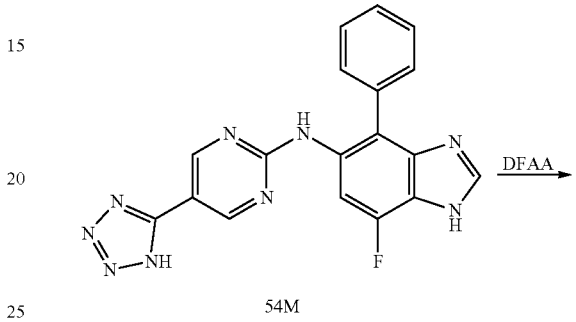

54M

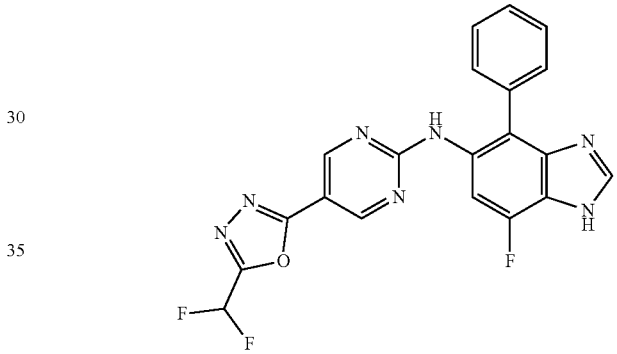

54

N-(2-bromo-5-fluorophenyl)acetamide (54B)

To a solution of 2-bromo-5-fluoroaniline (54A) (10.0 g, 52.9 mmol) in AcOH (80 mL) was added Ac$_2$O (5.95 g, 58.2 mmol). The mixture was stirred at 100° C. for 1.5 h and poured into ice-water (200 mL) and stirred for 30 min. The resulting solid was filtered, and the filter cake was washed with water. The solid was dried in vacuo to obtain (54B) (12.0 g, yield: 97%) as white solid which was used directly in the next step. LCMS: (ES+): m/z 232.1 [M+1]$^+$.

N-(2-bromo-5-fluoro-4-nitrophenyl)acetamide (54C')

To a solution of N-(2-bromo-5-fluorophenyl)acetamide (54B) (12.0 g, 52.0 mmol) in H$_2$SO$_4$ (50 mL) was added HNO$_3$ (16.4 g, 169 mmol, 65%) slowly at 0° C. The mixture was stirred at 0° C. for 1 h and poured into ice-water (200 mL). The solid was filtered, and the filter cake was washed with water. The solid was dried in vacuo to obtain (54C) (12.0 g, yield: 84%) as yellow solid which was used directly in the next step. LCMS: (ES+): m/z 277.0 [M+1]$^+$.

N-(4-amino-2-bromo-5-fluorophenyl)acetamide (54D)

To a solution of N-(2-bromo-5-fluoro-4-nitrophenyl)acetamide (54C) (12.0 g, 43.5 mmol) in EtOH/H$_2$O (10/1, 110 mL), was added iron powder (7.30 g, 130 mmol) and NH$_4$Cl (11.7 g, 271 mmol). The mixture was stirred at 100° C. for 2 h and cooled to rt. The mixture was filtered, and the filter cake was washed with EtOH (300 mL). The filtrate was concentrated, and the residue dissolved in EA (100 mL). The organics were washed with brine twice, and dried over anhydrous Na$_2$SO$_4$, filtered and concentrated to obtain (54D) (10.6 g, yield: 99%) as white solid which was used directly in the next step. LCMS: (ES+): m/z 247.0 [M+1]$^+$.

N,N'-(2-bromo-5-fluoro-1,4-phenylene)diacetamide (54E')

To a solution of N-(4-amino-2-bromo-5-fluorophenyl)acetamide (54D) (4.0 g, 16.3 mmol) in AcOH (20 mL) was added Ac$_2$O (1.82 g, 17.9 mmol) and the mixture was stirred at 100° C. for 1.5 hrs. The solution was cooled and poured into ice-water (100 mL) and stirred for 30 min. The solids were filtered, and the filter cake was washed with water. The solid was dried in vacuo to obtain (54E) (4.4 g, yield: 94%) as white solid which was used directly in the next step. LCMS: (ES+): m/z 289.0 [M+1]$^+$.

N,N'-(2-bromo-5-fluoro-3-nitro-1,4-phenylene)diacetamide (54F)

To a solution of N,N'-(2-bromo-5-fluoro-1,4-phenylene)diacetamide (54E) (4.0 g, 13.9 mmol) in H$_2$SO$_4$ (20 mL) was added HNO$_3$ (4.38 g, 45.2 mmol, 65%) at 0° C. slowly, and the mixture was stirred at 0° C. for 1 h. The solution was poured into ice-water (200 mL) and the solid was filtered. The filter cake was washed with water and the solid was dried in vacuo to obtain (54F) (1.6 g, yield: 35%) as yellow solid which was used directly in the next step. LCMS: (ES+): m/z 333.0 [M+1]$^+$.

N,N'-(4-fluoro-6-nitro-[1,1'-biphenyl]-2,5-diyl)diacetamide (54G)

To a suspension of N,N'-(2-bromo-5-fluoro-3-nitro-1,4-phenylene)diacetamide (54F) (700 mg, 2.10 mmol), phenylboronic acid (513 mg, 4.20 mmol) and K$_2$CO$_3$ (869 mg, 6.30 mmol) in 1,4-dioxane (20.0 mL) and water (2.0 mL) was added Pd(dppf)Cl$_2$ (154 mg, 0.21 mmol). The mixture was stirred at 90° C. for 12 h. The mixture was cooled to rt, poured into water and extracted with EA (2×50 mL). The combined organic phases were dried over anhydrous Na$_2$SO$_4$, filtered and concentrated. The residue was purified by preparative TLC (EtOAc/PE=1/3) to give (54G) (380 mg, yield: 55%) as yellow solid. LCMS: (ES+): m/z 332.1 [M+1]$^+$.

4-fluoro-6-nitro-[1,1'-biphenyl]-2,5-diamine (54H)

The solution of N,N'-(4-fluoro-6-nitro-[1,1'-biphenyl]-2,5-diyl)diacetamide (54G) (380 mg, 1.15 mmol) in EtOH (5.0 mL), was added H$_2$SO$_4$ (3.0 mL, 50%) and the mixture was stirred at 60° C. for 12 h. The solution was cooled, poured into ice-water and extracted with EA (20 mL×6). The combined organic layers were washed with brine twice and dried over anhydrous Na$_2$SO$_4$, filtered and concentrated. The residue was purified by preparative TLC (EA/PE=1/1) to give (54H) (200 mg, yield: 70%) as brown solid. LCMS: (ES+): m/z 248.1 [M+1]$^+$.

4-fluoro-[1,1'-biphenyl]-2,3,6-triamine (54I)

To a solution of 4-fluoro-6-nitro-[1,1'-biphenyl]-2,5-diamine (54H) (200 mg, 0.81 mmol) in MeOH (10 mL), was added Pd/C (100 mg) and the mixture was stirred at 30° C. for 2 h under an atmosphere of H$_2$. The mixture was filtered through Celite™ and, and the filter cake was washed with MeOH (30 mL). The filtrate was concentrated to obtain (54I) (150 mg, yield: 86%) as brown solid which was used directly in the next step. LCMS: (ES+): m/z 218.2 [M+1]$^+$.

7-fluoro-4-phenyl-1H-benzo[d]imidazol-5-amine (54K)

A solution of 4-fluoro-[1,1'-biphenyl]-2,3,6-triamine (54I) (150 mg, 0.69 mmol) in formic acid (5.0 mL) was stirred at 90° C. for 1 h. The mixture was cooled and concentrated in vacuo to give crude (54J). Crude (54J) was diluted with MeOH (2.0 mL) and 3N NaOH (3.0 mL) was added. The resulting mixture was stirred at 20° C. for 2 h, at which time, 1N HCl was added slowly to adjust pH to 8, and the mixture was extracted with EA (50 mL). The organic phase was dried over anhydrous Na$_2$SO$_4$, filtered and concentrated in vacuo to give (54K) (100 mg, Yield: 64%) as a brown solid which was used directly in the next step. LCMS: (ES+): m/z 228.1 [M+1]$^+$.

((7-fluoro-4-phenyl-1H-benzo[d]imidazol-5-yl)amino)pyrimidine-5-carbonitrile (54L)

To a mixture of 7-fluoro-4-phenyl-1H-benzo[d]imidazol-5-amine (54K) (100 mg, 0.44 mmol) and 2-chloropyrimidine-5-carbonitrile (73.0 mg, 0.53 mmol) in i-PrOH (5.0 mL) was added K$_2$CO$_3$ (121 mg, 0.88 mmol) and the mixture was stirred at 90° C. for 12 h. The mixture was cooled to rt, diluted with EA and washed with brine twice. The organic phase was dried over anhydrous Na$_2$SO$_4$, filtered and concentrated. The residue was recrystallized with EA/PE=1/1 to give 54L (100 mg, yield: 69%) as yellow solid. LCMS: (ES+): m/z 331.1 [M+1]$^+$.

N-(5-(5-(difluoromethyl)-1,3,4-oxadiazol-2-yl)pyrimidin-2-yl)-7-fluoro-4-phenyl-1H-benzo[d]imidazol-5-amine (54)

To a solution of ((7-fluoro-4-phenyl-1H-benzo[d]imidazol-5-yl)amino)pyrimidine-5-carbonitrile (54L) (100 mg, 0.30 mmol) and NaN$_3$ (65 mg, 1.0 mmol) in DMF (3.0 mL) was added CuI (11.4 mg, 0.060 mmol) and the mixture was stirred at 120° C. for 3 h at which time, LCMS showed the reaction was complete to give (54M). The mixture was then cooled to 25° C., DFAA (0.3 mL) was added, and the mixture was stirred at 90° C. for 3 h. The mixture was cooled to rt, 1N Na$_2$CO$_3$ (20 mL) was added, and the mixture was stirred at room temperature for 2 h. The mixture was extracted with EA (20 mL×2) and the combined organic layers were dried over anhydrous Na$_2$SO$_4$, filtered, and concentrated. The residue was purified by preparative HPLC to give 54 (19 mg, yield: 15%) as light-yellow solid. LCMS: (ES+): m/z 424.3 [M+1]$^+$ $^1$H NMR (400 MHz, DMSO-d$_6$): δ 9.77 (s, 1H), 8.84 (s, 2H), 8.38 (s, 1H), 7.23-7.65 (m, 8H).

HDAC Assay Protocol

Reagent:

Base Reaction buffer: 50 mM Tris-HCl, pH8.0, 137 mM NaCl, 2.7 mM KCl, and 1 mM MgCl$_2$. Add fresh: 1 mg/ml BSA, 1% DMSO Substrate:

Fluorogenic HDAC General Substrate: 50 µM, Arg-His-Lys-Lys(Ac)

(HDAC8 only substrate: 50 µM, Arg-His-Lys(Ac)-Lys(Ac))

Class2A Substrate: Boc-Lys(trifluoroacetyl)-AMC

For SIRTs 1-3, general Class1 HDAC substrate and 500 µM NAD+

For SIRT5, Ac-Lys-succ and 500 µM NAD+

Reaction Procedure:

Deacetylation Step:

1. Deliver 2× enzyme in wells of reaction plate except No Enzyme control wells. Add buffer in No En wells.
2. Deliver compounds in 100% DMSO into the enzyme mixture by Acoustic technology (Echo550; nanoliter range). Spin down and pre-incubation.
3. Deliver 2× Substrate Mixture (Fluorogenic HDAC Substrate and co-factor if applicable) in all reaction wells to initiate the reaction. Spin and shake.
4. Incubate for 30 min for Class 2A, 1 hr for HDAC1, 2, 3, and 6, and 2 hr for the rest of HDACs and SIRTs at 30° C. with seal.

Development Step:

5. Add Developer with Trichostatin A (or Nicotinamide for SIRTs) to stop the reaction and to generate fluorescent color.
6. Kinetic measurement for 1.5 hr with Envision with 15 min interval. (Ex/Em=360/460 nm)
7. Take endpoint reading for analysis after the development reaches plateau.

TABLE 1

| Example | Structure | IUPAC Name | % HDAC6 Inhibition @ 10 uM |
|---|---|---|---|
| 1 | 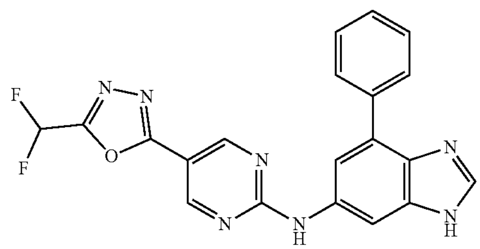 [SMILES: FC(F)c1nnc(-c2cnc(Nc3cc(-c4ccccc4)c4nc[nH]c4c3)nc2)o1] | N-(5-(5-(difluoromethyl)-1,3,4-oxadiazol-2-yl)pyrimidin-2-yl)-4-phenyl-1H-benzo[d]imidazol-6-amine | >90 |
| 2 | 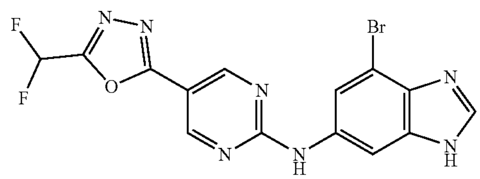 [SMILES: FC(F)c1nnc(-c2cnc(Nc3cc(Br)c4nc[nH]c4c3)nc2)o1] | 4-bromo-N-(5-(5-(difluoromethyl)-1,3,4-oxadiazol-2-yl)pyrimidin-2-yl)-1H-benzo[d]imidazol-6-amine | >90 |
| 3 | 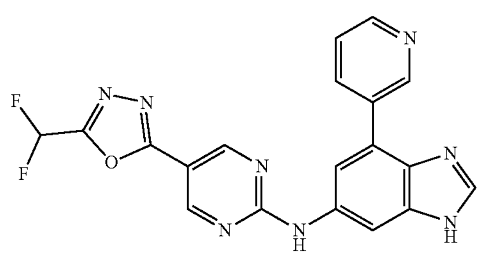 [SMILES: FC(F)c1nnc(-c2cnc(Nc3cc(-c4cccnc4)c4nc[nH]c4c3)nc2)o1] | N-(5-(5-(difluoromethyl)-1,3,4-oxadiazol-2-yl)pyrimidin-2-yl)-4-(pyridin-3-yl)-1H-benzo[d]imidazol-6-amine hydrochloride | >80 |
| 4 | 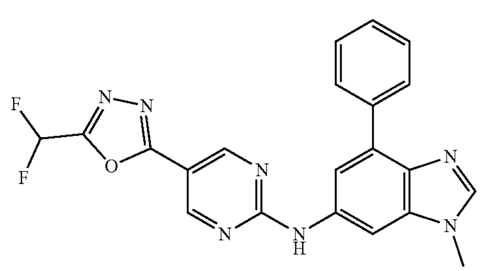 [SMILES: Cn1cnc2c(-c3ccccc3)cc(Nc3ncc(-c4nnc(C(F)F)o4)cn3)cc21] | N-(5-(5-(difluoromethyl)-1,3,4-oxadiazol-2-yl)pyrimidin-2-yl)-1-methyl-4-phenyl-1H-benzo[d]imidazol-6-amine | >70 |

TABLE 1-continued

| Example | Structure | IUPAC Name | % HDAC6 Inhibition @ 10 uM |
|---|---|---|---|
| 5 | 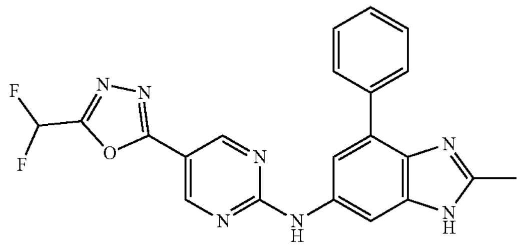 [SMILES: Cc1nc2c(-c3ccccc3)cc(Nc3ncc(-c4nnc(C(F)F)o4)cn3)cc2[nH]1] | N-(5-(5-(difluoromethyl)-1,3,4-oxadiazol-2-yl)pyrimidin-2-yl)-2-methyl-4-phenyl-1H-benzo[d]imidazol-6-amine | >90 |
| 6 | 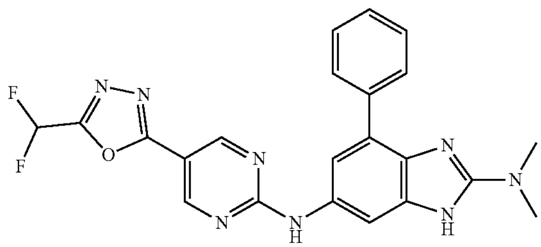 [SMILES: CN(C)c1nc2c(-c3ccccc3)cc(Nc3ncc(-c4nnc(C(F)F)o4)cn3)cc2[nH]1] | N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine 2,2,2-trifluoroacetate | >80 |
| 7 | 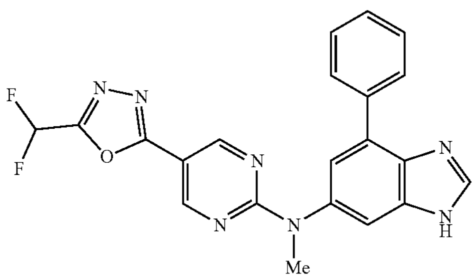 [SMILES: CN(c1cc(-c2ccccc2)c2nc[nH]c2c1)c1ncc(-c2nnc(C(F)F)o2)cn1] | N-(5-(5-(difluoromethyl)-1,3,4-oxadiazol-2-yl)pyrimidin-2-yl)-N-methyl-4-phenyl-1H-benzo[d]imidazol-6-amine | >40 |
| 8 | 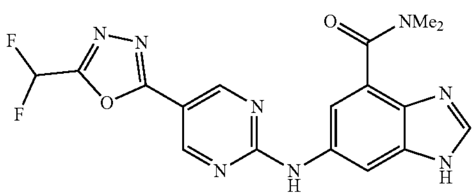 [SMILES: CN(C)C(=O)c1cc(Nc2ncc(-c3nnc(C(F)F)o3)cn2)cc2[nH]cnc12] | 6-((5-(5-(difluoromethyl)-1,3,4-oxadiazol-2-yl)pyrimidin-2-yl)amino)-N,N-dimethyl-1H-benzo[d]imidazole-4-carboxamide | >80 |
| 9 | 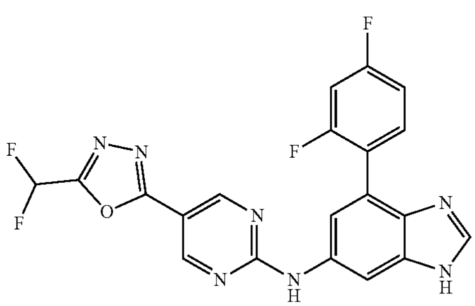 [SMILES: Fc1ccc(-c2cc(Nc3ncc(-c4nnc(C(F)F)o4)cn3)cc3[nH]cnc23)c(F)c1] | N-(5-(5-(difluoromethyl)-1,3,4-oxadiazol-2-yl)pyrimidin-2-yl)-4-(2,4-difluorophenyl)-1H-benzo[d]imidazol-6-amine | >90 |
| 10 | 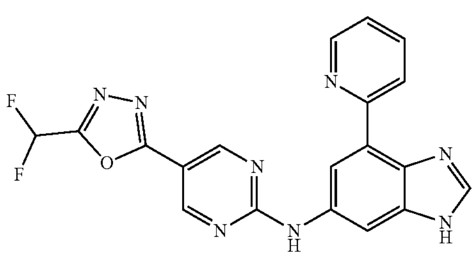 [SMILES: FC(F)c1nnc(-c2cnc(Nc3cc(-c4ccccn4)c4nc[nH]c4c3)nc2)o1] | N-(5-(5-difluoromethyl)-1,3,4-oxadiazol-2-yl)pyrimidin-2-yl)-4-(pyridin-2-yl)-1H-benzo[d]imidazol-6-amine | >90 |

TABLE 1-continued

| Example | Structure | IUPAC Name | % HDAC6 Inhibition @ 10 uM |
|---|---|---|---|
| 11 | 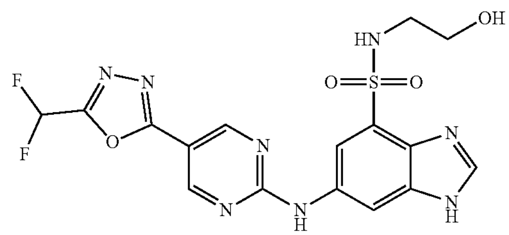 [SMILES: O=S(=O)(NCCO)c1cc(Nc2ncc(-c3nnc(C(F)F)o3)cn2)cc2[nH]cnc12] | 6-((5-(5-difluoromethyl)-1,3,4-oxodiazol-2-yl)pyrimidin-2-yl)amino)-N-(2-hydroxyethyl)-1H-benzo[d]imidazole-4-sulfonamide | >90 |
| 12 | 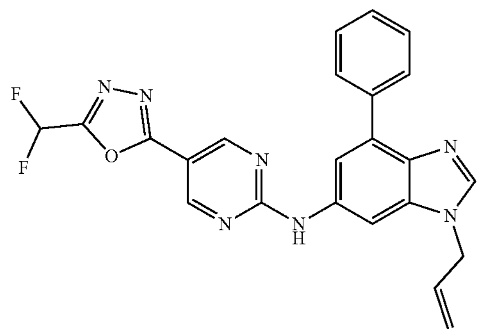 [SMILES: C=CCn1cnc2c(-c3ccccc3)cc(Nc3ncc(-c4nnc(C(F)F)o4)cn3)cc21] | 1-allyl-N-(5-(5-(difluoromethyl)-1,3,4-oxadiazol-2-yl)primidin-2-yl)-4-phenyl-1H-benzo[d]imidazol-6-amine | >90 |
| 13 | 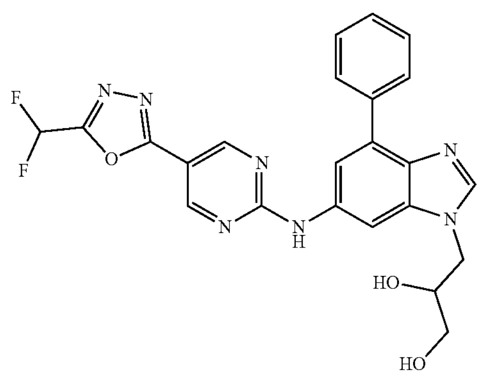 [SMILES: OCC(O)Cn1cnc2c(-c3ccccc3)cc(Nc3ncc(-c4nnc(C(F)F)o4)cn3)cc21] | 3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol | >90 |
| 14 | 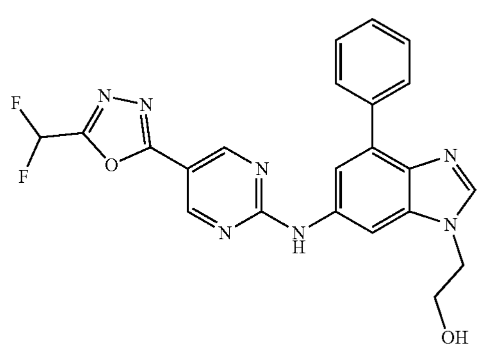 [SMILES: OCCn1cnc2c(-c3ccccc3)cc(Nc3ncc(-c4nnc(C(F)F)o4)cn3)cc21] | 2-(6-((5-(5-(difluromethyl)-1,3,4-oxadiazol-2-yl)pyrimidin-2-yl)amino)-4-phenyl-1H-benzo[d]imidazol-1-yl)ethan-1-ol | >90 |

TABLE 1-continued

| Example | Structure | IUPAC Name | % HDAC6 Inhibition @ 10 uM |
|---|---|---|---|
| 15 | 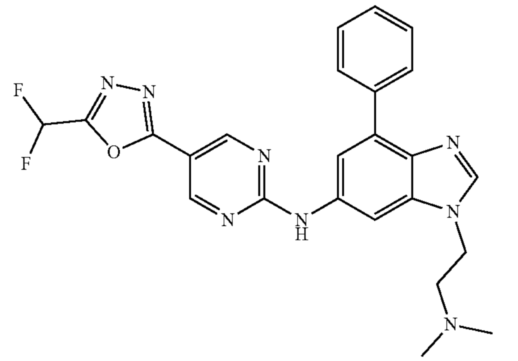 [SMILES: CN(C)CCn1cnc2c(-c3ccccc3)cc(Nc3ncc(-c4nnc(C(F)F)o4)cn3)cc21] | N-(5-(5-(difluoromethyl)-1,3,4-oxadiazol-2-yl)pyrimidin-2-yl)-1-(2-(dimethylamino)ethyl)-4-phenyl-1H-benzo[d]imidazol-6-amine | >90 |
| 16 | 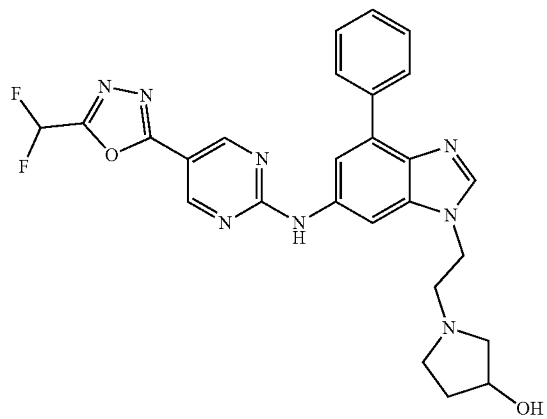 [SMILES: OC1CCN(CCn2cnc3c(-c4ccccc4)cc(Nc4ncc(-c5nnc(C(F)F)o5)cn4)cc32)C1] | 1-(2-(6-((5-(5-(difluoromethyl)-1,3,4-oxadiazol-2-yl)pyrimidin-2-yl)amino)-4-phenyl-1H-benzo[d]imidazol-1-yl)ethyl)pyrrolidin-3-ol | >90 |
| 17 | 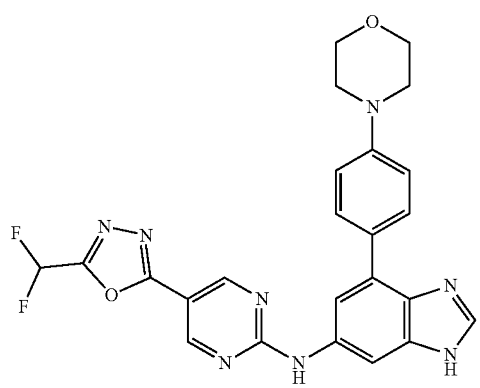 [SMILES: FC(F)c1nnc(-c2cnc(Nc3cc(-c4ccc(N5CCOCC5)cc4)c4nc[nH]c4c3)nc2)o1] | N-(5-(5-(difluoromethyl)-1,3,4-oxadiazol-2-yl)pyrimidin-2-yl)-4-(4-morpholinophenyl)-1H-benzo[d]imidazol-6-amine | >90 |
| 18 | 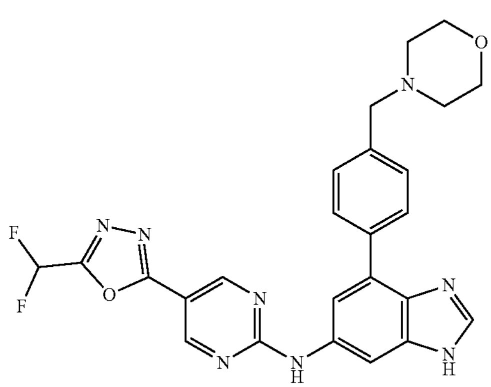 [SMILES: FC(F)c1nnc(-c2cnc(Nc3cc(-c4ccc(CN5CCOCC5)cc4)c4nc[nH]c4c3)nc2)o1] | N-(5-(5-(difluoromethyl)-1,3,4-oxadiazol-2-yl)pyrimidin-2-yl)-4-(4-(morpholinomethyl)phenyl)-1H-benzo[d]imidazol-6-amine | >90 |

TABLE 1-continued

| Example | Structure | IUPAC Name | % HDAC6 Inhibition @ 10 uM |
|---|---|---|---|
| 19 | 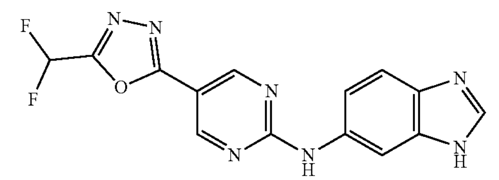 [SMILES: FC(F)c1nnc(-c2cnc(Nc3ccc4nc[nH]c4c3)nc2)o1] | N-(5-(5-(difluoromethyl)-1,3,4-oxadiazol-2-yl)pyrimidin-2-yl)-4-phenyl-1H-benzo[d]imidazol-6-amine | >90 |
| 20 | 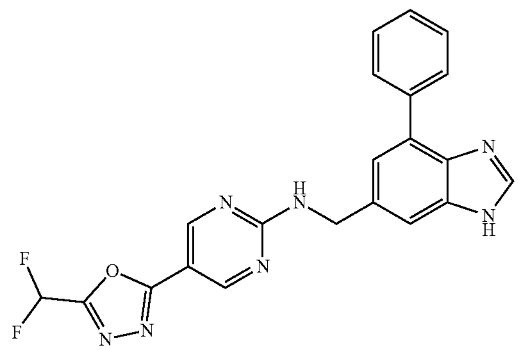 [SMILES: FC(F)c1nnc(-c2cnc(NCc3cc(-c4ccccc4)c4nc[nH]c4c3)nc2)o1] | 5-(5-(difluoromethyl)-1,3,4-oxadiazol-2-yl)-N-((4-phenyl-1H-benzo[d]imidazol-6-yl)methyl)pyrimidin-2-amine | >90 |
| 21 | 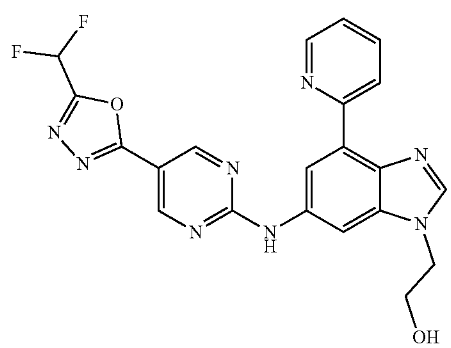 [SMILES: OCCn1cnc2c(-c3ccccn3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(pyridin-2-yl)-1H-benzo[d]imidazol-1-yl)ethan-1-ol | >90 |
| 22 | 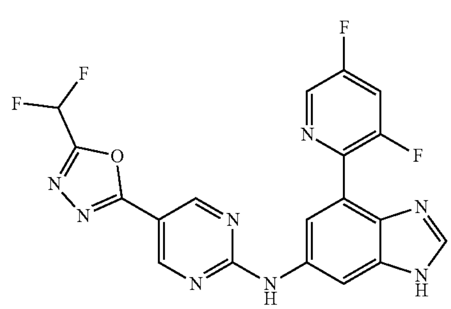 [SMILES: Fc1cnc(-c2cc(Nc3ncc(-c4nnc(C(F)F)o4)cn3)cc3[nH]cnc23)c(F)c1] | N-(5-(5-(difluoromethyl)-1,3,4-oxadiazol-2-yl)pyrimidin-2-yl)-4-(3,5-difluoropyridin-2-yl)-1H-benzo[d]imidazol-6-amine | >90 |
| 23 | 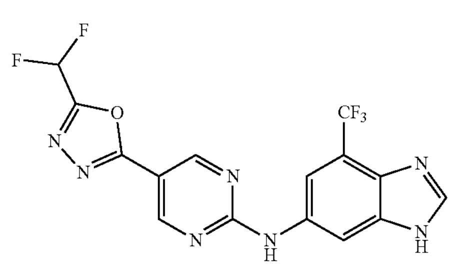 [SMILES: FC(F)c1nnc(-c2cnc(Nc3cc(C(F)(F)F)c4nc[nH]c4c3)nc2)o1] | N-(5-(5-(difluoromethyl)-1,3,4-oxadiazol-2-yl)pyrimidin-2-yl)-4-(trifluoromethyl)-1H-benzo[d]imidazol-6-amine | >90 |

TABLE 1-continued

| Example | Structure | IUPAC Name | % HDAC6 Inhibition @ 10 uM |
|---|---|---|---|
| 24 | 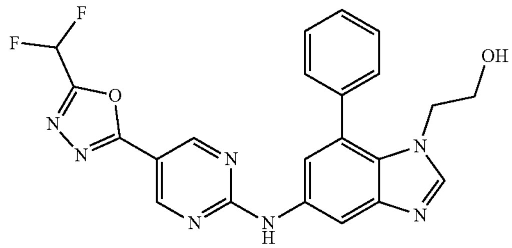 [SMILES: OCCn1cnc2cc(Nc3ncc(-c4nnc(C(F)F)o4)cn3)cc(-c3ccccc3)c21] | 2-(5-((5-(5-(difluoromethyl)-1,3,4-oxadiazol-2-yl)pyrimidin-2-yl)amino)-7-phenyl-1H-benzo[d]imidazol-1-yl)ethan-1-ol | >90 |
| 25 | 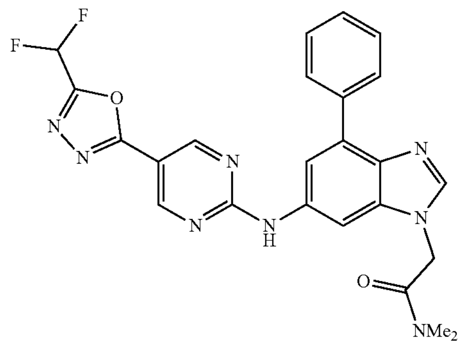 [SMILES: CN(C)C(=O)Cn1cnc2c(-c3ccccc3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-phenyl-1H-benzo[d]imidazol-1-yl)-N,N-dimethylacetamide | >90 |
| 26 | 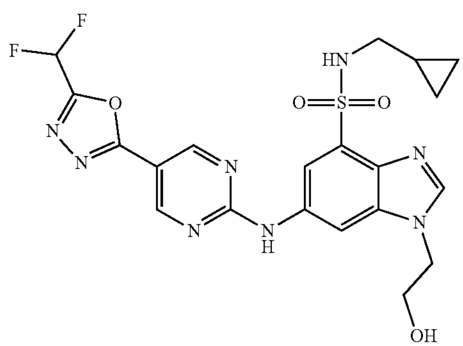 [SMILES: O=S(=O)(NCC1CC1)c1cc(Nc2ncc(-c3nnc(C(F)F)o3)cn2)cc2c1ncn2CCO] | N-(cyclopropylmethyl)-6-((5-(5-(difluoromethyl)-1,3,4-oxadiazol-2-yl)pyrimidin-2-yl)amino)-1-(2-hydroxyethyl)-1H-benzo[d]imidazole-4-sulfonamide | >90 |
| 27 | 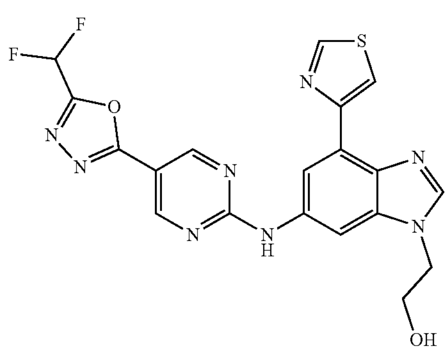 [SMILES: OCCn1cnc2c(-c3cscn3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(thiazol-4-yl)-1H-benzo[d]imidazol-1-yl)ethan-1-ol | |

TABLE 1-continued

| Example | Structure | IUPAC Name | % HDAC6 Inhibition @ 10 uM |
|---|---|---|---|
| 28 | 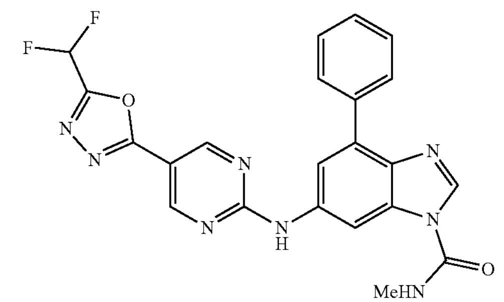 [SMILES: CNC(=O)n1cnc2c(-c3ccccc3)cc(Nc3ncc(-c4nnc(C(F)F)o4)cn3)cc21] | 6-((5-(5-(difluoromethyl)-1,3,4-oxadiazol-2-yl)pyrimidin-2-yl)amino)-N-methyl-4-phenyl-1H-benzo[d]imidazole-1-carboxamide | >90 |
| 29 | 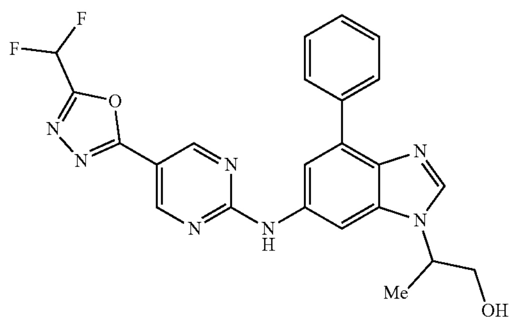 [SMILES: CC(CO)n1cnc2c(-c3ccccc3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-phenyl-1H-benzo[d]imidazol-1-yl)propan-1-ol | >90 |
| 30 | 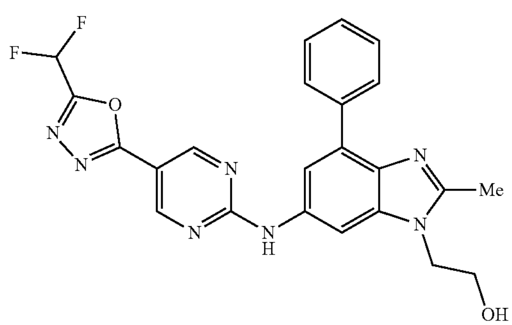 [SMILES: Cc1nc2c(-c3ccccc3)cc(Nc3ncc(-c4nnc(C(F)F)o4)cn3)cc2n1CCO] | 2-(6-((5-(5-(difluoromethyl)-1,3,4-oxadiazol-2-yl)pyrimidin-2-yl)amino)-2-methyl-4-phenyl-1H-benzo[d]imidazol-1-yl)ethan-1-ol | >90 |
| 31 | 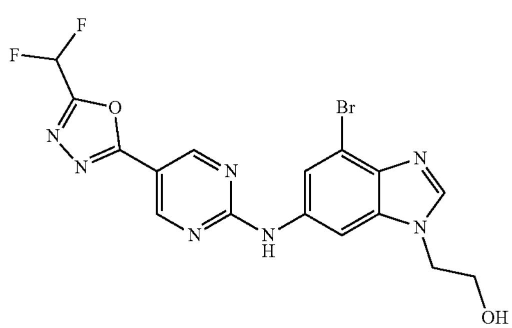 [SMILES: OCCn1cnc2c(Br)cc(Nc3ncc(-c4nnc(C(F)F)o4)cn3)cc21] | 2-(4-bromo-6-((5-(5-(difluoromethyl)-1,3,4-oxadiazol-2-yl)pyrimidin-2-yl)amino)-1H-benzo[d]imidazol-1-yl)ethan-1-ol | N/A |

TABLE 1-continued

| Example | Structure | IUPAC Name | % HDAC6 Inhibition @ 10 uM |
|---|---|---|---|
| 32 | 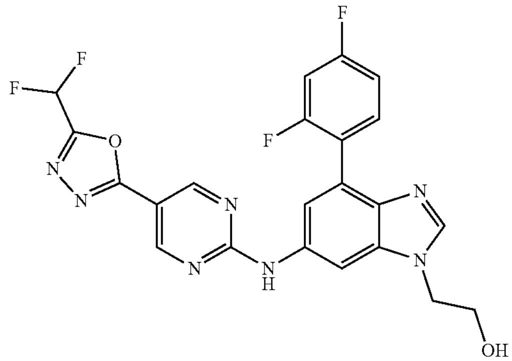 [SMILES: OCCn1cnc2c(-c3ccc(F)cc3F)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(2,4-difluorophenyl)-1H-benzo[d]imidazol-1-yl)ethan-1-ol | >90 |
| 33 | 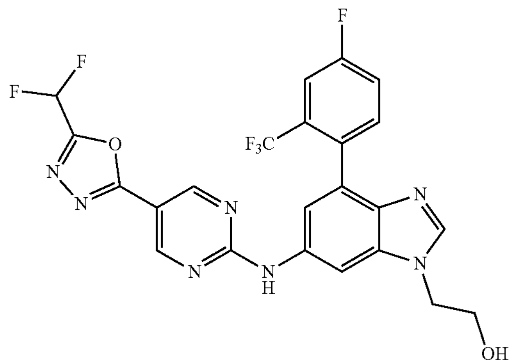 [SMILES: OCCn1cnc2c(-c3ccc(F)cc3C(F)(F)F)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(4-fluoro-2-(trifluoromethyl)phenyl)-1H-benzo[d]imidazol-1-yl)ethan-1-ol | >90 |
| 34 | 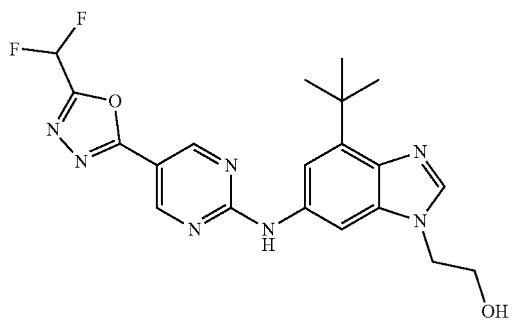 [SMILES: CC(C)(C)c1cc(Nc2ncc(-c3nnc(C(F)F)o3)cn2)cc2c1ncn2CCO] | 2-(4-(tert-butyl)-6-((5-(5-(difluoromethyl)-1,3,4-oxadiazol-2-yl)pyrimidin-2-yl)amino)-1H-benzo[d]imidazol-1-yl)ethan-1-ol | >90 |
| 35 | 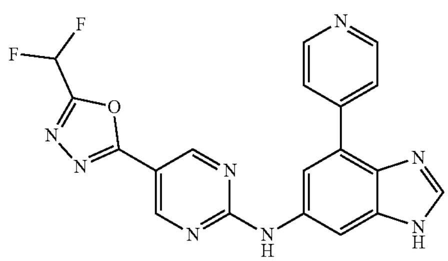 [SMILES: FC(F)c1nnc(-c2cnc(Nc3cc(-c4ccncc4)c4nc[nH]c4c3)nc2)o1] | N-(5-(5-(difluoromethyl)-1,3,4-oxadiazol-2-yl)pyrimidin-2-yl)-4-(pyridin-4-yl)-1H-benzo[d]imidazol-6-amine | >90 |
| 36 | 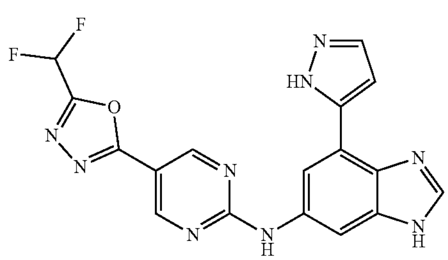 [SMILES: FC(F)c1nnc(-c2cnc(Nc3cc(-c4ccn[nH]4)c4nc[nH]c4c3)nc2)o1] | N-(5-(5-(difluoromethyl)-1,3,4-oxadiazol-2-yl)pyrimidin-2-yl)-4-(1H-pyrazol-5-yl)-1H-benzo[d]imidazol-6-amine | >90 |

TABLE 1-continued

| Example | Structure | IUPAC Name | % HDAC6 Inhibition @ 10 uM |
|---|---|---|---|
| 37 | 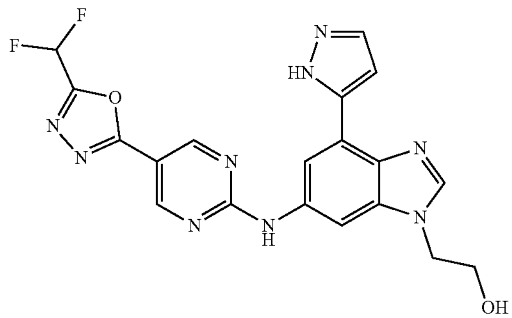 [SMILES: OCCn1cnc2c(-c3ccn[nH]3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(1H-pyrazol-5-yl)-1H-benzo[d]imidazol-1-yl)ethan-1-ol | >90 |
| 38 | 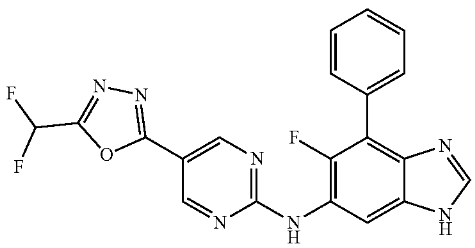 [SMILES: Fc1c(Nc2ncc(-c3nnc(C(F)F)o3)cn2)cc2[nH]cnc2c1-c1ccccc1] | N-(5-(5-(difluoromethyl)-1,3,4-oxadiazol-2-yl)pyrimidin-2-yl)-5-fluoro-4-phenyl-1H-benzo[d]imidazol-6-amine | >90 |
| 39 | 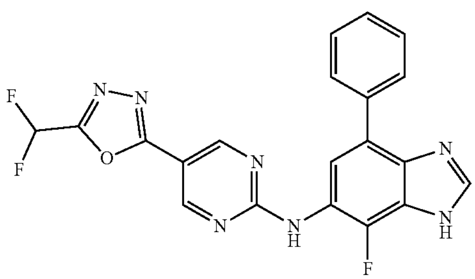 [SMILES: Fc1c(Nc2ncc(-c3nnc(C(F)F)o3)cn2)cc(-c2ccccc2)c2nc[nH]c12] | N-(5-(5-(difluoromethyl)-1,3,4-oxadiazol-2-yl)pyrimidin-2-yl)-7-fluoro-4-phenyl-1H-benzo[d]imidazol-6-amine | >90 |
| 40 | 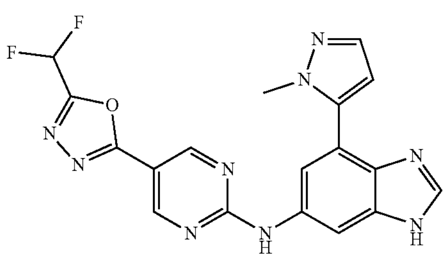 [SMILES: Cn1nccc1-c1cc(Nc2ncc(-c3nnc(C(F)F)o3)cn2)cc2[nH]cnc12] | N-(5-(5-(difluoromethyl)-1,3,4-oxadiazol-2-yl)pyrimidin-2-yl)-4-(1-methyl-1H-pyrazol-5-yl)-1H-benzo[d]imidazol-6-amine | >90 |
| 41 | 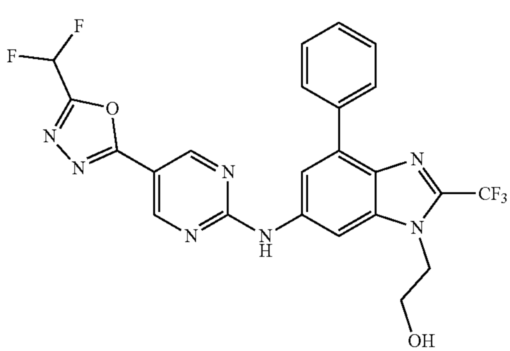 [SMILES: OCCn1c(C(F)(F)F)nc2c(-c3ccccc3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-phenyl-2-(trifluoromethyl)-1H-benzo[d]imidazol-1-yl)ethan-1-ol | >90 |

TABLE 1-continued

| Example | Structure | IUPAC Name | % HDAC6 Inhibition @ 10 uM |
|---|---|---|---|
| 42 | 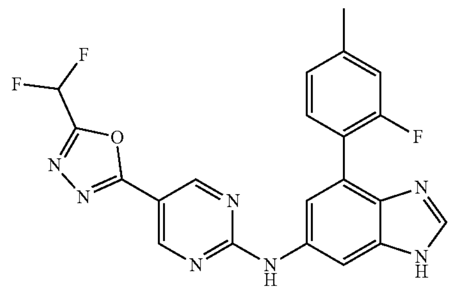 [SMILES: Cc1ccc(-c2cc(Nc3ncc(-c4nnc(C(F)F)o4)cn3)cc3[nH]cnc23)c(F)c1] | N-(5-(5-(difluoromethyl)-1,3,4-oxadiazol-2-yl)pyrimidin-2-yl)-4-(2-fluoro-4-iodophenyl)-1H-benzo[d]imidazol-6-amine | >90 |
| 43 | 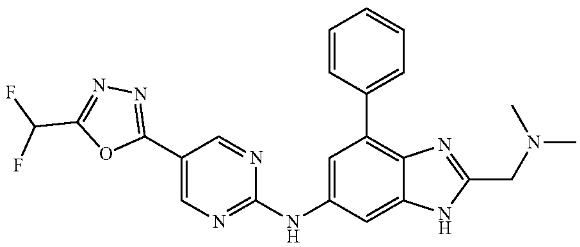 [SMILES: CN(C)Cc1nc2c(-c3ccccc3)cc(Nc3ncc(-c4nnc(C(F)F)o4)cn3)cc2[nH]1] | N-(5-(5-(difluoromethyl)-1,3,4-oxadiazol-2-yl)pyrimidin-2-yl)-2-((dimethylamino)methyl)-4-phenyl-1H-benzo[d]imidazol-6-amine | |
| 44 | 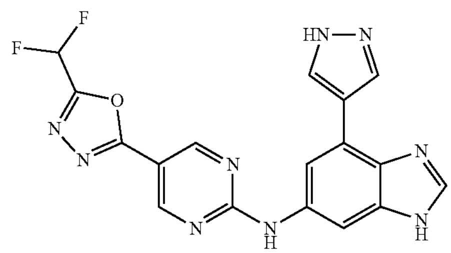 [SMILES: FC(F)c1nnc(-c2cnc(Nc3cc(-c4cn[nH]c4)c4nc[nH]c4c3)nc2)o1] | N-(5-(5-(difluoromethyl)-1,3,4-oxadiazol-2-yl)pyrimidin-2-yl)-4-(1H-pyrazol-4-yl)-1H-benzo[d]imidazol-6-amine | >90 |
| 45 | 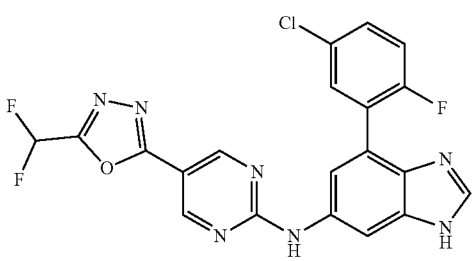 [SMILES: Fc1ccc(Cl)cc1-c1cc(Nc2ncc(-c3nnc(C(F)F)o3)cn2)cc2[nH]cnc12] | 4-(5-chloro-2-fluorophenyl)-N-(5-(5-(difluoromethyl)-1,3,4-oxadiazol-2-yl)pyrimidin-2-yl)-1H-benzo[d]imidazol-6-amine | >90 |
| 46 | 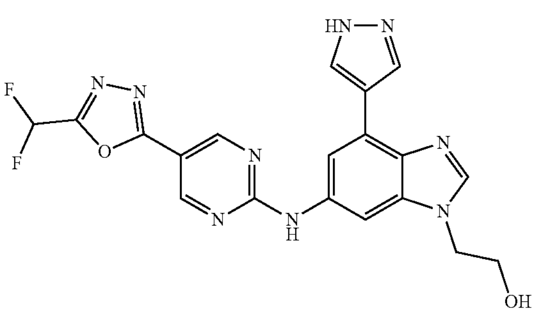 [SMILES: OCCn1cnc2c(-c3cn[nH]c3)cc(Nc3ncc(-c4nnc(C(F)F)o4)cn3)cc21] | 2-(6-((5-(5-(difluoromethyl)-1,3,4-oxadiazol-2-yl)pyrimidin-2-yl)amino)-4-(1H-pyrazol-4-yl)-1H-benzo[d]imidazol-1-yl)ethan-1-ol | >90 |

TABLE 1-continued

| Example | Structure | IUPAC Name | % HDAC6 Inhibition @ 10 uM |
|---|---|---|---|
| 47 | 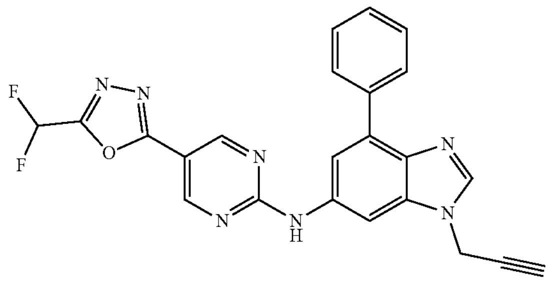 [SMILES: C#CCn1cnc2c(-c3ccccc3)cc(Nc3ncc(-c4nnc(C(F)F)o4)cn3)cc21] | N-(5-(5-(difluoromethyl)-1,3,4-oxadiazol-2-yl)pyrimidin-2-yl)-4-phenyl-1-(2,2,2-trifluoroethyl)-1H-benzo[d]imidazol-6-amine | >90 |
| 48 | 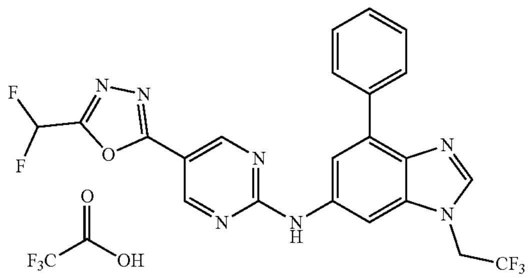 | 1-(6-((5-(5-(difluoromethyl)-1,3,4-oxadiazol-2-yl)pyrimidin-2-yl)amino)-1H-benzo[d]imidazol-4-yl)pyrrolidin-2-one | >90 |
| 49 | 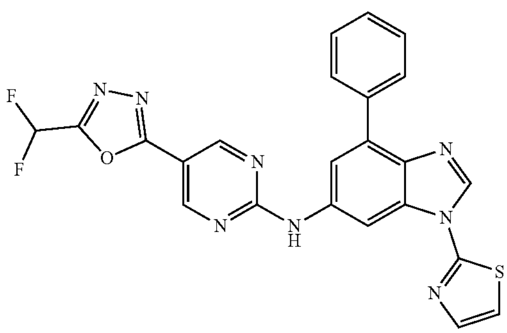 [SMILES: FC(F)c1nnc(-c2cnc(Nc3cc(-c4ccccc4)c4ncn(-c5nccs5)c4c3)nc2)o1] | N-(5-(5-(difluoromethyl)-1,3,4-oxadiazol-2-yl)pyrimidin-2-yl)-4-phenyl-1-(thiazol-2-yl)-1H-benzo[d]imidazol-6-amine | N/A |
| 50 | 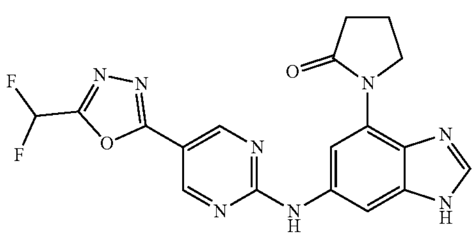 [SMILES: O=C1CCCN1c1cc(Nc2ncc(-c3nnc(C(F)F)o3)cn2)cc2[nH]cnc12] | 1-6-((5-(5-(difluoromethyl)-1,3,4-oxadiazol-2-yl)pyrimidin-2-yl)amino)-1H-benzo[d]imidazol-4-yl)pyrrolidin-2-one | N/A |
| 51 | 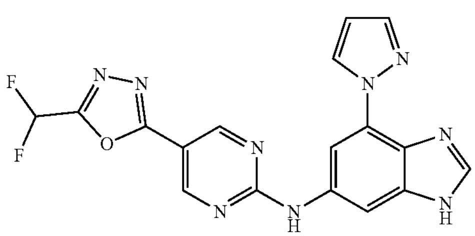 [SMILES: FC(F)c1nnc(-c2cnc(Nc3cc(-n4cccn4)c4nc[nH]c4c3)nc2)o1] | N-(5-(5-(difluoromethyl)-1,3,4-oxadiazol-2-yl)pyrimidin-2-yl)-4-(1H-pyrazol-1-yl)-1H-benzo[d]imidazol-6-amine | N/A |

TABLE 1-continued

| Example | Structure | IUPAC Name | % HDAC6 Inhibition @ 10 uM |
|---|---|---|---|
| 52 | 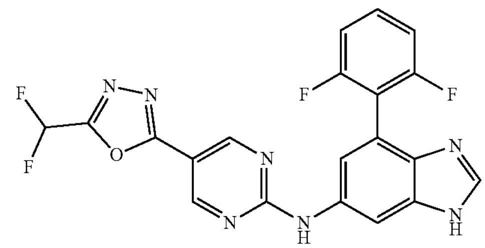 [SMILES: Fc1cccc(F)c1-c1cc(Nc2ncc(-c3nnc(C(F)F)o3)cn2)cc2[nH]cnc12] | N-(5-(5-(difluoronnethyl)-1,3,4-oxadiazol-2-yl)pyrimidin-2-yl)-4-(2,6-difluorophenyl)-1H-benzo[d]imidazol-6-amine | N/A |
| 53 | 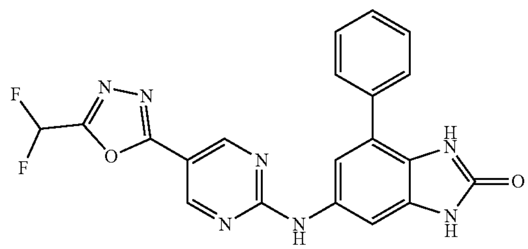 | N-(5-(5-(difluoromethyl)-1,3,4-oxadiazol-2-yl)pyrimidin-2-yl)-4-(2,6-difluorophenyl)-1H-benzo[d]imidazol-6-amine | N/A |
| 54 | 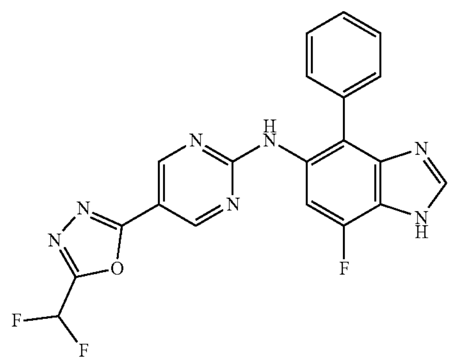 [SMILES: Fc1cc(Nc2ncc(-c3nnc(C(F)F)o3)cn2)c(-c2ccccc2)c2nc[nH]c12] | N-(5-(5-(difluoromethyl)-1,3,4-oxadiazol-2-yl)pyrimidin-2-yl)-7-fluoro-4-phenyl-1H-benzo[d]imidazol-5-amine | N/A |

| Isoform Selectivity: % HDAC1, 2, 3 and 6 Inhibition @ 10 uM | | | | |
|---|---|---|---|---|
| Example | HDAC1 | HDAC2 | HDAC3 | HDAC6 |
| 1 | <20 | <10 | <10 | >90 |

| Example | IC50 (uM) | Cell Type |
|---|---|---|
| 1 | 2.70 | U266B1 |
| Trichostatin (positive control) | 0.75 | U266B1 |

| | | Pharmacokinetic evaluation in male CD1 mice | | |
|---|---|---|---|---|
| Example | Dose | Cmax (ng/ml) | AUClast (h * ng/ml) | T1/2 h |
| 1 | 10 mg/kg (p.o.) | 1449 | 5821 | 1.75 |

| Study Type: | IV/PO PK | |
|---|---|---|
| N/Treatment: | 3 | |
| Doses: | IV | 2.0 mg/kg |
| | PO | 10 mg/kg |
| Formulations: | IV | 5% DMSO in 10% HP-β-CD in water |
| | PO | 1% CMC in water |
| Dosing Solution: | IV | 0.4 mg/mL |
| | PO | 1.0 mg/mL |
| Blood Sampling: | IV | 0.0833, 0.25, 0.5, 1, 2, 4, 8, 24 h |
| | PO | 0.25, 0.5, 1, 2, 4, 8, 24 h |

Tubulin Deacetylation Inhibition

Example 1 was dissolved with DMSO at 10 mM stock. Reference compound TSA was dissolved with DMSO at 10 mM stock. U266B1 human myeloma cell line was purchased from American Type Culture Collection (Manassas, Va.). U266B1 cells were grown in RPMI medium and supplemented with 15% heat-inactivated fetal bovine serum (FBS), 100 µg/ml penicillin, and 100 µg/ml streptomycin. Cultures were maintained at 37° C. in a humidified atmosphere of 5% $CO_2$ and 95% air. The results are shown in the Figure. 12% Bis-Tris gel and nitrocellulose membrane were purchased from Thermo Fisher. Anti-acetylated-Tubulin antibody (Catalogue #T7451) was purchased from Sigma-Aldrich. Anti-α-Tubulin antibody (Catalogue #sc-12462-R) antibody was purchased from Santa Cruz Biotechnology. Anti-Acetylated Histone H3 (K9) (Catalogue #9649) and anti-Histone H3 (Catalogue #3638) antibodies were purchased from Cell Signaling Technology. Anti-rabbit IgG IRDye 680RD or anti-mouse IgG IRDye 800CW secondary antibodies were purchased from LI-COR.

| | |
|---|---|
| HPLC | SHIMADZU (DGU-20A5R, Serial NO. L20705516860 IX; LC-30AD, Serial NO. L20555509526 AE and L20555509518 AE; SIL-30AC, Serial No. L20565504402 AE; CBM-20A, Serial No. L20235532357 CD;CTO-30A, Serial No. L20575501206 CD; Rack changer II, Serial No. L20585500968 SS) |
| MS | LCMS-8060 LC/MS/MS instrument (Serial NO. 011105500334 AE) |
| Column | Waters XSELECT HSS T3 2.5 μm 2.1 × 50 mm |
| Mobile Phase | A  5% Acetonitrile in Water (0.1% Formic acid)<br>B  95% Acetonitrile in Water (0.1% Formic acid) |
| Quantification | Internal Standard Method |

What is claimed:

1. A compound of Formula I:

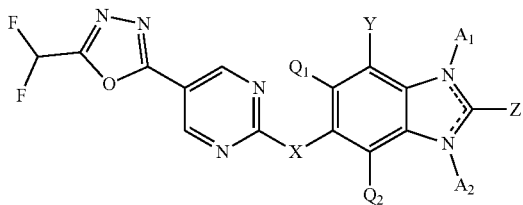

I or a pharmaceutically acceptable salt thereof,
wherein
X is $NR_1$ or O;
$Q_1$ and $Q_2$ are hydrogen or halogen;
Y is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nC(O)NR_2R_3$, —$(CH_2)_nNR_2S(O)_2R_4$, —$(CH_2)_nS(O)R_4$, —$(CH_2)_nS(O)_2R_4$ or —$(CH_2)_nOR_2$, wherein Y is substituted with 0-3 independent $R_5$ substituents;
Z is hydrogen, halogen, cyano, —$C_1$-$C_6$ alkyl, —$C_1$-$C_6$ alkenyl, —$C_1$-$C_6$ alkynyl, cycloalkyl, aryl, heterocyloalkyl, heteroaryl, —$(CH_2)_nNR_2R_3$, —$(CH_2)_nNR_2C(O)R_4$, —$(CH_2)_nC(O)R_4$, —$(CH_2)_nNR_2S(O)_2R_4$, —$(CH_2)_nS(O)R_4$, —$(CH_2)_nS(O)_2R_4$, —$(CH_2)_nOR_2$, —$OR_2$ or oxygen where oxygen and the carbon to which is attached form a double bond;
$A_1$ and $A_2$ are each independently absent, hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl, —$(CH_2)_nNR_2R_3$, —$(CH_2)_nC(O)NR_2R_3$, —$(CH_2)_nNR_2C(O)R_4$, —$(CH_2)_nNR_2S(O)_2R_4$, —$(CH_2)_nCH(OH)CH_2(CH_2)_nOH$, —$(CH_2)_nC(O)R_4$ or —$(CH_2)_nOR_5$, —$(CH_2)_nS(O)R_4$, —$(CH_2)_nS(O)_2R_4$ wherein $A_1$ and $A_2$ are substituted with 0-3 independent $R_5$ substituents;
or Y and $A_1$ taken together with the other atoms to which Y and $A_1$ are attached form a 5-10-membered heterocycloalkyl or heteroaryl ring;
or Z and $A_2$ taken together with the other atoms to which Z and $A_2$ are attached form a 5-10-membered heterocycloalkyl or heteroaryl ring;
or Z and $A_1$ taken together with the other atoms to which Z and $A_1$ are attached form a 5-10-membered heterocycloalkyl or heteroaryl ring;
$R_1$ is hydrogen or $C_1$-$C_6$ alkyl;
$R_2$ and $R_3$ are each independently, hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl or —$(CH_2)_nOR_5$ wherein $R_2$ and $R_3$ are substituted with 0-3 independent $R_5$ substituents; or $R_2$ and $R_3$ taken together with the atom(s) to which $R_2$ and $R_3$ are attached form a heterocycloalkyl ring, where the heterocycloalkyl ring is substituted with 0-2 substituents selected from —$C_1$-$C_3$ alkyl, halogen, hydroxyl and amino;
$R_4$ is hydrogen, —$C_1$-$C_6$ alkyl, —$C_1$-$C_6$ alkenyl, —$C_1$-$C_6$ alkynyl, cycloalkyl, aryl, heteroaryl, heterocyloalkyl, —$(CH_2)_nNR_6R_7$, —$(CH_2)_nOR_6$ wherein $R_4$ is substituted with 0-3 independent $R_5$ substituents; or $R_2$ and $R_4$ taken together with the atom(s) to which $R_2$ and $R_4$ are attached form a heterocycloalkyl ring;
each $R_5$ is independently hydrogen, halogen, cyano, acyl, carbamate, urea, alkoxyalkyl, —$C_1$-$C_6$ alkyl, —$C_1$-$C_6$ alkenyl, —$C_1$-$C_6$ alkynyl, heteroalkyl, haloalkyl, cycloalkyl, heterocycloalkyl, aryl, heteroaryl, arylalkyl, heteroarylalkyl, or heterocycloalkylalkyl;
$R_6$ and $R_7$ are each independently hydrogen, —$C_1$-$C_6$ alkyl and —$(CH_2)_nOH$; and
each n is independently 0, 1, 2, 3, 4, 5, 6, 7, 8, 9, or 10.

2. The compound of claim 1 or a pharmaceutically acceptable salt thereof, wherein Y is alkyl, alkenyl, alkynyl, cycloalkyl, aryl, —$(CH_2)_nR_4$ or —$(CH_2)_nOR_4$, wherein Y is substituted with 0-3 independent $R_5$ substituents.

3. The compound of claim 1 or a pharmaceutically acceptable salt thereof, wherein A is alkyl, alkenyl, alkynyl, cycloalkyl, aryl, heterocyloalkyl, or heteroaryl, wherein A is substituted with 0-3 independent $R_5$ substituents.

4. The compound of claim 1 or a pharmaceutically acceptable salt thereof, wherein Z is hydrogen, cyano, alkyl, alkenyl, alkynyl, cycloalkyl, aryl, heterocyloalkyl, heteroaryl, —$(CH_2)_nR_4$, —$(CH_2)_nNR_2R_3$, —$(CH_2)_nNR_2C(O)R_4$, —$(CH_2)_nC(O)R_4$, —$(CH_2)_nNR_2S(O)_2R_4$, —$(CH_2)_nS(O)R_4$, —$(CH_2)_nS(O)_2R_4$ or —$(CH_2)_nOR_2$.

5. The compound of claim 1, or a pharmaceutically acceptable salt thereof, wherein Y is aryl or heteroaryl, wherein each Y is substituted with 0-3 independent substituents.

6. The compound of claim 1, or a pharmaceutically acceptable salt thereof, wherein X is NH.

7. The compound of claim 1, wherein the compound of Formula I is a compound of Formula II

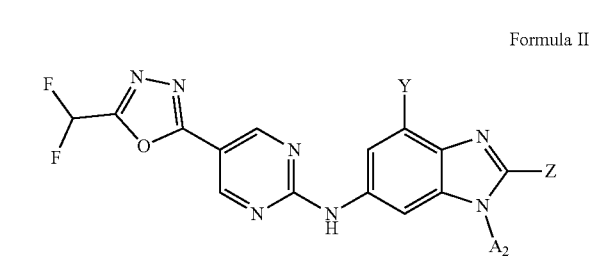

Formula II or a pharmaceutically acceptable salt thereof,
wherein:
Y is hydrogen, halogen, aryl, heteroaryl, —$(CH_2)_nC(O)NR_2R_3$ or —$(CH_2)_nS(O)_2R_4$;
$A_2$ is hydrogen, —$C_1$-$C_6$ alkyl, —$C_1$-$C_6$ alkenyl, —$(CH_2)_nOH$, —$(CH_2)_nNR_2R_3$ or —$(CH_2)_nCH(OH)CH_2(CH_2)_nOH$; and
Z is H, —$C_1$-$C_3$ alkyl or —$NR_2R_3$, where $R_2$ and $R_3$ are each independently —$C_1$-$C_3$ alkyl or —$C_1$-$C_3$ alkenyl.

8. A compound selected from the group consisting of:
N-(5-(5-(difluoromethyl)-1,3,4-oxadiazol-2-yl)pyrimidin-2-yl)-4-phenyl-1H-benzo[d]imidazol-6-amine;

4-bromo-N-(5-(5-(difluoromethyl)-1,3,4-oxadiazol-2-yl)pyrimidin-2-yl)-1H-benzo[d]imidazol-6-amine;

N-(5-(5-(difluoromethyl)-1,3,4-oxadiazol-2-yl)pyrimidin-2-yl)-4-(pyridin-3-yl)-1H-benzo[d]imidazol-6-amine hydrochloride;

N-(5-(5-(difluoromethyl)-1,3,4-oxadiazol-2-yl)pyrimidin-2-yl)-1-methyl-4-phenyl-1H-benzo[d]imidazol-6-amine;

N-(5-(5-(difluoromethyl)-1,3,4-oxadiazol-2-yl)pyrimidin-2-yl)-2-methyl-4-phenyl-1H-benzo[d]imidazol-6-amine;

N6-(5-(5-(difluoromethyl)-1,3,4-oxadiazol-2-yl)pyrimidin-2-yl)-N2,N2-dimethyl-4-phenyl-1H-benzo[d]imidazole-2,6-diamine 2,2,2-trifluoroacetate;

N-(5-(5-(difluoromethyl)-1,3,4-oxadiazol-2-yl)pyrimidin-2-yl)-N-methyl-4-phenyl-1H-benzo[d]imidazol-6-amine;

6-((5-(5-(difluoromethyl)-1,3,4-oxadiazol-2-yl)pyrimidin-2-yl)amino)-N,N-dimethyl-1H-benzo[d]imidazole-4-carboxamide;

N-(5-(5-(difluoromethyl)-1,3,4-oxadiazol-2-yl)pyrimidin-2-yl)-4-(2,4-difluorophenyl)-1H-benzo[d]imidazol-6-amine;

N-(5-(5-(difluoromethyl)-1,3,4-oxadiazol-2-yl)pyrimidin-2-yl)-4-(pyridin-2-yl)-1H-benzo[d]imidazol-6-amine;

6-((5-(5-(difluoromethyl)-1,3,4-oxadiazol-2-yl)pyrimidin-2-yl)amino)-N-(2-hydroxyethyl)-1H-benzo[d]imidazole-4-sulfonamide;

1-allyl-N-(5-(5-(difluoromethyl)-1,3,4-oxadiazol-2-yl)pyrimidin-2-yl)-4-phenyl-1H-benzo[d]imidazol-6-amine;

3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol;

3-(6-((5-(5-(difluoromethyl)-1,3,4-oxadiazol-2-yl)pyrimidin-2-yl)amino)-4-phenyl-1H-benzo[d]imidazol-1-yl)propane-1,2-diol;

N-(5-(5-(difluoromethyl)-1,3,4-oxadiazol-2-yl)pyrimidin-2-yl)-1-(2-(dimethylamino)ethyl)-4-phenyl-1H-benzo[d]imidazol-6-amine;

1-(2-(6-((5-(5-(difluoromethyl)-1,3,4-oxadiazol-2-yl)pyrimidin-2-yl)amino)-4-phenyl-1H-benzo[d]imidazol-1-yl)ethyl)pyrrolidin-3-ol;

N-(5-(5-(difluoromethyl)-1,3,4-oxadiazol-2-yl)pyrimidin-2-yl)-4-(4-morpholinophenyl)-1H-benzo[d]imidazol-6-amine;

N-(5-(5-(difluoromethyl)-1,3,4-oxadiazol-2-yl)pyrimidin-2-yl)-4-(4-(morpholinomethyl)phenyl)-1H-benzo[d]imidazol-6-amine;

N-(5-(5-(difluoromethyl)-1,3,4-oxadiazol-2-yl)pyrimidin-2-yl)-4-phenyl-1H-benzo[d]imidazol-6-amine;

and pharmaceutically acceptable salts thereof.

9. A method of inhibiting HDAC6 activity in a subject in need thereof comprising contacting a compound of claim 1, or a pharmaceutically acceptable salt thereof, with HDAC6.

10. The method of claim 9, further comprising administering a therapeutically effective amount of the compound, or a pharmaceutically acceptable salt thereof, to a subject in need thereof.

11. A method of modulating HDAC6 activity in a subject in need thereof, comprising administering to the subject a compound of claim 1, or a pharmaceutically acceptable salt thereof, in an amount and under conditions sufficient to modulate HDAC6 activity.

12. A method of treating a subject suffering from a disorder or disease associated with HDAC6, wherein the subject has been identified as in need of treatment for the disorder or disease, comprising administering to the subject a therapeutically effective amount of a compound of claim 1, or a pharmaceutically acceptable salt thereof.

13. The method of claim 12, wherein the disorder or disease is cancer, a proliferative disease, a neurodegenerative disease, pain, an autoimmune or inflammatory disorder, an infection, a metabolic disorder, a hematologic disorder, a cardiovascular disease, or a combination thereof.

14. The method of claim 12, wherein the disorder or disease is cancer or a proliferative disease, wherein the cancer or proliferative disease is selected from the group consisting of a carcinoma, a sarcoma, a leukemia, a blastoma, a lymphoma, a myeloma, or a melanoma, multiple myeloma, melanoma, breast cancer, pancreatic cancer, ovarian cancer, prostate cancer, hepatocellular cancer, renal cancer, leukemia, T-cell lymphoma, cardiac cancer, bone cancer, glioblastoma, neuroblastoma, oral squamous cell carcinoma, urothelial cancer, lung cancer, cervical cancer, rectal cancer, liver cancer, pancreatic cancer, brain cancer, kidney cancer, stomach cancer, skin cancer, colon cancer, head and neck squamous cell carcinoma, Burkitt's Lymphoma, esophageal cancer, Hodgkin's lymphoma, bladder cancer, or gastric cancer and a combination thereof.

15. The method of claim 12, wherein the disorder or disease is selected from the group consisting of epilepsy, attention deficit disorder, depression, anxiety, Alzheimer's disease, Parkinson's Disease, Huntington's Disease, amyotrophic lateral sclerosis, spinal muscular atrophy, essential tremor, central nervous system trauma, multiple sclerosis, Charcot-Marie-Tooth (MCT), cerebral ischemia, stroke, Gulf War Illness and a combination thereof.

16. The method of claim 12, wherein the disorder or disease is an infection caused by a virus, fungus, or bacteria, or a combination thereof.

17. The method of claim 12, wherein the disorder or disease is selected from the group consisting of metabolic syndrome, diabetes, obesity, high blood pressure, heart failure, cyst growth in autosomal dominant polycystic kidney disease (ADPKD), pulmonary fibrosis, idiopathic pulmonary fibrosis, liver fibrosis, cystic fibrosis, or a combination thereof.

18. The method of claim 12, wherein the disorder or disease is selected from the group consisting of cardiovascular stress, pressure overload, chronic ischemia, infarction-reperfusion injury, hypertension, atherosclerosis, peripheral artery disease, heart failure, hypertrophy, angina, arrhythmias, hypercholesterolemia, atherosclerosis, or stroke, or a combination thereof.

19. A pharmaceutical composition comprising a compound of claim 1, or a pharmaceutically acceptable salt thereof, and a pharmaceutically acceptable carrier.

20. The pharmaceutical composition of claim 19, further comprising an additional therapeutic agent.

21. The pharmaceutical composition of claim 19, further comprising an anti-cancer agent.

22. The pharmaceutical composition of claim 20, wherein the additional therapeutic agent is selected from the group consisting of platinum-based chemotherapeutic agents, *vinca* alkaloids, Akt inhibitors, alkylating agents, androgen receptor antagonists, anti-estrogens, Bcl-2 inhibitors, BRAF kinase inhibitors, BTK inhibitors, CAR-T Cells, anti-CD38 antibodies, CDK inhibitors, anti-CTLA-4 antibodies, ERK/MAPK inhibitors, farnesyltransferase inhibitors, IL-6 inhibitors, immunomodulatory agents, immuno-oncology agents, JAK2/FLT3 inhibitors, kinesin spindle protein inhibitors, MEK inhibitors, anti-PD-1 antibodies, anti-PD- LI antibodies, PI3K inhibitors, proteasome inhibitors, radiation (sensitizer), radioisotopes (sensitizer), synthetic retinoids (AM80), taxanes, tyrosine kinase inhibitors, VDR agonists, VEGF inhibitors, and oncolytic viruses, all trans tetinoic acid (ATRA), arsenic trioxide, berberine, bevacizumab, bortezomib, cabazitaxel, carfilzomib, cisplatin, carboplatin, oxaliplatin, clarithromycin, cyclophosphamide, cytarabine, darzalex, dexamethasone, docetaxel, elotuzumab, enzalutamide, epirubicin, fluorouracil (5-FU), gefitinib, gemcitabine hydrochloride, ibrutinib, idelalisib, indatuximab, ixazomib, ravtansine, ipilimumab, lenalidomide, lonafarnib, methotrexate, nab-paclitaxel, nivolumab, paclitaxel, pacritinib, pomalidomide, sorafenib, temozolomide, thalidomide, vemurafenib, vinblastine, vindesine, vinorelbine, and vincristine.

23. The method of claim 9, wherein the subject is an animal other than a human.

* * * * *